US008865610B2

(12) United States Patent
Sydora et al.

(10) Patent No.: US 8,865,610 B2
(45) Date of Patent: Oct. 21, 2014

(54) PHOSPHINYL GUANIDINE COMPOUNDS, METAL SALT COMPLEXES, CATALYST SYSTEMS, AND THEIR USE TO OLIGOMERIZE OR POLYMERIZE OLEFINS

(75) Inventors: Orson L. Sydora, Houston, TX (US); Brooke L. Small, Kingwood, TX (US); Michael J. Carney, Eau Claire, WI (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 93 days.

(21) Appl. No.: 13/490,319

(22) Filed: Jun. 6, 2012

(65) Prior Publication Data
US 2013/0331629 A1 Dec. 12, 2013

(51) Int. Cl.
*B01J 31/02* (2006.01)
*C07F 9/02* (2006.01)

(52) U.S. Cl.
USPC .......................... 502/117; 502/155; 544/225

(58) Field of Classification Search
None
See application file for complete search history.

(56) References Cited

U.S. PATENT DOCUMENTS

| | | | |
|---|---|---|---|
| 6,166,154 A | 12/2000 | Oskam et al. | |
| 7,285,607 B2 | 10/2007 | Blann et al. | |
| 7,378,537 B2 | 5/2008 | Small et al. | |
| 7,786,336 B2 | 8/2010 | Zhang et al. | |
| 7,994,363 B2 | 8/2011 | Gao et al. | |
| 2007/0043181 A1 | 2/2007 | Knudsen et al. | |
| 2012/0172645 A1 | 7/2012 | Sydora | |
| 2012/0309965 A1 | 12/2012 | Sydora et al. | |

FOREIGN PATENT DOCUMENTS

| | | |
|---|---|---|
| EP | 0585683 A2 | 3/1994 |
| EP | 2 239 056 A1 | 10/2010 |
| WO | 2004056479 A1 | 7/2004 |
| WO | 2005123633 A1 | 12/2005 |
| WO | 2007007272 A2 | 1/2007 |
| WO | 2008146215 A1 | 12/2008 |
| WO | 2011082192 A1 | 7/2011 |
| WO | 2012092415 A1 | 7/2012 |
| WO | 2013184579 A1 | 12/2013 |

OTHER PUBLICATIONS

Negrebetskii, V.V., et al., "Phosphorotropic Tautomeric Migrations of Phosphorus(III)-Containing Groups in the N—C—N Triad of Amidines," Institute of Organic Chemistry, Academy of Sciences of the Ukrainian SSR, vol. 52, No. 1, pp. 40-49 (printed pp. 36-44), Jan. 1982, Plenum Publishing Corporation.
International Search Report, PCT/US2013/043902, dated Aug. 1, 2013.
McGuinness D S et al: "Novel CR-PNP Complexes as Catalysts for the Trimerisation of Ethylene", Chemical Communications—Chemcom; Royal Society of Chemistry, GB, Jan. 1, 2003, pp. 334-335.
Lise Baiget et al: "N-Phosphino-amidines and -guanidines: synthesis, structure and P,N-chelate chemistry". Dalton Transactions, No. 8, Jan. 1, 2008, p. 1043.
Agapie, Theodor, et al., "Mechanistic studies of olefin and alkyne trimerization with chromium catalysts: deuterium labeling and studies of regiochemistry using a model chromacyclopentane complex," J. Am. Chem. Soc., 2007, pp. 14281-14295, vol. 129, No. 46, American Chemical Society.
Agapie, Theodor, et al., "Mechanistic studies of the ethylene trimerization reaction with chromium-diphosphine catalysts: experimental evidence for a mechanism involving metallacyclic intermediates ," J. Am. Chem. Soc., 2004, pp. 1304-1305, vol. 126, No. 5, American Chemical Society.
Aluri, Bhaskar Reddy, et al., Coordination chemistry of new selective ethylene trimerisation ligand Ph2PN(iPr)P(Ph)NH(R) (R=iPr, Et) and tests in catalysis, XP-55023528, Dalton Transactions, 2010, pp. 7911-7920, vol. 39, The Royal Society of Chemistry.
Blann, Kevin, et al., "Ethylene tetramerisation: Subtle effects exhibited by N-substituted diphospinoamine ligands," Journal of Catalysis, 2007, pp. 244-249, vol. 249, Elsevier Inc.
Bollmann, Annette, et al., "Ethylene tetramerization: a new route to produce 1-octene in exceptionally high selectivities," J. Am. Chem. Soc., 2004, pp. 14712-14713, vol. 126, No. 45, American Chemical Society.
Brückner, Angelika, et al., "Monitoring Structure and Valence State of Chromium Sites during Catalyst Formation and Ethylene Oligomerization by in Situ EPR Spectroscopy," Organometallicss, 2008, vol. 27, pp. 3849-3856, American Chemical Society.
Chemical Abstracts Service, Data Registry, No. 74141-00-7/RN, Nov. 16, 1984, 2 pages, American Chemical Society, ACS on STN.
Filing receipt and specification for provisional patent application entitled "Phosphinyl amidine compounds, metal complexes, catalyst systems, and their use to oligomerize or polymerize olefins," by Orson L. Sydora, et al., filed Dec. 31, 2009 as U.S. Appl. No. 61/291,459.
Foreign communication from a related counterpart application—International Preliminary Report on Patentability, PCT/US2010/062281, Jul. 4, 2012, 7 pages.
Foreign communication from a related counterpart application—International Search Report and Written Opinion, PCT/US2011/067709, Apr. 12, 2012, 10 pages.
Foreign communication from a related counterpart application—International Preliminary Report on Patentability, PCT/US2011/067709, Jul. 2, 2013, 7 pages.

(Continued)

*Primary Examiner* — Samantha Shterengarts
(74) *Attorney, Agent, or Firm* — Conley Rose, P.C.; Rodney B. Carroll; Lynda S. Jolly

(57) ABSTRACT

The present application relates to $N^2$-phosphinyl guanidine metal salt complexes. The present application also relates to catalyst systems comprising $N^2$-phosphinyl guanidine metal salt complexes and processes for making catalyst systems comprising $N^2$-phosphinyl guanidine metal salt complexes. The present application also relates to utilizing $N^2$-phosphinyl guanidine metal salt complexes in processes of oligomerizing or polymerizing olefins.

24 Claims, No Drawings

(56) References Cited

OTHER PUBLICATIONS

Jabri, Amir, et al., "Isolation of a Cationic Chromium(II) Species in a Catalytic System for Ethylene Tri- and Tetramerization," XP-002457472, Organometallics, 2006, pp. 715-718, vol. 25, No. 3, American Chemical Society.
Killian, Esna, et al., "The use of bis(diphenylphosphino)amines with N-aryl functionalities in selective ethylene tri- and tetramerization," Journal of Molecular Catalysis A: Chemical, vol. 270, 2007, pp. 214-218, Elsevier B.V.
Kuhlmann, Sven, et al., "Chromium catalyzed tetramerization of ethylene in a continuous tube reactor—Proof of concept and kinetic aspects," Journal of Catalysis, vol. 262, 2009, pp. 83-91, Elsevier Inc.
Kuhlmann, Sven, et al., "N-substituted diphosphinoamines: Toward rational ligand design for the efficient tetramerization of ethylene," XP-005755888, Journal of Catalysis, 2007, pp. 279-284, vol. 245, Elsevier Inc.
MacAdams, Leonard A., et al., "A Chromium Catalyst for the Polymerization of Ethylene as a Homogeneous Model for the Phillips Catalyst," JACS Communications, J. Am. Chem. Soc., vol. 127, No. 4, 2005, pp. 1082-1083, American Chemical Society.
Advisory Action dated Sep. 18, 2013 (2 pages), U.S. Appl. No. 13/519,825, filed Aug. 27, 2012.
Notice of Allowance dated Oct. 31, 2013 (10 pages), U.S. Appl. No. 13/519,825, filed Aug. 27, 2012.
Office Action dated Feb. 25, 2013 (21 pages), U.S. Appl. No. 13/519,825, filed Aug. 27, 2012.
Office Action (Final) dated Jun. 19, 2013 (8 pages), U.S. Appl. No. 13/519,825, filed Aug. 27, 2012.
Office Action dated Oct. 7, 2013 (21 pages), U.S. Appl. No. 12/980,457, filed Dec. 29, 2010.
Rucklidge, Adam J., et al., "Ethylene tetramerization with cationic chromium(I) complexes," Organometallics, 2007, pp. 2782-2787, vol. 26, No. 10, American Chemical Society.
Sydora, Orson L., "Catalyst Activation Study: PNR/Cr Systems," Aug. 19, 2010, pp. 4-17.
Thomas, Barbara J., et al., "Paramagnetic alkychromium compounds as homogeneous catalysts for the polymerization of ethylene," J. Am. Chem. Soc., vol. 113, No. 3, 1991, pp. 893-902, American Chemical Society.
Walsh, Richard, et al., "Reaction kinetics of an ethylene tetramerisation catalyst," Applied Catalysis A: General, vol. 302, 2006, pp. 184-191, Elsevier B.V.
Wang, Dongping, et al., "Influence of the built-in pyridinium salt on asymmetric epoxidation of substituted chromenes catalysed by chiral (Pyrrolidine salen)Mn(III) complexes," Journal of Molecular Catalysis A: Chemical, 2007, pp. 278-283, vol. 270, Elsevier B.V.
Weng, Zhiqiang, et al., "Chromium(III) catalysed ethylene tetramerization promoted by bis(phosphino)amines with an N-functionalized pendant," Dalton Transactions, 2007, 1 page cover page plus pp. 3493-3498, The Royal Society of Chemistry.
White, Paul A., et al., "α-Olefin Polymerization with Ether-Coordinated Chromium(III) Alkyls," Organometallics, vol. 15, 1996, pp. 5473-5475, American Chemical Society.
Zhuze, T. P., et al., "Solubilities of ethylene in hexane, cyclohexane, and benzene under pressure," pp. 335-337 (translated from Izvestiya Akademii Nauk SSSR, Otdelenie Khimicheskikh Nauk, No. 2, pp. 364-366, Feb. 1960).
Acid-catalyzed rearrangements of phosphinoamidines, 1992, vol. 61, No. 7, pp. 1581-1589 plus 1 cover page, International Academic Publishing Co.
Baiget, Lise, et al., "N-Phosphino-amidines and -guanidines: synthesis, structure and P,N-chelate chemistry," Dalton Transactions, 2008, pp. 1043-1054, The Royal Society of Chemistry.
Benito-Garagorri, David, et al., "Achiral and Chiral Transition Metal Complexes with Modularly Designed Tridentate PNP Pincer-Type Ligands Based on N-Heterocyclic Diamines," Organometallics, 2006, vol. 25, pp. 1900-1913, American Chemical Society.
Benito-Garagorri, David, et al., "Iron(II) Complexes Bearing Tridentate PNP Pincer-Type Ligands as Catalysts for the Selective Formation of 3-Hydroxyacrylates from Aromatic Aldehydes and Ethyldiazoacetate," Organometallics, 2007, vol. 26, pp. 217-222, American Chemical Society.
Benito-Garagorri, David, et al., "Kinetically Controlled Formation of Octahedral trans-Dicarbonyl Iron(II) PNP Pincer Complexes: The Decisive Role of Spin-State Changes," Organometallics, 2010, vol. 29, pp. 4932-4942, American Chemical Society.
Benito-Garagorri, David, et al., "Striking Differences Between the Solution and Solid-State Reactivity of Iron PNP Pincer Complexes with Carbon Monoxide," Organometallics, 2009, vol. 28, pp. 6902-6914, American Chemical Society.
Braunstein, Pierre, et al., "Erratum to "Synthesis of nickel phenyl complexes with new chelating $\bullet^2$-P,N ligands derived from α-iminoazatriphenylphosphoranes"", Journal of Organometallic Chemistry, 1999, vol. 582, pp. 370-377, Elsevier Science S.A.
Braunstein, Pierre, et al., "Synthesis of nickel phenyl complexes with new chelating $\bullet^2$-P,N ligands derived from α-iminoazatriphenylphosphoranes," Journal of Organometallic Chemistry, 1997, vol. 529, pp. 387-393, Elsevier Science S.A.
Dyer, Philip W., et al., "Rigid N-Phosphino Guanidine P,N Ligands and Their Use in Nickel-Catalyzed Ethylene Oligomerization," Organometallics, 2008, vol. 27, pp. 5082-5087, American Chemical Society.
Foreign communication from a corresponding application—International Search Report and Written Opinion, PCT/US2010/062281, Mar. 25, 2011, 14 pages.
Hartke, Klaus, et al., "Zur 1,3(N→N)-Wanderung N-heterosubstituierter N,N'-Dimethylbenzamidine," Chem. Ber., 1980, vol. 113, pp. 1394-1405, Verlag Chemie.
McNaught, A.D., et al., "Compendium of Chemical Terminology," The Gold Book, International Union of Pure and Applied Chemistry, Second Edition, 1997, 1 page, http:www.chem.qmul.ac.uk/iupac/bibliog/gold.html.
Munchenberg, Jochen, et al., "N-(N', N', N'',N''-tetramethyl) guanidine-substituted phosphines as monodentate, bidentate or tridentate ligands in transition metal chemistry," Journal or Organometallic Chemistry, 1997, vol. 529, pp. 361-374, Elsevier Science S.A.
Negrebetskii, V.V., et al., "Phosphorotropic tautomeric migrations of trivalent phosphorus groups in the nitrogen—carbon—nitrogen triad of amidines," Inst. Org. Khim., XP 002625773, 1982, vol. 52, No. 1, 1 page.
Ostrowska, K., et al., "Amidines (imidamides) N-substituted by metals, halogens, oxygen, and other heteroatoms," Science of Synthesis, XP 002625772, 2005, vol. 22, pp. 489-563, 1 page.
Periodic Table of Elements, Feb. 4, 1985, C&EN, p. 27.
Shalimov, A.A., et al., "N-Substituted N-Phosphinotrifluoroacetamides in the Staudinger Reaction," Russian Journal of General Chemistry, vol. 75, No. 9, 2005, pp. 1376-1378, Pleiades Publishing, Inc.
Sun, Mingtai, et al., "Synthesis, structures and ethylene polymerization behavior of half-metallocene chromium(III) catalysts bearing salicylaldiminato ligands," XP 002625776, New Journal of Chemistry, 2010, vol. 34, pp. 2979-2987.
Yeh, Chun-Wei, et al., "Role of Ligand Conformation in the Structural Diversity of Divalent Complexes Containing Phosphinic Amide Ligand," Inorganic Chemistry Communications, vol. 14, 2011, pp. 1212-1216, Elsevier B.V.
Filing receipt and specification for patent application entitled "Phosphinyl amidine compounds, metal complexes, catalyst systems, and their use to oligomerize or polymerize olefins," by Orson L. Sydora, et al., filed Jan. 31, 2014 as U.S. Appl. No. 14/169,517.
Office Action (Final) dated Mar. 14, 2014 (14 pages), U.S. Appl. No. 12/980,457, filed Dec. 29, 2010.
Foreign communication from a related counterpart application—Japanese Office Action, JP 2012-547252, Feb. 7, 2014, 6 pages.

PHOSPHINYL GUANIDINE COMPOUNDS, METAL SALT COMPLEXES, CATALYST SYSTEMS, AND THEIR USE TO OLIGOMERIZE OR POLYMERIZE OLEFINS

TECHNICAL FIELD

This disclosure relates to $N^2$-phosphinyl guanidine compounds and metal salt complexes of $N^2$-phosphinyl guanidine compounds. The disclosure also relates to methods of producing the $N^2$-phosphinyl guanidine compounds and metal salt complexes of $N^2$-phosphinyl guanidine compounds. The disclosure further relates to catalyst systems utilizing the $N^2$-phosphinyl guanidine compounds, metal salt complexes of $N^2$-phosphinyl guanidine compounds, and their use in the oligomerization or polymerization of olefins.

BACKGROUND

Olefins are important items of commerce. Their many applications include employment as intermediates in the manufacture of detergents, as precursors to more environmentally-friendly refined oils, as monomers, and as precursors for many other types of products. An important subset of olefins are alpha-olefins, and one method of making alpha olefins is via oligomerization of ethylene, which is a catalytic reaction involving various types of catalysts and/or catalyst systems.

Applications and demand for olefin oligomers (e.g., alpha olefins) continue to multiply, and competition to supply them correspondingly intensifies. Thus, additional novel and improved catalysts and methods for olefin oligomerization and/or polymerization are desirable.

SUMMARY

In an aspect, the present disclosure is directed to an $N^2$-phosphinyl guanidine metal salt complex comprising a metal salt complexed to an $N^2$-phosphinyl guanidine compound; or alternatively, a chromium salt complexed to an $N^2$-phosphinyl guanidine compound. In another aspect, the present disclosure is directed to a composition comprising an $N^2$-phosphinyl guanidine metal salt complex comprising a chromium salt complexed to an $N^2$-phosphinyl guanidine compound. In some embodiments, the $N^2$-phosphinyl guanidine metal salt complex can have Structure MGu1, Structure MGu2, Structure MGu3, Structure MGu4, or Structure MGu5; or alternatively, can have Structure CrGu1, Structure CrGu2, Structure CrGu3, Structure CrGu4, or Structure CrGu5. In some embodiments, where the metal salt is a chromium salt, the chromium salt can comprise a chromium(III) carboxylate, a chromium(III) β-diketonate, or a chromium (III) halide; or alternatively a chromium(III) halide.

In another aspect, the present disclosure is directed to a catalyst system comprising an $N^2$-phosphinyl guanidine metal salt complex comprising a metal salt complexed to an $N^2$-phosphinyl guanidine compound and a metal alkyl compound; or alternatively, chromium salt complexed to an $N^2$-phosphinyl guanidine compound and a metal alkyl compound. In some embodiments, the metal alkyl compound can be an aluminoxane. In some embodiments, aluminoxane can comprise methylaluminoxane (MAO), modified methylaluminoxane (MMAO), ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, and mixtures thereof; or alternatively, modified methylaluminoxane (MMAO). In a further aspect, the present disclosure is directed to processes of preparing a catalyst system comprising contacting an $N^2$-phosphinyl guanidine metal salt complex and a metal alkyl compound; or alternatively, contacting an $N^2$-phosphinyl guanidine chromium salt complex and a metal alkyl compound. In an embodiment, the catalyst system can be aged in the substantial absence of an olefin.

In yet another aspect, the present disclosure is directed to an oligomerization process comprising a) contacting i) an olefin, and ii) a catalyst system comprising (a) an $N^2$-phosphinyl guanidine metal salt complex (or alternatively, an $N^2$-phosphinyl guanidine chromium salt complex), and (b) a metal alkyl compound (or alternatively, an aluminoxane), to form an oligomer product and b) recovering an oligomer. In some embodiments, the catalyst system, the olefin, and hydrogen can be contacted to form an oligomer product. In some embodiments, the olefin can comprise ethylene. In an embodiment where the olefin comprises ethylene, the oligomer product can comprise a liquid oligomer product comprising from 60 to 99.9 wt. % $C_6$ and $C_8$ olefins. In another embodiment where the olefin comprises ethylene, a $C_6$ oligomer product can comprise at least 90 wt. % 1-hexene; or alternatively, a $C_8$ oligomer product comprises at least 90 wt. % 1-octene.

DETAILED DESCRIPTION

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the Periodic Table are indicated using the numbering scheme indicated in the version of the periodic table of elements published in Chemical and Engineering News, 63(5), 27, 1985. In some instances a group of elements can be indicated using a common name assigned to the group; for example alkali metals for Group 1 elements, alkaline earth metals for Group 2 elements, transition metals for Group 3-12 elements, and halogens for Group 17 elements.

Regarding claim transitional terms or phrases, the transitional term "comprising", which is synonymous with "including," "containing," "having," or "characterized by," is inclusive or open-ended and does not exclude additional, unrecited elements or process steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter the composition or process to which the term is applied. For example, a feedstock consisting of a material A can include impurities typically present in a commercially produced or commercially available sample of the recited compound or composition. When a claim includes different features and/or feature classes (for example, a process step, feedstock features, and/or product features, among other possibilities), the transitional terms comprising, consisting essentially of, and consisting of apply only to the feature class which is utilized and it is possible to have different transitional terms or phrases utilized with different features within a claim. For example, a process can comprise several recited steps (and other non-recited steps) but utilize a catalyst system preparation consisting of specific or alternatively consist of specific steps and/or utilize a catalyst system comprising recited components and other non-recited components.

While compositions and methods are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound unless otherwise specified.

Herein, features of the subject matter can be described such that, within particular aspects and/or embodiments, a combination of different features may be envisioned. For each and every aspect and/or embodiment disclosed herein, all combinations of features that do not detrimentally affect the compounds, processes, and/or methods described herein are contemplated with or without explicit description of the particular combination. Additionally, unless explicitly recited otherwise, any aspect and/or embodiment disclosed herein can be combined to describe inventive features of the present application.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethylpropane while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogen atoms, as necessary for the situation, removed from the alkane. Throughout, the disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group.

"Substituted" is intended to be non-limiting and include inorganic substituents or organic substituents. Moreover, other identifiers or qualifying terms can be utilized to indicate the presence or absence of a particular substituent, a particular regiochemistry and/or stereochemistry, or the presence or absence of a branched underlying structure or backbone.

A guanidine group is a group having the general structure

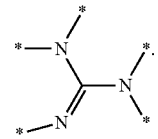

Within the guanidine core, the nitrogen participating in a double bond with the central carbon atom is referred to as the $N^1$ nitrogen and the two nitrogen atoms participating in a single bond with the central carbon atom are referred to as the $N^2$ nitrogen and the $N^3$ nitrogen. Similarly, the groups attached to the $N^1$, $N^2$ and $N^3$ nitrogen atoms are referred to as the $N^1$ group, $N^2$ group, and $N^3$ group respectively. An $N^2$-phosphinyl guanidine group has the general structure

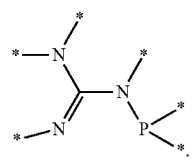

Within an $N^2$-phosphinyl guanidine group, the nitrogen participating in a double bond with the central carbon atom of the guanidine core is referred to as the $N^1$ nitrogen, the nitrogen atom participating in a single bond with the central carbon atom of the guanidine core and a bond with the phosphorus atom of the phosphinyl group is referred to as the $N^2$ nitrogen, and the remaining nitrogen atom participating in a single bond with the central carbon atom of the guanidine core is referred to as the $N^3$ nitrogen. It should be noted that a guanidine core or an $N^2$-phosphinyl guanidine group can be a portion of a larger group (or compound) which does not contain guanidine in it name. For example, while the compound 7-dimethylphosphinylimidazo[1,2-a]imidazole could be classified as a compound having an imidazo[1,2-a]imidazole core (or a compound having a phosphinylimidazo[1,2-a]imidazole group), 7-dimethylphosphinylimidazo[1,2-a]imidazole would still be classified as a compound having a guanidine core (or as a compound having an $N^2$-phosphinyl guanidine group) since it contains the defined general structure of the guanidine core (or the $N^2$-phosphinyl guanidine group).

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. In one aspect, the hydrogen atom(s) removed to form the "organyl group," "organylene group," or "organic group" can be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—C≡N), a carbamoyl group (—C(O)NH$_2$), an N-hydrocarbylcarbamoyl group (—C(O)NHR), or N,N'-dihydrocarbylcarbamoyl group (—C(O)NR$_2$), among other possibilities. In another aspect, the hydrogen atom(s) removed to form the "organyl group," "organylene group," or "organic group" can be attached to a carbon atom not belonging to, and remote from, a functional group, for example, —CH$_2$C(O)CH$_3$, —CH$_2$NR$_2$, and the like. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" definition includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group having a free valence on a heteroatom which i) does not substantially interfere with the process described herein in which the material having an inert functional group takes part and/or ii) does not complex with the metal salt of the metal salt complex. The term "does not complex with the metal salt of the metal salt complex" can include groups that could complex with a metal salt but in particular molecules described herein does not necessarily complex with a metal salt due to positional relationship of the inert function group within a ligand. Thus, the inertness of a particular functional group is not only related to the functional group's inherent inability to complex the metal compound but can also be related to the functional group's position within the metal salt complex. Non-limiting examples of inert functional groups which do not substantially interfere with processes described herein and/or ii) do not complex with the metal salt of the metal salt complex can include a halide (fluoride, chloride, bromide, and iodide), nitro, hydrocarboxy groups (e.g, alkoxy, and/or aroxy, among others), and/or hydrocarbosulfidyl groups (e.g., RS—), among others.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g., halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, tertiary carbon atom, respectively, of an alkane. The n-alkyl group can be derived by removal of a hydrogen atom from a terminal carbon atom of a linear alkane. The groups $RCH_2$ ($R \neq H$), $R_2CH$($R \neq H$), and $R_3C$ ($R \neq H$) represent exemplary primary, secondary, and tertiary alkyl groups, respectively.

A cycloalkane is a saturated cyclic hydrocarbon, with or without side chains, for example, cyclobutane. Unsaturated cyclic hydrocarbons having one or more endocyclic double or one triple bond are called cycloalkenes and cycloalkynes, respectively. Cycloalkenes and cycloalkynes having only one, only two, only three, etc. . . . endocyclic double or triple bonds, respectively, can be identified by use of the term "mono," "di," "tri, etc . . . within the name of the cycloalkene or cycloalkyne. Cycloalkenes and cycloalkynes can further identify the position of the endocyclic double or triple bonds.

A "cycloalkyl group" is a univalent group derived by removing a hydrogen atom from a ring carbon atom of a cycloalkane. For example, a 1-methylcyclopropyl group and a 2-methylcyclopropyl group are illustrated as follows.

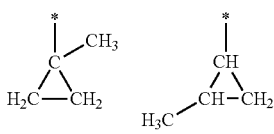

Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane. It should be noted that according to the definitions provided herein, general cycloalkane groups (including cycloalkyl groups and cycloalkylene groups) include those having zero, one, or more than one hydrocarbyl substituent groups attached to a cycloalkane ring carbon atom (e.g., a methylcyclopropyl group) and is member of the group of hydrocarbon groups. However, when referring to a cycloalkane group having a specified number of cycloalkane ring carbon atoms (e.g., cyclopentane group or cyclohexane group, among others), the base name of the cycloalkane group having a defined number of cycloalkane ring carbon atoms refers to the unsubstituted cycloalkane group (including having no hydrocarbyl groups located on cycloalkane group ring carbon atom). Consequently, a substituted cycloalkane group having a specified number of ring carbon atoms (e.g., substituted cyclopentane or substituted cyclohexane, among others) refers to the respective group having one or more substituent groups (including halogens, hydrocarbyl groups, and/or hydrocarboxy groups, among other substituent groups) attached to a cycloalkane group ring carbon atom. When the substituted cycloalkane group having a defined number of cycloalkane ring carbon atoms is a member of the group of hydrocarbon groups (or a member of the general group of cycloalkane groups), each substituent of the substituted cycloalkane group having a defined number of cycloalkane ring carbon atoms is limited to hydrocarbyl substituent group. One can readily discern and select general groups, specific groups, and/or individual substituted cycloalkane group(s) having a specific number of ring carbons atoms which can be utilized as member of the hydrocarbon group (or a member of the general group of cycloalkane groups).

The term "olefin" whenever used in this specification and claims refers to compounds that have at least one carbon-carbon double bond that is not part of an aromatic ring or ring system. The term "olefin" includes aliphatic and aromatic, cyclic and acyclic, and/or linear and branched compounds having at least one carbon-carbon double bond that is not part of an aromatic ring or ring system unless specifically stated otherwise. The term "olefin," by itself, does not indicate the presence or absence of heteroatoms and/or the presence or absence of other carbon-carbon double bonds unless explicitly indicated. Olefins having only one, only two, only three, etc. . . . carbon-carbon double bonds can be identified by use of the term "mono," "di," "tri," etc . . . within the name of the olefin. The olefins can be further identified by the position of the carbon-carbon double bond(s).

The term "alkene" whenever used in this specification and claims refers a linear or branched hydrocarbon olefin that has one or more carbon-carbon double bonds. Alkenes having only one, only two, only three, etc. . . . such multiple bond can be identified by use of the term "mono," "di," "tri," etc . . . within the name. For example, alkamonoenes, alkadienes, and alkatrienes refer to a linear or branched hydrocarbon olefins having only one carbon-carbon double bond (general formula $C_nH_{2n}$), only two carbon-carbon double bonds (general formula $C_nH_{2n-2}$), and only three carbon-carbon double bonds (general formula $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replace with a halogen atom.

An "alkenyl group" is a univalent group derived from an alkene by removal of a hydrogen atom from any carbon atom of the alkene. Thus, "alkenyl group" includes groups in which the hydrogen atom is formally removed from an $sp^2$ hybridized (olefinic) carbon atom and groups in which the hydrogen atom is formally removed from any other carbon atom. For example and unless otherwise specified, 1-propenyl (—CH═CHCH₃), 2-propenyl [(CH₃)C═CH₂], and 3-propenyl (—CH₂CH═CH₂) groups are all encompassed with the term "alkenyl group." Similarly, an "alkenylene group" refers to a group formed by formally removing two hydrogen atoms from an alkene, either two hydrogen atoms from one carbon atom or one hydrogen atom from two different carbon atoms. An "alkene group" refers to a generalized group formed by removing one or more hydrogen atoms (as necessary for the particular group) from an alkene. When the hydrogen atom is removed from a carbon atom participating in a carbon-carbon double bond, the regiochemistry of the carbon from which the hydrogen atom is removed, and regiochemistry of the carbon-carbon double bond can both be specified. Alkene groups can also have more than one carbon-carbon double bond. Alkene groups can also be further identified by the position of the carbon-carbon double bond.

The term "alpha olefin" as used in this specification and claims refers to an olefin that has a carbon-carbon double bond between the first and second carbon atom of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of heteroatoms and/or the presence or absence of other carbon-carbon double bonds unless explicitly indicated. The terms "hydrocarbon alpha olefin" or "alpha olefin hydrocarbon" refer to alpha olefin compounds containing only hydrogen and carbon.

The term "linear alpha olefin" as used herein refers to a linear olefin having a carbon-carbon double bond between the first and second carbon atom. The term "linear alpha olefin" by itself does not indicate the presence or absence of heteroatoms and/or the presence or absence of other carbon-carbon double bonds, unless explicitly indicated. The terms "linear hydrocarbon alpha olefin" or "linear alpha olefin hydrocarbon" refer to linear alpha olefin compounds containing only hydrogen and carbon.

The term "normal alpha olefin" whenever used in this specification and claims refers to a linear hydrocarbon monoolefin having a carbon carbon double bond between the first and second carbon atom. It is noted that "normal alpha olefin" is not synonymous with "linear alpha olefin" as the term "linear alpha olefin" can include linear olefinic compounds having a double bond between the first and second carbon atoms and having heteroatoms and/or additional double bonds.

The term "consists essentially of normal alpha olefin(s)," or variations thereof, whenever used in this specification and claims refers to commercially available normal alpha olefin product(s). The commercially available normal alpha olefin product can contain non-normal alpha olefin impurities such as vinylidenes, internal olefins, branched alpha olefins, paraffins, and diolefins, among other impurities, which are not removed during the normal alpha olefin production process. One readily recognizes that the identity and quantity of the specific impurities present in the commercial normal alpha olefin product will depend upon the source of commercial normal alpha olefin product. Consequently, the term "consists essentially of normal alpha olefins" and its variants is not intended to limit the amount/quantity of the non-linear alpha olefin components any more stringently than the amounts/quantities present in a particular commercial normal alpha olefin product unless explicitly stated.

A "heterocyclic compound" is a cyclic compound having at least two different elements as ring member atoms. For example, heterocyclic compounds can comprise rings containing carbon and nitrogen (for example, tetrahydropyrrole), carbon and oxygen (for example, tetrahydrofuran), or carbon and sulfur (for example, tetrahydrothiophene), among others. Heterocyclic compounds and heterocyclic groups can be either aliphatic or aromatic.

A "heterocyclyl group" is a univalent group formed by removing a hydrogen atom from a heterocyclic ring or ring system carbon atom of a heterocyclic compound. By specifying that the hydrogen atom is removed from a heterocyclic ring or ring system carbon atom, a "heterocyclyl group" is distinguished from a "cycloheteryl group," in which a hydrogen atom is removed from a heterocyclic ring or ring system heteroatom. For example, a pyrrolidin-2-yl group illustrated below is one example of a "heterocyclyl group," and a pyrrolidin-1-yl group illustrated below is one example of a "cycloheteryl group."

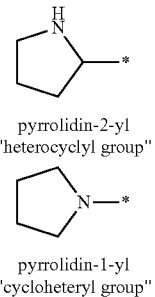

pyrrolidin-2-yl
"heterocyclyl group"

pyrrolidin-1-yl
"cycloheteryl group"

Similarly, a "heterocyclylene group" or more simply, a "heterocyclene group," refers to a group formed by removing two hydrogen atoms from a heterocyclic compound, at least one of which is from a heterocyclic ring or ring system carbon. Thus, in a "heterocyclylene group," at least one hydrogen is removed from a heterocyclic ring or ring system carbon atom, and the other hydrogen atom can be removed from any other carbon atom, including for example, the same heterocyclic ring or ring system carbon atom, a different heterocyclic ring or ring system ring carbon atom, or a non-ring carbon atom. A "heterocyclic group" refers to a generalized group formed by removing one or more hydrogen atoms (as necessary for the particular group and at least one of which is a heterocyclic ring carbon atom) from a heterocyclic compound. Generally, a heterocyclic compound can be aliphatic or aromatic unless otherwise specified.

A "cycloheteryl group" is a univalent group formed by removing a hydrogen atom from a heterocyclic ring or ring system heteroatom of a heterocyclic compound, as illustrated. By specifying that the hydrogen atom is removed from a heterocyclic ring or ring system heteroatom and not from a ring carbon atom, a "cycloheteryl group" is distinguished from a "heterocyclyl group" in which a hydrogen atom is removed from a heterocyclic ring or ring system carbon atom. Similarly, a "cycloheterylene group" refers to a group formed by removing two hydrogen atoms from an heterocyclic compound, at least one of which is removed from a heterocyclic ring or ring system heteroatom of the heterocyclic compound; the other hydrogen atom can be removed from any other atom, including for example, a heterocyclic ring or ring system ring carbon atom, another heterocyclic ring or ring system heteroatom, or a non-ring atom (carbon or heteroatom). A "cyclohetero group" refers to a generalized group formed by removing one or more hydrogen atoms (as necessary for the particular group and at least one of which is from a heterocyclic ring or ring system heteroatom) from a heterocyclic compound.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from the carbon atom of an aliphatic compound. Thus, an aliphatic compound is an acyclic or cyclic, saturated or unsaturated carbon compound, excluding aromatic compounds. That is, an aliphatic compound is a non-aromatic organic compound. Aliphatic compounds and therefore aliphatic groups can contain organic functional group(s) and/or atom(s) other than carbon and hydrogen.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2). While arene compounds and heteroarene compounds are mutually exclusive members of the group of aromatic compounds, a compound that has both an arene group and a heteroarene group are generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon—the methylene group in diphenylmethane; oxygen—diphenyl ether; nitrogen—triphenyl amine; among others linking groups). As disclosed herein, the term "substituted" can be used to describe an aromatic group, arene, or heteroarene wherein a non-hydrogen moiety formally replaces a hydrogen in the compound, and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" can have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

An arene is an aromatic hydrocarbon, with or without side chains (e.g., benzene, toluene, or xylene, among others). An "aryl group" is a group derived from the formal removal of a hydrogen atom from an aromatic ring carbon of an arene. It should be noted that the arene can contain a single aromatic hydrocarbon ring (e.g., benzene, or toluene), contain fused aromatic rings (e.g., naphthalene or anthracene), and contain one or more isolated aromatic rings covalently linked via a bond (e.g., biphenyl) or non-aromatic hydrocarbon group(s) (e.g., diphenylmethane). One example of an "aryl group" is ortho-tolyl (o-tolyl), the structure of which is shown here.

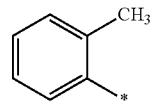

Similarly, an "arylene group" refers to a group formed by removing two hydrogen atoms (at least one of which is from an aromatic ring carbon) from an arene. An "arene group" refers to a generalized group formed by removing one or more hydrogen atoms (as necessary for the particular group and at least one of which is an aromatic ring carbon) from an arene. However, if a group contains separate and distinct arene and heteroarene rings or ring systems (e.g., the phenyl and benzofuran moieties in 7-phenylbenzofuran) its classification depends upon the particular ring or ring system from which the hydrogen atom was removed, that is, an arene group if the removed hydrogen came from the aromatic hydrocarbon ring or ring system carbon atom (e.g., the 2 carbon atom in the phenyl group of 6-phenylbenzofuran and a heteroarene group if the removed hydrogen carbon came from a heteroaromatic ring or ring system carbon atom (e.g., the 2 or 7 carbon atom of the benzofuran group or 6-phenylbenzo-furan). It should be noted that according the definitions provided herein, general arene groups (including an aryl group and an arylene group) include those having zero, one, or more than one hydrocarbyl substituent groups located on an aromatic hydrocarbon ring or ring system carbon atom (e.g., a toluene group or a xylene group, among others) and is a member of the group of hydrocarbon groups. However, a phenyl group (or phenylene group) and/or a naphthyl group (or naphthylene group) refer to the specific unsubstituted arene groups (including no hydrocarbyl group located on an aromatic hydrocarbon ring or ring system carbon atom). Consequently, a substituted phenyl group or substituted naphthyl group refers to the respective arene group having one or more substituent groups (including halogens, hydrocarbyl groups, and/or hydrocarboxy groups, among others) located on an aromatic hydrocarbon ring or ring system carbon atom. When the substituted phenyl group and/or substituted naphtyl group is a member of the group of hydrocarbon groups (or a member of the general group of arene groups), each substituent is limited to a hydrocarbyl substituent group. One having ordinary skill in the art can readily discern and select general phenyl and/or naphthyl groups, specific phenyl and/or naphthyl groups, and/or individual substituted phenyl or substituted naphthyl groups which can be utilized as a member of the group of hydrocarbon groups (or a member of the general group of arene groups).

A heteroarene is aromatic compound, with or without side chains, having a heteroatom within the aromatic ring or aromatic ring system (e.g., pyridine, indole, or benzofuran, among others). A "heteroaryl group" is a class of "heterocyclyl group" and is a univalent group formed by removing a hydrogen atom from a heteroaromatic ring or ring system carbon atom of a heteroarene compound. By specifying that the hydrogen atom is removed from a ring carbon atom, a "heteroaryl group" is distinguished from an "arylheteryl group," in which a hydrogen atom is removed from a heteroaromatic ring or ring system heteroatom. For example, an indol-2-yl group illustrated below is one example of a "heteroaryl group," and an indol-1-yl group illustrated below is one example of an "arylheteryl" group."

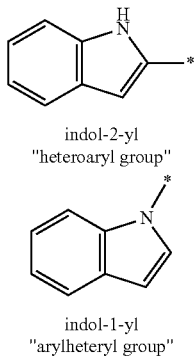

indol-2-yl
"heteroaryl group"

indol-1-yl
"arylheteryl group"

Similarly, a "heteroarylene group" refers to a group formed by removing two hydrogen atoms from a heteroarene compound, at least one of which is from a heteroarene ring or ring system carbon atom. Thus, in a "heteroarylene group," at least one hydrogen is removed from a heteroarene ring or ring system carbon atom, and the other hydrogen atom can be removed from any other carbon atom, including for example, a heteroarene ring or ring system carbon atom, or a non-heteroarene ring or ring system atom. A "heteroarene group" refers to a generalized group formed by removing one or more hydrogen atoms (as necessary for the particular group and at least one of which is a heteroarene ring or ring system carbon atom) from a heteroarene compound. If a hydrogen atom is removed from a heteroaromatic ring or ring system heteroatom and from a heteroaromatic ring or ring system carbon atom or an aromatic hydrocarbon ring or ring system carbon atom, the group is classified as an "arylheterylene group" or an "arylhetero group."

An "arylheteryl group" is a class of "cycloheteryl group" and is a univalent group formed by removing a hydrogen atom from a heteroaromatic ring or ring system heteroatom, as illustrated. By specifying that the hydrogen atom is removed from of a heteroaromatic ring or ring system heteroatom and not from a heteroaromatic ring or ring system carbon atom, an "arylheteryl group" is distinguished from a "heteroaryl group" in which a hydrogen atom is removed from a heteroaromatic ring or a ring system carbon atom. Similarly, an "arylheterylene group" refers to a group formed by removing two hydrogen atoms from a heteroaryl compound, at least one of which is removed from a heteroaromatic ring or ring system heteroatom of the heteroaryl compound; the other hydrogen atom can be removed from any other atom, including for example, a heteroaromatic ring or ring system carbon atom, another heteroaromatic ring or ring system heteroatom, or a non-ring atom (carbon or heteroatom) from a heteroaromatic compound. An "arylhetero group" refers to a generalized group formed by removing one or more hydrogen atoms (as necessary for the particular group and at least one of which is from a heteroaromatic ring or ring system) heteroatom from a heteroarene compound.

An "aralkyl group" is an aryl-substituted alkyl group having a free valance at a non-aromatic carbon atom (e.g., a benzyl group, or a 2-phenyleth-1yl group, among others). Similarly, an "aralkylene group" is an aryl-substituted alkylene group having two free valencies at a single non-aromatic carbon atom or a free valence at two non-aromatic carbon atoms while an "aralkane group" is a generalized is an aryl-substituted alkane group having one or more free valencies at a non-aromatic carbon atom(s). A "heteroaralkyl group" is a heteroaryl-substituted alkyl group having a free valence at a non-heteroaromatic ring or ring system carbon atom. Similarly a "heteroaralkylene group" is a heteroaryl-substituted alkylene group having two free valencies at a single non-heteroaromatic ring or ring system carbon atom or a free valence at two non-heteroaromatic ring or ring system carbon atoms while a "heteroaralkane group" is a generalized aryl-substituted alkane group having one or more free valencies at a non-heteroaromatic ring or ring system carbon atom(s). It should be noted that according the definitions provided herein, general aralkane groups include those having zero, one, or more than one hydrocarbyl substituent groups located on an aralkane aromatic hydrocarbon ring or ring system carbon atom and is a member of the group of hydrocarbon groups. However, specific aralkane groups specifying a particular aryl group (e.g., the phenyl group in a benzyl group or a 2-phenylethyl group, among others) refer to the specific unsubstituted aralkane groups (including no hydrocarbyl group located on the aralkane aromatic hydrocarbon ring or ring system carbon atom). Consequently, a substituted aralkane group specifying a particular aryl group refers to a respective aralkane group having one or more substituent groups (including halogens, hydrocarbyl groups, and/or hydrocarboxy groups, among others). When the substituted aralkane group specifying a particular aryl group is a member of the group of hydrocarbon groups (or a member of the general group of aralkane groups), each substituent is limited to a hydrocarbyl substituent group. One can readily discern and select substituted aralkane groups specifying a particular aryl group which can be utilized as a member of the group of hydrocarbon groups (or a member of the general group of aralkane groups).

A "halide" has its usual meaning; therefore, examples of halides include fluoride, chloride, bromide, and iodide.

An "organoheteryl group" is a univalent group containing carbon, which are thus organic, but which have their free valence at an atom other than carbon. Thus, organoheteryl and organyl groups are complementary and mutually exclusive. Organoheteryl groups can be cyclic or acyclic, and/or aliphatic or aromatic, and thus encompasses aliphatic "cycloheteryl groups" (e.g., pyrrolidin-1-yl or morpholin-1-yl, among others), aromatic "arylheteryl groups" (e.g., pyrrol-1-yl or indol-1-yl, among others), and acyclic groups (e.g., organylthio, trihydrocarbylsilyl, aryloxy, or alkoxy, among others). Similarly, an "organoheterylene group" is a divalent group containing carbon and at least one heteroatom having two free valencies, at least one of which is at a heteroatom. An "organohetero group" is a generalized group containing carbon and at least one heteroatom having one or more free valencies (as necessary for the particular group and at least one of which is at a heteroatom) from an organohetero compound.

An "organoaluminum compound," is used to describe any compound that contains an aluminum-carbon bond. Thus, organoaluminum compounds include hydrocarbyl aluminum compounds such as trialkyl-, dialkyl-, or monoalkylaluminum compounds; hydrocarbyl alumoxane compounds, and aluminate compounds which contain an aluminum-organyl bond such as tetrakis(p-tolyl)aluminate salts.

Within this disclosure the normal rules of organic nomenclature will prevail. For instance, when referencing substituted compounds or groups, references to substitution patterns are taken to indicate that the indicated group(s) is (are)

located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using comprising or some other alternative language. For example, a reference to a phenyl group comprising a substituent at the 4 position refers to a group having a non-hydrogen atom at the 4-position and hydrogen or any non-hydrogen group at the 2, 3, 5, and 6 positions.

The term "reactor effluent," and it derivatives (e.g., oligomerization reactor effluent) generally refers to all the material which exits the reactor. The term "reactor effluent," and its derivatives, can also be prefaced with other descriptors that limit the portion of the reactor effluent being referenced. For example, while the term "reactor effluent" would refer to all material exiting the reactor (e.g., product and solvent or diluent, among others), the term "olefin reactor effluent" refers to the effluent of the reactor which contains an olefin (i.e. carbon-carbon) double bond.

The term "oligomerization," and its derivatives, refers to processes which produce a mixture of products containing at least 70 weight percent products containing from 2 to 30 monomer units. Similarly, an "oligomer" is a product that contains from 2 to 30 monomer units and an "oligomerization product" or "oligomer product" includes all product made by the "oligomerization" process including the "oligomers" and products which are not "oligomers" (e.g., product which contain more than 30 monomer units). It should be noted that the monomer units in the "oligomer" or "oligomerization product" do not have to be the same. For example, an "oligomer" or "oligomerization product" of an "oligomerization" process using ethylene and propylene as monomers can contain both ethylene and/or propylene units.

The term "polymerization," and its derivatives, refers to processes which produce a mixture of products containing at least 70 weight percent products containing greater than 30 monomer units Similarly, "polymer" is a product that contains greater than 30 monomer units while an "polymerization product" or "polymer product" includes all products made by the "polymerization" process including the "polymers" and products which are not "polymers" (e.g., product which contain less than or equal to 30 monomer units). It should be noted that the monomer units in the "polymer" or "polymerization product" do not have to be the same. For example, a "polymer" or "polymerization product" of a "polymerization" process using ethylene and propylene as monomers can contain both ethylene and/or propylene units.

The term "trimerization," and it derivatives, refers to a process which produces a mixture of products containing at least 70 weight percent products containing three and only three monomer units. A "trimer" is a product which contains three and only three monomer units while a "trimerization product" or "trimer product" includes all products made by the trimerization process including trimer and product which are not trimer (e.g., dimers or tetramers). Generally, an olefin trimerization reduces number of olefinic bonds, i.e., carbon-carbon double bonds, by two when considering the number of olefin bonds in the monomer units and the number of olefin bonds in the trimer. It should be noted that the monomer units in the "trimer" or "trimerization product" do not have be the same. For example, a "trimer" of a "trimerization" process using ethylene and butene as monomers can contain ethylene and/or butene monomer units. That is to say the "trimer" can include $C_6$, $C_8$, $C_{10}$, and $C_{12}$ products. In another example, a "trimer" of a "trimerization" process using ethylene as the monomer can contain ethylene monomer units. It should also be noted that a single molecule can contain two monomer units. For example, dienes such as 1,3-butadiene and 1,4-pentadiene have two monomer units within one molecule.

The term "tetramerization," and it derivatives, refers to a process which produces a mixture of products containing at least 70 weight percent products containing four and only four monomer units. A "tetramer" is a product which contains four and only four monomer units while a "tetramerization product" or tetramer product" includes all products made by the tetramerization process including tetramer and product which are not tetramer (e.g., dimers or trimer). Generally, an olefin tetramerization reduces number of olefinic bonds, i.e., carbon-carbon double bonds, by three when considering the number of olefin bonds in the monomer units and the number of olefin bonds in the tetramer. It should be noted that the monomer units in the "tetramer" or "tetramerization product" do not have be the same. For example, a "tetramer" of a "tetramerization" process using ethylene and butene as monomers can contain ethylene and/or butene monomer units. In an example, a "tetramer" of a "tetramerization" process using ethylene as the monomer can contain ethylene monomer units. It should also be noted that a single molecule can contain two monomer units. For example, dienes such as 1,3-butadiene and 1,4-pentadiene have two monomer units within one molecule.

The term "trimerization and tetramerization," and it derivatives, refers to a process which produces a mixture of products containing at least 70 weight percent products containing three and/or four and only three and/or four monomer units. A "trimerization and tetramerization product" and "trimer and tetramer product" includes all products made by the "trimerization and tetramerization" process including trimer, tetramer, and product which are not tetramer (e.g., dimers). In an example, a "trimerization and tetramerization" process using ethylene as the monomer produces a mixture of products containing at least 70 weight percent hexene and/or octene.

The term or variation of the terms an "oligomerized product having X carbon atoms" and "$C_X$ oligomer product," wherein X can be any positive non-zero integer, refers to materials produced by monomer oligomerization which have X carbon atoms. Thus, the term "oligomerized product having X carbon atoms" and "$C_X$ oligomer product" excludes materials having X carbon atoms which were not produced by the olefin oligomerization (e.g., solvent) and oligomer products which do not have X carbon atoms. These terms can also include other descriptive words (e.g., olefin, liquid, and mixture, among others) without detracting from the essence of the term referring to materials having X carbon atoms, produced by monomer oligomerization, and fitting the additional descriptive terms.

This disclosure encompasses $N^2$-phosphinyl guanidine compounds, methods for making $N^2$-phosphinyl guanidine compounds, metal salt complexes comprising $N^2$-phosphinyl guanidine compounds, methods of making metal salt complexes comprising $N^2$-phosphinyl guanidine compounds, catalyst systems comprising $N^2$-phosphinyl guanidine compounds, methods of making catalyst systems comprising $N^2$-phosphinyl guanidine compounds, and methods of oligomerizing olefins utilizing catalysts system comprising $N^2$-phosphinyl guanidine compounds, among other aspects an embodiments. These aspects of this disclosure are further described herein. While these aspects can be disclosed under these headings, the heading does not limit the disclosure found therein. Additionally the various aspects and embodiments disclosed herein can be combined in any manner.

N²-Phosphinyl Guanidine Compounds Generally, the N²-phosphinyl guanidine compounds encompassed by this disclosure have at least one N²-phosphinyl guanidine group. In an embodiment, the N²-phosphinyl guanidine compounds comprise only one N²-phosphinyl guanidine; or alternatively, comprise only two N²-phosphinyl guanidine groups.

In an aspect, the compounds encompassed by the present disclosure include an N²-phosphinyl guanidine compound. Generally, the N²-phosphinyl guanidine compounds encompassed by this disclosure comprise an N²-phosphinyl guanidine group; or alternatively, comprise two N²-phosphinyl guanidine groups. In an embodiment, the N²-phosphinyl guanidine compounds comprise only one N²-phosphinyl guanidine group; or alternatively, comprise only two N²-phosphinyl guanidine groups. In an embodiment, the compounds, regardless of the number of N²-phosphinyl guanidine groups, or structure, can be non-metallic (i.e., a non-metallic N²-phosphinyl guanidine compound or a non-metallic compound having an N²-phosphinyl guanidine group). In some embodiments, the guanidine group of the N²-phosphinyl guanidine compounds can be an acyclic guanidine group (a guanidine group wherein the three nitrogen atoms and the central carbon atom of the amine group are not contained in a ring). In some embodiments, the guanidine group of the N²-phosphinyl guanidine compounds can be a cyclic guanidine group (a guanidine group wherein one or more of the nitrogen atoms and the central carbon atom of the amine group are contained in a ring).

In an aspect, the N²-phosphinyl guanidine compound can have Structure Gu1, Gu2, Gu3, Gu4, or Gu5: alternatively, Structure Gu1; alternatively, Structure Gu2; alternatively, Structure Gu3; alternatively, Structure Gu4; or alternatively, Structure Gu5.

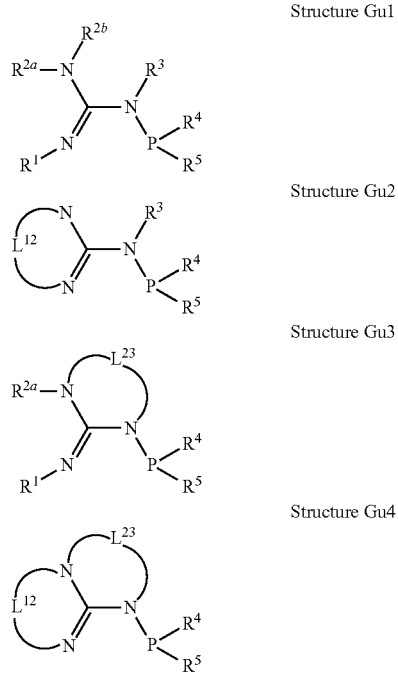

Structure Gu1

Structure Gu2

Structure Gu3

Structure Gu4

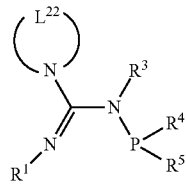

Structure Gu5

In an embodiment, the N²-phosphinyl guanidine compound comprising only one N²-phosphinyl guanidine group can be characterized by having the Structure Gu1, Gu2, Gu3, Gu4, or Gu5; alternatively, Structure Gu1; alternatively, Structure Gu2; alternatively, Structure Gu3; alternatively, Structure Gu4; or alternatively, Structure Gu5. In an embodiment, an N²-phosphinyl guanidine compound having more than one N²-phosphinyl guanidine groups can be characterized by having Structure Gu1, Gu2, Gu3, Gu4, or Gu5 wherein $R^1$, $R^{2a}$, $R^{2b}$, $R^3$, $R^4$, $R^5$, $L^{12}$, $L^{22}$, and/or $L^{23}$ include the other N²-phosphinyl guanidine group(s). In an embodiment, the N²-phosphinyl guanidine compound comprising only two N²-phosphinyl guanidine groups can be characterized by having Structure Gu1, Gu2, Gu3, Gu4, or Gu5 wherein R1, $R^{2a}$, $R^{2b}$, $R^3$, $R^4$, $R^5$, $L^{12}$, $L^{22}$ and/or $L^{23}$ include the second N²-phosphinyl guanidine group. In some embodiments where an N²-phosphinyl guanidine compound can more than one N²-phosphinyl guanidine group, one or more of the atom of one N²-phosphinyl guanidine group can be shared with another N²-phosphinyl guanidine group within the N²-phosphinyl guanidine compound having more than one N²-phosphinyl guanidine group. $R^1$, $R^{2a}$, $R^{2b}$, $R^3$, $R^4$, $R^5$, $L^{12}$, $L^{22}$, and $L^{23}$ within N²-phosphinyl guanidine compound Structures Gu1, Gu2, Gu3, Gu4, or Gu5 are independently described herein and can be utilized without limitation to further describe the N²-phosphinyl guanidine compounds having Structures Gu1, Gu2, Gu3, Gu4, and/or Gu5. In other embodiments, the N²-phosphinyl guanidine compounds can have any specific structure disclosed herein.

Generally, $R^1$ can be an organyl group; alternatively, an organyl group consisting essentially of inert functional groups; or alternatively, a hydrocarbyl group. In an embodiment, $R^1$ can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, $R^1$ can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In an embodiment, $R^1$ can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In yet other embodiments, $R^1$ can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group.

In an aspect, $R^1$ can be a $C_1$ to $C_{30}$ alkyl group, a $C_4$ to $C_{30}$ cycloalkyl group, a $C_4$ to $C_{30}$ substituted cycloalkyl group, a $C_6$ to $C_{30}$ aryl group, or a $C_6$ to $C_{30}$ substituted aryl group; alternatively, a $C_4$ to $C_{30}$ cycloalkyl group or a $C_4$ to $C_{30}$ substituted cycloalkyl group; alternatively, a $C_6$ to $C_{30}$ aryl group or a $C_6$ to $C_{30}$ substituted aryl group; alternatively, a $C_1$ to $C_{30}$ alkyl group; alternatively, a $C_4$ to $C_{30}$ cycloalkyl group; alternatively, a $C_4$ to $C_{30}$ substituted cycloalkyl group; alternatively, a $C_6$ to $C_{30}$ aryl group; or alternatively, a $C_6$ to $C_{30}$ substituted aryl group. In an embodiment, $R^1$ can be a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group; alternatively, a $C_4$ to $C_{20}$ cycloalkyl group or a $C_4$ to $C_{20}$ substituted cycloalkyl group; alternatively, a $C_6$ to $C_{20}$ aryl group or a $C_6$ to $C_{20}$ substituted aryl group; alternatively, a $C_1$ to $C_{15}$ alkyl group; alternatively, a $C_4$ to $C_{20}$ cycloalkyl group; alternatively, a $C_4$ to $C_{20}$ substituted cycloalkyl group; alternatively, a $C_6$ to $C_{20}$ aryl group; or alternatively, a $C_6$ to $C_{20}$ substituted aryl group. In other embodiments, $R^1$ can be a $C_1$ to $C_{10}$ alkyl group, a $C_4$ to $C_{15}$ cycloalkyl group, a $C_4$ to $C_{15}$ substituted cycloalkyl group, a $C_6$ to $C_{15}$ aryl group, or a $C_6$ to $C_{15}$ substituted aryl group; alternatively, a $C_4$ to $C_{15}$ cycloalkyl group or a $C_4$ to $C_{15}$ substituted cycloalkyl group; alternatively, a $C_6$ to $C_{15}$ aryl group or a $C_6$ to $C_{15}$ substituted aryl group; alternatively, a $C_1$ to $C_{10}$ alkyl group; alternatively, a $C_4$ to $C_{15}$ cycloalkyl group; alternatively, a $C_4$ to $C_{15}$ substituted cycloalkyl group; alternatively, a $C_6$ to $C_{15}$ aryl group; or alternatively, a $C_6$ to $C_{15}$ substituted aryl group. In further embodiments, $R^1$ can be a $C_1$ to $C_5$ alkyl group. Substituents (general and specific) are independently disclosed herein and can be utilized without limitation to further describe substituted groups which can be utilized as $R^1$.

In an embodiment, $R^1$ can be a methyl group, an ethyl group, a propyl group, a butyl group, a pentyl group, a hexyl group, a heptyl group, an octyl group, a nonyl group, or a decyl group. In some embodiments, $R^1$ can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, an n-propyl group; alternatively, an iso-propyl group; alternatively, a tert-butyl group; or alternatively, a neopentyl group. In some embodiments, the alkyl groups which can be utilized as $R^1$ can be substituted. Each substituent of a substituted alkyl group independently can be a halogen or a hydrocarboxy group; alternatively, a halogen; or alternatively, a hydrocarboxy group. Halogens and hydrocarboxy groups (general and specific) that can be utilized as substituents are independently disclosed herein and can be utilized without limitation to further describe the substituted alkyl group which can be utilized as $R^1$.

In an embodiment, $R^1$ can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, $R^1$ can be a cyclopentyl group, a substituted cyclopentyl group, a cyclohexyl group, or a substituted cyclohexyl group. In other embodiments, $R^1$ can be a cyclopentyl group or a substituted cyclopentyl group; or alternatively, a cyclohexyl group or a substituted cyclohexyl group. In further embodiments, $R^1$ can be a cyclopentyl group; alternatively, a substituted cyclopentyl group; a cyclohexyl group; or alternatively, a substituted cyclohexyl group. Substituents (general and specific) are independently disclosed herein and can be utilized without limitation to further describe the substituted cycloalkyl group which can be utilized as $R^1$.

In an aspect, $R^1$ can have Structure G1:

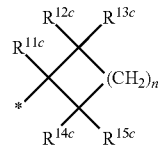

Structure G1 wherein the undesignated valency is attached to the $N^1$ nitrogen atom of the $N^2$-phosphinyl guanidine group. Generally, $R^{11c}$, $R^{12c}$, $R^{13c}$, $R^{14c}$, and $R^{15c}$ can independently be hydrogen or a non-hydrogen substituent, and n can be an integer from 1 to 5. In an embodiment wherein $R^1$ has Structure G1, $R^{11c}$, $R^{13c}$, $R^{14c}$, and $R^{15c}$ can be hydrogen and $R^{12c}$ can be any non-hydrogen substituent disclosed herein; or alternatively, $R^{11c}$, $R^{13c}$, and $R^{15c}$ can be hydrogen and $R^{12c}$ and $R^{14c}$ independently can be any non-hydrogen substituent disclosed herein. In an embodiment, n can be an integer from 1 to 4; or alternatively, from 2 to 4. In other embodiments, n can be 2 or 3; alternatively, 2; or alternatively 3. Substituents (general and specific) are independently disclosed herein and can be utilized without limitation to further describe a non-hydrogen substituent which can be utilized without limitation as $R^{11c}$, $R^{12c}$, $R^{13c}$, $R^{14c}$, and/or $R^{15c}$ for the $R^1$ group having Structure G1.

In an embodiment wherein $R^1$ has Structure G1, $R^{11c}$, $R^{13c}$, $R^{14c}$, and $R^{15c}$ can be hydrogen and $R^{12c}$ can be any non-hydrogen substituent indicated herein; or alternatively, $R^{11c}$, $R^{13c}$, and $R^{15c}$ can be hydrogen and $R^{12c}$ and $R^{14c}$ can be any non-hydrogen substituent indicated herein. In some embodiments, wherein $R^1$ has Structure G1, $R^{11c}$, $R^{13c}$, $R^{14c}$, and $R^{15c}$ can be hydrogen and $R^{12c}$ can be any alkyl group, alkoxy group, or halogen indicated herein; or alternatively, $R^{11c}$, $R^{13c}$, and $R^{15c}$ can be hydrogen and $R^{12c}$ and $R^{14c}$ can be any alkyl group, alkoxy group, or halogen indicated herein. In other embodiments, wherein $R^1$ has Structure G1, $R^{11c}$, $R^{13c}$, $R^{14c}$, and $R^{15c}$ can be hydrogen and $R^{12c}$ can be any alkyl group substituent indicated herein; or alternatively, $R^{11c}$, $R^{13c}$, and $R^{15c}$ can be hydrogen and $R^{12c}$ and $R^{14c}$ can be any alkyl group substituent indicated herein. In another embodiment wherein $R^1$ has Structure G1, $R^{11c}$, $R^{12c}$, $R^{13c}$, $R^{14c}$, and $R^{15c}$ can be hydrogen. In an embodiment, $R^{11c}$, $R^{12c}$, $R^{13c}$, $R^{14c}$, and $R^{15c}$ independently can be hydrogen, or an alkyl group; alternatively, $R^{11c}$, $R^{12c}$, and $R^{14c}$ can be hydrogen and $R^{13c}$ and $R^{15c}$ can be alkyl groups; or alternatively, $R^{11c}$ can be hydrogen and $R^{12c}$, $R^{13c}$, $R^{14c}$, and $R^{15c}$ can be alkyl groups. Specific substituent halogens, hydrocarbyl groups, hydrocarboxy groups, alkyl group, and alkoxy groups are independently disclosed herein and can be utilized without limitation to further describe the $R^1$ group having Structure G1.

In an aspect, $R^1$ can be a phenyl group, a substituted phenyl group, a naphthyl group, or a substituted naphthyl group; alternatively, a phenyl group or a substituted phenyl group; alternatively, a naphthyl group or a substituted naphthyl group; alternatively, a phenyl group or a naphthyl group; or alternatively, a substituted phenyl group or a substituted naphthyl group. In some embodiments, $R^1$ independently can be a phenyl group; alternatively, a substituted phenyl group; alternatively, a naphthyl group; or alternatively, a substituted naphthyl group. In an embodiment, the $R^1$ substituted phenyl group can be a 2-substituted phenyl group, a 3-substituted phenyl group, a 4-substituted phenyl group, a 2,4-disubstituted phenyl group, a 2,6-disubstituted phenyl group, 3,5-disubstituted phenyl group, or a 2,4,6-trisubstituted phenyl group. In other embodiments, the $R^1$ substituted phenyl group can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,6-di-substituted phenyl group or a 2,4,6-trisubstituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents (general and specific) are independently disclosed herein and can be utilized without limitation to further describe any substituted phenyl group which can be utilized as $R^1$.

In an embodiment, $R^1$ can be a naphth-1-yl group, a substituted naphth-1-yl group, a naphth-2-yl group, or a substituted naphth-2-yl group. In some embodiments, $R^1$ can be a naphth-1-yl group or a substituted naphth-1-yl group; alternatively, a naphth-2-yl group or a substituted naphth-2-yl group; alternatively, a naphth-1-yl group; alternatively, a substituted naphth-1-yl group; alternatively, a naphth-2-yl group; or alternatively, a substituted naphth-2-yl group. In other embodiments, $R^1$ can be a 2-substituted naphth-1-yl group, a 3-substituted naphth-1-yl group, a 4-substituted naphth-1-yl group, or a 8-substituted naphth-1-yl group; alternatively, a 2-substituted naphth-1-yl group; alternatively, a 3-substituted naphth-1-yl group; alternatively, a 4-substituted naphth-1-yl group; or alternatively, a 8-substituted naphth-1-yl group. In further embodiments, $R^1$ can be a 1-substituted naphth-2-yl group, a 3-substituted naphth-2-yl group, a 4-substituted naphth-2-yl group, or a 1,3-disubstituted naphth-2-yl group; alternatively, a 1-substituted naphth-2-yl group; alternatively, a 3-substituted naphth-2-yl group; alternatively, a 4-substituted naphth-2-yl group; or alternatively, a 1,3-disubstituted naphth-2-yl group. Substituents (general and specific) are independently disclosed herein can be utilized without limitation to further describe any substituted naphthyl groups which can be utilized as $R^1$.

In an aspect, $R^1$ can have Structure G2:

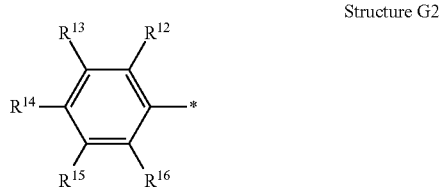

Structure G2 wherein the undesignated valency is attached to the $N^1$ nitrogen atom of the $N^2$-phosphinyl guanidine group. Generally, $R^{12}$, $R^{13}$, $R^{14}$, $R^{15}$, and $R^{16}$ independently can be hydrogen or a non hydrogen substituent. In an embodiment wherein $R^1$ has Structure G2, $R^{12}$, $R^{13}$, $R^{14}$, $R^{15}$, and $R^{16}$ can be hydrogen, $R^{13}$, $R^{14}$, $R^{15}$, and $R^{16}$ can be hydrogen and $R^{12}$ can be a non hydrogen substituent, $R^{12}$, $R^{14}$, $R^{15}$, and $R^{16}$ can be hydrogen and $R^{13}$ can be a non-hydrogen substituent, $R^{12}$, $R^{13}$, $R^{15}$, and $R^{16}$ can be hydrogen and $R^{14}$ can be a non-hydrogen substituent, $R^{13}$, $R^{15}$, and $R^{16}$ can be hydrogen and $R^{12}$ and $R^{14}$ can be non-hydrogen substituents, $R^{13}$, $R^{14}$, and $R^{15}$ can be hydrogen and $R^{12}$ and $R^{16}$ can be non-hydrogen substituents, $R^{12}$, $R^{14}$, and $R^{16}$ can be hydrogen and $R^{13}$ and $R^{15}$ can be non-hydrogen substituents, or $R^{13}$ and $R^{15}$ can be hydrogen and $R^{12}$, $R^{14}$, and $R^{16}$ can be non-hydrogen substituents. In some embodiments wherein $R^1$ has Structure G2, $R^{13}$, $R^{14}$, $R^{15}$, and $R^{16}$ can be hydrogen and $R^{12}$ can be a non-hydrogen substituent, $R^{12}$, $R^{13}$, $R^{15}$, and $R^{16}$ can be hydrogen and $R^{14}$ can be a non-hydrogen substituent, $R^{13}$, $R^{15}$, and $R^{16}$ can be hydrogen and $R^{12}$ and $R^{14}$ can be non-hydrogen substituents, $R^{13}$, $R^{14}$, and $R^{15}$ can be hydrogen and $R^{12}$ and $R^{16}$ can be non-hydrogen substituents, or $R^{13}$ and $R^{15}$ can be hydrogen and $R^{12}$, $R^{14}$, and $R^{16}$ can be non hydrogen substituents; alternatively, $R^{13}$, $R^{14}$, $R^{15}$, and $R^{16}$ can be hydrogen and $R^{12}$ can be a non-hydrogen substituent, $R^{12}$, $R^{13}$, $R^{15}$, and $R^{16}$ can be hydrogen and $R^{14}$ can be a non-hydrogen substituent; alternatively, $R^{13}$, $R^{15}$, and $R^{16}$ can be hydrogen and $R^{12}$ and $R^{14}$ can be non-hydrogen substituents, $R^{13}$, $R^{14}$, and $R^{15}$ can be hydrogen and $R^{12}$ and $R^{16}$ can be non-hydrogen substituents, or $R^{13}$ and $R^{15}$ can be hydrogen and $R^{12}$, $R^{14}$, and $R^{16}$ can be non-hydrogen substituents; or alternatively, $R^{13}$, $R^{15}$, and $R^{16}$ can be hydrogen and $R^{12}$ and $R^{14}$ can be non-hydrogen substituents, or $R^{13}$, $R^{14}$, and $R^{15}$ can be hydrogen and $R^{12}$ and $R^{16}$ can be non-hydrogen substituents. In other embodiments wherein $R^1$ has Structure G2, $R^{12}$, $R^{13}$, $R^{14}$, $R^{15}$, and $R^{16}$ can be hydrogen; alternatively, $R^{13}$, $R^{14}$, $R^{15}$, and $R^{16}$ can be hydrogen and $R^{12}$ can be a non hydrogen substituent; alternatively, $R^{12}$, $R^{14}$, $R^{15}$, and $R^{16}$ can be hydrogen and $R^{13}$ can be a non-hydrogen substituent; alternatively, $R^{12}$, $R^{13}$, $R^{15}$, and $R^{16}$ can be hydrogen and $R^{14}$ can be a non-hydrogen substituent; alternatively, $R^{13}$, $R^{15}$, and $R^{16}$ can be hydrogen and $R^{12}$ and $R^{14}$ can be non-hydrogen substituents; alternatively, $R^{13}$, $R^{14}$, and $R^{15}$ can be hydrogen and $R^{12}$ and $R^{16}$ can be non-hydrogen substituents; alternatively, $R^{12}$, $R^{14}$, and $R^{16}$ can be hydrogen and $R^{13}$ and $R^{15}$ and can be non-hydrogen substituents; or alternatively, $R^{13}$ and $R^{15}$ can be hydrogen and $R^{12}$, $R^{14}$, and $R^{16}$ can be non-hydrogen substituents. Substituents (general and specific) are independently disclosed herein and can be utilized without limitation as $R^{12}$, $R^{13}$, $R^{15}$, and $R^{16}$ for the $R^1$ group having Structure G2.

In an aspect, $R^1$ can be a $C_1$ to $C_{30}$ organoheteryl group; alternatively, a $C_1$ to $C_{20}$ organoheteryl group; alternatively, a $C_1$ to $C_{15}$ organoheteryl group; alternatively, a $C_1$ to $C_{10}$ organoheteryl group; or alternatively, a $C_1$ to $C_5$ organoheteryl group. In an embodiment, $R^1$ can be a $C_4$ to $C_{30}$ cycloheteryl group; alternatively, a $C_4$ to $C_{20}$ cycloheteryl group; alternatively, a $C_4$ to $C_{15}$ cycloheteryl group; or alternatively, a $C_4$ to $C_{10}$ cycloheteryl group. In some embodiments, the cycloheteryl group which can be utilized as $R^1$ can be a substituted cycloheteryl group.

In some embodiments, $R^1$ can be a $C_1$ to $C_{30}$ hydrocarbyl aminyl group, a $C_2$ to $C_{30}$ dihydrocarbyl aminyl group, a $C_4$ to $C_{30}$ cycloaminyl group, or a $C_4$ to $C_{30}$ substituted cycloaminyl group; alternatively, a $C_1$ to $C_{30}$ hydrocarbyl aminyl group or a $C_2$ to $C_{30}$ dihydrocarbyl aminyl group; alternatively, a $C_4$ to $C_{30}$ cycloaminyl group or a $C_4$ to $C_{30}$ substituted cycloaminyl group; alternatively, a $C_2$ to $C_{30}$ dihydrocarbyl aminyl group or a $C_4$ to $C_{30}$ cycloaminyl group; alternatively, a $C_1$ to $C_{30}$ hydrocarbyl aminyl group; alternatively, a $C_2$ to $C_{30}$ dihydrocarbyl aminyl group; alternatively, a $C_4$ to $C_{30}$ cycloaminyl group; or alternatively, a $C_4$ to $C_{30}$ substituted cycloaminyl group. In other embodiments, $R^1$ can be a $C_1$ to $C_{20}$ hydrocarbyl aminyl group, a $C_2$ to $C_{20}$ dihydrocarbyl aminyl group, a $C_4$ to $C_{20}$ cycloaminyl group, or a $C_4$ to $C_{20}$ substituted cycloaminyl group; alternatively, a $C_1$ to $C_{20}$ hydrocarbyl aminyl group or a $C_2$ to $C_{20}$ dihydrocarbyl aminyl group; alternatively, a $C_4$ to $C_{20}$ cycloaminyl group or a $C_4$ to $C_{20}$ substituted cycloaminyl group; alternatively, a $C_2$ to $C_{20}$ dihydrocarbyl aminyl group or a $C_4$ to $C_{20}$ cycloaminyl group; alternatively, a $C_1$ to $C_{20}$ hydrocarbyl aminyl group; alternatively, a $C_2$ to $C_{20}$ dihydrocarbyl aminyl group; alternatively, a $C_4$ to $C_{20}$ cycloaminyl group; or alternatively, a $C_4$ to $C_{20}$ substituted cycloaminyl group. In yet other embodiments, $R^1$ can be an a $C_1$ to $C_{10}$ hydrocarbyl aminyl group, a $C_2$ to $C_{15}$ dihydrocarbyl aminyl group, a $C_4$ to $C_{15}$ cycloaminyl group, or a $C_4$ to $C_{15}$ substituted cycloaminyl group; alternatively, a $C_1$ to $C_{10}$ hydrocarbyl aminyl group or a $C_2$ to $C_{15}$ dihydrocarbyl aminyl group; alternatively, a $C_4$ to $C_{15}$ cycloaminyl group or a $C_4$ to $C_{15}$ substituted cycloaminyl group; alternatively, a $C_2$ to $C_{15}$ dihydrocarbyl aminyl group or a $C_4$ to $C_{15}$ cycloaminyl group; alternatively, a $C_1$ to $C_{10}$ hydrocarbyl aminyl group; alternatively, a $C_2$ to $C_{15}$ dihydrocarbyl aminyl group; alternatively, a $C_4$ to $C_{15}$ cycloaminyl group; or alternatively, a $C_4$ to $C_{15}$ substituted cycloaminyl group. In further embodiments, $R^1$ can be an a $C_1$ to $C_5$ hydrocarbyl aminyl group, a $C_2$ to $C_{10}$ dihydrocarbyl aminyl group, a $C_4$ to $C_{10}$ cycloaminyl group, or a $C_4$ to $C_{10}$ substituted cycloaminyl group; alternatively, a $C_1$ to $C_5$ hydrocarbyl aminyl group or a $C_2$ to $C_{10}$ dihydrocarbyl aminyl group; alternatively, a $C_4$ to $C_{10}$ cycloaminyl group or a $C_4$ to $C_{10}$ substituted cycloaminyl group; alternatively, a $C_2$ to $C_{10}$ dihydrocarbyl aminyl group or a $C_4$ to $C_{10}$ cycloaminyl group; alternatively, a $C_1$ to $C_5$ hydrocarbyl aminyl group; alternatively, a $C_2$ to $C_{10}$ dihydrocarbyl aminyl group; alternatively, a $C_4$ to $C_{10}$ cycloaminyl group; or alternatively, a $C_4$ to $C_{10}$ substituted cycloaminyl group.

In an embodiment, each hydrocarbyl group of a hydrocarbyl aminyl group or a dihydrocarbyl aminyl group can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In an embodiment, each hydrocarbyl group of a hydrocarbyl aminyl group or a dihydrocarbyl aminyl group independently can be an alkyl group, a cycloalkyl group, an aryl group, or an aralkyl group; alternatively, an alkyl group; alternatively, a cycloalkyl group; alternatively, an aryl group; or alternatively, or aralkyl group. Alkyl groups, cycloalkyl groups, aryl group, and aralkyl groups have been described herein a potential $R^1$, $R^2$, $R^3$, $R^4$, and $R^5$ groups (among other potential group) and these alkyl groups, cycloalkyl groups, aryl group, and aralkyl groups can be utilized without limitation to further describe the hydrocarbyl aminyl group and/or a dihydrocarbyl aminyl group that can be utilized a $R^1$.

In an embodiment, $R^1$ can be a pyrrolidin-1-yl group, a substituted pyrrolidin-1-yl group, a piperidin-1-yl group, a substituted piperidin-1-yl group, a morphilin-1-yl group, a substituted morphilin-1-yl group, a pyrrol-1-yl group, or a substituted pyrrol-1-yl group. In some embodiments, $R^1$ can be a pyrrolidin-1-yl group, a substituted pyrrolidin-1-yl group, a piperidin-1-yl group, or a substituted piperidin-1-yl group; a pyrrolidin-1-yl group or a substituted pyrrolidin-1-yl group; alternatively, a piperidin-1-yl group or a substituted piperidin-1-yl group; alternatively, a morphilin-1-yl group or a substituted morphilin-1-yl group; alternatively, a pyrrol-1-yl group or a substituted pyrrol-1-yl group; alternatively, a pyrrolidin-1-yl group, a piperidin-1-yl group, a morphilin-1-yl group, or a pyrrol-1-yl group; alternatively, a pyrrolidin-1-yl group or a piperidin-1-yl group; alternatively, a pyrrolidin-1-yl group; alternatively, a substituted pyrrolidin-1-yl group; alternatively, a piperidin-1-yl group; alternatively, a substituted piperidin-1-yl group; alternatively, a morphilin-1-yl group; alternatively, a substituted morphilin-1-yl group; alternatively, a pyrrol-1-yl group; or alternatively, a substituted pyrrol-1-yl group. Generally, these specific cycloaminyl groups can have the same number of carbon atoms as the cycloaminyl and substituted cycloaminyl group described herein. Substituents (general and specific) are independently disclosed herein and these substituents can be utilized without limitation to further describe the substituted cycloaminyl groups (general or specific) which can be utilized as $R^1$.

In an aspect, when the $N^1$ nitrogen atom of the $N^2$-phosphinyl guanidine group is attached to an atom (carbon or a heteroatom) of a ring or ring system group (cycloalkane group, aliphatic heterocyclic group, cyclohetero group, aromatic group, arene group, heteroarene group, arylhetero group, or any other disclosed herein), the cyclic $R^1$ group can comprise at least one substituent at an atom adjacent to the atom attached to $N^1$ nitrogen atom of the $N^2$-phosphinyl guanidine group. In an embodiment, when the $N^1$ nitrogen atom of the $N^2$-phosphinyl guanidine group is attached to an atom (carbon or a heteroatom) of a ring or ring system group (e.g., cycloalkane group, aliphatic heterocyclic group, cyclohetero group, aromatic group, arene group, heteroarene group, or arylhetero group, or any other disclosed herein) the cyclic $R^1$ group can comprise at least one substituent at each atom adjacent to the atom attached to $N^1$ nitrogen atom of the $N^2$-phosphinyl guanidine group. In another embodiment, when the $N^1$ nitrogen atom of the $N^2$-phosphinyl guanidine group is attached to an atom (carbon or a heteroatom) of a ring or ring system group (e.g., cycloalkane group, aliphatic heterocyclic group, cyclohetero group, aromatic group, arene group, heteroarene group, or arylhetero group, or any other disclosed herein), the cyclic $R^1$ group can consist of one substituent at each atom adjacent to the atom attached to $N^1$ nitrogen atom of the $N^2$-phosphinyl guanidine group. In other embodiments, when the $N^1$ nitrogen atom of the $N^2$-phosphinyl guanidine group is attached to an atom (carbon or a heteroatom) of a ring or ring system group (e.g., cycloalkane group, aliphatic heterocyclic group, cyclohetero group, aromatic group, arene group, heteroarene group, or arylhetero group, or any other disclosed herein), the cyclic $R^1$ group can comprise only one substituent at an atom adjacent to the atom attached to $N^1$ nitrogen atom of the $N^2$-phosphinyl guanidine group. In another embodiment, when the $N^1$ nitrogen atom of the $N^2$-phosphinyl guanidine group is attached to an atom (carbon or a heteroatom) of a ring or ring system group (e.g., cycloalkane group, aliphatic heterocyclic group, cyclohetero group, aromatic group, arene group, heteroarene group, or arylhetero group, or any other disclosed herein), the cyclic $R^1$ group can comprise only one substituent at each atom adjacent to the atom attached to $N^1$ nitrogen atom of the $N^2$-phosphinyl guanidine group. In yet another embodiment, when the $N^1$ nitrogen atom of the $N^2$-phosphinyl guanidine group is attached to an atom (carbon or a heteroatom) of a ring or ring system group (e.g., cycloalkane group, aliphatic heterocyclic group, cyclohetero group, aromatic group, arene group, heteroarene group, or arylhetero group, or any other disclosed herein), the cyclic $R^1$ group can consist of only one substituent located at each atom adjacent to the atom attached to $N^1$ nitrogen atom of the $N^2$-phosphinyl guanidine group.

In an embodiment, when the $N^1$ nitrogen atom of the $N^2$-phosphinyl guanidine group is attached to a carbon atom of a cycloalkane or arene ring or ring system, the cyclic $R^1$ group can comprise at least one substituent located on a carbon atom adjacent to the carbon atom attached to $N^1$ nitrogen atom of the $N^2$-phosphinyl guanidine group. In some embodiments, when the $N^1$ nitrogen atom of the $N^2$-phosphinyl guanidine group is attached to a carbon atom of a cycloalkane or arene ring or ring system, the cyclic $R^1$ group can comprise at least one substituent located on each carbon atom adjacent to the carbon atom attached to $N^1$ nitrogen atom of the $N^2$-phosphinyl guanidine group. In another embodiment, when the $N^1$ nitrogen atom of the $N^2$-phosphinyl guanidine group is attached to a carbon atom of a cycloalkane or arene ring or ring system, the cyclic $R^1$ group can consist of one substituent located on each carbon atom adjacent to the carbon atom attached to $N^1$ nitrogen atom of the $N^2$-phosphinyl guanidine group. In other embodiments, when the $N^1$ nitrogen atom of the $N^2$-phosphinyl guanidine group is attached to a carbon atom of a cycloalkane or arene ring or ring system, the cyclic $R^1$ group can comprise only one substituent located on a carbon atom adjacent to the carbon atom attached to $N^1$ nitrogen atom of the $N^2$-phosphinyl guanidine group. In another embodiment, when the $N^1$ nitrogen atom of the $N^2$-phosphinyl guanidine group is attached to a carbon atom of a cycloalkane or arene ring or ring system, the cyclic $R^1$ group can comprise only one substituent located on each carbon atom adjacent to the carbon atom attached to $N^1$ nitrogen atom of the $N^2$-phosphinyl guanidine group. In yet another embodiment, when the $N^1$ nitrogen atom of the $N^2$-phosphinyl guanidine group is attached to a carbon atom of a cycloalkane or arene ring or ring system, the cyclic $R^1$ group can consist of only one substituent located on each carbon atom adjacent to the carbon atom attached to $N^1$ nitrogen atom of the $N^2$-phosphinyl guanidine group.

In a non-limiting embodiment, $R^1$ can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group, or a 2,4,6-trialkylphenyl group; alternatively, a 2,4-dialkylphenyl group or a 2,6-dialkylphenyl group; alternatively, a 2,6-dialkylphenyl group, or a 2,4,6-trialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 3-alkylphenyl group; alternatively, a 4-alkylphenyl group; alternatively, a 2,4-dialkylphenyl group; alternatively, a 2,6-dialkylphenyl group; alternatively, a 3,5-dialkylphenyl group; or alternatively, a 2,4,6-trialkylphenyl group. In another non-limiting embodiment, $R^1$ can be a naphth-1-yl group, a naphth-2-yl group, a 2-alkylnaphth-1-yl group, a 1-alkylnaphth-2-yl group, a 3-alkylnapth-2-yl group, or a 1,3-dialkylnaphth-2-yl group; alternatively, a naphth-1-yl group or a 2-alkylnaphth-1-yl group; alternatively, a naphth-2-yl group, a 1-alkylnaphth-2-yl group, a 3-alkylnapth-2-yl group, or a 1,3-dialkylnaphth-2-yl group; alternatively, a naphth-1-yl group; alternatively, a naphth-2-yl group; alternatively, a 2-alkylnaphth-1-yl group; alternatively, a 1-alkylnaphth-2-yl group; alternatively, a 3-alkylnapth-2-yl group; or alternatively, a 1,3-dialkylnaphth-2-yl group. In other non-limiting embodiments, $R^1$ can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkyl-cyclopentyl group; or alternatively, a 2,5-dialkylcyclopentyl group. Alkyl group substituents (general and specific) are independently described herein and can be utilized, without limitation, to further describe the alkylphenyl, dialkylphenyl, trialkylphenyl, naphthyl, dialkylnaphthyl, alkylcyclohexyl, dialkylcyclohexyl, alkylcyclopentyl, or dialkylcyclopentyl groups that can be utilized $R^1$. Generally, the alkyl substituents of a dialkyl or trialkyl phenyl, naphthyl, cyclohexyl, or cyclopentyl group can be the same; or alternatively, the alkyl substituents of a dialkyl or trialkyl phenyl, naphthyl, cyclohexyl, or cyclopentyl group can be different.

In another non-limiting embodiment, $R^1$ can be a phenyl group, a 2-alkoxyphenyl group, a 3-alkoxyphenyl group, 4-alkoxyphenyl group, or a 3,5-dialkoxyphenyl group; alternatively, a 2-alkoxyphenyl group or a 4-alkoxyphenyl group; alternatively, a 3-alkoxyphenyl group or a 3,5-dialkoxyphenyl group; alternatively, a 2-alkoxyphenyl group; alternatively, a 3-alkoxyphenyl group; alternatively, a 4-alkoxyphenyl group; alternatively, a 3,5-dialkoxyphenyl group. Alkoxy group substituents (general and specific) are independently described herein and can be utilized, without limitation, to further describe the alkoxyphenyl or dialkoxyphenyl groups that can be utilized $R^1$. Generally, the alkoxy substituents of a dialkoxyphenyl group can be the same; or alternatively, the alkoxy substituents of a dialkoxyphenyl group can be different.

In other non-limiting embodiments, $R^1$ can be a phenyl group, a 2-halophenyl group, a 3-halophenyl group, a 4-halophenyl group, a 2,6-dihalophenylgroup, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group; alternatively, a 2,6-dihalophenyl group; or alternatively, a 3,5-dihalophenyl group. Halides are independently described herein and can be utilized, without limitation, to further describe the halophenyl or dihalophenyl groups that can be utilized $R^1$. Generally, the halides of a dihalophenyl group can be the same; or alternatively, the halides of a dihalophenyl group can be different.

In a non-limiting embodiment, $R^1$ can be a 2-methylphenyl group, a 2-ethylphenyl group, a 2-n-propylphenyl group, a 2-isopropylphenyl group, a 2-tert-butylphenyl group, a 3-methylphenyl group, a 2,6-dimethylphenyl group, a 2,6-diethylphenyl group, a 2,6-di-n-propylphenyl group, a 2,6-diisopropyl-phenyl group, a 2,6-di-tert-butylphenyl group, a 2-isopropyl-6-methylphenyl group, a 3,5-dimethyl group, or a 2,4,6-trimethylphenyl group; alternatively, a 2-methylphenyl group, a 2-ethylphenyl group, a 2-n-propylphenyl group, a 2-isopropylphenyl group, or a 2-tert-butylphenyl group; alternatively, a 2,6-dimethylphenyl group, a 2,6-diethylphenyl group, a 2,6-di-n-propylphenyl group, a 2,6-diisopropylphenyl group, a 2,6-di-tert-butylphenyl group, or a 2-isopropyl-6-methylphenyl group; alternatively, a 2-methylphenyl group; alternatively, a 2-ethylphenyl group; alternatively, a 2-n-propylphenyl group; alternatively, a 2-isopropylphenyl group; alternatively, a 2-tert-butylphenyl group; alternatively, a 3-methylphenyl group; alternatively, a 2,6-dimethylphenyl group; alternatively, a 2,6-diethylphenyl group; alternatively, a 2,6-di-n-propylphenyl group; alternatively, a 2,6-diisopropylphenyl group; alternatively, a 2,6-di-tert-butylphenyl group; alternatively, a 2-isopropyl-6-methylphenyl group; alternatively, a 3,5-dimethylphenyl group; or alternatively, a 2,4,6-trimethylphenyl group. In another non-limiting embodiment, $R^1$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group, a 2-ethylcyclohexyl group, a 2-isopropylcyclohexyl group, or a 2-tert-butylcyclohexyl group; alternatively, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group; alternatively, a 2-ethylcyclohexyl group; alternatively, a 2-isopropyl-cyclohexyl group; alternatively, a 2-tert-butylcyclohexyl group; alternatively, a 2,6-dimethylcyclohexyl group; alternatively, a 2,6-diethylcyclohexyl group; alternatively, a 2,6-diisopropylcyclohexyl group; or alternatively, a 2,6-di-tert-butylcyclohexyl group. In another non-limiting embodiment, $R^1$ can be a 2-methyl-naphth-1-yl group, a 2-ethylnaphth-1-yl group, a 2-n-propyl-naphth-1-yl group, a 2-isopropylnaphth-1-yl group, or a 2-tert-butylnaphth-1-yl group; alternatively, a 2-methyl-naphth-1-yl group; alternatively, a 2-ethylnaphth-1-yl group; alternatively, a 2-n-propylnaphth-1-yl group; alternatively, a 2-isopropylnaphth-1-yl group; or alternatively, a 2-tert-butyl-naphth-1-yl group.

In a non-limiting embodiment, $R^1$ can be a 3-methoxyphenyl group, a 3-ethoxyphenyl group, a 3-isopropoxyphenyl group, a 3-tert-butoxyphenyl group, a 4-methoxyphenyl group, a 4-ethoxyphenyl group, a 4-isopropoxyphenyl group, a 4-tert-butoxyphenyl group, a 3,5-dimethoxyphenyl group, a 3,5-diethoxyphenyl group, a 3,5-diisopropoxyphenyl group, or a 3,5-di-tert-butoxyphenyl group; alternatively, a 3-methoxyphenyl group, a 3-ethoxyphenyl group, a 3-isopropoxyphenyl group, or a 3-tert-butoxyphenyl group; alternatively, a 4-methoxyphenyl group, a 4-ethoxyphenyl group, a 4-isopropoxyphenyl group, or a 4-tert-butoxyphenyl group; or alternatively, a 3,5-dimethoxyphenyl group, a 3,5-diethoxyphenyl group, a 3,5-diisopropoxyphenyl group, or a 3,5-di-tert-butoxyphenyl group. In other non-limiting embodiments, $R^1$ can be a 3-methoxyphenyl group; alternatively, a 3-ethoxyphenyl group; alternatively, a 3-isopropoxyphenyl group; alternatively, a 3-tert-butoxyphenyl group; alternatively, a 4-methoxyphenyl group; alternatively, a 4-ethoxyphenyl group; alternatively, a 4-isopropoxyphenyl group; alternatively, a 4-tert-butoxyphenyl group; alternatively, a 3,5-dimethoxyphenyl group; alternatively, a 3,5-diethoxyphenyl group; alternatively, a 3,5-diisopropoxyphenyl group; or alternatively, a 3,5-di-tert-butoxyphenyl group.

In an aspect, $R^{2a}$ and $R^{2b}$ independently can be hydrogen, an organyl group, or a triorganylsilyl group; alternatively, hydrogen or an organyl group; alternatively, hydrogen or a triorganylsilyl group; alternatively, hydrogen; alternatively, an organyl group; or alternatively, a triorganylsilyl group. In another aspect, $R^{2a}$ and/or $R^{2b}$ independently can be hydrogen, an organyl group consisting essentially of inert functional groups, or a tri(organyl group consisting essentially of inert functional groups)silyl group; alternatively, hydrogen or an organyl group consisting essentially of inert functional groups; alternatively, hydrogen or a tri(organyl group consisting essentially of inert functional groups)silyl group; alternatively, an organyl group consisting essentially of inert functional groups or a tri(organyl group consisting essentially of inert functional groups)silyl group; alternatively, an organyl group consisting essentially of inert functional groups; or alternatively, a tri(organyl group consisting essentially of inert functional groups)silyl group. In an aspect, $R^{2a}$ and $R^{2b}$ independently can be hydrogen, a hydrocarbyl group, or a trihydrocarbylsilyl group; alternatively, hydrogen or a hydrocarbyl group; alternatively, hydrogen or a trihydrocarbylsilyl group; alternatively, a hydrocarbyl or a trihydrocarbylsilyl group; alternatively, a hydrocarbyl group; or alternatively, a trihydrocarbylsilyl group. Organyl groups, general and specific, are disclosed herein (e.g., as potential selections for $R^1$) and any aspect or embodiment of these organyl groups disclosed herein can be utilized as $R^{2a}$ and/or $R^{2b}$ or as each independent organyl group of the triorganylsilyl group which can be utilized as $R^{2a}$ and/or $R^{2b}$. Organyl groups consisting essentially of inert functional groups, general and specific, are disclosed herein (e.g., as potential selections for $R^1$) and any aspect or embodiment of these organyl groups consisting essentially of inert functional group disclosed herein can be utilized as $R^{2a}$ and/or $R^{2b}$ or as each independent organyl group consisting essentially of inert functional groups of the tri(organyl group consisting essentially of inert functional groups)silyl group which can be utilized as $R^{2a}$ and/or $R^{2b}$. Hydrocarbyl groups, general and specific, are disclosed herein (e.g., as potential selections for $R^1$) and any aspect or embodiment of these hydrocarbyl groups disclosed herein can be utilized as $R^{2a}$ and/or $R^{2b}$ or as each independent hydrocarbyl group of trihydrocarbylsilyl group which can be utilized as $R^{2a}$ and/or $R^{2b}$. In yet other embodiments, $R^{2a}$ and/or $R^{2b}$ independently can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group.

In an aspect, $R^{2a}$ and $R^{2b}$ independently can be a $C_1$ to $C_{30}$ alkyl group, a $C_4$ to $C_{30}$ cycloalkyl group, a $C_4$ to $C_{30}$ substituted cycloalkyl group, a $C_6$ to $C_{30}$ aryl group, or a $C_6$ to $C_{30}$ substituted aryl group; alternatively, a $C_4$ to $C_{30}$ cycloalkyl group or a $C_4$ to $C_{30}$ substituted cycloalkyl group; alternatively, a $C_6$ to $C_{30}$ aryl group or a $C_6$ to $C_{30}$ substituted aryl group; alternatively, a $C_1$ to $C_{30}$ alkyl group; alternatively, a $C_4$ to $C_{30}$ cycloalkyl group; alternatively, a $C_4$ to $C_{30}$ substituted cycloalkyl group; alternatively, a $C_6$ to $C_{30}$ aryl group; or alternatively, a $C_6$ to $C_{30}$ substituted aryl group. In an embodiment $R^{2a}$ and $R^{2b}$ independently can be a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group; alternatively, a $C_4$ to $C_{20}$ cycloalkyl group or a $C_4$ to $C_{20}$ substituted cycloalkyl group; alternatively, a $C_6$ to $C_{20}$ aryl group or a $C_6$ to $C_{20}$ substituted aryl group; alternatively, a $C_1$ to $C_{15}$ alkyl group; alternatively, a $C_4$ to $C_{20}$ cycloalkyl group; alternatively, a $C_4$ to $C_{20}$ substituted cycloalkyl group; alternatively, a $C_6$ to $C_{20}$ aryl group; or alternatively, a $C_6$ to $C_{20}$ substituted aryl group. In other embodiments, $R^{2a}$ and $R^{2b}$ independently can be a $C_1$ to $C_{10}$ alkyl group, a $C_4$ to $C_{15}$ cycloalkyl group, a $C_4$ to $C_{15}$ substituted cycloalkyl group, a $C_6$ to $C_{15}$ aryl group, or a $C_6$ to $C_{15}$ substituted aryl group; alternatively, a $C_4$ to $C_{15}$ cycloalkyl group or a $C_4$ to $C_{15}$ substituted cycloalkyl group; alternatively, a $C_6$ to $C_{15}$ aryl group or a $C_6$ to $C_{15}$ substituted aryl group; alternatively, a $C_1$ to $C_{10}$ alkyl group; alternatively, a $C_4$ to $C_{15}$ cycloalkyl group; alternatively, a $C_4$ to $C_{15}$ substituted cycloalkyl group; alternatively, a $C_6$ to $C_{15}$ aryl group; or alternatively, a $C_6$ to $C_{15}$ substituted aryl group. In further embodiments, $R^{2a}$ and $R^{2b}$ independently can be a $C_1$ to $C_5$ alkyl group. Substituents (general and specific) are independently disclosed herein and can be utilized without limitation to further describe substituted groups which can be utilized as $R^{2a}$ and/or $R^{2b}$.

In an embodiment, $R^{2a}$ and $R^{2b}$ independently can be a methyl group, an ethyl group, a propyl group, a butyl group, a pentyl group, a hexyl group, a heptyl group, an octyl group, a nonyl group, or a decyl group. In some embodiments, $R^{2a}$ and $R^{2b}$ independently can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, an n-propyl group; alternatively, an iso-propyl group; alternatively, a tert-butyl group; or alternatively, a neopentyl group. In some embodiments, the alkyl groups which can be utilized as $R^{2a}$ and/or $R^{2b}$ can be substituted. Each substituent of a substituted alkyl group independently can be a halogen or a hydrocarboxy group; alternatively, a halogen; or alternatively, a hydrocarboxy group. Halogens and hydrocarboxy groups (general and specific) are independently disclosed herein (e.g., as general substituents and substituents for substituted $R^1$ groups) and can be utilized without limitation to further describe the substituted alkyl group which can be utilized as $R^{2a}$ and/or $R^{2b}$.

In an embodiment $R^{2a}$ and $R^{2b}$ independently can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, $R^{2a}$ and $R^{2b}$ independently can be a cyclopentyl group, a substituted cyclopentyl group, a cyclohexyl group, or a substituted cyclohexyl group. In other embodiments, $R^{2a}$ and $R^{2b}$ independently can be a cyclopentyl group or a substituted cyclopentyl group; or alternatively, a cyclohexyl group or a substituted cyclohexyl group. In further embodiments, $R^{2a}$ and $R^{2b}$ independently can be a cyclopentyl group; alternatively, a substituted cyclopentyl group; a cyclohexyl group; or alternatively, a substituted cyclohexyl group. Substituents (general and specific) are independently disclosed herein and can be utilized without limitation to further describe the substituted cycloalkyl group which can be utilized as $R^{2a}$ and/or $R^{2b}$.

In an aspect, $R^{2a}$ and $R^{2b}$ independently can have Structure G3 and Structure G4, respectively:

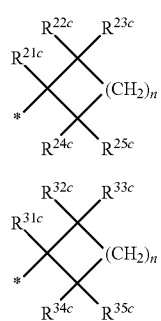

Structure G3

Structure G4 wherein, the undesignated valency of Structure G3 and Structure G4 is attached to the $N^3$ nitrogen atom of the $N^2$-phosphinyl guanidine group. Generally, $R^{21c}$, $R^{23c}$, $R^{24c}$, and $R^{25c}$ of Structure G3 and $R^{31c}$, $R^{33c}$, $R^{34c}$, and $R^{35c}$ of Structure G4 independently can be hydrogen or a non-hydrogen substituent, and each n independently can be an integer from 1 to 5. In an embodiment wherein $R^{2a}$ has Structure G3, $R^{21c}$, $R^{23c}$, $R^{24c}$, and $R^{25c}$ can be hydrogen and $R^{22c}$ can be any non-hydrogen substituent disclosed herein; or alternatively, $R^{21c}$, $R^{23c}$, and $R^{25c}$ can be hydrogen and $R^{22c}$ and $R^{24c}$ independently can be any non-hydrogen substituent disclosed herein. In an embodiment wherein $R^{2b}$ has Structure G4, $R^{31c}$, $R^{33c}$, $R^{34c}$, and $R^{35c}$ can be hydrogen and $R^{32c}$ can be any non-hydrogen substituent disclosed herein; or alternatively, $R^{31c}$, $R^{33c}$, and $R^{35c}$ can be hydrogen and $R^{32c}$ and $R^{34c}$ independently can be any non-hydrogen substituent disclosed herein. In an embodiment, each n independently can be an integer from 1 to 4; or alternatively, from 2 to 4. In other embodiments, each n independently can be 2 or 3; alternatively, 2; or alternatively 3. Substituents (general and specific) are independently disclosed herein and can be utilized without limitation as $R^{21c}$, $R^{23c}$, $R^{24c}$, and $R^{25c}$ for the $R^{2a}$ group having Structure G3 and/or $R^{31c}$, $R^{33c}$, $R^{34c}$, and $R^{35c}$ for the $R^{2b}$ group having Structure G4.

In an embodiment, $R^{2a}$ and $R^{2b}$ independently can be a phenyl group or a substituted phenyl group. In some embodiments, $R^{2a}$ and $R^{2b}$ can be a phenyl group; or alternatively, a substituted phenyl group. In an embodiment, the $R^{2a}$ and $R^{2b}$ substituted phenyl group independently can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other embodiments, the $R^2$ and $R^{2b}$ substituted phenyl group independently can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,6-disubstituted phenyl group or a 2,4,6-trisubstituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents (general and specific) are independently disclosed herein and can be utilized without limitation to further describe any substituted phenyl group which can be utilized as $R^{2a}$ and/or $R^{2b}$.

In an aspect, $R^{2a}$ and $R^{2b}$ independently can have Structure G5 and Structure G6, respectively:

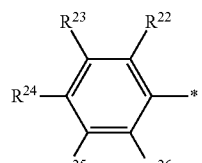

Structure G5

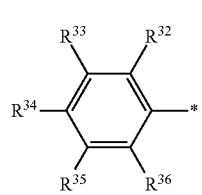

Structure G6 wherein the undesignated valency of Structure G5 and Structure G6 is attached to the $N^3$ nitrogen atom of the $N^2$-phosphinyl guanidine group. Generally, $R^{22}$, $R^{23}$, $R^{24}$, $R^{25}$, and $R^{26}$ of Structure G5 and $R^{32}$, $R^{33}$, $R^{34}$, $R^{35}$, and $R^{36}$ of Structure G6 independently can be hydrogen or a non-hydrogen substituent. In an embodiment, $R^{22}$, $R^{23}$, $R^{24}$, $R^{25}$, and $R^{26}$ of Structure G5 can be hydrogen, $R^{23}$, $R^{24}$, $R^{25}$, and $R^{26}$ can be hydrogen and $R^{22}$ can be a non-hydrogen substituent, $R^{22}$, $R^{24}$, $R^{25}$, and $R^{26}$ can be hydrogen and $R^{23}$ can be a non-hydrogen substituent, $R^{22}$, $R^{23}$, $R^{25}$, and $R^{26}$ can be hydrogen and $R^{24}$ can be a non-hydrogen substituent, $R^{23}$, $R^{25}$, and $R^{26}$ can be hydrogen and $R^{22}$ and $R^{24}$ can be non-hydrogen substituents, $R^{23}$, $R^{24}$, and $R^{25}$ can be hydrogen and $R^{22}$ and $R^{26}$ can be non-hydrogen substituents, $R^{22}$, $R^{24}$, and $R^{26}$ can be hydrogen and $R^{23}$ and $R^{25}$ can be non-hydrogen substituents, or $R^{23}$ and $R^{25}$ can be hydrogen and $R^{22}$, $R^{24}$, and $R^{26}$ can be non-hydrogen substituents. In some embodiments, $R^{23}$, $R^{24}$, $R^{25}$, and $R^{26}$ of Structure G5 can be hydrogen and $R^{22}$ can be a non-hydrogen substituent, $R^{22}$, $R^{23}$, $R^{25}$, and $R^{26}$ can be hydrogen and $R^{24}$ can be a non-hydrogen substituent, $R^{23}$, $R^{25}$, and $R^{26}$ can be hydrogen and $R^{22}$ and $R^{24}$ can be non-hydrogen substituents, $R^{23}$, $R^{24}$, and $R^{25}$ can be hydrogen and $R^{22}$ and $R^{26}$ can be non-hydrogen substituents, or $R^{23}$ and $R^{25}$ can be hydrogen and $R^{22}$, $R^{24}$, and $R^{26}$ can be non-hydrogen substituents; alternatively, $R^{23}$, $R^{24}$, $R^{25}$, and $R^{26}$ can be hydrogen and $R^{22}$ can be a non-hydrogen substituent, $R^{22}$, $R^{23}$, $R^{25}$, and $R^{26}$ can be hydrogen and $R^{24}$ can be a non-hydrogen substituent, $R^{23}$, $R^{25}$, and $R^{26}$ can be hydrogen and $R^{22}$ and $R^{24}$ can be non-hydrogen substituents, or $R^{23}$, $R^{24}$, and $R^{25}$ can be hydrogen and $R^{22}$ and $R^{26}$ can be non-hydrogen substituents; alternatively, $R^{22}$, $R^{24}$, $R^{25}$, and $R^{26}$ can be hydrogen and $R^{23}$ can be a non-hydrogen substituent, or $R^{22}$, $R^{24}$, and $R^{26}$ can be hydrogen and $R^{23}$ and $R^{25}$ can be non-hydrogen substituents; alternatively, $R^{23}$, $R^{24}$, $R^{25}$, and $R^{26}$ can be hydrogen and $R^{22}$ can be a non-hydrogen substituent, or $R^{22}$, $R^{23}$, $R^{25}$, and $R^{26}$ can be hydrogen and $R^{24}$ can be a non-hydrogen substituent; alternatively, $R^{23}$, $R^{25}$, and $R^{26}$ can be hydrogen and $R^{22}$ and $R^{24}$ can be non-hydrogen substituents, $R^{23}$, $R^{24}$, and $R^{25}$ can be hydrogen and $R^{22}$ and $R^{26}$ can be non-hydrogen substituents, or $R^{23}$ and $R^{25}$ can be hydrogen and $R^{22}$, $R^{24}$, and $R^{26}$ can be non-hydrogen substituents; or alternatively, $R^{23}$, $R^{25}$, and $R^{26}$ can be hydrogen and $R^{22}$ and $R^{24}$ can be non-hydrogen substituents, or $R^{23}$, $R^{24}$, and $R^{25}$ can be hydrogen and $R^{22}$ and $R^{26}$ can be non-hydrogen substituents. In other embodiments, $R^{22}$, $R^{23}$, $R^{24}$, $R^{25}$, and $R^{26}$ of Structure G5 can be hydrogen; alternatively, $R^{23}$, $R^{24}$, $R^{25}$, and $R^{26}$ can be hydrogen and $R^{22}$ can be a non-hydrogen substituent; alternatively, $R^{22}$, $R^{24}$, $R^{25}$, and $R^{26}$ can be hydrogen and $R^{23}$ can be a non-hydrogen substituent; alternatively, $R^{22}$, $R^{23}$, $R^{25}$, and $R^{26}$ can be hydrogen and $R^{24}$ can be a non-hydrogen substituent; alternatively, $R^{23}$, $R^{25}$, and $R^{26}$ can be hydrogen and $R^{22}$ and $R^{24}$ can be non-hydrogen substituents; alternatively, $R^{23}$, $R^{24}$, and $R^{25}$ can be hydrogen and $R^{22}$ and $R^{26}$ can be non-hydrogen substituents; alternatively, $R^{22}$, $R^{24}$, and $R^{26}$ can be hydrogen and $R^{23}$ and $R^{25}$ and can be non-hydrogen substituents; or alternatively, $R^{23}$ and $R^{25}$ can be hydrogen and $R^{22}$, $R^{24}$, and $R^{26}$ can be non-hydrogen substituents. In an embodiment, $R^{32}$, $R^{33}$, $R^{34}$, $R^{35}$, and $R^{36}$ of Structure G6 can be hydrogen, $R^{33}$, $R^{34}$, $R^{35}$, and $R^{36}$ can be hydrogen and $R^{32}$ can be a non-hydrogen substituent, $R^{32}$, $R^{34}$, $R^{35}$, and $R^{36}$ can be hydrogen and $R^{33}$ can be a non-hydrogen substituent, $R^{32}$, $R^{33}$, $R^{35}$, and $R^{36}$ can be hydrogen and $R^{34}$ can be a non-hydrogen substituent, $R^{33}$, $R^{35}$, and $R^{36}$ can be hydrogen and $R^{32}$ and $R^{34}$ can be non-hydrogen substituents, $R^{33}$, $R^{34}$, and $R^{35}$ can be hydrogen and $R^{32}$ and $R^{36}$ can be non-hydrogen substituents, $R^{32}$, $R^{34}$, and $R^{36}$ can be hydrogen and $R^{33}$ and $R^{35}$ can be non-hydrogen substituents, or $R^{33}$ and $R^{35}$ can be hydrogen and $R^{32}$, $R^{34}$, and $R^{36}$ can be non-hydrogen substituents. In some embodiments, $R^{33}$, $R^{34}$, $R^{35}$, and $R^{36}$ of Structure G6 can be hydrogen and $R^{32}$ can be a non-hydrogen substituent, $R^{32}$, $R^{33}$, $R^{35}$, and $R^{36}$ can be hydrogen and $R^{34}$ can be a non-hydrogen substituent, $R^{33}$, $R^{35}$, and $R^{36}$ can be hydrogen and $R^{32}$ and $R^{34}$ can be non-hydrogen substituents, $R^{33}$, $R^{34}$, and $R^{35}$ can be hydrogen and $R^{32}$ and $R^{36}$ can be non-hydrogen substituents, or $R^{33}$ and $R^{35}$ can be hydrogen and $R^{32}$, $R^{34}$, and $R^{36}$ can be non-hydrogen substituents; alternatively, $R^{33}$, $R^{34}$, $R^{35}$, and $R^{36}$ can be hydrogen and $R^{32}$ can be a non-hydrogen substituent, $R^{32}$, $R^{33}$, $R^{35}$, and $R^{36}$ can be hydrogen and $R^{34}$ can be a non-hydrogen substituent, $R^{33}$, $R^{35}$, and $R^{36}$ can be hydrogen and $R^{32}$ and $R^{34}$ can be non-hydrogen substituents, or $R^{33}$, $R^{34}$, and $R^{35}$ can be hydrogen and $R^{32}$ and $R^{36}$ can be non-hydrogen substituents; alternatively, $R^{32}$, $R^{34}$, $R^{35}$, and $R^{36}$ can be hydrogen and $R^{33}$ can be a non-hydrogen substituent, or $R^{32}$, $R^{34}$, and $R^{36}$ can be hydrogen and $R^{33}$ and $R^{35}$ can be non-hydrogen substituents; alternatively, $R^{33}$, $R^{34}$, $R^{35}$, and $R^{36}$ can be hydrogen and $R^{32}$ can be a non-hydrogen substituent, or $R^{32}$, $R^{33}$, $R^{35}$, and $R^{36}$ can be hydrogen and $R^{34}$ can be a non-hydrogen substituent; alternatively, $R^{33}$, $R^{35}$, and $R^{36}$ can be hydrogen and $R^{32}$ and $R^{34}$ can be non-hydrogen substituents, $R^{33}$, $R^{34}$, and $R^{35}$ can be hydrogen and $R^{32}$ and $R^{36}$ can be non-hydrogen substituents, or $R^{33}$ and $R^{35}$ can be hydrogen and $R^{32}$, $R^{34}$, and $R^{36}$ can be non-hydrogen substituents; or alternatively, $R^{33}$, $R^{35}$, and $R^{36}$ can be hydrogen and $R^{32}$ and $R^{34}$ can be non-hydrogen substituents, or $R^{33}$, $R^{34}$, and $R^{35}$ can be hydrogen and $R^{32}$ and $R^{36}$ can be non-hydrogen substituents. In other embodiments, $R^{32}$, $R^{33}$, $R^{34}$, $R^{35}$, and $R^{36}$ of Structure G6 can be hydrogen; alternatively, $R^{33}$, $R^{34}$, $R^{35}$, and $R^{36}$ can be hydrogen and $R^{32}$ can be a non-hydrogen substituent; alternatively, $R^{32}$, $R^{34}$, $R^{35}$, and $R^{36}$ can be hydrogen and $R^{33}$ can be a non-hydrogen substituent; alternatively, $R^{32}$, $R^{33}$, $R^{35}$, and $R^{36}$ can be hydrogen and $R^{34}$ can be a non-hydrogen substituent; alternatively, $R^{33}$, $R^{35}$, and $R^{36}$ can be hydrogen and $R^{32}$ and $R^{34}$ can be non-hydrogen substituents; alternatively, $R^{33}$, $R^{34}$, and $R^{35}$ can be hydrogen and $R^{32}$ and $R^{36}$ can be non-hydrogen substituents; alternatively, $R^{32}$, $R^{34}$, and $R^{36}$ can be hydrogen and $R^{33}$ and $R^{35}$ and can be non-hydrogen substituents; or alternatively, $R^{33}$ and $R^{35}$ can be hydrogen and $R^{32}$, $R^{34}$, and $R^{36}$ can be non-hydrogen substituents. Substituents (general and specific) are independently disclosed herein and can be utilized without limitation as $R^{22}$, $R^{23}$, $R^{24}$, $R^{25}$, and/or $R^{26}$ for the $R^{2a}$ group having Structure G5 and/or $R^{32}$, $R^{33}$, $R^{34}$, $R^{35}$, and/or $R^{36}$ for the $R^{2b}$ group having Structure G6.

In a non-limiting embodiment, $R^{2a}$ and $R^{2b}$ independently can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group, or a 2,4,6-trialkylphenyl group; alternatively, a 2,4-dialkylphenyl group or a 2,6-dialkylphenyl group; alternatively, a 2,6-dialkylphenyl group, or a 2,4,6-trialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 3-alkylphenyl group; alternatively, a 4-alkylphenyl group; alternatively, a 2,4-dialkylphenyl group; alternatively, a 2,6-dialkylphenyl group; alternatively, a 3,5-dialkylphenyl group; or alternatively, a 2,4,6-trialkylphenyl group. In another non-limiting embodiment, $R^{2a}$ and $R^{2b}$ independently can be a phenyl group, a 2-alkoxyphenyl group, a 3-alkoxyphenyl group, a 4-alkoxyphenyl group, or 3,5-dialkoxyphenyl group; alternatively, a 2-alkoxyphenyl group or a 4-alkoxyphenyl group; alternatively, a 3-alkoxyphenyl group or 3,5-dialkoxyphenyl group; alternatively, a 2-alkoxyphenyl group; alternatively, 3-alkoxyphenyl group; alternatively, a 4-alkoxyphenyl group; alternatively, 3,5-dialkoxyphenyl group. In other non-limiting embodiments, $R^{2a}$ and $R^{2b}$ independently can be a phenyl group, a 2-halophenyl group, a 3-halophenyl group, a 4-halophenyl group, a 2,6-dihalophenylgroup, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group; alternatively, a 2,6-dihalophenylgroup; or alternatively, a 3,5-dihalophenyl group. Halides, alkyl group substituents (general and specific), and alkoxy group substituents (general and specific) are independently described herein and can be utilized, without limitation, to further describe the alkylphenyl, dialkylphenyl, trialkylphenyl, alkoxyphenyl, dialkoxyphenyl, halophenyl, or dihalophenyl groups that can be utilized as $R^{2a}$ and/or $R^{2b}$. Generally, the halides, alkyl substituents, or alkoxy substituents of a dialkyl, trialkyl phenyl, dialkoxyphenyl, or dihalophenyl groups can be the same; or alternatively the halo, alkyl substituents, or alkoxy substituents of alkylphenyl, dialkylphenyl, trialkylphenyl, dialkoxyphenyl, or dihalophenyl groups can be different.

In a non-limiting embodiment, $R^{2a}$ and $R^{2b}$ independently can be a 2-methylphenyl group, a 2-ethylphenyl group, a 2-isopropylphenyl group, a 2-tert-butylphenyl group, a 4-methylphenyl group, a 4-ethylphenyl group, a 4-isopropylphenyl group, or a 4-tert-butylphenyl group; alternatively, a 2-methylphenyl group, a 2-ethylphenyl group, a 2-isopropylphenyl group, or a 2-tert-butylphenyl group; alternatively, a 4-methylphenyl group, a 4-ethylphenyl group, a 4-isopropylphenyl group, or a 4-tert-butylphenyl group; alternatively, a 2-methylphenyl group; alternatively, a 2-ethylphenyl group; alternatively, a 2-isopropylphenyl group; alternatively, a 2-tert-butylphenyl group; alternatively, a 4-methylphenyl group; alternatively, a 4-ethylphenyl group; alternatively, a 4-isopropylphenyl group; or alternatively, a 4-tert-butylphenyl group. In another non-limiting embodiment, $R^{2a}$ and $R^{2b}$ independently can be a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; alternatively, a 4-methoxyphenyl group, a 4-ethoxyphenyl group, a 4-isopropoxyphenyl group, or a 4-tert-butoxyphenyl group; alternatively, a 2-methoxyphenyl group; alternatively, a 2-ethoxyphenyl group; alternatively, a 2-isopropoxyphenyl group; alternatively, a 2-tert-butoxyphenyl group; alternatively, a 4-methoxyphenyl group; alternatively, a 4-ethoxyphenyl group; alternatively, a 4-isopropoxyphenyl group; or alternatively, a 4-tert-butoxyphenyl group. In other non-limiting embodiments, $R^{2a}$ and $R^{2b}$ independently can be a 2-fluorophenyl group, a 2-chlorophenyl group, a 3-fluorophenyl group, a 3-chlorophenyl group, a 4-fluorophenyl group, a 4-chlorophenyl group, a 3,5-difluorophenyl group, or a 3,5-dichlorophenyl group; alternatively, a 2-fluorophenyl group or a 2-chlorophenyl group; alternatively, a 3-fluorophenyl group or a 3-chloro-phenyl group; alternatively, a 4-fluorophenyl group or a 4-chlorophenyl group; alternatively, a 3,5-difluorophenyl group or a 3,5-dichlorophenyl group; alternatively, a 3-fluorophenyl group, a 3-chlorophenyl group, a 3,5-difluorophenyl group or a 3,5-dichlorophenyl group; alternatively, a 3-fluorophenyl group or a 3,5-difluorophenyl group; alternatively, a 2-fluorophenyl group; alternatively, a 2-chlorophenyl group; alternatively, a 3-fluorophenyl group; alternatively, a 3-chlorophenyl group; alternatively, a 4-fluorophenyl group; alternatively, a 4-chlorophenyl; alternatively, a 3,5-difluorophenyl group; or alternatively, a 3,5-dichlorophenyl group.

In an embodiment, $R^{2a}$ and $R^{2b}$ independently can be a trihydrocarbylsilyl group. The trihydrocarbylsilyl group can have the general formula $SiR_3$ where R is a hydrocarbyl group of the type disclosed herein. In some embodiments, each hydrocarbyl group, of the trihydrocarbylsilyl group substituent of $R^{2a}$ and/or $R^{2b}$, independently can be an alkyl group, an aryl group, or an aralkyl group; alternatively, an alkyl group; alternatively, an aryl group; or alternatively, an aralkyl group. In an embodiment, each alkyl substituent, which can be utilized as R for any trihydrocarbylsilyl group substituent of $R^{2a}$ and/or $R^{2b}$ (general or specific), independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, each aryl substituent, which can be utilized as R for any trihydrocarbylsilyl group of $R^{2a}$ and/or $R^{2b}$ (general or specific), independently can be a phenyl group, a tolyl group, a xylyl group, or a 2,4,6-trimethylphenyl group; alternatively, a phenyl group; alternatively, a tolyl group; alternatively, a xylyl group; or alternatively, a 2,4,6-trimethylphenyl group. In an embodiment, each aralkyl substituent, which can be utilized as R for any trihydrocarbylsilyl group substituent of $R^{2a}$ and/or $R^{2b}$ (general or specific), independently can be a benzyl group.

In an embodiment, the trihydrocarbylsilyl group which can be utilized as $R^2$ and $R^{2b}$ independently can be a trialkylsilyl group, a triarylsilyl group, or a trialkaryl silyl group; alternatively, trialkylsilyl group; alternatively, a triarylsilyl group; or alternatively, a trialkaryl silyl group. In some embodiments, each trihydrocarbyl group which can be utilized as $R^2$ and/or $R^{2b}$ independently can be a trimethylsilyl group, a triethylsilyl group, a tripropylsilyl group, a triphenylsilyl group, or a tribenzylsilyl group; alternatively, a trimethylsilyl group, a triethylsilyl group, or a tripropylsilyl group; alternatively, a trimethylsilyl group; alternatively, a triethylsilyl group; alternatively, a tripropylsilyl group; alternatively, a triphenylsilyl group; or alternatively, a tribenzylsilyl group.

In an aspect, $R^3$ can be hydrogen. In another aspect, $R^3$ can be an organyl group; alternatively, an organyl group consisting essentially of inert functional groups; or alternatively, a hydrocarbyl group. Organyl groups (general and specific) are disclosed herein (e.g., as potential selections for $R^1$) and any aspect or embodiment of these organyl groups disclosed herein can be utilized as $R^3$. Organyl groups consisting essentially of inert functional groups (general and specific) are disclosed herein (e.g., as potential selections for $R^1$) and aspect or embodiment of these organyl groups consisting essentially of inert functional group disclosed herein can be utilized as $R^3$. Hydrocarbyl groups (general and specific) are disclosed herein (e.g., as potential selections for $R^1$) and aspect or embodiment of these hydrocarbyl groups disclosed herein can be utilized as $R^3$. In yet other embodiments, $R^3$ can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group.

In an aspect, $R^3$ can be a $C_1$ to $C_{30}$ alkyl group, a $C_4$ to $C_{30}$ cycloalkyl group, a $C_4$ to $C_{30}$ substituted cycloalkyl group, a $C_6$ to $C_{30}$ aryl group, or a $C_6$ to $C_{30}$ substituted aryl group; alternatively, a $C_4$ to $C_{30}$ cycloalkyl group or a $C_4$ to $C_{30}$ substituted cycloalkyl group; alternatively, a $C_6$ to $C_{30}$ aryl group or a $C_6$ to $C_{30}$ substituted aryl group; alternatively, a $C_1$ to $C_{30}$ alkyl group; alternatively, a $C_4$ to $C_{30}$ cycloalkyl group; alternatively, a $C_4$ to $C_{30}$ substituted cycloalkyl group; alternatively, a $C_6$ to $C_{30}$ aryl group; or alternatively, a $C_6$ to $C_{30}$ substituted aryl group. In an embodiment, $R^3$ can be a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group; alternatively, a $C_4$ to $C_{20}$ cycloalkyl group or a $C_4$ to $C_{20}$ substituted cycloalkyl group; alternatively, a $C_6$ to $C_{20}$ aryl group or a $C_6$ to $C_{20}$ substituted aryl group; alternatively, a $C_1$ to $C_{15}$ alkyl group; alternatively, a $C_4$ to $C_{20}$ cycloalkyl group; alternatively, a $C_4$ to $C_{20}$ substituted cycloalkyl group; alternatively, a $C_6$ to $C_{20}$ aryl group; or alternatively, a $C_6$ to $C_{20}$ substituted aryl group. In other embodiments, $R^3$ can be a $C_1$ to $C_{10}$ alkyl group, a $C_4$ to $C_{15}$ cycloalkyl group, a $C_4$ to $C_{15}$ substituted cycloalkyl group, a $C_6$ to $C_{15}$ aryl group, or a $C_6$ to $C_{15}$ substituted aryl group; alternatively, a $C_4$ to $C_{15}$ cycloalkyl group or a $C_4$ to $C_{15}$ substituted cycloalkyl group; alternatively, a $C_6$ to $C_{15}$ aryl group or a $C_6$ to $C_{15}$ substituted aryl group; alternatively, a $C_1$ to $C_{10}$ alkyl group; alternatively, a $C_4$ to $C_{15}$ cycloalkyl group; alternatively, a $C_4$ to $C_{15}$ substituted cycloalkyl group; alternatively, a $C_6$ to $C_{15}$ aryl group; or alternatively, a $C_6$ to $C_{15}$ substituted aryl group. In further embodiments, $R^3$ can be a $C_1$ to $C_5$ alkyl group. Substituents (general and specific) are independently disclosed herein and can be utilized without limitation to further describe substituted groups which can be utilized as $R^3$.

In an embodiment, $R^3$ can be a methyl group, an ethyl group, a propyl group, a butyl group, a pentyl group, a hexyl group, a heptyl group, an octyl group, a nonyl group, or a decyl group. In some embodiments, $R^3$ can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, an n-propyl group; alternatively, an iso-propyl group; alternatively, a tert-butyl group; or alternatively, a neopentyl group. In some embodiments, the alkyl groups which can be utilized as $R^3$ can be substituted. Each substituent of a substituted alkyl group independently can be a halogen or a hydrocarboxy group; alternatively, a halogen; or alternatively, a hydrocarboxy group. Halogens and hydrocarboxy groups (general and specific) are independently disclosed herein (e.g., as general substituents and substituents for substituted $R^1$ groups) and can be utilized without limitation to further describe the substituted alkyl group which can be utilized as $R^3$.

In an embodiment, $R^3$ can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, $R^3$ can be a cyclopentyl group, a substituted cyclopentyl group, a cyclohexyl group, or a substituted cyclohexyl group. In other embodiments, $R^3$ can be a cyclopentyl group or a substituted cyclopentyl group; or alternatively, a cyclohexyl group or a substituted cyclohexyl group. In further embodiments, $R^3$ can be a cyclopentyl group; alternatively, a substituted cyclopentyl group; a cyclohexyl group; or alternatively, a substituted cyclohexyl group. Substituents (general and specific) are independently disclosed herein and can be utilized without limitation to further describe the substituted cycloalkyl group which can be utilized as $R^3$.

In an aspect, $R^3$ can have Structure G11:

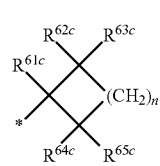

Structure G11 wherein, the undesignated valency is attached to the $N^2$ nitrogen atom of the $N^2$-phosphinyl guanidine group. Generally, $R^{61c}$, $R^{62c}$, $R^{63c}$, $R^{64c}$, and $R^{65c}$ independently can be hydrogen or a non-hydrogen substituent, and n can be an integer from 1 to 5. In an embodiment wherein $R^3$ has Structure G11, $R^{61c}$, $R^{63c}$, $R^{64c}$, and $R^{65c}$ can be hydrogen and $R^{62c}$ can be any non-hydrogen substituent disclosed herein; or alternatively, $R^{61c}$, $R^{63c}$, and $R^{65c}$ can be hydrogen and $R^{62c}$ and $R^{64c}$ independently can be any non-hydrogen substituent disclosed herein. In an embodiment, n can be an integer from 1 to 4; or alternatively, from 2 to 4. In other embodiments, n can be 2 or 3; alternatively, 2; or alternatively 3. Substituents (general and specific) are independently disclosed herein and can be utilized without limitation to further describe a non-hydrogen substituent which can be utilized without limitation as $R^{61c}$, $R^{62c}$, $R^{63c}$, $R^{64c}$, and/or $R^{65c}$ for the $R^3$ group having Structure G11.

In an embodiment, $R^3$ can be a phenyl group or a substituted phenyl group. In some embodiments, $R^3$ can be a phenyl group; or alternatively, a substituted phenyl group. In an embodiment, the $R^3$ substituted phenyl group can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other embodiments, the $R^3$ substituted phenyl group can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,6-disubstituted phenyl group or a 2,4,6-trisubstituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents (general and specific) are independently disclosed herein and can be utilized without limitation to further describe any substituted phenyl group which can be utilized as $R^3$.

In an aspect, $R^3$ can have Structure G12:

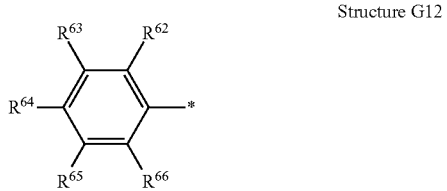

Structure G12 wherein the undesignated valency is attached to the $N^1$ nitrogen atom of the $N^2$-phosphinyl guanidine group. Generally, $R^{62}$, $R^{63}$, $R^{64}$, $R^{65}$, and $R^{66}$ independently can be hydrogen or a non-hydrogen substituent. In an embodiment wherein $R^3$ has Structure G12, $R^{62}$, $R^{63}$, $R^{64}$, $R^{65}$, and $R^{66}$ can be hydrogen, $R^{63}$, $R^{64}$, $R^{65}$, and $R^{66}$ can be hydrogen and $R^{62}$ can be a non-hydrogen substituent, $R^{62}$, $R^{64}$, $R^{65}$, and $R^{66}$ can be hydrogen and $R^{63}$ can be a non-hydrogen substituent, $R^{62}$, $R^{63}$, $R^{65}$, and $R^{66}$ can be hydrogen and $R^{64}$ can be a non-hydrogen substituent, $R^{63}$, $R^{65}$, and $R^{66}$ can be hydrogen and $R^{62}$ and $R^{64}$ can be non-hydrogen substituents, $R^{63}$, $R^{64}$, and $R^{65}$ can be hydrogen and $R^{62}$ and $R^{66}$ can be non-hydrogen substituents, $R^{62}$, $R^{64}$, and $R^{66}$ can be hydrogen and $R^{63}$ and $R^{65}$ can be non-hydrogen substituents, or $R^{63}$ and $R^{65}$ can be hydrogen and $R^{62}$, $R^{64}$, and $R^{66}$ can be non-hydrogen substituents. In some embodiments wherein $R^3$ has Structure G12, $R^{63}$, $R^{64}$, $R^{65}$, and $R^{66}$ can be hydrogen and $R^{62}$ can be a non-hydrogen substituent, $R^{62}$, $R^{63}$, $R^{65}$, and $R^{66}$ can be hydrogen and $R^{64}$ can be a non-hydrogen substituent, $R^{63}$, $R^{65}$, and $R^{66}$ can be hydrogen and $R^{62}$ and $R^{64}$ can be non-hydrogen substituents, $R^{63}$, $R^{64}$, and $R^{65}$ can be hydrogen and $R^{62}$ and $R^{66}$ can be non-hydrogen substituents, or $R^{63}$ and $R^{65}$ can be hydrogen and $R^{62}$, $R^{64}$, and $R^{66}$ can be non-hydrogen substituents; alternatively, $R^{63}$, $R^{64}$, $R^{65}$, and $R^{66}$ can be hydrogen and $R^{62}$ can be a non-hydrogen substituent, $R^{62}$, $R^{63}$, $R^{65}$, and $R^{66}$ can be hydrogen and $R^{64}$ can be a non-hydrogen substituent, $R^{63}$, $R^{65}$, and $R^{66}$ can be hydrogen and $R^{62}$ and $R^{64}$ can be non-hydrogen substituents, or $R^{63}$, $R^{64}$, and $R^{65}$ can be hydrogen and $R^{62}$ and $R^{66}$ can be non-hydrogen substituents; alternatively, $R^{62}$, $R^{64}$, $R^{65}$, and $R^{66}$ can be hydrogen and $R^{63}$ can be a non-hydrogen substituent, or $R^{62}$, $R^{64}$, and $R^{66}$ can be hydrogen and $R^{63}$ and $R^{65}$ can be non-hydrogen substituents; alternatively, $R^{63}$, $R^{64}$, $R^{65}$, and $R^{66}$ can be hydrogen and $R^{62}$ can be a non-hydrogen substituent, or $R^{62}$, $R^{63}$, $R^{65}$, and $R^{66}$ can be hydrogen and $R^{64}$ can be a non-hydrogen substituent; alternatively, $R^{63}$, $R^{65}$, and $R^{66}$ can be hydrogen and $R^{62}$ and $R^{64}$ can be non-hydrogen substituents, or $R^{63}$, $R^{64}$, and $R^{65}$ can be hydrogen and $R^{62}$ and $R^{66}$ can be non-hydrogen substituents. In other embodiments wherein $R^3$ has Structure G12, $R^{62}$, $R^{63}$, $R^{64}$, $R^{65}$, and $R^{66}$ can be hydrogen; alternatively, $R^{63}$, $R^{64}$, $R^{65}$, and $R^{66}$ can be hydrogen and $R^{62}$ can be a non-hydrogen substituent; alternatively, $R^{62}$, $R^{64}$, $R^{65}$, and $R^{66}$ can be hydrogen and $R^{63}$ can be a non-hydrogen substituent; alternatively, $R^{62}$, $R^{63}$, $R^{65}$, and $R^{66}$ can be hydrogen and $R^{64}$ can be a non-hydrogen substituent; alternatively, $R^{63}$, $R^{65}$, and $R^{66}$ can be hydrogen and $R^{62}$ and $R^{64}$ can be non-hydrogen substituents; alternatively, $R^{63}$, $R^{64}$, and $R^{65}$ can be hydrogen and $R^{62}$ and $R^{66}$ can be non-hydrogen substituents; alternatively, $R^{62}$, $R^{64}$, and $R^{66}$ can be hydrogen and $R^{63}$ and $R^{65}$ can be non-hydrogen substituents; or alternatively, $R^{63}$ and $R^{65}$ can be hydrogen and $R^{62}$, $R^{64}$, and $R^{66}$ can be non-hydrogen substituents. Substituents (general and specific) are independently disclosed herein and can be utilized without limitation as $R^{62}$, $R^{63}$, $R^{64}$, $R^{65}$, and $R^{66}$ for the $R^3$ group having Structure G12.

In a non-limiting embodiment, $R^3$ can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group, or a 2,4,6-trialkylphenyl group; alternatively, a 2,4-dialkylphenyl group or a 2,6-dialkylphenyl group; alternatively, a 2,6-dialkylphenyl group, or a 2,4,6-trialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 3-alkylphenyl group; alternatively, a 4-alkylphenyl group; alternatively, a 2,4-dialkylphenyl group; alternatively, a 2,6-dialkylphenyl group; alternatively, a 3,5-dialkylphenyl group; or alternatively, a 2,4,6-trialkylphenyl group. In another non-limiting embodiment, $R^3$ can be a phenyl group, a 2-alkoxyphenyl group, a 3-alkoxyphenyl group, a 4-alkoxyphenyl group, or a 3,5-dialkoxyphenyl group; alternatively, a 2-alkoxyphenyl group or a 4-alkoxyphenyl group; alternatively, a 3-alkoxyphenyl group or 3,5-dialkoxyphenyl group; alternatively, a 2-alkoxyphenyl group; alternatively, a 3-alkoxyphenyl group; alternatively, a 4-alkoxyphenyl group; alternatively, a 3,5-dialkoxyphenyl group. In other non-limiting embodiments, $R^3$ can be a phenyl group, a 2-halophenyl group, a 3-halophenyl group, a 4-halophenyl group, a 2,6-dihalophenylgroup, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group; alternatively, a 2,6-dihalophenylgroup; or alternatively, a 3,5-dihalophenyl group. Halides, alkyl group substituents (general and specific), and alkoxy group substituents (general and specific) are independently described herein and can be utilized, without limitation, to further describe the alkylphenyl, dialkylphenyl, trialkylphenyl, alkoxyphenyl, dialkoxyphenyl, halophenyl, or dihalophenyl groups that can be utilized $R^3$. Generally, the halides, alkyl substituents, or alkoxy substituents of a dialkyl, trialkyl phenyl, dialkoxyphenyl, or dihalophenyl group can be the same; or alternatively the halo, alkyl substituents, or alkoxy substituents of alkylphenyl, dialkylphenyl, trialkylphenyl, dialkoxyphenyl, or dihalophenyl groups can be different.

In a non-limiting embodiment, $R^3$ can be a 2-methylphenyl group, a 2-ethylphenyl group, a 2-isopropylphenyl group, a 2-tert-butylphenyl group, a 4-methylphenyl group, a 4-ethylphenyl group, a 4-isopropylphenyl group, a 4-tert-butylphenyl group, a 2,6-dimethylphenyl group, a 2,6-diethylphenyl group, a 2,6-diisopropylphenyl group, or a 2,6-di-tert-butylphenyl group; alternatively, a 2-methylphenyl group, a 2-ethylphenyl group, a 2-isopropylphenyl group, or a 2-tert-butylphenyl group, a 4-methylphenyl group, a 4-ethylphenyl group, a 4-isopropylphenyl group, or a 4-tert-butylphenyl group; alternatively, a 2-methylphenyl group, a 2-ethylphenyl group, a 2-isopropylphenyl group, or a 2-tert-butylphenyl group; alternatively, a 4-methylphenyl group, a 4-ethylphenyl group, a 4-isopropylphenyl group, or a 4-tert-butylphenyl group; or alternatively, a 2,6-dimethylphenyl group, a 2,6-diethylphenyl group, a 2,6-di-n-propylphenyl group, a 2,6-diisopropylphenyl group, or a 2,6-di-tert-butylphenyl group. In another non-limiting embodiment, $R^3$ can be a 2-methylphenyl group; alternatively, a 2-ethylphenyl group; alternatively, a 2-isopropylphenyl group; alternatively, a 2-tert-butylphenyl group; alternatively, a 4-methylphenyl group; alternatively, a 4-ethylphenyl group; alternatively, a 4-isopropylphenyl group; or alternatively, a 4-tert-butylphenyl group.

In an aspect, $R^4$ and $R^5$ independently can be an organyl group; alternatively, an organyl group consisting essentially of inert functional groups; or alternatively, a hydrocarbyl group. Organyl groups (general and specific) are disclosed herein (e.g., as potential selections for $R^1$) and these organyl groups can be utilized as $R^4$ and/or $R^5$. Organyl groups consisting essentially of inert functional groups, general and specific, are disclosed herein (e.g., as potential selections for $R^1$) and these organyl groups consisting essentially of inert functional group can be utilized as $R^4$ and/or $R^5$. Hydrocarbyl groups, general and specific, are disclosed herein (e.g., as potential selections for $R^1$) and these hydrocarbyl groups can be utilized as $R^4$ and/or $R^5$. In yet other embodiments, $R^4$ and $R^5$ independently can be selected from a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group. In an aspect, $R^4$ and $R^5$ can be joined to form a ring (regardless of particular type of group—organyl, organyl consisting of inert functional groups, hydrocarbyl, or any species within) containing the phosphorus atom of the $N^2$-phosphinyl guanidine group.

In another aspect, $R^4$ and $R^5$ independently can be a $C_1$ to $C_{30}$ alkyl group, a $C_4$ to $C_{30}$ cycloalkyl group, a $C_4$ to $C_{30}$ substituted cycloalkyl group, a $C_3$ to $C_{30}$ aliphatic heterocyclic group, a $C_3$ to $C_{30}$ substituted aliphatic heterocyclic group, a $C_6$ to $C_{30}$ aryl group, a $C_6$ to $C_{30}$ substituted aryl group, a $C_3$ to $C_{30}$ heteroaryl group, or a $C_3$ to $C_{30}$ substituted heteroaryl group; alternatively, a $C_1$ to $C_{30}$ alkyl group, a $C_4$ to $C_{30}$ cycloalkyl group, a $C_4$ to $C_{30}$ substituted cycloalkyl group, a $C_6$ to $C_{30}$ aryl group, or a $C_6$ to $C_{30}$ substituted aryl group; alternatively, a $C_4$ to $C_{30}$ cycloalkyl group or a $C_4$ to $C_{30}$ substituted cycloalkyl group; alternatively, a $C_3$ to $C_{30}$ aliphatic heterocyclic group or a $C_3$ to $C_{30}$ substituted aliphatic heterocyclic group; alternatively, a $C_6$ to $C_{30}$ aryl group or a $C_6$ to $C_{30}$ substituted aryl group; alternatively, a $C_3$ to $C_{30}$ heteroaryl group or a $C_3$ to $C_{30}$ substituted heteroaryl group; alternatively, a $C_1$ to $C_{30}$ alkyl group; alternatively, a $C_4$ to $C_{30}$ cycloalkyl group; alternatively, a $C_4$ to $C_{30}$ substituted cycloalkyl group; alternatively, a $C_3$ to $C_{30}$ aliphatic heterocyclic group; alternatively, a $C_3$ to $C_{30}$ substituted aliphatic heterocyclic group; alternatively, a $C_6$ to $C_{30}$ aryl group; alternatively, a $C_6$ to $C_{30}$ substituted aryl group; alternatively, a $C_3$ to $C_{30}$ heteroaryl group; or alternatively, a $C_3$ to $C_{30}$ substituted heteroaryl group. In an embodiment, $R^4$ and $R^5$ independently can be a $C_1$ to $C_{15}$ alkyl group, a $C_4$ to $C_{20}$ cycloalkyl group, a $C_4$ to $C_{20}$ substituted cycloalkyl group, a $C_3$ to $C_{20}$ aliphatic heterocyclic group, a $C_3$ to $C_{20}$ substituted aliphatic heterocyclic group, a $C_6$ to $C_{20}$ aryl group, a $C_6$ to $C_{20}$ substituted aryl group, a $C_3$ to $C_{20}$ heteroaryl group, or a $C_3$ to $C_{20}$ substituted heteroaryl group; alternatively, a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group; alternatively, a $C_4$ to $C_{20}$ cycloalkyl group or a $C_4$ to $C_{20}$ substituted cycloalkyl group; alternatively, a $C_3$ to $C_{20}$ aliphatic heterocyclic group or a $C_3$ to $C_{20}$ substituted aliphatic heterocyclic group; alternatively, a $C_6$ to $C_{20}$ aryl group or a $C_6$ to $C_{20}$ substituted aryl group; alternatively, a $C_3$ to $C_{20}$ heteroaryl group or a $C_3$ to $C_{20}$ substituted heteroaryl group; alternatively, a $C_1$ to $C_{15}$ alkyl group; alternatively, a $C_4$ to $C_{20}$ cycloalkyl group; alternatively, a $C_4$ to $C_{20}$ substituted cycloalkyl group; alternatively, a $C_3$ to $C_{20}$ aliphatic heterocyclic group; alternatively, a $C_3$ to $C_{20}$ substituted aliphatic heterocyclic group; alternatively, a $C_6$ to $C_{20}$ aryl group; alternatively, a $C_6$ to $C_{20}$ substituted aryl group; alternatively, a $C_3$ to $C_{20}$ heteroaryl group; or alternatively, a $C_3$ to $C_{20}$ substituted heteroaryl group. In other embodiments, $R^4$ and $R^5$ independently can be a $C_1$ to $C_{10}$ alkyl group, a $C_4$ to $C_{15}$ cycloalkyl group, a $C_4$ to $C_{15}$ substituted cycloalkyl group, a $C_3$ to $C_{15}$ aliphatic heterocyclic group, a $C_3$ to $C_{15}$ substituted aliphatic heterocyclic group, a $C_6$ to $C_{15}$ aryl group, a $C_6$ to $C_{15}$ substituted aryl group, a $C_3$ to $C_{15}$ heteroaryl group, or a $C_3$ to $C_{15}$ substituted heteroaryl group; alternatively, a $C_1$ to $C_{10}$ alkyl group, a $C_4$ to $C_{15}$ cycloalkyl group, a $C_4$ to $C_{15}$ substituted cycloalkyl group, a $C_6$ to $C_{15}$ aryl group, or a $C_6$ to $C_{15}$ substituted aryl group; alternatively, a $C_4$ to $C_{15}$ cycloalkyl group or a $C_4$ to $C_{15}$ substituted cycloalkyl group; alternatively, a $C_3$ to $C_{15}$ aliphatic heterocyclic group or a $C_3$ to $C_{15}$ substituted aliphatic heterocyclic group; alternatively, a $C_6$ to $C_{15}$ aryl group or a $C_6$ to $C_{15}$ substituted aryl group; alternatively, a $C_3$ to $C_{15}$ heteroaryl group or a $C_3$ to $C_{15}$ substituted heteroaryl group; alternatively, a $C_1$ to $C_{10}$ alkyl group; alternatively, a $C_4$ to $C_{15}$ cycloalkyl group; alternatively, a $C_4$ to $C_{15}$ substituted cycloalkyl group; alternatively, a $C_3$ to $C_{15}$ aliphatic heterocyclic group; alternatively, a $C_3$ to $C_{15}$ substituted aliphatic heterocyclic group; alternatively, a $C_6$ to $C_{15}$ aryl group; alternatively, a $C_6$ to $C_{15}$ substituted aryl group; alternatively, a $C_3$ to $C_{15}$ heteroaryl group; or alternatively, a $C_3$ to $C_{15}$ substituted heteroaryl group. In further embodiments, $R^4$ and $R^5$ independently can be $C_1$ to $C_5$ alkyl group. Substituents (general and specific) are independently disclosed herein and can be utilized without limitation to further describe substituted groups which can be utilized as $R^4$ and/or $R^5$.

In a further aspect, $R^4$ and $R^5$ independently can be a methyl group, an ethyl group, a propyl group, a butyl group, a pentyl group, a hexyl group, a heptyl group, an octyl group, a nonyl group, or a decyl group. In some embodiments, $R^4$ and/or $R^5$ independently can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, an n-propyl group; alternatively, an iso-propyl group; alternatively, a tert-butyl group; or alternatively, a neopentyl group. In some embodiments, the alkyl groups which can be utilized as $R^4$ and/or $R^5$ can be substituted. Each substituent of a substituted alkyl group independently can be a halogen or a hydrocarboxy group; alternatively, a halogen; or alternatively, a hydrocarboxy group. Halogens, and hydrocarboxy groups (general and specific) are independently disclosed herein (e.g., as general substituents and/or as substituents for substituted $R^1$ groups) and can be utilized without limitation to further describe the substituted alkyl group which can be utilized as $R^4$ and/or $R^5$.

In a further aspect, $R^4$ and $R^5$ independently can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, $R^4$ and/or $R^5$ independently can be a cyclopentyl group, a substituted cyclopentyl group, a cyclohexyl group, or a substituted cyclohexyl group. In other embodiments, $R^4$ and/or $R^5$ can be a cyclopentyl group or a substituted cyclopentyl group; or alternatively, a cyclohexyl group or a substituted cyclohexyl group. In further embodiments, $R^4$ and/or $R^5$ independently can be a cyclopentyl group; alternatively, a substituted cyclopentyl group; a cyclohexyl group; or alternatively, a substituted cyclohexyl group. Substituents (general and specific) are independently disclosed herein and can be utilized without limitation to further describe the substituted cycloalkyl group which can be utilized as $R^4$ and/or $R^5$.

In an aspect, $R^4$ can have Structure G7:

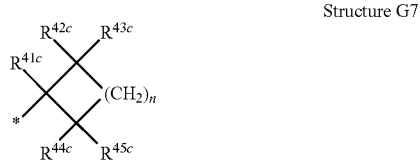

Structure G7 wherein, the undesignated valency is attached to the phosphorus atom of the $N^2$-phosphinyl guanidine group. Generally, $R^{41c}$, $R^{42c}$, $R^{43c}$, $R^{44c}$, and $R^{45c}$ independently can be hydrogen or a non-hydrogen substituent, and n can be an integer from 1 to 5. In an embodiment wherein $R^4$ has Structure G7, $R^{41c}$, $R^{43c}$, $R^{44c}$, and $R^{45c}$ can be hydrogen and $R^{32c}$ can be any non-hydrogen substituent disclosed herein; or alternatively, $R^{41c}$, $R^{43c}$, and $R^{45c}$ can be hydrogen and $R^{42c}$ and $R^{44c}$ independently can be any non-hydrogen substituent disclosed herein. In an embodiment, n can be an integer from 1 to 4; or alternatively, from 2 to 4. In other embodiments, n can be 2 or 3; alternatively, 2; or alternatively 3. Substituents (general and specific) are independently disclosed herein and can be utilized without limitation to further describe a non-hydrogen substituent which can be utilized without limitation as $R^{41c}$, $R^{42c}$, $R^{43c}$, $R^{44c}$, and/or $R^{45c}$ for the $R^4$ group having Structure G7.

In an aspect, $R^5$ can have Structure G8:

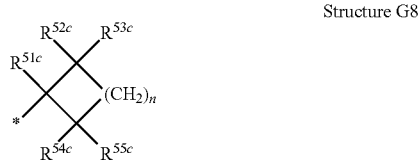

Structure G8 wherein, the undesignated valency is attached to the phosphorus atom of the $N^2$-phosphinyl guanidine group. Generally, $R^{51c}$, $R^{52c}$, $R^{53c}$, $R^{54c}$, and $R^{55c}$ independently can be hydrogen or a non-hydrogen substituent, and n can be an integer from 1 to 5. In an embodiment wherein $R^5$ has Structure G8, $R^{51c}$, $R^{53c}$, $R^{54c}$, and $R^{55c}$ can be hydrogen and $R^{32c}$ can be any non-hydrogen substituent disclosed herein; or alternatively, $R^{51c}$, $R^{53c}$, and $R^{55c}$ can be hydrogen and $R^{52c}$ and $R^{54c}$ independently can be any non-hydrogen substituent disclosed herein. In an embodiment, n can be an integer from 1 to 4; or alternatively, from 2 to 4. In other embodiments, n can be 2 or 3; alternatively, 2; or alternatively 3. Substituents (general and specific) are independently disclosed herein and can be utilized without limitation to further describe a non-hydrogen substituent which can be utilized without limitation as $R^{51c}$, $R^{52c}$, $R^{53c}$, $R^{54c}$, and/or $R^{55c}$ for the $R^5$ group having Structure G8.

In an aspect, $R^4$ and $R^5$ independently can be a phenyl group, a substituted phenyl group, a naphthyl group, or a substituted naphthyl group. In an embodiment, $R^4$ and $R^5$ independently can be a phenyl group or a substituted phenyl group; alternatively, a naphthyl group or a substituted naphthyl group; alternatively, a phenyl group or a naphthyl group; or alternatively, a substituted phenyl group or a substituted naphthyl group. In some embodiments, $R^4$ and $R^5$ independently can be a phenyl group; alternatively, a substituted phenyl group; alternatively, a naphthyl group; or alternatively, a substituted naphthyl group. Substituents (general and specific) are independently disclosed herein and can be utilized without limitation to further describe any substituted phenyl group and/or substituted naphthyl group which can be utilized as $R^4$ and/or $R^5$.

In an embodiment, the $R^4$ and/or $R^5$ substituted phenyl group can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other embodiments, the $R^4$ and/or $R^5$ substituted phenyl group can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,6-disubstituted phenyl group or a 2,4,6-trisubstituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents (general and specific) are independently disclosed herein and can be utilized without limitation to further describe any substituted phenyl group which can be utilized as $R^4$ and/or $R^5$.

In an embodiment, $R^4$ and $R^5$ independently can be a naphth-1-yl group, a substituted naphth-1-yl group, a naphth-2-yl group, or a substituted naphth-2-yl group. In some embodiments, $R^4$ and $R^5$ independently can be a naphth-1-yl group or a substituted naphth-1-yl group; alternatively, a naphth-2-yl group or a substituted naphth-2-yl group; alternatively, a naphth-1-yl group; alternatively, a substituted naphth-1-yl group; alternatively, a naphth-2-yl group; or alternatively, a substituted naphth-2-yl group. In other embodiments, $R^4$ and $R^5$ independently can be a 2-substituted naphth-1-yl group, a 3-substituted naphth-1-yl group, a 4-substituted naphth-1-yl group, or a 8-substituted naphth-1-yl group; alternatively, a 2-substituted naphth-1-yl group; alternatively, a 3-substituted naphth-1-yl group; alternatively, a 4-substituted naphth-1-yl group; or alternatively, a 8-substituted naphth-1-yl group. In further embodiments, $R^4$ and $R^5$ independently can be a 1-substituted naphth-2-yl group, a 3-substituted naphth-2-yl group, a 4-substituted naphth-2-yl group, or a 1,3-disubstituted naphth-2-yl group; alternatively, a 1-substituted naphth-2-yl group; alternatively, a 3-substituted naphth-2-yl group; alternatively, a 4-substituted naphth- 2-yl group; alternatively, a 1,3-disubstituted naphth-2-yl group. Substituents (general and specific) are independently disclosed herein and can be utilized without limitation to further describe any substituted naphthyl group which can be utilized as $R^4$ and/or $R^5$.

In an aspect, $R^4$ can have Structure G9:

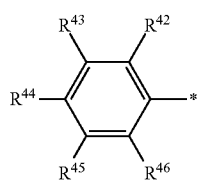

Structure G9 wherein the undesignated valency is attached to the phosphorus atom of the $N^2$-phosphinyl guanidine group. Generally, $R^{42}$, $R^{43}$, $R^{44}$, $R^{45}$, and $R^{46}$ can independently be hydrogen or a non-hydrogen substituent. In an embodiment wherein $R^4$ has Structure G9, $R^{42}$, $R^{43}$, $R^{44}$, $R^{45}$, and $R^{46}$ can be hydrogen, $R^{43}$, $R^{44}$, $R^{45}$, and $R^{46}$ can be hydrogen and $R^{42}$ can be a non-hydrogen substituent, $R^{42}$, $R^{44}$, $R^{45}$, and $R^{46}$ can be hydrogen and $R^{43}$ can be a non-hydrogen substituent, $R^{42}$, $R^{43}$, $R^{45}$, and $R^{46}$ can be hydrogen and $R^{44}$ can be a non-hydrogen substituent, $R^{43}$, $R^{45}$, and $R^{46}$ can be hydrogen and $R^{42}$ and $R^{44}$ can be non-hydrogen substituents, $R^{43}$, $R^{44}$, and $R^{45}$ can be hydrogen and $R^{42}$ and $R^{46}$ can be non-hydrogen substituents, $R^{42}$, $R^{44}$, and $R^{46}$ can be hydrogen and $R^{43}$ and $R^{45}$ can be non-hydrogen substituents, or $R^{43}$ and $R^{45}$ can be hydrogen and $R^{42}$, $R^{44}$, and $R^{46}$ can be non-hydrogen substituents. In some embodiments wherein $R^4$ has Structure G9, $R^{43}$, $R^{44}$, $R^{45}$, and $R^{46}$ can be hydrogen and $R^{42}$ can be a non-hydrogen substituent, $R^{42}$, $R^{43}$, $R^{45}$, and $R^{46}$ can be hydrogen and $R^{44}$ can be a non-hydrogen substituent, $R^{43}$, $R^{45}$, and $R^{46}$ can be hydrogen and $R^{42}$ and $R^{44}$ can be non-hydrogen substituents, $R^{43}$, $R^{44}$, and $R^{45}$ can be hydrogen and $R^{42}$ and $R^{46}$ can be non-hydrogen substituents, or $R^{43}$ and $R^{45}$ can be hydrogen and $R^{42}$, $R^{44}$, and $R^{46}$ can be non-hydrogen substituents; alternatively, $R^{43}$, $R^{44}$, $R^{45}$, and $R^{46}$ can be hydrogen and $R^{42}$ can be a non-hydrogen substituent, $R^{42}$, $R^{43}$, $R^{45}$, and $R^{46}$ can be hydrogen and $R^{44}$ can be a non-hydrogen substituent, $R^{43}$, $R^{45}$, and $R^{46}$ can be hydrogen and $R^{42}$ and $R^{44}$ can be non-hydrogen substituents, or $R^{43}$, $R^{44}$, and $R^{45}$ can be hydrogen and $R^{42}$ and $R^{46}$ can be non-hydrogen substituents; alternatively, $R^{42}$, $R^{44}$, $R^{45}$, and $R^{46}$ can be hydrogen and $R^{43}$ can be a non-hydrogen substituent, or $R^{42}$, $R^{44}$, and $R^{46}$ can be hydrogen and $R^{43}$ and $R^{45}$ can be non-hydrogen substituents; alternatively, $R^{43}$, $R^{44}$, $R^{45}$, and $R^{46}$ can be hydrogen and $R^{42}$ can be a non-hydrogen substituent, or $R^{42}$, $R^{43}$, $R^{45}$, and $R^{46}$ can be hydrogen and $R^{44}$ can be a non-hydrogen substituent; alternatively, $R^{43}$, $R^{45}$, and $R^{46}$ can be hydrogen and $R^{42}$ and $R^{44}$ can be non-hydrogen substituents, $R^{43}$, $R^{44}$, and $R^{45}$ can be hydrogen and $R^{42}$ and $R^{46}$ can be non-hydrogen substituents, or $R^{43}$ and $R^{45}$ can be hydrogen and $R^{42}$, $R^{44}$, and $R^{46}$ can be non-hydrogen substituents; or alternatively, $R^{43}$, $R^{45}$, and $R^{46}$ can be hydrogen and $R^{42}$ and $R^{44}$ can be non-hydrogen substituents, or $R^{43}$, $R^{44}$, and $R^{45}$ can be hydrogen and $R^{42}$ and $R^{46}$ can be non-hydrogen substituents. In other embodiments wherein $R^4$ has Structure G9, $R^{42}$, $R^{43}$, $R^{44}$, $R^{45}$, and $R^{46}$ can be hydrogen; alternatively, $R^{43}$, $R^{44}$, $R^{45}$, and $R^{46}$ can be hydrogen and $R^{42}$ can be a non-hydrogen substituent; alternatively, $R^{42}$, $R^{44}$, $R^{45}$, and $R^{46}$ can be hydrogen and $R^{43}$ can be a non-hydrogen substituent; alternatively, $R^{42}$, $R^{43}$, $R^{45}$, and $R^{46}$ can be hydrogen and $R^{44}$ can be a non-hydrogen substituent; alter- natively, $R^{43}$, $R^{45}$, and $R^{46}$ can be hydrogen and $R^{42}$ and $R^{44}$ can be non-hydrogen substituents; alternatively, $R^{43}$, $R^{44}$, and $R^{45}$ can be hydrogen and $R^{42}$ and $R^{46}$ can be non hydrogen substituents; alternatively, $R^{42}$, $R^{44}$, and $R^{46}$ can be hydrogen and $R^{43}$ and $R^{45}$ and can be non-hydrogen substituents; or alternatively, $R^{43}$ and $R^{45}$ can be hydrogen and $R^{42}$, $R^{44}$, and $R^{46}$ can be non-hydrogen substituents. Substituents (general and specific) are independently disclosed herein and can be utilized without limitation as $R^{42}$, $R^{43}$, $R^{44}$, $R^{45}$, and $R^{46}$ for the $R^4$ group having Structure G9.

In an aspect, $R^5$ can have Structure G10:

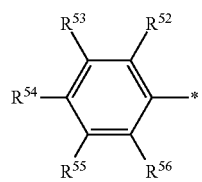

Structure G10 wherein the undesignated valency is attached to the phosphorus atom of the $N^2$-phosphinyl guanidine group. Generally, $R^{52}$, $R^{53}$, $R^{54}$, $R^{55}$, and $R^{56}$ independently can be hydrogen or a non-hydrogen substituent. In an embodiment wherein $R^5$ has Structure G10, $R^{52}$, $R^{53}$, $R^{54}$, $R^{55}$, and $R^{56}$ can be hydrogen, $R^{53}$, $R^{54}$, $R^{55}$, and $R^{56}$ can be hydrogen and $R^{52}$ can be a non-hydrogen substituent, $R^{52}$, $R^{54}$, $R^{55}$, and $R^{56}$ can be hydrogen and $R^{53}$ can be a non-hydrogen substituent, $R^{52}$, $R^{53}$, $R^{55}$, and $R^{56}$ can be hydrogen and $R^{54}$ can be a non-hydrogen substituent, $R^{53}$, $R^{55}$, and $R^{56}$ can be hydrogen and $R^{52}$ and $R^{54}$ can be non-hydrogen substituents, $R^{53}$, $R^{54}$, and $R^{55}$ can be hydrogen and $R^{52}$ and $R^{56}$ can be non-hydrogen substituents, $R^{52}$, $R^{54}$, and $R^{56}$ can be hydrogen and $R^{53}$ and $R^{55}$ can be non-hydrogen substituents, or $R^{53}$ and $R^{55}$ can be hydrogen and $R^{52}$, $R^{54}$, and $R^{56}$ can be non-hydrogen substituents. In some embodiments wherein $R^5$ has Structure G10, $R^{53}$, $R^{54}$, $R^{55}$, and $R^{56}$ can be hydrogen and $R^{52}$ can be a non-hydrogen substituent, $R^{52}$, $R^{53}$, $R^{55}$, and $R^{56}$ can be hydrogen and $R^{54}$ can be a non-hydrogen substituent, $R^{53}$, $R^{55}$, and $R^{56}$ can be hydrogen and $R^{52}$ and $R^{54}$ can be non-hydrogen substituents, $R^{53}$, $R^{54}$, and $R^{55}$ can be hydrogen and $R^{52}$ and $R^{56}$ can be non-hydrogen substituents, or $R^{53}$ and $R^{55}$ can be hydrogen and $R^{52}$, $R^{54}$, and $R^{56}$ can be non-hydrogen substituents; alternatively, $R^{53}$, $R^{54}$, $R^{55}$, and $R^{56}$ can be hydrogen and $R^{52}$ can be a non-hydrogen substituent, $R^{52}$, $R^{53}$, $R^{55}$, and $R^{56}$ can be hydrogen and $R^{54}$ can be a non-hydrogen substituent, $R^{53}$, $R^{55}$, and $R^{56}$ can be hydrogen and $R^{52}$ and $R^{54}$ can be non-hydrogen substituents, or $R^{53}$, $R^{54}$, and $R^{55}$ can be hydrogen and $R^{52}$ and $R^{56}$ can be non-hydrogen substituents; alternatively, $R^{52}$, $R^{54}$, $R^{55}$, and $R^{56}$ can be hydrogen and $R^{53}$ can be a non-hydrogen substituent, or $R^{52}$, $R^{54}$, and $R^{56}$ can be hydrogen and $R^{53}$ and $R^{55}$ can be non-hydrogen substituents; alternatively, $R^{53}$, $R^{54}$, $R^{55}$, and $R^{56}$ can be hydrogen and $R^{52}$ can be a non-hydrogen substituent, or $R^{52}$, $R^{53}$, $R^{55}$, and $R^{56}$ can be hydrogen and $R^{54}$ can be a non-hydrogen substituent; alternatively, $R^{53}$, $R^{55}$, and $R^{56}$ can be hydrogen and $R^{52}$ and $R^{54}$ can be non-hydrogen substituents, $R^{53}$, $R^{54}$, and $R^{55}$ can be hydrogen and $R^{52}$ and $R^{56}$ can be non-hydrogen substituents, or $R^{53}$ and $R^{55}$ can be hydrogen and $R^{52}$, $R^{54}$, and $R^{56}$ can be non-hydrogen substituents; or alternatively, $R^{53}$, $R^{55}$, and $R^{56}$ can be hydrogen and $R^{52}$ and $R^{54}$ can be non-hydrogen substituents, or $R^{53}$, $R^{54}$, and $R^{55}$ can be hydrogen and $R^{52}$ and $R^{56}$ can be non-hydrogen substituents. In other embodiments wherein $R^5$ has Structure G10, $R^{52}$, $R^{53}$, $R^{54}$, $R^{55}$, and $R^{56}$ can be hydrogen;

alternatively, $R^{53}$, $R^{54}$, $R^{55}$, and $R^{56}$ can be hydrogen and $R^{52}$ can be a non-hydrogen substituent; alternatively, $R^{52}$, $R^{54}$, $R^{55}$, and $R^{56}$ can be hydrogen and $R^{53}$ can be a non-hydrogen substituent; alternatively, $R^{52}$, $R^{53}$, $R^{55}$, and $R^{56}$ can be hydrogen and $R^{54}$ can be a non-hydrogen substituent; alternatively, $R^{53}$, $R^{55}$, and $R^{56}$ can be hydrogen and $R^{52}$ and $R^{54}$ can be non-hydrogen substituents; alternatively, $R^{53}$, $R^{54}$, and $R^{55}$ can be hydrogen and $R^{52}$ and $R^{56}$ can be non-hydrogen substituents; alternatively, $R^{52}$, $R^{54}$, and $R^{56}$ can be hydrogen and $R^{53}$ and $R^{55}$ and can be non-hydrogen substituents; or alternatively, $R^{53}$ and $R^{55}$ can be hydrogen and $R^{52}$, $R^{54}$, and $R^{56}$ can be non-hydrogen substituents. Substituents (general and specific) are independently disclosed herein and can be utilized without limitation as $R^{52}$, $R^{53}$, $R^{54}$, $R^{55}$, and $R^{56}$ for the $R^5$ group having Structure G10.

In an aspect, $R^4$ and $R^5$ independently can be a pyridinyl group, a substituted pyridinyl group, a furyl group, a substituted furyl group, a thienyl group, or a substituted thienyl group. In an embodiment, $R^4$ and $R^5$ independently can be a pyridinyl group or a substituted pyridinyl group; alternatively, a furyl group or a substituted furyl group; or alternatively, a thienyl group or a substituted thienyl group. In some embodiments, $R^4$ and $R^5$ independently can be a pyridinyl group, a furyl group, or a thienyl group. In other embodiments, $R^4$ and $R^5$ can be a pyridinyl group; alternatively, a substituted pyridinyl group; alternatively, a furyl group; alternatively, a substituted furyl group; alternatively, a thienyl group; or alternatively, a substituted thienyl group.

In an embodiment, the pyridinyl (or substituted pyridinyl) $R^4$ and $R^5$ group independently can be a pyridin-2-yl group, a substituted pyridin-2-yl group, a pyridin-3-yl group, a substituted pyridin-3-yl group, a pyridin-4-yl group, or a substituted pyridin-4-yl group; or alternatively, a pyridin-2-yl group, a pyridin-3-yl group, or a pyridin-4-yl group. In some embodiments, the pyridinyl (or substituted pyridinyl) $R^4$ and $R^5$ group independently can be a pyridin-2-yl group or a substituted pyridin-2-yl group; alternatively, a pyridin-3-yl group or a substituted pyridin-3-yl group; alternatively a pyridin-4-yl group or a substituted pyridin-4-yl group; alternatively, a pyridin-2-yl group; alternatively, a substituted pyridin-2-yl group; alternatively, a pyridin-3-yl group; alternatively, a substituted pyridin-3-yl group; alternatively, a pyridin-4-yl group; or alternatively, a substituted pyridin-4-yl group. In an embodiment, the substituted pyridinyl $R^4$ and $R^5$ group independently can be a 2-substituted pyridin-3-yl group, a 4-substituted pyridin-3-yl group, a 5-substituted pyridin-3-yl group, a 6-substituted pyridin-3-yl group, a 2,4-disubstituted pyridin-3-yl group, a 2,6-disubstituted pyridin-3-yl group, or a 2,4,6-trisubstituted pyridin-3-yl group; alternatively, 2-substituted pyridin-3-yl group, a 4-substituted pyridin-3-yl group, or a 6-substituted pyridin-3-yl group; alternatively, a 2,4-disubstituted pyridin-3-yl group or a 2,6-disubstituted pyridin-3-yl group; alternatively, a 2-substituted pyridin-3-yl group; alternatively, a 4-substituted pyridin-3-yl group; alternatively, a 5-substituted pyridin-3-yl group; alternatively, a 6-substituted pyridin-3-yl group; alternatively, a 2,4-disubstituted pyridin-3-yl group; alternatively, a 2,6-disubstituted pyridin-3-yl group; or alternatively, a 2,4,6-trisubstituted pyridin-3-yl group. In an embodiment, the substituted pyridinyl $R^4$ and $R^5$ group independently can be a 2-substituted pyridin-4-yl group, a 3-substituted pyridin-4-yl group, a 5-substituted pyridin-4-yl group, a 6-substituted pyridin-4-yl group, a 2,6-disubstituted pyridin-4-yl group, or a 3,5-disubstituted pyridin-4-yl group; alternatively, 2-substituted pyridin-4-yl group or a 6-substituted pyridin-4-yl group; alternatively, a 3-substituted pyridin-4-yl group or a 5-substituted pyridin-4-yl group; alternatively, a 2-substituted pyridin-4-yl group; alternatively, a 3-substituted pyridin-4-yl group; alternatively, a 5-substituted pyridin-4-yl group; alternatively, a 6-substituted pyridin-4-yl group; alternatively, a 2,6-disubstituted pyridin-4-yl group; or alternatively, a 3,5-disubstituted pyridin-4-yl group. Substituents (general and specific) are independently disclosed herein and can be utilized without limitation to further describe the substituted pyridinyl groups which can be utilized as $R^4$ and/or $R^5$.

In an embodiment, each furyl (or substituted furyl) $R^4$ and $R^5$ group can be independently selected from a fur-2-yl group, a substituted fur-2-yl group, a fur-3-yl group, or a substituted fur-3-yl group; or alternatively, a fur-2-yl or a fur-3-yl group. In some embodiments, the furyl (or substituted furyl) $R^4$ and $R^5$ group can be independently selected from a fur-2-yl group or a substituted fur-2-yl group; alternatively, a fur-3-yl group or a substituted fur-3-yl group; alternatively, a fur-2-yl group; alternatively, a substituted fur-2-yl group; alternatively, a fur-3-yl group; or alternatively, a substituted fur-3-yl group. In an embodiment, the substituted furyl $R^4$ and $R^5$ group can be a 2-substituted fur-3-yl group, a 4-substituted fur-3-yl group, or a 2,4-disubstituted fur-3-yl group; alternatively, a 2-substituted fur-3-yl group; alternatively, a 4-substituted fur-3-yl group; or alternatively, a 2,4-disubstituted fur-3-yl group. Substituents (general and specific) are independently disclosed herein and can be utilized without limitation to further describe the substituted furyl groups which can be utilized as $R^4$ and/or $R^5$.

In an embodiment, the thienyl (or substituted thienyl) $R^4$ and $R^5$ group can be independently selected from a thien-2-yl group, a substituted thien-2-yl group, a thien-3-yl group, or a substituted thien-3-yl group; or alternatively, a thien-2-yl group or a thien-3-yl group. In some embodiments, the thienyl (or substituted thienyl) $R^4$ and $R^5$ group can be independently selected from a thien-2-yl group or a substituted thien-2-yl group; alternatively, a thien-3-yl group or a substituted thien-3-yl group; alternatively, a thien-2-yl group; alternatively, a substituted thien-2-yl group; alternatively, a thien-3-yl group; or alternatively, a substituted thien-3-yl group. In an embodiment, the substituted thienyl $R^4$ and $R^5$ group can be a 2-substituted thien-3-yl group, a 4-substituted thien-3-yl group, or a 2,4-disubstituted thien-3-yl group; alternatively, a 2-substituted thien-3-yl group; alternatively, a 4-substituted thien-3-yl group; or alternatively, a 2,4-disubstituted thien-3-yl group. Substituents (general and specific) are independently disclosed herein and can be utilized without limitation to further describe the substituted thienyl groups which can be utilized as $R^4$ and/or $R^5$.

In an aspect, $R^4$ and $R^5$ can be joined to form a cyclic group including the phosphorus atom. In an embodiment when $R^4$ and $R^5$ are joined to form a cyclic group including the phosphorus atom of the $N^2$-phosphinyl guanidine group, the phosphinyl group can be a phosphol-1-yl group, a substituted phosphol-1-yl group, a 2,3-dihydrophosphol-1-yl group, a substituted 2,3-dihydro-phosphol-1-yl group, a 3,5-dihydrophosphol-1-yl group, a substituted 3,5-dihydrophosphol-1-yl group, a phospholan-1-yl group, a substituted phospholan-1-yl group, a 1,2-dihydrophosphinin-1-yl group, a substituted, 1,2-dihydrophosphinin-1-yl group, a 1,4-dihydrophosphinin-1-yl group, a substituted 1,4-dihydrophosphinin-1-yl group, a 1,2,3,4-tetrahydrophosphinin-1-yl group, a substituted 1,2,3,4-tetrahydrophosphinin-1-yl group, a 1,2,3,6-tetrahydrophosphinin-1-yl group, a substituted 1,2,3,6-tetrahydrophosphinin-1-yl group, a phosphinan-1-yl group, or a substituted phosphinan-1-yl group. In some embodiments when $R^4$ and $R^5$ are joined to form a cyclic group including the phosphorus atom of the $N^2$-phosphinylguanidine group, the phosphinyl group can be a phosphol-1-yl group or a substituted phosphol-1-yl group; alternatively, a 2,3-dihydrophosphol-1-yl group or a substituted 2,3-dihydrophosphol-1-yl group; alternatively, a 3,5-dihydrophosphol-1-yl group or a substituted 3,5-dihydrophosphol-1-yl group; alternatively, a phospholan-1-yl group or a substituted phospholan-1-yl group; alternatively, a 1,2-dihydrophosphinin-1-yl group or a substituted, 1,2-dihydrophosphinin-1-yl group; alternatively, a 1,4-dihydrophosphinin-1-yl group or a substituted 1,4-dihydrophosphinin-1-yl group; alternatively, a 1,2,3,4-tetrahydrophosphinin-1-yl group or a substituted 1,2,3,4-tetrahydrophosphinin-1-yl group; alternatively, a 1,2,3,6-tetrahydrophosphinin-1-yl group or a substituted 1,2,3,6-tetrahydrophosphinin-1-yl group; or alternatively, a phosphinan-1-yl group or a substituted phosphinan-1-yl group. In some embodiments when $R^4$ and $R^5$ are joined to form a cyclic group including the phosphorus atom of the $N^2$-phosphinyl guanidine group, the phosphinyl group can be a phosphol-1-yl group, a 2,3-dihydrophosphol-1-yl group, a 3,5-dihydrophosphol-1-yl group, a phospholan-1-yl group, a 1,2-dihydrophosphinin-1-yl group, a 1,4-dihydrophosphinin-1-yl group, a 1,2,3,4-tetrahydrophosphinin-1-yl group, a 1,2,3,6-tetrahydrophosphinin-1-yl group, or a phosphinan-1-yl group. In other embodiments when $R^4$ and $R^5$ are joined to form a cyclic group including the phosphorus atom of the $N^2$-phosphinylguanidine group, the phosphinyl group can be a substituted phosphol-1-yl group, a substituted 2,3-dihydrophosphol-1-yl group, a substituted 3,5-dihydrophosphol-1-yl group, a substituted phospholan-1-yl group, a substituted, 1,2-dihydrophosphinin-1-yl group, a substituted 1,4-dihydrophosphinin-1-yl group, a substituted 1,2,3,4-tetrahydrophosphinin-1-yl group, a substituted 1,2,3,6-tetrahydrophosphinin-1-yl group, or a substituted phosphinan-1-yl group. In yet other embodiments when $R^4$ and $R^5$ are joined to form a cyclic group including the phosphorus atom of the $N^2$-phosphinyl guanidine group, a phospholan-1-yl group, a substituted phospholan-1-yl group, a phosphinan-1-yl group, or a substituted phosphinan-1-yl group; alternatively, a phospholan-1-yl group or a phosphinan-1-yl group; or alternatively, a substituted phospholan-1-yl group or a substituted phosphinan-1-yl group. In further embodiments when $R^4$ and $R^5$ are joined to form a cyclic group including the phosphorus atom of the $N^2$-phosphinyl guanidine group, the phosphinyl group can be a phosphol-1-yl group; alternatively, a substituted phosphol-1-yl group; alternatively, a 2,3-dihydro-phosphol-1-yl group; alternatively, a substituted 2,3-dihydrophosphol-1-yl group; alternatively, a 3,5-dihydrophosphol-1-yl group; alternatively, a substituted 3,5-dihydrophosphol-1-yl group; alternatively, a phospholan-1-yl group; alternatively, a substituted phospholan-1-yl group; alternatively, a 1,2-dihydrophosphinin-1-yl group; alternatively, a substituted, 1,2-dihydrophosphinin-1-yl group; alternatively, a 1,4-dihydrophosphinin-1-yl group; alternatively, a substituted 1,4-dihydrophosphinin-1-yl group; alternatively, a 1,2,3,4-tetrahydrophosphinin-1-yl group; alternatively, a substituted 1,2,3,4-tetrahydrophosphinin-1-yl group; alternatively, a 1,2,3,6-tetrahydrophosphinin-1-yl group; alternatively, a substituted 1,2,3,6-tetrahydrophosphinin-1-yl group; alternatively, a phosphinan-1-yl group; or alternatively, a substituted phosphinan-1-yl group. Substituents (general and specific) are independently disclosed herein and can be utilized without limitation to further describe substituted groups where $R^4$ and $R^5$ are joined to form a cyclic group including the phosphorus atom.

In an embodiment when $R^4$ and $R^5$ are joined to form a cyclic group including the phosphorus atom of the $N^2$-phosphinyl guanidine group, the cyclic group including the phosphorus atom can comprise at least one substituent on a carbon atom adjacent to the phosphorus atom attached to the $N^2$ nitrogen atom of the $N^2$-phosphinyl guanidine group. In some embodiments when $R^4$ and $R^5$ are joined to form a cyclic group including the phosphorus atom of the $N^2$-phosphinyl guanidine group, the cyclic group including the phosphorus atom can comprise at least one substituent on each carbon atom adjacent to the phosphorus atom attached to the $N^2$ nitrogen atom of the $N^2$-phosphinyl guanidine group. In other embodiments when $R^4$ and $R^5$ are joined to form a cyclic group including the phosphorus atom of the $N^2$-phosphinyl guanidine group, the cyclic group including the phosphorus atom can comprise, or consist of, only one substituent on a carbon atom adjacent to the phosphorus atom attached to the $N^2$ nitrogen atom of the $N^2$-phosphinyl guanidine group. In yet other embodiments when $R^4$ and $R^5$ are joined to form a cyclic group including the phosphorus atom of the $N^2$-phosphinyl guanidine group, the cyclic group including the phosphorus atom can comprise, or consist of, only one substituent on each carbon atom adjacent to the phosphorus atom attached to the $N^2$ nitrogen atom of the $N^2$-phosphinyl guanidine group.

In an embodiment, $R^4$ and $R^5$ independently can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group, or a 2,4,6-trialkylphenyl group; alternatively, a 2,4-dialkylphenyl group or a 2,6-dialkylphenyl group; alternatively, a 2,6-dialkylphenyl group, or a 2,4,6-trialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 3-alkylphenyl group; alternatively, a 4-alkylphenyl group; alternatively, a 2,4-dialkylphenyl group; alternatively, a 2,6-dialkylphenyl group; alternatively, a 3,5-dialkylphenyl group; or alternatively, a 2,4,6-trialkylphenyl group. In another non-limiting embodiment, $R^4$ and $R^5$ independently can be a napht-1-yl group, a 2-naphth-2-yl group, a 2-alkylnaphth-1-yl group, a 1-alkylnaphth-2-yl group, a 3-alkylnapth-2-yl group, or a 1,3-dialkylnaphth-2-yl group; alternatively, a napht-1-yl group or a 2-alkylnaphth-1-yl group; alternatively, a naphth-2-yl group, a 1-alkylnaphth-2-yl group, a 3-alkylnapth-2-yl group, or a 1,3-dialkylnaphth-2-yl group; alternatively, a napht-1-yl group; alternatively, a 2-naphth-2-yl group; alternatively, a 2-alkylnaphth-1-yl group; alternatively, a 1-alkylnaphth-2-yl group; alternatively, a 3-alkylnapth-2-yl group; or alternatively, a 1,3-dialkylnaphth-2-yl group. In other non-limiting embodiments, $R^4$ and $R^5$ independently can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, cyclopentyl group; alternatively, a 2-alkyl-cyclopentyl group; or alternatively, a 2,5-dialkylcyclopentyl group. Alkyl group substituents (general and specific) are independently described herein and can be utilized, without limitation, to further describe the alkylphenyl, dialkylphenyl, trialkylphenyl, naphthyl, dialkylnaphthyl, alkylcyclohexyl, dialkylcyclohexyl, alkylcyclopentyl, or dialkylcyclopentyl groups that can be utilized as $R^4$ and/or $R^5$. Generally, the alkyl substituents of a dialkyl or trialkyl phenyl, naphthyl, cyclohexyl, or cyclopentyl group can be the same; or alternatively the alkyl substituents of a dialkyl or trialkyl phenyl, naphthyl, cyclohexyl, or cyclopentyl group can be different.

In another non-limiting embodiment, $R^4$ and $R^5$ independently can be a phenyl group, a 2-alkoxyphenyl group, a 3-alkoxyphenyl group, a 4-alkoxyphenyl group, or 3,5-dialkoxyphenyl group; alternatively, a 2-alkoxyphenyl group or a 4-alkoxyphenyl group; alternatively, a 3-alkoxyphenyl group or 3,5-dialkoxyphenyl group; alternatively, a 2-alkoxyphenyl group; alternatively, a 3-alkoxyphenyl group; alternatively, a 4-alkoxyphenyl group; alternatively, a 3,5-dialkoxyphenyl group. Alkoxy group substituents (general and specific) are independently described herein and can be utilized, without limitation, to further describe the alkoxyphenyl or dialkoxyphenyl groups that can be utilized as $R^4$ and/or $R^5$. Generally, the alkoxy substituents of a dialkoxyphenyl groups can be the same; or alternatively the alkoxy substituents of a dialkoxyphenyl group can be different.

In other non-limiting embodiments, $R^4$ and $R^5$ independently can be a phenyl group, a 2-halophenyl group, a 3-halophenyl group, a 4-halophenyl group, a 2,6-dihalophenylgroup, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group; alternatively, a 2,6-dihalophenylgroup; or alternatively, a 3,5-dihalophenyl group. Halides are independently described herein and can be utilized, without limitation, to further describe the halophenyl or dihalophenyl groups that can be utilized as $R^4$ and/or $R^5$. Generally, the halides of a dihalophenyl group can be the same; or alternatively the halides of a dihalophenyl group can be different.

In a non-limiting embodiment, $R^4$ and $R^5$ independently can be a 2-methylphenyl group, a 2-ethylphenyl group, a 2-isopropylphenyl group, a 2-tert-butylphenyl group, a 3-methylphenyl group, a 2,6-dimethylphenyl group, a 2,6-diethylphenyl group, a 2,6-diisopropylphenyl group, a 2,6-di-tert-butyl-phenyl group, a 3,5-dimethyl group, or a 2,4,6-trimethylphenyl group; alternatively, a 2-methylphenyl group, a 2-ethylphenyl group, a 2-isopropylphenyl group, or a 2-tert-butylphenyl group; alternatively, a 2,6-dimethylphenyl group, a 2,6-diethylphenyl group, a 2,6-diisopropylphenyl group, or a 2,6-di-tert-butylphenyl group; alternatively, 2-methylphenyl group; alternatively, a 2-ethylphenyl group; alternatively, a 2-isopropylphenyl group; alternatively, a 2-tert-butylphenyl group; alternatively, a 3-methylphenyl group; alternatively, a 2,6-dimethylphenyl group; alternatively, a 2,6-diethylphenyl group; alternatively, a 2,6-diisopropylphenyl group; alternatively, a 2,6-di-tert-butylphenyl group; alternatively, a 3,5-dimethyl group; or alternatively, a 2,4,6-trimethylphenyl group. In another non-limiting embodiment, $R^4$ and $R^5$ independently can be cyclohexyl group, a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group, a 2-ethylcyclohexyl group, a 2-isopropylcyclohexyl group, or a 2-tert-butylcyclohexyl group; alternatively, a 2,6-dimethylcyclohexyl group, a 2,6-diethylcyclohexyl group, a 2,6-diisopropylcyclohexyl group, or a 2,6-di-tert-butylcyclohexyl group; alternatively, a cyclohexyl group; alternatively, a 2-methylcyclohexyl group; alternatively, a 2-ethylcyclohexyl group; alternatively, a 2-isopropylcyclohexyl group; alternatively, a 2-tert-butylcyclohexyl group; alternatively, a 2,6-dimethylcyclohexyl group; alternatively, a 2,6-diethylcyclohexyl group; alternatively, a 2,6-diisopropylcyclohexyl group; or alternatively, a 2,6-di-tert-butylcyclohexyl group. In another non-limiting embodiment, $R^4$ and/or $R^5$ independently can be a 2-methylnaphth-1-yl group, a 2-ethylnaphth-1-yl group, a 2-n-propylnaphth-1-yl group, a 2-isopropylnaphth-1-yl group, or a 2-tert-butylnaphth-1-yl group; alternatively, a 2-methylnaphth-1-yl group; alternatively, a 2-ethylnaphth-1-yl group; alternatively, a 2-n-propylnaphth-1-yl group; alternatively, a 2-isopropylnaphth-1-yl group; or alternatively, a 2-tert-butylnaphth-1-yl group.

In a non-limiting embodiment, $R^4$ and $R^5$ independently can be a 2-methoxyphenyl group, a 2-ethoxyphenyl group, a 2-isopropoxyphenyl group, a 2-tert-butoxyphenyl group, a 3-methoxyphenyl group, a 3-ethoxyphenyl group, a 3-isopropoxyphenyl group, a 3-tert-butoxyphenyl group, a 4-methoxyphenyl group, a 4-ethoxyphenyl group, a 4-isopropoxyphenyl group, a 4-tert-butoxyphenyl group, a 2,4-dimethoxyphenyl group, a 2,4-diethoxyphenyl group, a 2,4-diisopropoxyphenyl group, a 2,4-di-tert-butoxyphenyl group, a 3,5-dimethoxyphenyl group, a 3,5-diethoxyphenyl group, a 3,5-diisopropoxyphenyl group, a 3,5-di-tert-butoxyphenyl group, a 2,6-dimethoxyphenyl group, a 2,6-diethoxyphenyl group, a 2,6-diisopropoxyphenyl group, a 2,6-di-tert-butoxyphenyl group, or a 2,4,6-trimethoxyphenyl group; alternatively, a 2-methoxyphenyl group, a 2-ethoxyphenyl group, a 2-isopropoxyphenyl group, or a 2-tert-butoxyphenyl group; alternatively, a 3-methoxyphenyl group, a 3-ethoxyphenyl group, a 3-isopropoxyphenyl group, or a 3-tert-butoxyphenyl group; alternatively, a 4-methoxyphenyl group, a 4-ethoxyphenyl group, a 4-isopropoxyphenyl group, or a 4-tert-butoxyphenyl group; alternatively, a 2,4-dimethoxyphenyl group, a 2,4-diethoxyphenyl group, a 2,4-diisopropoxyphenyl group, or a 2,4-di-tert-butoxyphenyl group; alternatively, a 3,5-dimethoxyphenyl group, a 3,5-diethoxyphenyl group, a 3,5-diisopropoxyphenyl group, or a 3,5-di-tert-butoxyphenyl group; or alternatively, a 2,6-dimethoxyphenyl group, a 2,6-diethoxyphenyl group, a 2,6-diisopropoxyphenyl group, or a 2,6-di-tert-butoxyphenyl group. In other non-limiting embodiments, $R^4$ and $R^5$ independently can be a 2-methoxyphenyl group; alternatively, a 2-ethoxyphenyl group; alternatively, a 2-isopropoxyphenyl group; alternatively, a 2-tert-butoxyphenyl group; alternatively, a 3-methoxyphenyl group; alternatively, a 3-ethoxyphenyl group; alternatively, a 3-isopropoxyphenyl group; alternatively, a 3-tert-butoxyphenyl group; alternatively, a 4-methoxyphenyl group; alternatively, a 4-ethoxyphenyl group; alternatively, a 4-isopropoxyphenyl group; alternatively, a 4-tert-butoxyphenyl group; alternatively, a 2,4-dimethoxyphenyl group; alternatively, a 2,4-diethoxyphenyl group; alternatively, a 2,4-diisopropoxyphenyl group; alternatively, a 2,4-di-tert-butoxyphenyl group; alternatively; alternatively, a 3,5-dimethoxyphenyl group; alternatively, a 3,5-diethoxyphenyl group; alternatively, a 3,5-diisopropoxyphenyl group; alternatively, a 3,5-di-tert-butoxyphenyl group; alternatively, a 2,6-dimethoxyphenyl group; alternatively, a 2,6-diethoxyphenyl group; alternatively, a 2,6-diisopropoxyphenyl group; alternatively, a 2,6-di-tert-butoxyphenyl group; or alternatively, a 2,4,6-trimethoxyphenyl group. In another non-limiting embodiment, $R^4$ and/or $R^5$ independently can be a 2-fluorophenyl group, a 2-chlorophenyl group, a 3-fluorophenyl group, a 3-chlorophenyl group, a 4-fluorophenyl group, a 4-chlorophenyl group, a 3,5-difluorophenyl group, or a 3,5-dichlorophenyl group; alternatively, a 2-fluorophenyl group or a 2-chlorophenyl group; alternatively, a 3-fluorophenyl group or a 3-chloro-phenyl group; alternatively, a 4-fluorophenyl group or a 4-chlorophenyl group; alternatively, a 3,5-difluorophenyl group or a 3,5-dichlorophenyl group; alternatively, a 3-fluorophenyl group, a 3-chlorophenyl group, a 3,5-difluorophenyl group or a 3,5-dichlorophenyl group; or alternatively, a 3-fluorophenyl group or a 3,5-difluorophenyl group. In another non-limiting embodiments, $R^4$ and/or $R^5$ independently can be a 2-fluorophenyl group; alternatively, a 2-chlorophenyl group; alternatively, a 3-fluorophenyl group; alternatively, a 3-chlorophenyl group; alternatively, a 4-fluorophenyl group; alternatively, a 4-chlorophenyl; alternatively, a 3,5-difluorophenyl group; or alternatively, a 3,5-dichlorophenyl group. Generally, the $R^4$ and/or $R^5$ groups of the phosphinyl group independently can be any $R^4$ or $R^5$ group described herein and utilized in any combination to further describe the phosphinyl group of any $N^2$-phosphinyl guanidine compound described herein. In an embodiment, $R^4$ and $R^5$ can be the same. In other embodiments, $R^4$ and $R^5$ can be different.

Phosphinyl Group

In an aspect, the phosphinyl group of the $N^2$-phosphinyl guanidine compound can be a diphenylphosphinyl group, a dialkylphosphinyl group, a bis(mono-halo substituted phenyl)phosphinyl group, a bis(mono-alkyl substituted phenyl) phosphinyl group, or a bis(mono-alkoxy substituted phenyl) phosphinyl group; alternatively, a diphenylphosphinyl group; alternatively, a dialkylphosphinyl group; alternatively, a bis(mono-halo substituted phenyl)phosphinyl group; alternatively, a bis(mono-alkyl substituted phenyl)phosphinyl group; alternatively, a bis(mono-alkoxy substituted phenyl) phosphinyl group. In another aspect, the phosphinyl group of the $N^2$-phosphinyl guanidine compound can be an (alkyl)(phenyl)phosphinyl group, a (mono-halo substituted phenyl)(phenyl)phosphinyl group, a (mono-alkyl substituted phenyl)(phenyl)phosphinyl group, a (mono-alkoxy substituted phenyl)(phenyl)phosphinyl group, a (mono-alkyl substituted phenyl)(mono-halo substituted phenyl) phosphinyl group, or a (mono-alkyl substituted phenyl)(mono-alkoxy substituted phenyl) phosphinyl group; alternatively, an (alkyl)(phenyl) phosphinyl group; alternatively, a (mono-halo substituted phenyl)(phenyl)phosphinyl group; alternatively, a (mono-alkyl substituted phenyl)(phenyl)phosphinyl group; alternatively, a (mono-alkoxy substituted phenyl)(phenyl)phosphinyl group; alternatively, a (mono-alkyl substituted phenyl)(mono-halo substituted phenyl) phosphinyl group; or alternatively, a (mono-alkyl substituted phenyl)(mono-alkoxy substituted phenyl) phosphinyl group. In another aspect, the phosphinyl group of the $N^2$-phosphinyl guanidine compound can be a bis(dihalo substituted phenyl)phosphinyl group, a bis(dialkyl substituted phenyl)phosphinyl group, a bis(dialkoxy substituted phenyl)phosphinyl group, a bis(trialkylphenyl)phosphinyl group, or a bis(trialkoxyphenyl) phosphinyl group; alternatively, bis(dihalo substituted phenyl)phosphinyl group; alternatively, a bis(dialkyl substituted phenyl)phosphinyl group; alternatively, a bis(dialkoxy substituted phenyl)phosphinyl group; alternatively, a bis(trialkylphenyl)phosphinyl group; or alternatively, a bis(trialkoxyphenyl)phosphinyl group. Halogens, alkyl group substituents (general and specific), and alkoxy group substituents (general and specific) are independently described herein (e.g., as substituents for substituted $R^1$ groups) and can be utilized, without limitation to further describe the phosphinyl group which can be utilized in the $N^2$-phosphinyl guanidine compound.

In a non-limiting aspect, the phosphinyl group of the $N^2$-phosphinyl guanidine compound can be a dimethylphosphinyl group, a diethylphosphinyl group, a diisopropylphosphinyl group, a di-tert-butylphosphinyl group, or a di-neopentylphosphinyl group. In a non-limiting embodiment, the phosphinyl group of the $N^2$-phosphinyl guanidine compound can be a dimethylphosphinyl group; alternatively, a diethyl phosphinyl group; alternatively, a diisopropylphosphinyl group; alternatively, a di-tert-butylphosphinyl group; or alternatively, a di-neo-pentylphosphinyl group. In a non-limiting aspect, the phosphinyl group of the $N^2$-phosphinyl guanidine compound can be a (methyl)(phenyl)phosphinyl group, a (ethyl)(phenyl)phosphinyl group, a (isopropyl)(phenyl)phosphinyl group, a (tert-butyl)(phenyl)phosphinyl group, or a (neo-pentyl)(phenyl)phosphinyl group. In an embodiment, the phosphinyl group of the $N^2$-phosphinyl guanidine compound can be a (methyl)(phenyl)phosphinyl group; alternatively, a (ethyl)(phenyl) phosphinyl group; alternatively, a (isopropyl)(phenyl)phosphinyl group; alternatively, a (tert-butyl)(phenyl)phosphinyl group; or alternatively, a (neo-pentyl)(phenyl)phosphinyl group. In some non-limiting embodiments, the phosphinyl group of the $N^2$-phosphinyl guanidine compound can be a dicyclopentyl phosphinyl group, a dicyclohexyl phosphinyl group; alternatively, a dicyclopentylphosphinyl group; or alternatively, a dicyclohexylphosphinyl group.

In yet another non non-limiting aspect, the phosphinyl group of the $N^2$-phosphinyl guanidine compound can be a bis(2-fluorophenyl)phosphinyl group, a bis(2-chlorophenyl) phosphinyl group, a bis(3-fluorophenyl)phosphinyl group, a bis(3-chlorophenyl)phosphinyl group, a bis(4-fluorophenyl) phosphinyl group, or a bis(4-chlorophenyl)phosphinyl group. In some non-limiting embodiments, the phosphinyl group of the $N^2$-phosphinyl guanidine compound can be a bis(2-fluorophenyl)phosphinyl group, a bis(3-fluorophenyl)phosphinyl group, or a bis(4-fluorophenyl)phosphinyl group; or alternatively, a bis(2-chlorophenyl)phosphinyl group, a bis(3-chlorophenyl)phosphinyl group, or a bis(4-chlorophenyl)phosphinyl group. In other non-limiting embodiments, the phosphinyl group of the $N^2$-phosphinyl guanidine compound can be a bis(2-fluorophenyl)phosphinyl group; alternatively, a bis(2-chlorophenyl)phosphinyl group; alternatively, a bis(3-fluorophenyl)phosphinyl group; alternatively, a bis(3-chloro-phenyl)phosphinyl group; alternatively, a bis(4-fluorophenyl)phosphinyl group; or alternatively, a bis(4-chlorophenyl)phosphinyl group.

In yet another non non-limiting aspect, the phosphinyl group of the $N^2$-phosphinyl guanidine compound can be a (2-fluorophenyl)(phenyl)phosphinyl group, a (2-chlorophenyl)(phenyl)phosphinyl group, a (3-fluorophenyl)(phenyl) phosphinyl group, a (3-chlorophenyl)(phenyl)phosphinyl group, a (4-fluorophenyl)(phenyl)phosphinyl group, or a (4-chlorophenyl)(phenyl)phosphinyl group. In some non-limiting embodiments, the phosphinyl group of the $N^2$-phosphinyl guanidine compound can be a (2-fluorophenyl)(phenyl)phosphinyl group, a (3-fluorophenyl)(phenyl)phosphinyl group, or a (4-fluoro-phenyl)(phenyl)phosphinyl group; or alternatively, a (2-chlorophenyl)(phenyl)phosphinyl group, a (3-chlorophenyl)(phenyl)phosphinyl group, or a (4-chlorophenyl)(phenyl)phosphinyl group. In other non-limiting embodiments, the phosphinyl group of the $N^2$-phosphinyl guanidine compound can be a (2-fluorophenyl)(phenyl)phosphinyl group; alternatively, a (2-chlorophenyl)(phenyl)phosphinyl group; alternatively, a (3-fluorophenyl)(phenyl)phosphinyl group; alternatively, a (3-chlorophenyl)(phenyl) phosphinyl group; alternatively, a (4-fluorophenyl)(phenyl) phosphinyl group; or alternatively, a (4-chlorophenyl) (phenyl)phosphinyl group.

In yet another non non-limiting aspect, the phosphinyl group of the $N^2$-phosphinyl guanidine compound can be a diphenylphosphinyl group, a bis(2-methylphenyl)phosphinyl group, a bis(2-ethyl-phenyl)phosphinyl group, a bis(2-isopropylphenyl)phosphinyl group, a bis(2-tert-butylphenyl)phosphinyl group, a bis(3-methylphenyl)phosphinyl group, a bis(3-ethylphenyl)phosphinyl group, bis(3-isopropyl-phenyl)phosphinyl group, a bis(3-tert-butylphenyl)phosphinyl group, a diphenylphosphinyl group, a bis(4-methylphenyl)phosphinyl group, a bis(4-ethylphenyl)phosphinyl group, a bis(4-isopropylphenyl)phosphinyl group, or a bis(4-tert-butylphenyl)phosphinyl group. In a non-limiting embodiment, the phosphinyl group of the $N^2$-phosphinyl guanidine compound can be a bis(2-methylphenyl)phosphinyl group, a bis(2-ethylphenyl)phosphinyl group, a bis(2-isopropylphenyl)phosphinyl group, or a bis(2-tert-butylphenyl)phosphinyl group; alternatively, a diphenylphosphinyl group, a bis(3-methylhenyl)phosphinyl group, a bis(3-ethylphenyl)phosphinyl group, a bis(3-isopropylphenyl)phosphinyl group, or a bis(3-tert-butylphenyl)phosphinyl group; or alternatively, a diphenylphosphinyl group, a bis(4-methylphenyl)phosphinyl group, a bis(4-ethylphenyl)phosphinyl group, a bis(4-isopropylphenyl)phosphinyl group, or a bis(4-tert-butylphenyl)phosphinyl group. In other non-limiting embodiments, the phosphinyl group of the $N^2$-phosphinyl guanidine compound can be a diphenylphosphinyl group; alternatively, a bis(2-methylphenyl)phosphinyl group; alternatively, a bis(2-ethylphenyl)phosphinyl group; alternatively, a bis(2-isopropylphenyl)phosphinyl group; alternatively, a bis(2-tert-butylphenyl)phosphinyl group; alternatively, a bis(3-methylphenyl)phosphinyl group; alternatively, a bis(3-ethylphenyl)phosphinyl group; alternatively, a bis(3-isopropylphenyl)phosphinyl group; alternatively, a bis(3-tert-butylphenyl)phosphinyl group; alternatively, a diphenylphosphinyl group; alternatively, a bis(4-methylphenyl)phosphinyl group; alternatively, a bis(4-ethylphenyl)phosphinyl group; alternatively, a bis(4-isopropylphenyl)phosphinyl group; or alternatively, a bis(4-tert-butylphenyl)phosphinyl group.

In yet another non non-limiting aspect, the phosphinyl group of the $N^2$-phosphinyl guanidine compound can be a diphenylphosphinyl group, a (2-methylphenyl)(phenyl)phosphinyl group, a (2-ethyl-phenyl)(phenyl)phosphinyl group, a (2-isopropylphenyl)(phenyl)phosphinyl group, a (2-tert-butyl-phenyl)(phenyl)phosphinyl group, a (3-methylphenyl)(phenyl)phosphinyl group, a (3-ethylphenyl)(phenyl)phosphinyl group, a (3-isopropylphenyl)(phenyl)phosphinyl group, a (3-tert-butylphenyl)(phenyl)phosphinyl group, a diphenylphosphinyl group, a (4-methylphenyl)(phenyl)phosphinyl group, a (4-ethylphenyl)(phenyl)phosphinyl group, a (4-isopropylphenyl)(phenyl)phosphinyl group, or a (4-tert-butylphenyl)(phenyl)phosphinyl group. In a non-limiting embodiment, the phosphinyl group of the $N^2$-phosphinyl guanidine compound can be a (2-methylphenyl)(phenyl)phosphinyl group, a (2-ethyl-phenyl)(phenyl)phosphinyl group, a (2-isopropylphenyl)(phenyl)phosphinyl group, or a (2-tert-butyl-phenyl)(phenyl)phosphinyl group; alternatively, a diphenylphosphinyl group, a (3-methylphenyl)(phenyl)phosphinyl group, a (3-ethylphenyl)(phenyl)phosphinyl group, a (3-isopropylphenyl)(phenyl)phosphinyl group, or a (3-tert-butylphenyl)(phenyl)phosphinyl group; or alternatively, a diphenyl-phosphinyl group, a (4-methylphenyl)(phenyl)phosphinyl group, a (4-ethylphenyl)(phenyl)phosphinyl group, a (4-isopropylphenyl)(phenyl)phosphinyl group, or a (4-tert-butylphenyl)(phenyl)phosphinyl group. In other non-limiting embodiments, the phosphinyl group of the $N^2$-phosphinyl guanidine compound can be a diphenylphosphinyl group; alternatively, a (2-methylphenyl)(phenyl)phosphinyl group; alternatively, a (2-ethylphenyl)(phenyl)phosphinyl group; alternatively, a (2-isopropylphenyl)(phenyl)phosphinyl group; alternatively, a (2-tert-butylphenyl)(phenyl)phosphinyl group; alternatively, a (3-methylphenyl)(phenyl)phosphinyl group; alternatively, a (3-ethylphenyl)(phenyl) phosphinyl group; alternatively, a (3-isopropylphenyl)(phenyl)phosphinyl group; alternatively, a (3-tert-butylphenyl)(phenyl)phosphinyl group; alternatively, a diphenylphosphinyl group; alternatively, a (4-methylphenyl)(phenyl)phosphinyl group; alternatively, a (4-ethylphenyl)(phenyl)phosphinyl group; alternatively, a (4-isopropylphenyl)(phenyl)phosphinyl group; or alternatively, a (4-tert-butylphenyl)(phenyl)phosphinyl group.

In yet another non non-limiting aspect, the phosphinyl group of the $N^2$-phosphinyl guanidine compound can be a diphenylphosphinyl group, a bis(2-methoxyphenyl)phosphinyl group, a bis(2-ethoxyphenyl)phosphinyl group, a bis(2-isopropoxyphenyl)phosphinyl group, a bis(2-tert-butoxyphenyl)phosphinyl group, a bis(3-methoxyphenyl)phosphinyl group, a bis(3-ethoxyphenyl)phosphinyl group, a bis(3-isopropoxyphenyl)phosphinyl group, a bis(3-tert-butoxyphenyl)phosphinyl group, a diphenoxyphosphinyl group, a bis(4-methoxyphenyl)phosphinyl group, a bis(4-ethoxyphenyl)phosphinyl group, bis(4-isopropoxyphenyl)phosphinyl group, or a bis(4-tert-butoxyphenyl)phosphinyl group. In a non-limiting embodiment, the phosphinyl group of the $N^2$-phosphinyl guanidine compound can be a bis(2-methoxyphenyl)phosphinyl group, a bis(2-ethoxyphenyl)phosphinyl group, a bis(2-isopropoxyphenyl)phosphinyl group, or a bis(2-tert-butoxyphenyl)phosphinyl group; alternatively, a diphenoxyphosphinyl group, a bis(3-methoxyphenyl)phosphinyl group, a bis(3-ethoxyphenyl)phosphinyl group, a bis(3-isopropoxyphenyl)phosphinyl group, or a bis(3-tert-butoxyphenyl)phosphinyl group; or alternatively, a diphenoxyphosphinyl group, a bis(4-methoxyphenyl)phosphinyl group, a bis(4-ethoxyphenyl)phosphinyl group, a bis(4-isopropoxyphenyl)phosphinyl group, or a bis(4-tert-butoxyphenyl)phosphinyl group. In other non-limiting embodiments, the phosphinyl group of the $N^2$-phosphinyl guanidine compound can be a diphenylphosphinyl group; alternatively, a bis(2-methoxyphenyl)phosphinyl group; alternatively, a bis(2-ethoxyphenyl)phosphinyl group; alternatively, a bis(2-isopropoxyphenyl)phosphinyl group; alternatively, a bis(2-tert-butoxyphenyl)phosphinyl group; alternatively, a bis(3-methoxyphenyl)phosphinyl group; alternatively, a bis(3-ethoxyphenyl)phosphinyl group; alternatively, a bis(3-isopropoxyphenyl)phosphinyl group; alternatively, a bis(3-tert-butoxyphenyl)phosphinyl group; alternatively, a diphenoxyphosphinyl group; alternatively, a bis(4-methoxyphenyl)phosphinyl group; alternatively, a bis(4-ethoxyphenyl)phosphinyl group; alternatively, a bis(4-isopropoxyphenyl)phosphinyl group; or alternatively, a bis (4-tert-butoxyphenyl)phosphinyl group.

In yet another non non-limiting aspect, the phosphinyl group of the $N^2$-phosphinyl guanidine compound can be a diphenylphosphinyl group, a (2-methoxyphenyl)(phenyl)phosphinyl group, a (2-ethoxyphenyl)(phenyl)phosphinyl group, a (2-isopropoxyphenyl)(phenyl)phosphinyl group, a (2-tert-butoxyphenyl)(phenyl)phosphinyl group, a (3-methoxyphenyl)(phenyl)phosphinyl group, a (3-ethoxyphenyl)(phenyl)phosphinyl group, a (3-isopropoxyphenyl)(phenyl)phosphinyl group, a (3-tert-butoxyphenyl)(phenyl)phosphinyl group, a diphenoxyphosphinyl group, a (4-methoxyphenyl)(phenyl)phosphinyl group, a (4-ethoxyphenyl)(phenyl)phosphinyl group, a (4-isopropoxyphenyl)(phenyl)phosphinyl group, or a (4-tert-butoxyphenyl)(phenyl)phosphinyl group. In a non-limiting embodiment, the phosphinyl group of the $N^2$-phosphinyl guanidine compound can be a (2-methoxyphenyl)(phenyl)phosphinyl group, a (2-ethoxyphenyl)(phenyl)phosphinyl group, a (2-isopropoxyphenyl)(phenyl)phosphinyl group, or a (2-tert-butoxyphenyl)(phenyl)phosphinyl group; alternatively, a diphenoxyphosphinyl group, a (3-methoxyphenyl)(phenyl) phosphinyl group, a (3-ethoxyphenyl)(phenyl)phosphinyl group, a (3-isopropoxyphenyl)(phenyl)phosphinyl group, or a (3-tert-butoxyphenyl)(phenyl)phosphinyl group; or alternatively, a diphenoxyphosphinyl group, a (4-methoxyphenyl)(phenyl)phosphinyl group, a (4-ethoxyphenyl)(phenyl)phosphinyl group, a (4-isopropoxyphenyl)(phenyl)phosphinyl group, or a (4-tert-butoxyphenyl)(phenyl)phosphinyl group. In other non-limiting embodiments, the phosphinyl group of the $N^2$-phosphinyl guanidine compound can be a diphenylphosphinyl group; alternatively, a (2-methoxyphenyl)(phenyl)phosphinyl group; alternatively, a (2-ethoxyphenyl)(phenyl)phosphinyl group; alternatively, a (2-isopropoxyphenyl)(phenyl)phosphinyl group; alternatively, a (2-tert-butoxyphenyl)(phenyl)phosphinyl group; alternatively, a (3-methoxyphenyl)(phenyl)phosphinyl group; alternatively, a (3-ethoxyphenyl)(phenyl)phosphinyl group; alternatively, a (3-isopropoxyphenyl)(phenyl)phosphinyl group; alternatively, a (3-tert-butoxyphenyl)(phenyl)phosphinyl group; alternatively, a diphenoxyphosphinyl group; alternatively, a (4-methoxyphenyl)(phenyl)phosphinyl group; alternatively, a (4-ethoxyphenyl)(phenyl)phosphinyl group; alternatively, a (4-isopropoxyphenyl)(phenyl)phosphinyl group; or alternatively, a (4-tert-butoxyphenyl)(phenyl)phosphinyl group.

In an aspect, embodiment, $R^1$ and $R^2$ can be joined to form a group, $L^{12}$, wherein $L^{12}$, the $N^1$ nitrogen atom, and the $N^3$ nitrogen atom can form a ring or a ring system. In another aspect, $R^{2b}$ and $R^3$ can be joined to form a group, $L^{23}$, wherein $L^{23}$, the $N^1$ nitrogen, and the $N^2$ nitrogen atom can from a ring or a ring system. In an embodiment, $L^{12}$ and/or $L^{23}$ can be an organylene group; alternatively, an organylene group consisting of inert functional groups; or alternatively, a hydrocarbylene group. The organylene group which can be utilized as $L^{12}$ and $L^{23}$ independently can be a $C_2$ to $C_{20}$ organylene group; alternatively, a $C_2$ to $C_{15}$ organylene group; alternatively, a $C_2$ to $C_{10}$ organylene group; or alternatively, a $C_2$ to $C_5$ organylene group. The organylene group consisting of inert functional groups which can be utilized as $L^{12}$ and $L^{23}$ independently can be a $C_2$ to $C_{20}$ organylene group consisting of inert functional groups; alternatively, a $C_2$ to $C_{15}$ organylene group consisting of inert functional groups; alternatively, a $C_2$ to $C_{10}$ organylene group consisting of inert functional groups; or alternatively, a $C_2$ to $C_5$ organylene group consisting of inert functional groups. The hydrocarbylene group which can be utilized as $L^{12}$ and $L^{23}$ independently can be a $C_2$ to $C_{20}$ hydrocarbylene group; alternatively, a $C_2$ to $C_{15}$ hydrocarbylene group; alternatively, a $C_2$ to $C_{10}$ hydrocarbylene group; or alternatively, a $C_2$ to $C_5$ hydrocarbylene group. In some embodiments wherein the $N^2$-phosphinyl guanidine compound includes $L^{12}$ and $L^{23}$, $L^{12}$ and $L^{23}$ can be the same. In other embodiments wherein the $N^2$-phosphinyl guanidine compound includes $L^{12}$ and $L^{23}$, $L^{12}$ and $L^{23}$ can be different.

In an embodiment, $L^{12}$ and/or $L^{23}$ can have any structure provided in Table 1. In embodiments, $L^{12}$ and/or $L^{23}$ can have Structure 1L, Structure 2L, Structure 3L, Structure 4L or Structure 5L. In some embodiments, $L^{12}$ and $L^{23}$ independently can have Structure 2L or Structure 3L; alternatively, Structure 4L or Structure 5L. In other embodiments, $L^{12}$ and $L^{23}$ independently can have Structure 1L; alternatively, Structure 2L; alternatively, Structure 3L; alternatively, Structure 4L; or alternatively, Structure 5L. In some embodiments, $L^{12}$ can have Structure 6L. It should be noted that when $L^{12}$ has Structure 6L the corresponding $R^{2b}$ is null because of the double bond link (depicted as real but can be through aromatic resonance) with the $N^3$ nitrogen atom of the $N^2$-phosphinyl guanidine group.

TABLE 1

Potential Structure for Linking Groups $L^{12}$ and/or $L^{23}$.

| | |
|---|---|
| —$(CR^{L1}R^{L2})_m$— | Structure 1L |
| —$CR^{L3}R^{L4}$—$CR^{L5}R^{L6}$— | Structure 2L |
| —$CR^{L3}R^{L4}$—$CR^{L7}R^{L8}$—$CR^{L5}R^{L6}$— | Structure 3L |
| —$CR^{11L}$=$CR^{12L}$— | Structure 4L |
| 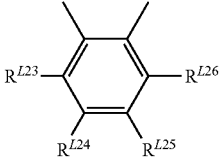 | Structure 5L |
| =$CR^{27}$—$CR^{28}$=$CR^{29}$— | Structure 6L |

Within the structures of Table 1, the undesignated valencies represent the points at which $L^{12}$ and/or $L^{23}$, when present, attach to the respective nitrogen atoms of the $N^2$-phosphinyl guanidine group. Generally, m can be an integer ranging from 2 to 5. In further embodiments, m can be 2 or 3; alternatively, m can be 2; or alternatively, m can be 3. $R^{L1}$ and $R^{L2}$ of the linking group having Structure 1L, $R^{L3}$, $R^{L4}$, $R^{L5}$, and $R^{L6}$ of the linking group having Structure 2L, $R^{L3}$, $R^{L4}$ $R^{L5}$, $R^{L6}$, $R^{L7}$, and $R^{L8}$, of the linking group having Structure 3L, $R^{L11}$ and $R^{L12}$ of the linking group having Structure 4L, $R^{L22}$, $R^{L23}$, $R^{L24}$, $R^{L25}$, and $R^{L26}$ of the linking group having Structure 5L, $R^{L27}$, $R^{L28}$, and $R^{L29}$ of the linking group having Structure 6L independently can be a hydrogen or a non-hydrogen substituent group (any general or specific described herein); or alternatively, hydrogen. Non-hydrogen substituent group (general and specific) are independently disclosed herein and can be utilized without limitation to further describe the linking group having Structure 1L, Structure 2L, Structure 3L, Structure 4L, and/or Structure 5L. In an embodiment, $L^{12}$ and $L^{23}$ independently can be an eth-1,2-ylene group (—$CH_2CH_2$—), an ethen-1,2-ylene group (—CH=CH—), a prop-1,3-ylene group (—$CH_2CH_2CH_2$—), a 1-methylethen-1,2-ylene group (—$C(CH_3)$=CH—), a but-1,3-ylene group (—$CH_2CH_2CH(CH_3)$—), a 3-methylbut-1,3-ylene group (—$CH_2CH_2C(CH_3)_2$—), or a phen-1,2-ylene group. In some non-limiting embodiments, $L^{12}$ and $L^{23}$ independently be an eth-1,2-ylene group (—$CH_2CH_2$—), a prop-1,3-ylene group (—$CH_2CH_2CH_2$—), a 1-methylethen-1,2-ylene group (—$C(CH_3)$=CH—), a but-1,3-ylene group (—$CH_2CH_2CH(CH_3)$—), or a 3-methylbut-1,3-ylene group (—$CH_2CH_2C(CH_3)_2$—); alternatively, an eth-1,2-ylene group (—$CH_2CH_2$—), an ethen-1,2-ylene group (—CH=CH—), a prop-1,3-ylene group (—$CH_2CH_2CH_2$—), or a phen-1,2-ylene group; alternatively, an eth-1,2-ylene group (—$CH_2CH_2$—) or a prop-1,3-ylene group (—$CH_2CH_2CH_2$—); alternatively, an ethen-1,2-ylene group (—CH=CH—) or a phen-1,2-ylene group. In other embodiments, $L^{12}$ and/or $L^{23}$ can be an eth-1,2-ylene group (—$CH_2CH_2$—); alternatively, an ethen-1,2-ylene group (—CH=CH—); alternatively, a prop-1,3-ylene group (—$CH_2CH_2CH_2$—); alternatively, a 1-methylethen-1,2-ylene group (—$C(CH_3)$=CH—); alternatively, a but-1,3-ylene group (—$CH_2CH_2CH(CH_3)$—); alternatively, a 3-methylbut-1,3-ylene group (—$CH_2CH_2C(CH_3)_2$—); or alternatively, a phen-1,2-ylene group. In some embodiments, $L^{12}$ can be a —CH=CH—CH= group. In an embodiment, $L^{12}$ can have a structure that can comprise at least one substituent located on the carbon atom attached to the $N^1$ nitrogen atom of the $N^2$-phosphinyl guanidine group; alternatively, can comprise only one substituent located on the carbon atom attached to the $N^1$ nitrogen atom of the $N^2$-phosphinyl guanidine group; or alternatively, can comprise two substituents located on the carbon atom attached to the $N^1$ nitrogen atom of the $N^2$-phosphinyl guanidine group. In another embodiment, $L^{12}$ can have a structure that can consist of one substituent located on the carbon atom attached to $N^1$ nitrogen atom of the $N^2$-phosphinyl guanidine group; or alternatively, can consist of two substituents located on the carbon atom attached to $N^1$ nitrogen atom of the $N^2$-phosphinyl guanidine group. In an embodiment, $L^{23}$ can have a structure that can comprise at least one substituent located on the carbon atom attached to the $N^2$ nitrogen atom of the $N^2$-phosphinyl guanidine group; alternatively, can comprise only one substituent located on the carbon atom attached to the $N^2$ nitrogen atom of the $N^2$-phosphinyl guanidine group; or alternatively, can comprise two substituents located on the carbon atom attached to the $N^2$ nitrogen atom of the $N^2$-phosphinyl guanidine group. In another embodiment, $L^{23}$ can have a structure that can consist of one substituent located on the carbon atom attached to $N^2$ nitrogen atom of the $N^2$-phosphinyl guanidine group; or alternatively, can consist of two substituents located on the carbon atom attached to $N^2$ nitrogen atom of the $N^2$-phosphinyl guanidine group.

In an embodiment, $R^{2a}$ and $R^{2b}$ can be joined to form a group, $L^{22}$, wherein $R^{2a}$, $R^{2b}$, and the $N^3$ nitrogen (or $L^{22}$ and the $N^3$ nitrogen) forms a ring or ring system. In an embodiment, $L^{22}$ can be an organylene group; alternatively, an organylene group consisting of inert functional groups; or alternatively, a hydrocarbylene group. The organylene group which can be utilized as $L^{22}$ can be a $C_3$ to $C_{20}$ organylene group; alternatively, a $C_3$ to $C_{15}$ organylene group; or alternatively, a $C_3$ to $C_{10}$ organylene group. The organylene group consisting of inert functional groups which can be utilized as $L^{22}$ can be a $C_3$ to $C_{20}$ organylene group consisting of inert functional groups; alternatively, a $C_3$ to $C_{15}$ organylene group consisting of inert functional groups; or alternatively, a $C_3$ to $C_{10}$ organylene group consisting of inert functional groups. The hydrocarbylene group which can be utilized as $L^{22}$ can be a $C_4$ to $C_{20}$ hydrocarbylene group; alternatively, a $C_4$ to $C_{15}$ hydrocarbylene group; or alternatively, a $C_4$ to $C_{10}$ hydrocarbylene group.

In an embodiment, $L^{22}$ can have any structure provided in Table 2. In some embodiments, $L^{22}$ can have Structure 11L, Structure 12L, Structure 13L, Structure 14L, or Structure 15L. In other embodiments, $L^{22}$ can have Structure 2L or Structure 3L; alternatively, Structure 4L or Structure 5L. In other embodiments, the linking group can have Structure 1L; alternatively, Structure 2L; alternatively, Structure 3L; alternatively, Structure 4L; or alternatively, Structure 5L.

Within the structures of Table 2, the undesignated valencies represent the points at which $L^{22}$, when present, attaches to the $N^3$ nitrogen atom of the $N^2$-phosphinyl guanidine group. Generally, n can be an integer ranging from 4 to 7. In further embodiments, n can be 4 or 5; alternatively, n can be 4; or alternatively, n can be 5. $R^{L31}$ and $R^{L32}$ of the linking group having Structure 11L, $R^{L41}$, $R^{L42}$, $R^{L43}$, $R^{L44}$, $R^{L45}$, $R^{L46}$, $R^{L47}$, and $R^{L48}$ of the linking group having Structure 12L, $R^{L41}$, $R^{L42}$, $R^{L43}$, $R^{L44}$, $R^{L45}$, $R^{L46}$, $R^{L47}$, $R^{L48}$, $R^{L49}$, and $R^{L50}$ of the linking group having Structure 13L, $R^{L41}$, $R^{L42}$, $R^{L43}$, $R^{L44}$, $R^{L45}$, $R^{L46}$, $R^{L47}$, and $R^{L48}$ of the linking group having Structure 14L, $R^{L41}$, $R^{L42}$, $R^{L43}$, $R^{L44}$, $R^{L45}$, $R^{L46}$, $R^{L47}$, and $R^{L48}$ of the linking group having Structure 15L, and $R^{L51}$, $R^{L52}$, $R^{L53}$, and $R^{L54}$ of the linking group having Structure 16L independently can be a hydrogen or a non-hydrogen substituent group (any general or specific described herein); alternatively, hydrogen. Non-hydrogen substituent groups (general and specific) are independently disclosed herein and can be utilized without limitation to further describe the linking group having Structure 11L, Structure 12L, Structure 13L, Structure 14L, Structure 15L, and/or Structure 16L. In an embodiment, $L^{22}$ can be a but-1,4-ylene group, a pent-1,4-ylene group, a pent-1,5-ylene group, a hex-2,5-ylene group, a hex-1,5-ylene group, a hept-2,5-ylene group, a buta-1,3-dien-1,4-ylene group, or a bis(eth-2-yl)ether group; alternatively, a but-1,4-ylene group, a pent-1,5-ylene group, or a bis(eth-2-yl)ether group; alternatively, a but-1,4-ylene group; alternatively, a pent-1,5-ylene group; alternatively, a buta-1,3-dien-1,4-ylene group; or alternatively, a bis(eth-2-yl)ether group.

In an embodiment, the $N^2$-phosphinyl guanidine compound comprising at least one $N^2$-phosphinyl guanidine group can have Structure Gu6, Gu7, Gu8, Gu9, Gu10, Gu11, Gu12, Gu13, Gu14, Gu15, Gu16, Gu17, Gu18, Gu19, Gu20, Gu21, Gu22, Gu23, Gu24, Gu25, or Gu26; alternatively, Structure Gu6, Gu7, Gu8, Gu9, Gu10, Gu11, Gu12, Gu13, Gu14, or Gu15; alternatively, Structure Gu11, Gu18, Gu21, Gu22, Gu23, Gu24, or Gu25; alternatively, Structure Gu19 or Gu20; alternatively, Structure Gu6; alternatively, Structure Gu7; alternatively, Structure Gu8; alternatively, Structure Gu9; alternatively, Structure Gu10; alternatively, Structure Gu11; alternatively, Structure Gu12; alternatively, Structure Gu13; alternatively, Structure Gu14; alternatively, Structure Gu15; alternatively, Structure Gu16; alternatively, Structure Gu11; alternatively, Structure Gu18; alternatively, Structure Gu19; alternatively, Structure Gu20; alternatively, Structure Gu21; alternatively, Structure Gu22; alternatively, Structure Gu23; alternatively, Structure Gu24; alternatively, Structure Gu25; or alternatively, Structure Gu26.

TABLE 2

Potential Structure for Linking Groups $L^{22}$.

| | |
|---|---|
| —$(CR^{L31}R^{L32})_n$— <br> Structure 11L | —$CR^{L41}R^{L42}$—$CR^{L45}R^{L46}CR^{L47}R^{L48}CR^{L43}R^{L44}$— <br> Structure 12L |
| —$CR^{L41}R^{L42}$—$CR^{L45}R^{L46}$—$CR^{L49}R^{L50}$—$CR^{L47}R^{L48}$—$CR^{L43}R^{L44}$— <br> Structure 13L | |
| —$CR^{L41}R^{L42}$—$CR^{L45}R^{L46}$—O—$CR^{L47}R^{L48}$—$CR^{L43}R^{L44}$— <br> Structure 15L | —$CR^{L51}$=$CR^{L53}$—$CR^{L54}$=$CR^{L52}$— <br> Structure 16L |

Structure Gu6
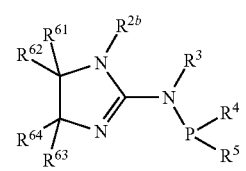
Structure Gu7
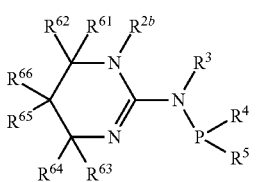
Structure Gu8
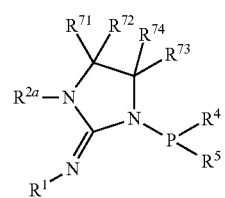
Structure Gu9
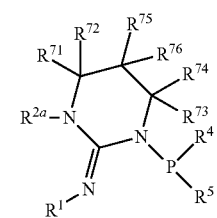
Structure Gu10
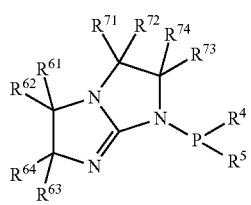
Structure Gu11
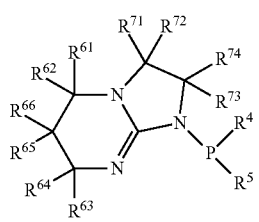
Structure Gu12
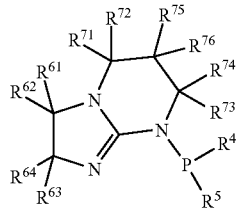
Structure Gu13
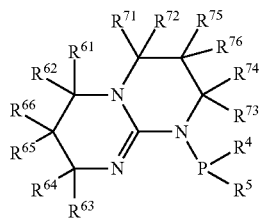
Structure Gu14
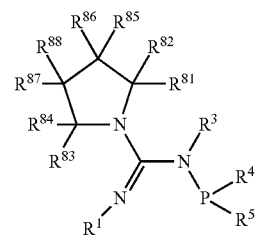
Structure Gu15
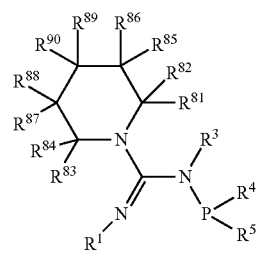
Structure Gu16
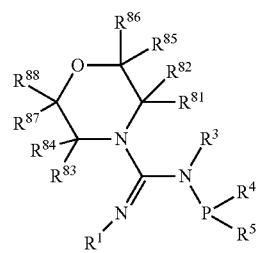
Structure Gu17
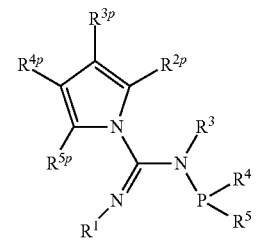
Structure Gu18
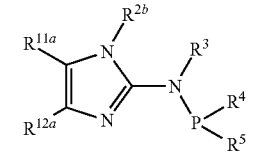
Structure Gu19
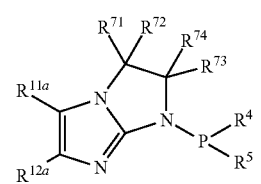

-continued

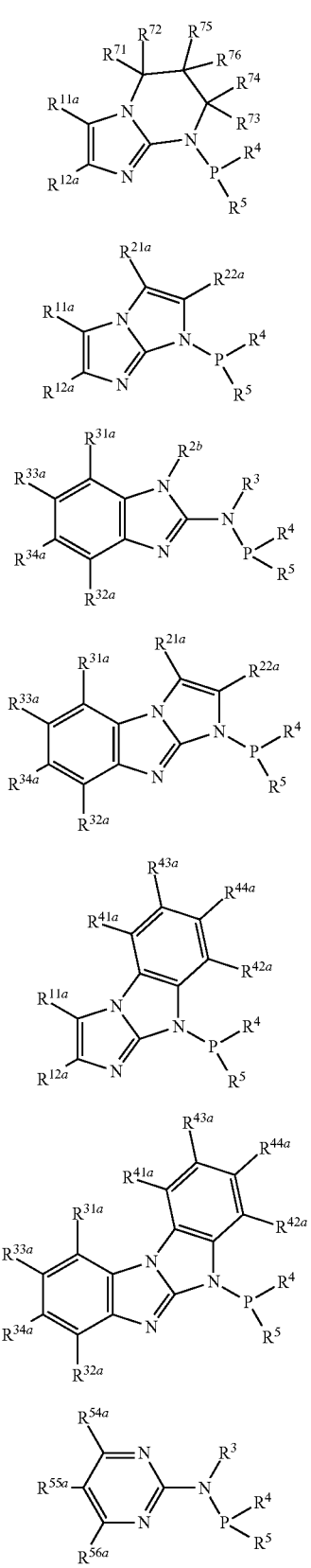

Structure Gu20

Structure Gu21

Structure Gu22

Structure Gu23

Structure Gu24

Structure Gu25

Structure Gu26

Within the N²-phosphinyl guanidine compounds having Structures Gu6 to Gu26, $R^1$, $R^{2a}$, $R^{2b}$, $R^3$, $R^4$, and $R^5$ have been previously described for the N²-phosphinyl guanidine compound Structures Gu1-Gu5. Any aspect or embodiment of these $R^1$, $R^{2a}$, $R^{2b}$, $R^3$, $R^4$, and $R^5$ descriptions (general or specific) can be utilized, without limitation, to further describe any of the ligand Structures Gu6-Gu26 in which $R^1$, $R^{2a}$, $R^{2b}$, $R^3$, $R^4$, and/or $R^5$ appears. Within the N²-phosphinyl guanidine compound having Structures Gu6-Gu26, $R^{61}$-$R^{64}$ of Structures Gu6, Gu10, and/or Gu12, $R^{61}$-$R^{66}$ of Structures Gu7, Gu11, and/or Gu13, $R^{71}$-$R^{74}$ of Structures Gu8, Gu10, Gu11, and/or Gu19, $R^{71}$-$R^{76}$ of Structures Gu9, Gu12, Gu13 and/or Gu20, $R^{81}$-$R^{88}$ of Structures Gu14 and/or Gu16, $R^{81}$-$R^{90}$ of Structure Gu15, $R^{2p}$-$R^{5p}$ of Structure Gu11, $R^{11a}$-$R^{12a}$ of Structures Gu18, Gu19, Gu20, Gu21, and/or Gu24, $R^{21a}$-$R^{22a}$ of Structures Gu21 and/or Gu23, $R^{31a}$-$R^{34a}$ of Structures Gu22, Gu23, and/or Gu25, $R^{41a}$-$R^{44a}$ of Structures Gu24 and/or Gu25, and/or $R^{54a}$-$R^{56a}$ of Structure Gu26 independently can be hydrogen or any substituent group (general or specific) described herein; or alternatively, hydrogen. In an embodiment, the N²-phosphinyl guanidine compound can have Structure Gu I, Gu II, Gu III, Gu IV, Gu V, Gu VI, Gu VII, Gu VIII, Gu IX, Gu X, Gu XI, Gu XII, Gu XIII, Gu XIV, Gu XV, Gu XVI, Gu XVII, Gu XVIII, Gu XIX, Gu XX, Gu XXI, Gu XXII, or Gu XXIII; alternatively, Structure Gu I, Gu II, or Gu III; alternatively, Structure Gu IV or Gu V; alternatively, Structure Gu VII, Gu VIII, Gu IX, Gu X, Gu XI, Gu XII, Gu XIII, Gu XIV, or Gu XV; alternatively, Structure Gu VII, Gu VIII, Gu IX, Gu X, Gu XI, or GU XXIII; alternatively, Structure Gu XII, Gu XIII, Gu XIV, or Gu XV; alternatively, Structure Gu XVII, Gu XVIII, Gu XIX, Gu XX, Gu XXI, or Gu XXII; alternatively, Structure Gu I; alternatively, Structure Gu II; alternatively, Structure Gu III; alternatively, Structure Gu IV; alternatively, Structure Gu V; alternatively, Structure Gu VI; alternatively, Structure Gu VII; alternatively, Structure Gu VIII; alternatively, Structure Gu IX; alternatively, Structure Gu X; alternatively, Structure Gu XI; alternatively, Structure Gu XII; alternatively, Structure Gu XIII; alternatively, Structure Gu XIV; alternatively, Structure Gu XV; alternatively, Structure Gu XVI; alternatively, Structure Gu XVII; alternatively, Structure Gu XVIII; alternatively, Structure Gu XIX; alternatively, Structure Gu XX; alternatively, Structure Gu XXI; alternatively, Structure Gu XXII; or alternatively, Structure Gu XXIII.

Structure Gu I

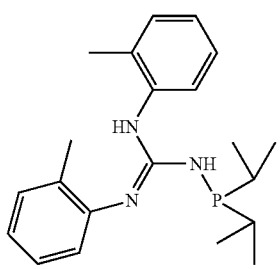

Structure Gu II

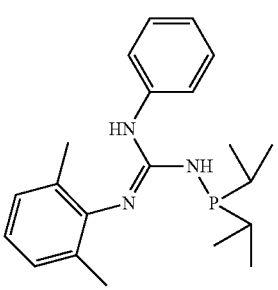

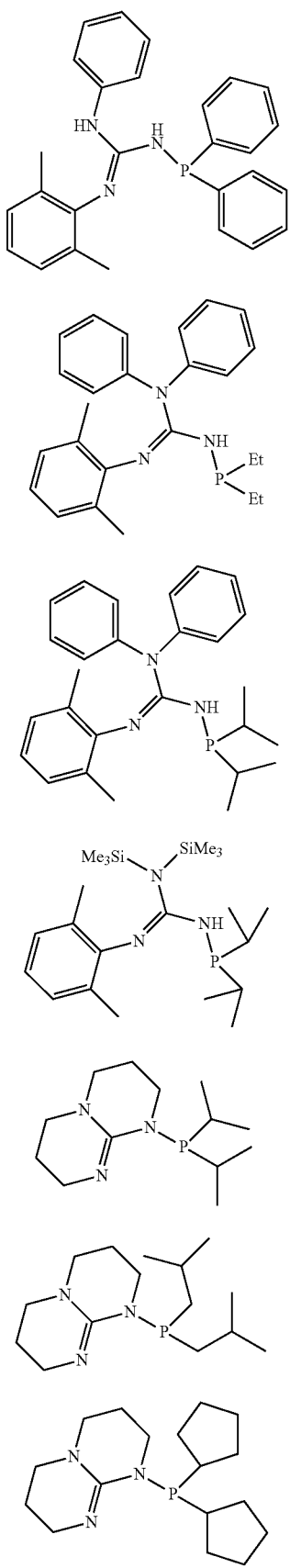
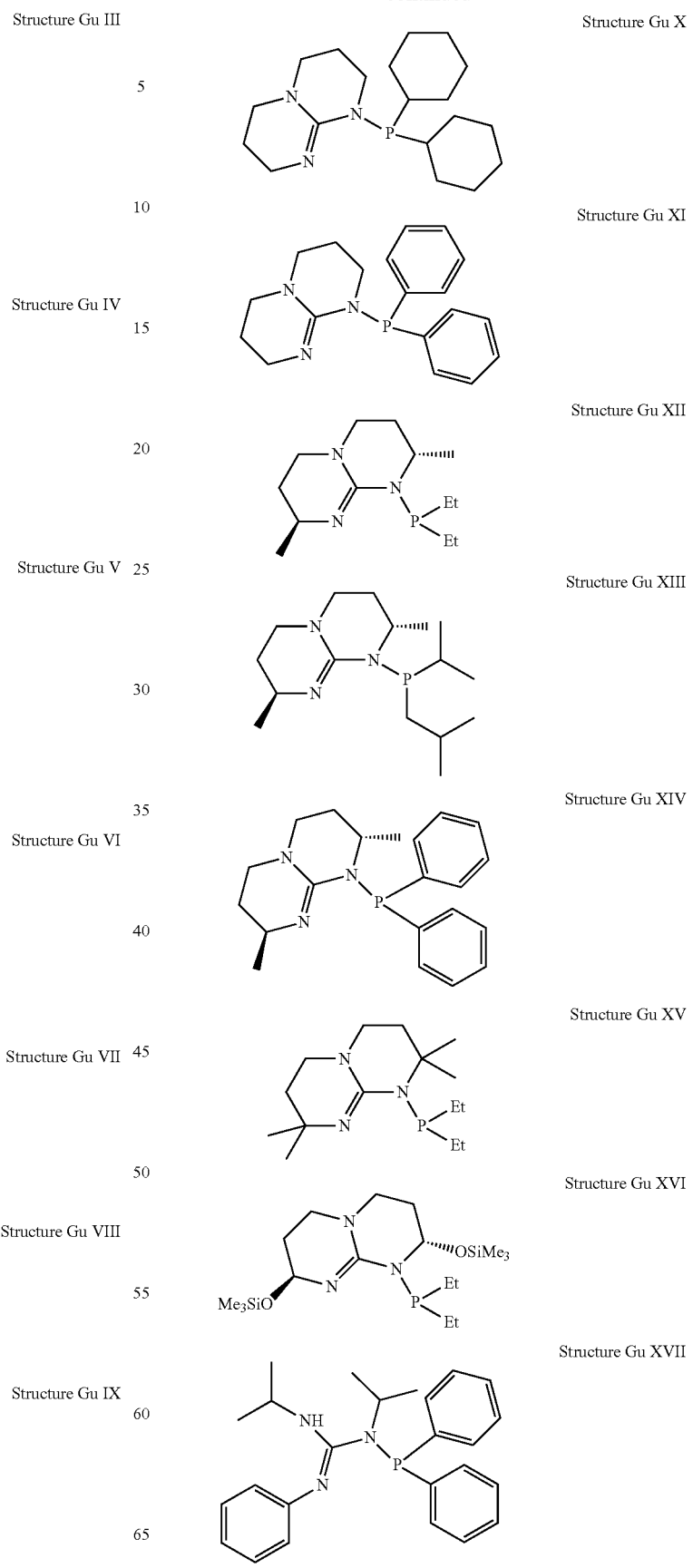

-continued

Structure Gu XVIII

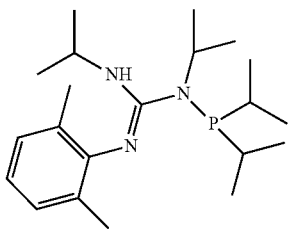

Structure Gu XIX

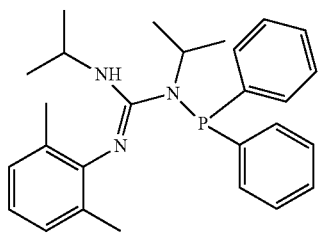

Structure Gu XX

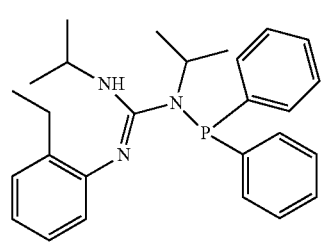

Structure Gu XXI

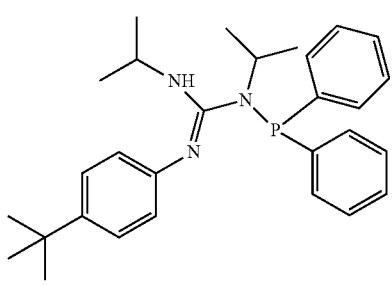

Structure Gu XXII

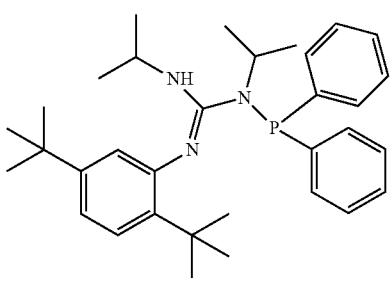

Structure Gu XXIII

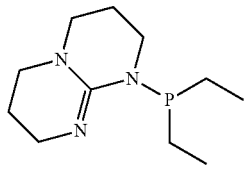

N²-Phosphinyl Guanidine Metal Salt Complexes

In an aspect, this disclosure provides for a composition comprising an N²-phosphinyl guanidine metal salt complex; or alternatively, an N²-phosphinyl guanidine metal salt complex. Generally, the N²-phosphinyl guanidine metal salt complex can comprise a metal salt complexed to an N²-phosphinyl guanidine compound. In some embodiments, the N²-phosphinyl guanidine metal salt complex can further comprise a neutral ligand, Q. N²-phosphinyl guanidine compounds are generally described herein and can be utilized, without limitation, to further describe the N²-phosphinyl guanidine metal salt complex comprising a metal salt complexed to an N²-phosphinyl guanidine compound. In an embodiment, a metal compound complexed to an N²-phosphinyl guanidine compound (or the N²-phosphinyl guanidine metal salt complex) can have Structure MGu1, MGu2, MGu3, MGu4, or MGu5; alternatively, Structure MGu1; alternatively, Structure MGu2; alternatively, Structure MGu3; alternatively, Structure MGu4; or alternatively, Structure MGu5.

Structure MGu1

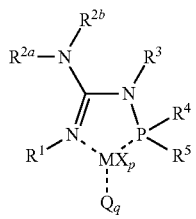

Structure MGu2

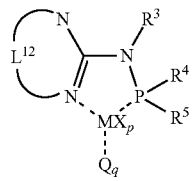

Structure MGu3

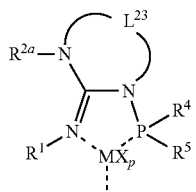

Structure MGu4

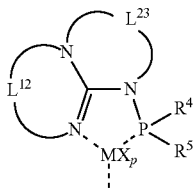

Structure MGu5

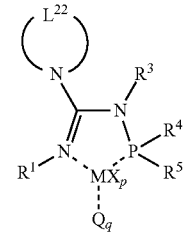

In other embodiments, the metal salt complexed to an N²-phosphinyl guanidine compound (or the N²-phosphinyl guanidine metal salt complex) have Structure MGu6, MGu7, MGu8, MGu9, MGu10, MGu11, MGu12, MGu13, MGu14, MGu15, MGu16, MGu17, MGu18, MGu19, MGu20, MGu21, MGu22, MGu23, MGu24, MGu25, or MGu26; alternatively, Structure MGu6, MGu7, MGu8, MGu9, MGu10, MGu11, MGu12, MGu13, MGu14, or MGu15; alternatively, Structure MGu17, MGu18, MGu21, MGu22, MGu23, MGu24, or MGu25; alternatively, Structure MGu19 or MGu20; alternatively, Structure MGu6; alternatively, Structure MGu7; alternatively, Structure MGu8; alternatively, Structure MGu9; alternatively, Structure MGu10; alternatively, Structure MGu11; alternatively, Structure MGu12; alternatively, Structure MGu13; alternatively, Structure MGu14; alternatively, Structure MGu15; alternatively, Structure MGu16; alternatively, Structure MGu17; alternatively, Structure MGu18; alternatively, Structure MGu19; alternatively, Structure MGu20; alternatively, Structure MGu21; alternatively, Structure MGu22; alternatively, Structure MGu23; alternatively, Structure MGu24; alternatively, Structure MGu25; or alternatively, Structure MGu26.

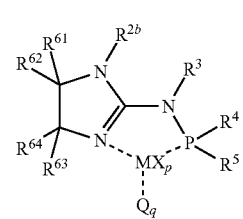

Structure MGu6

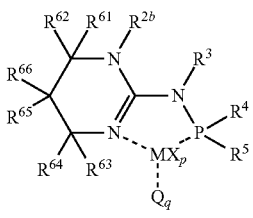

Structure MGu7

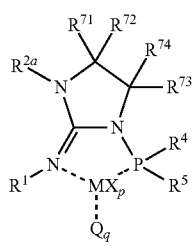

Structure MGu8

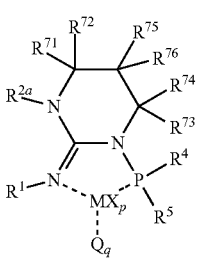

Structure MGu9

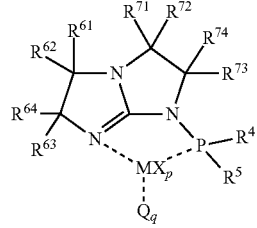

Structure MGu10

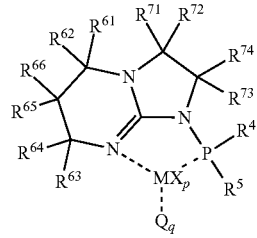

Structure MGu11

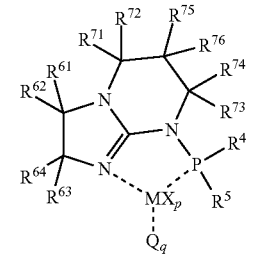

Structure MGu12

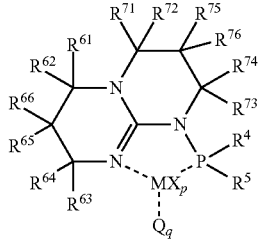

Structure MGu13

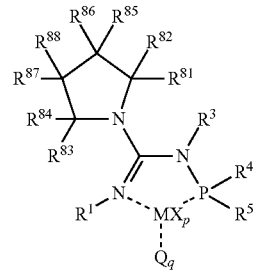

Structure MGu14

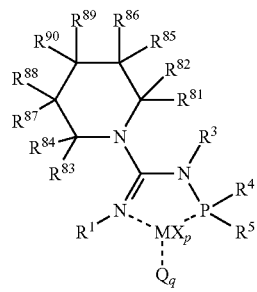

Structure MGu15

-continued

Structure MGu16
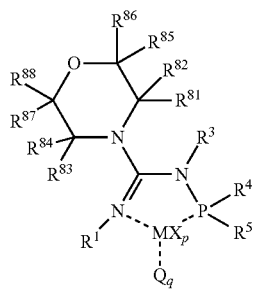

Structure MGu17
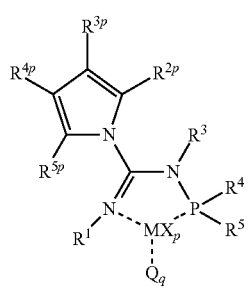

Structure MGu18
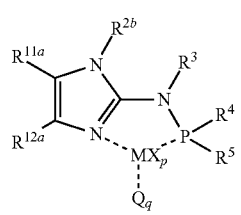

Structure MGu19
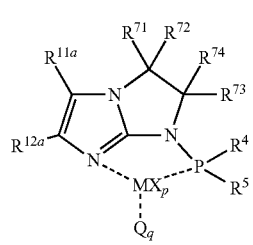

Structure MGu20
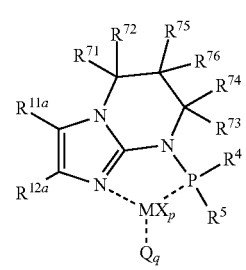

Structure MGu21
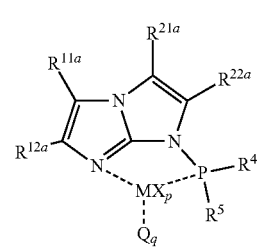

-continued

Structure MGu22
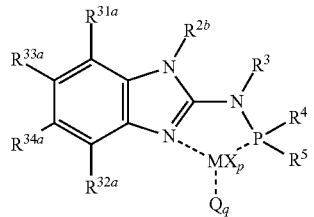

Structure MGu23
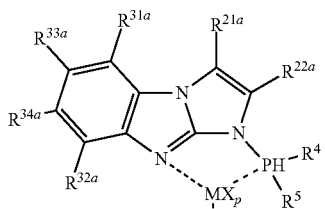

Structure MGu24
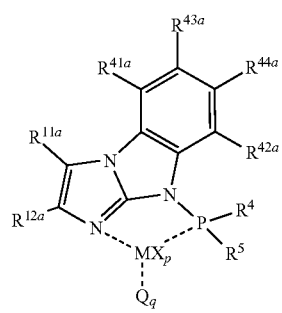

Structure MGu25
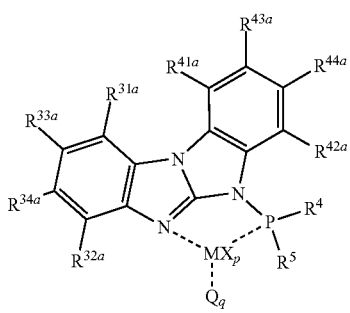

Structure MGu26
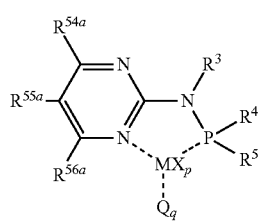

Within the $N^2$-phosphinyl guanidine metal salt complexes having Structures MGu1 to MGu26, $R^1$, $R^{2a}$, $R^{2b}$ $R^3$, $R^4$, and $R^5$ have been previously described for the $N^2$-phosphinyl guanidine compound having Structures Gu1-Gu5 and any aspect or embodiment of these descriptions (general or specific) can be utilized, without limitation, to further describe any of the $N^2$-phosphinyl guanidine metal salt complex Structures MGu1-MGu26 in which $R^1$, $R^{2a}$, $R^{2b}$ $R^3$, $R^4$, and/or $R^5$ appears. Within the $N^2$-phosphinyl guanidine compound having Structures MGu6-MGu26, $R^{61}$-$R^{66}$, $R^{71}$-$R^{76}$, $R^{81}$-$R^{90}$, $R^{11a}$-$R^{12a}$, $R^{21a}$-$R^{22a}$, $R^{31a}$-$R^{34a}$, $R^{41a}$-$R^{44a}$, and $R^{54a}$—$R^{56a}$ have been previously described for the $N^2$-phosphinyl guanidine compounds having Structures Gu6-Gu26 and any aspect or embodiment of these descriptions (general or specific) can be utilized, without limitation, to further describe any of the $N^2$-phosphinyl guanidine metal salt complex Structures MGu1-MGu26 in which $R^{61}$-$R^{66}$, $R^{71}$-$R^{76}$, $R^{81}$-$R^{90}$, $R^{11a}$-$R^{12a}$, $R^{21a}$-$R^{22a}$, $R^{31a}$-$R^{34a}$, $R^{41a}$-$R^{44a}$, and/or $R^{54a}$-$R^{56a}$ appears. In yet other embodiments, the $N^2$-phosphinyl guanidine metal salt complexes can have Structure MGu I, MGu II, MGu III, MGu IV, MGu V, MGu VI, MGu VII, MGu VIII, MGu IX, MGu X, MGu XI, MGu XII, MGu XIII, MGu XIV, Gu MXV, Gu MXVI, Gu MXVII, Gu MXVIII, Gu MXIX, Gu MXX, Gu MXXI, Gu MXXII, or Gu MXXIII; alternatively, Structure MGu I, MGu II, or MGu III; alternatively, Structure MGu IV or MGu V; alternatively, Structure MGu VII, MGu VIII, MGu IX, MGu X, MGu XI, MGu XII, MGu XIII, MGu XIV, or MGu XV; alternatively, Structure MGu VII, MGu VIII, MGu IX, MGu XI, or MGu XXIII; alternatively, Structure MGu XII, MGu XIII, MGu XIV, or MGu XV; alternatively, Structure MGu I; alternatively, Structure MGu II; alternatively, Structure MGu III; alternatively, Structure MGu IV; alternatively, Structure MGu V; alternatively, Structure MGu VI; alternatively, Structure MGu VII; alternatively, Structure MGu VIII; alternatively, Structure MGu IX; alternatively, Structure MGu X; alternatively, Structure MGu XI; alternatively, Structure MGu XII; alternatively, Structure MGu XIII; alternatively, Structure MGu XIV; alternatively, Structure MGu XV; alternatively, Structure MGu XVI; alternatively, Structure MGu XVII; alternatively, Structure MGu XVIII; alternatively, Structure MGu XIX; alternatively, Structure MGu XX; alternatively, Structure MGu XXI; alternatively, Structure MGu XXII; or alternatively, Structure MGu XXIII.

Structure MGu I

Structure MGu II

Structure MGu III

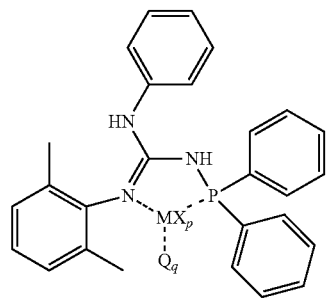

Structure MGu IV

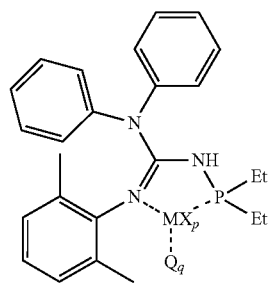

Structure MGu V

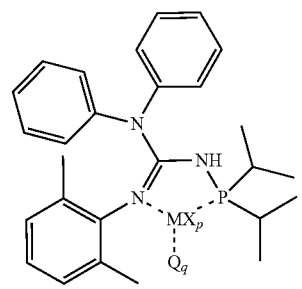

Structure MGu VI

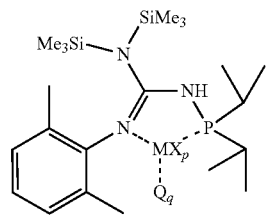

Structure MGu VII

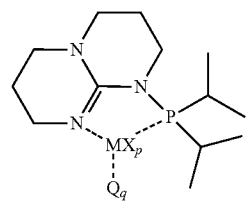

Structure MGu VIII

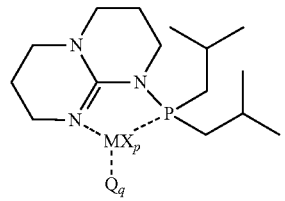

Structure MGu IX
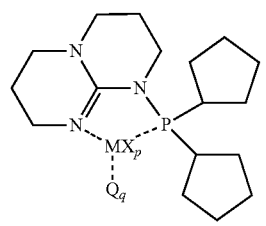
Structure MGu X
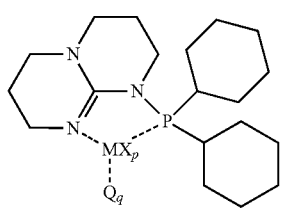
Structure MGu XI
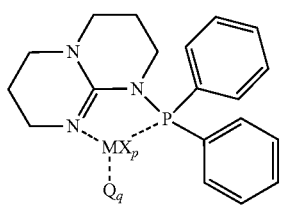
Structure MGu XII
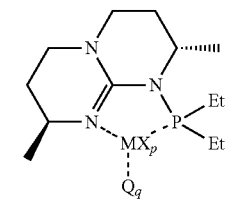
Structure MGu XIII
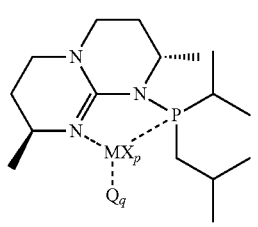
Structure MGu XIV
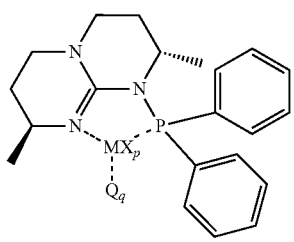
Structure MGu XV
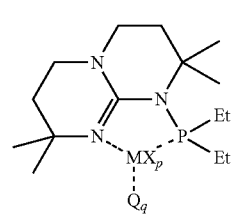
Structure MGu XVI
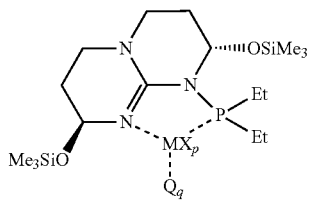
Structure MGu XVII
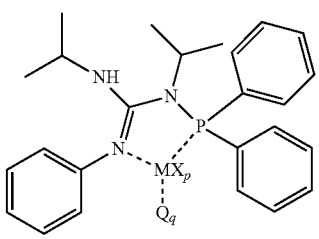
Structure MGu XVIII
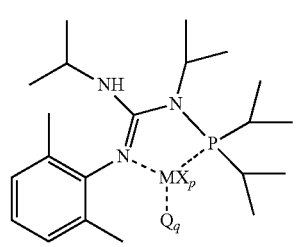
Structure MGu XIX
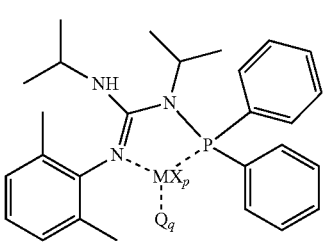
Structure MGu XX
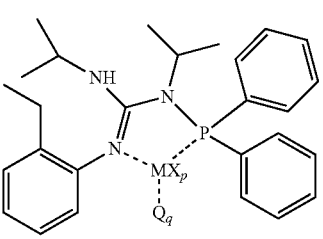
Structure MGu XXI
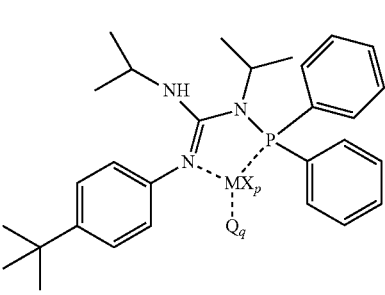

Structure MGu XXII

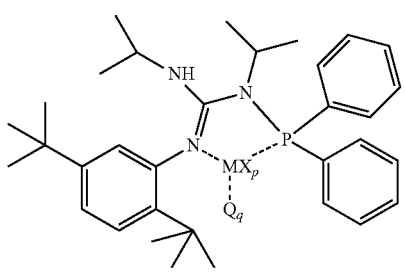

Structure MGu XXIII

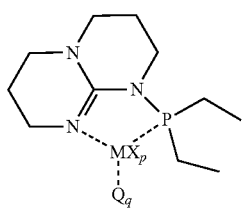

Aspects and embodiments of the metal salts ($MX_P$ or $MX_pQ_q$), the neutral ligand (Q), and the number of neutral ligands (q), if present, are described herein and these aspects and embodiments, can be utilized without limitation to further describe the $N^2$-phosphinyl guanidine metal salt complexes having Structures MGu1 to MGu26 and $N^2$-phosphinyl guanidine metal salt complexes having Structures MGu I to MGu XVI. Other metal salts ($MX_p$ or $MX_pQ_a$) complexed to any $N^2$-phosphinyl guanidine compound (or any $N^2$-phosphinyl guanidine metal salt complex) can be envisioned (and are readily apparent) by showing the ligation bonds of $MX_n$ to any ligand provided herein in a manner similar to the depictions of the metal compound, $MX_n$, complexed to respective $N^2$-phosphinyl guanidine compound depicted herein. Depictions of $N^2$-phosphinyl guanidine metal salt complex with general metal salts can have the structure designation $MX_n$-GuY or $MX_n$Gu X where M represents the metal of the metal salt (general or specific) without any neutral ligands (which may or may not be present in the $N^2$-phosphinyl guanidine metal salt complex), Y represents the Arabic numeral designation of the respective $N^2$-phosphinyl guanidine compound within this description, and X represents the Roman numeral designation of the respective $N^2$-phosphinyl guanidine compound within this description. Depictions of $N^2$-phosphinyl guanidine metal salt complex with a specific metal salt can have the structure designation $MX_n$GuY or $MX_n$Gu X where $MX_n$ is the specific metal salt without any neutral ligands (which may or may not be present in the $N^2$-phosphinyl guanidine metal salt complex), Y represents the Arabic numeral designation of the respective $N^2$-phosphinyl guanidine compound within this description, and X represents the Roman numeral designation of the respective $N^2$-phosphinyl guanidine compound within this description. Further, the neutral ligand (if present) and number of neutral ligands can be either generally provided as $Q_q$ or specifically designated by providing a designation of the ligand(s) and the number of ligands present. For example for designation illustrative purposes, general chromium salt $N^2$-phosphinyl guanidine complexes for the $N^2$-phosphinyl guanidine metal salt complexes having Structures MGu1 to MGu26 and Structures MGu I to MGu XVI, general chromium trichloride $N^2$-phosphinyl guanidine complexes for the $N^2$-phosphinyl guanidine metal salt complexes having Structures MGu1 to MGu26, and some specific $CrCl_3$.THF $N^2$-phosphinyl guanidine complexes for the $N^2$-phosphinyl guanidine metal salt complexes having Structures MGu I to MGu XVI are provided with their appropriate Structure designations.

Structure CrGu1

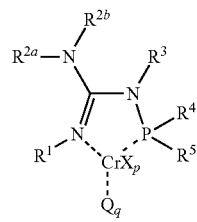

Structure CrGu2

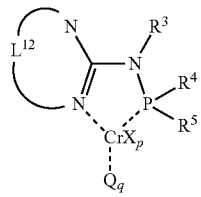

Structure CrGu3

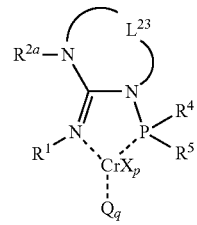

Structure CrGu4

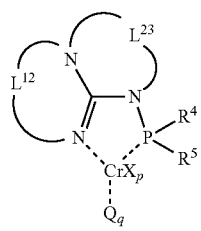

Structure CrGu5

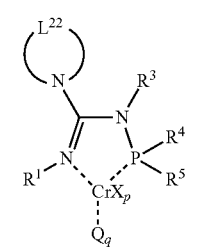

Structure CrGu6

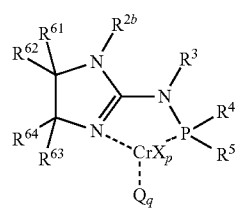

-continued
Structure CrGu7
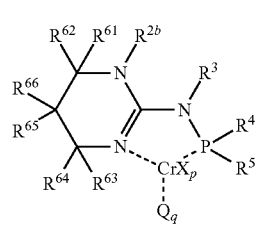
Structure CrGu8
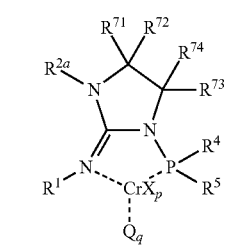
Structure CrGu9
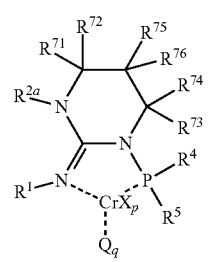
Structure CrGu10
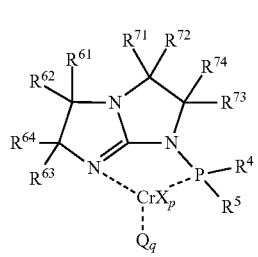
Structure CrGu11
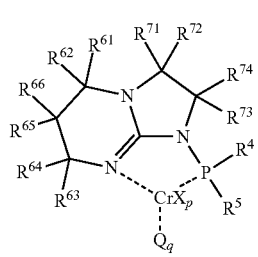
Structure CrGu12
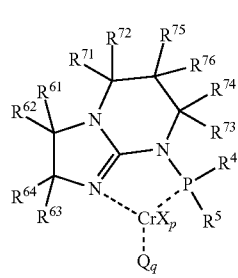
-continued
Structure CrGu13
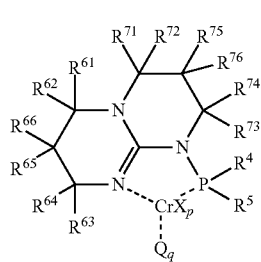
Structure CrGu14
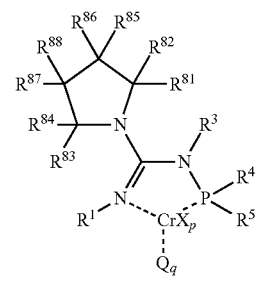
Structure CrGu15
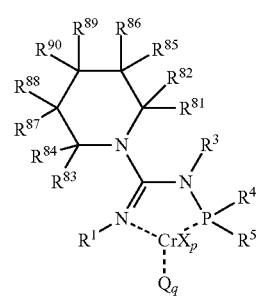
Structure CrGu16
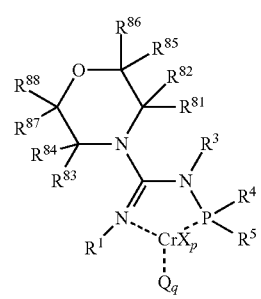
Structure CrGu17
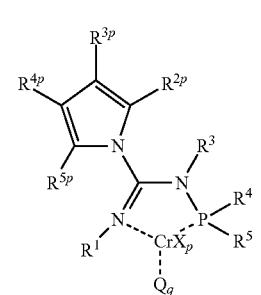
Structure CrGu18
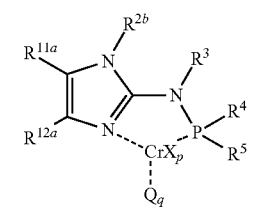

Structure CrGu19
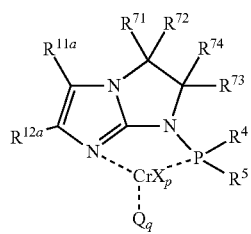
Structure CrGu20
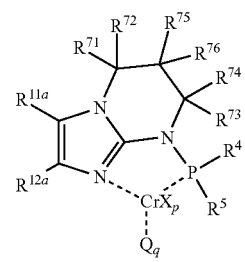
Structure CrGu21
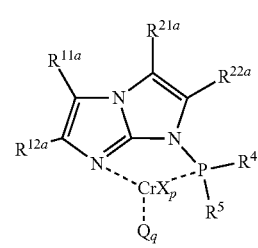
Structure CrGu22
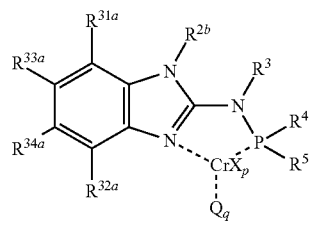
Structure CrGu23
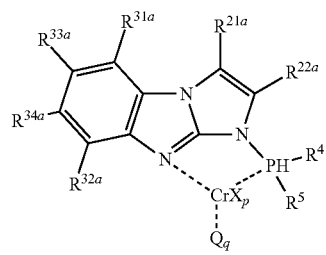
Structure CrGu24
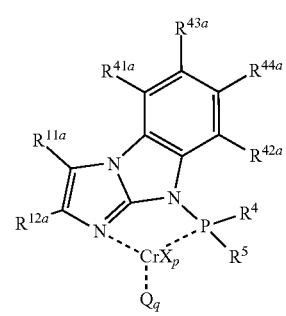
Structure CrGu25
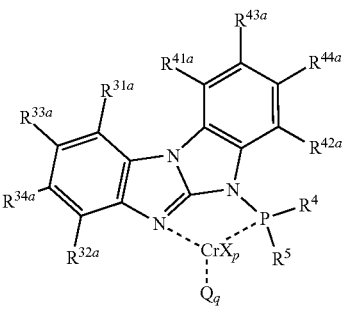
Structure CrGu26
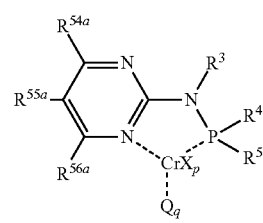
Structure CrGu I
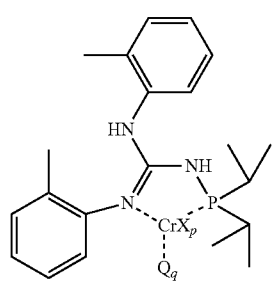
Structure CrGu II
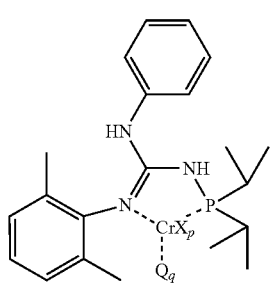
Structure CrGu III
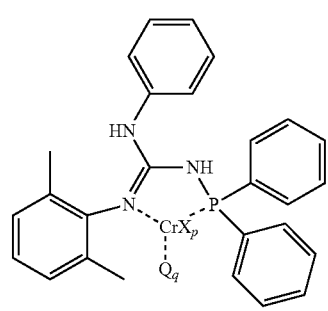

Structure CrGu IV
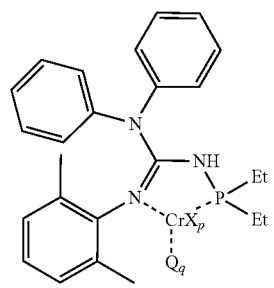
Structure CrGu V
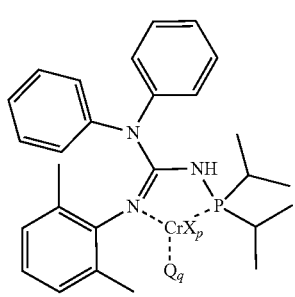
Structure CrGu VI
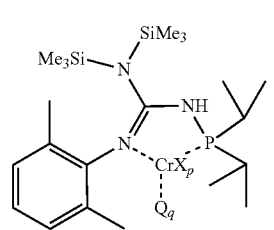
Structure CrGu VII
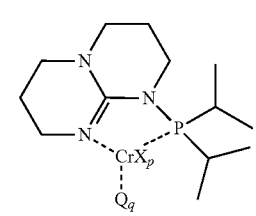
Structure CrGu VIII
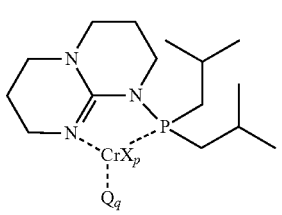
Structure CrGu IX
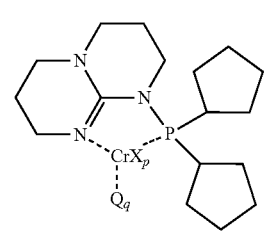
Structure CrGu X
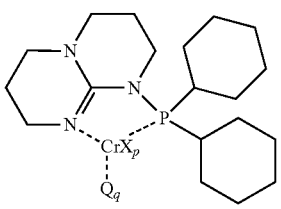
Structure CrGu XI
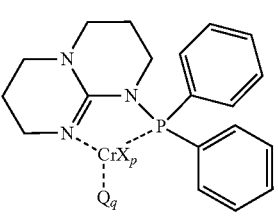
Structure CrGu XII
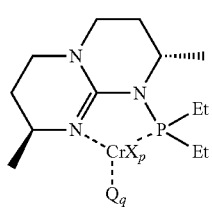
Structure CrGu XIII
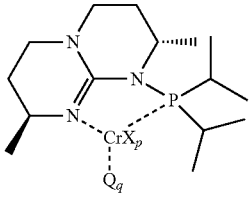
Structure CrGu XIV
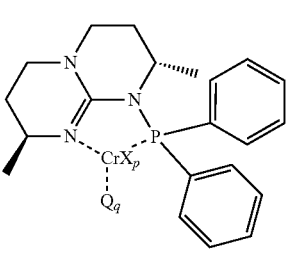
Structure CrGu XV
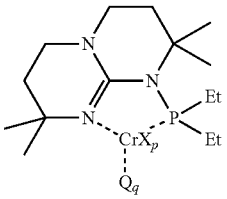
Structure CrGu XVI
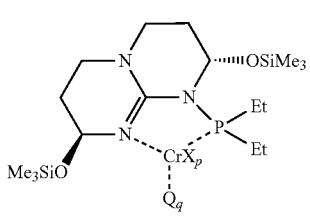

Structure CrGu XVII
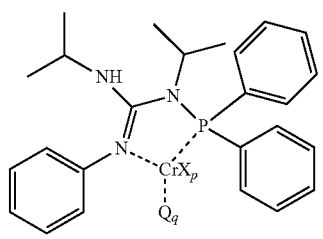
Structure CrGu XVIII
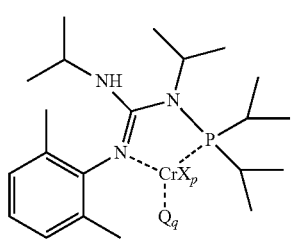
Structure CrGu XIX
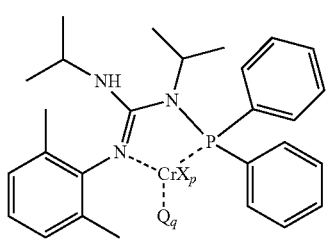
Structure CrGu XX
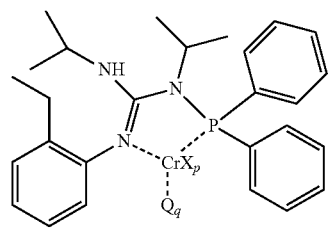
Structure CrGu XXI
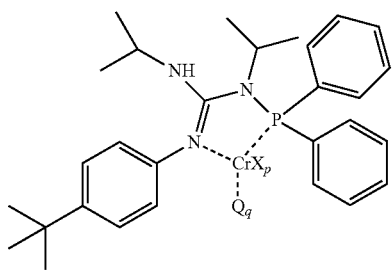
Structure CrGu XXII
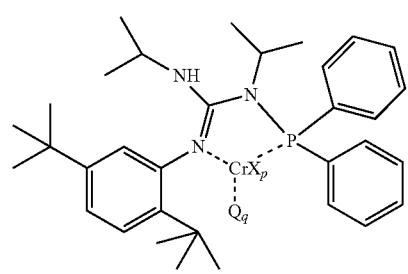
Structure CrGu XXIII
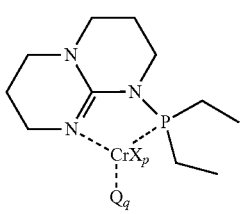
Structure CrCl$_3$·THF Gu I
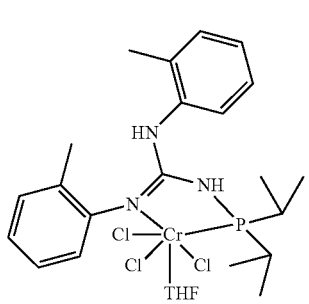
Structure CrCl$_3$·THF Gu II
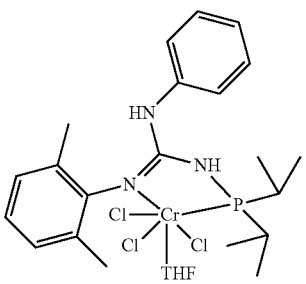
Structure CrCl$_3$·THF Gu III
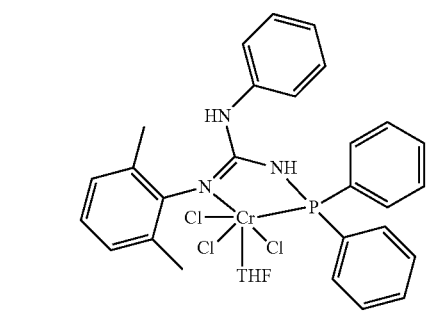
Structure CrCl$_3$·THF Gu IV
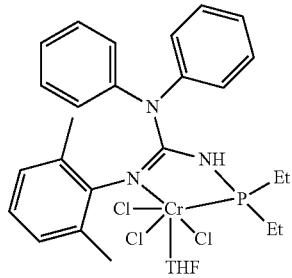

Structure CrCl₃•THF Gu V
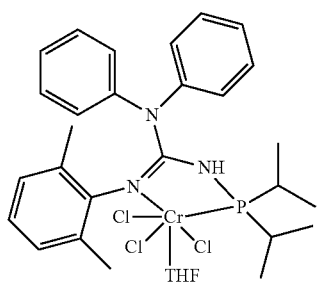
Structure CrCl₃•THF Gu VI
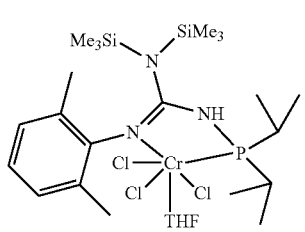
Structure CrCl₃•THF Gu VII
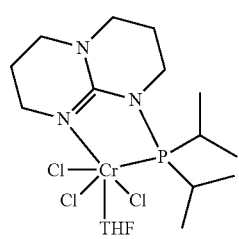
Structure CrCl₃•THF Gu VIII
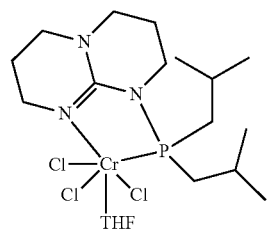
Structure CrCl₃•THF Gu IX
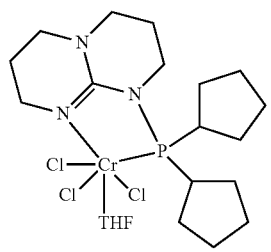
Structure CrCl₃•THF Gu X
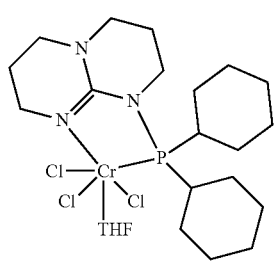
Structure CrCl₃•THF Gu XI
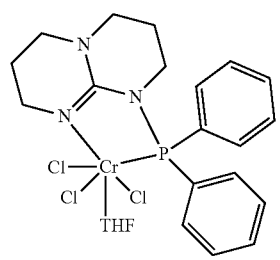
Structure CrCl₃•THF Gu XII
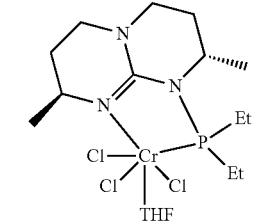
Structure CrCl₃•THF Gu XIII
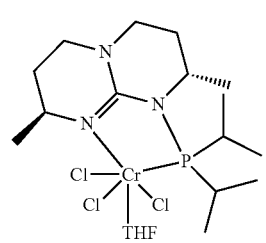
Structure CrCl₃•THF Gu XIV
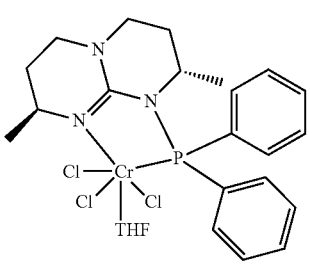
Structure CrCl₃•THF Gu XV
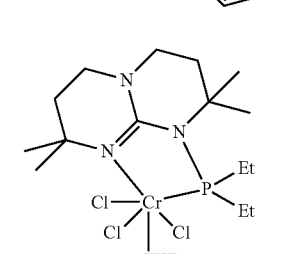
Structure CrCl₃•THF Gu XVI
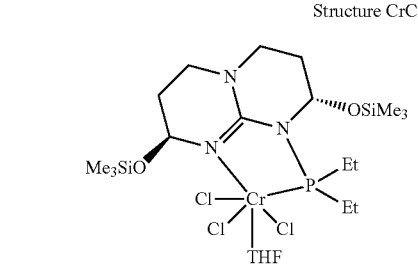

-continued

Structure CrCl₃·THF Gu XVII

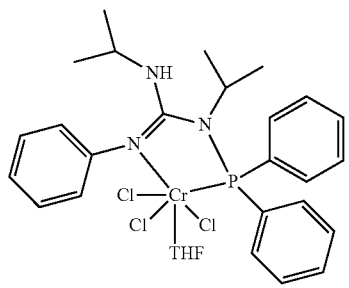

Structure CrCl₃·THF Gu XVIII

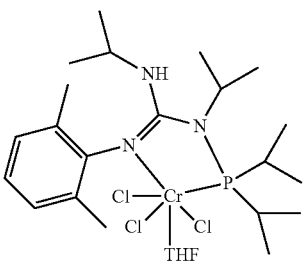

Structure CrCl₃·THF Gu XIX

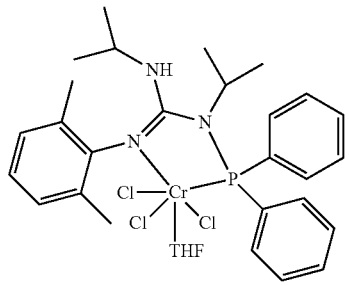

Structure CrCl₃·THF Gu XX

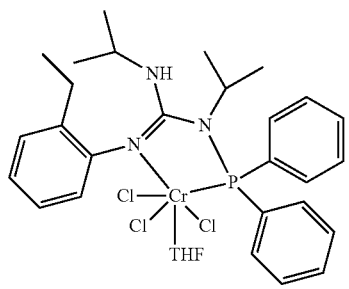

Structure CrCl₃·THF Gu XXI

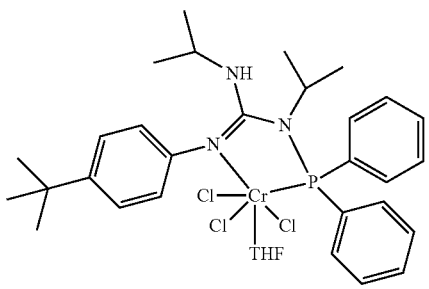

-continued

Structure CrCl₃·THF Gu XXII

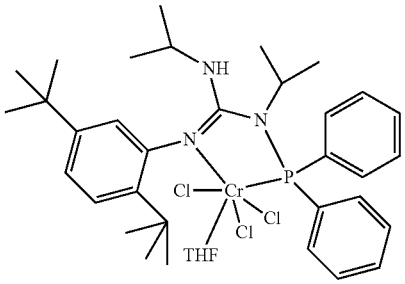

Structure CrCl₃·THF Gu XXIII

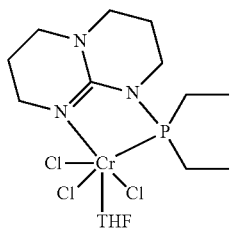

Metal Salt

Generally, the metal salt, $MX_p$ or $MX_pQ_q$, of the $N^2$-phosphinyl guanidine metal salt complex comprising a metal salt complexed to an $N^2$-phosphinyl guanidine compound can comprise a cationic metal, M, and a monoanionic ligand, X. In some embodiments, the metal salt can further comprise a neutral ligand which may or may not be present in the $N^2$-phosphinyl guanidine metal salt complex comprising a metal salt complexed to an $N^2$-phosphinyl guanidine compound.

Generally, the metal atom of the metal salt, $MX_p$ or $MX_pQ_q$, can be any metal atom. In an aspect, the metal atom of the metal salt can be a transition metal. In an embodiment, the metal salts can comprise a Group 3-12 metal; alternatively, a Group 4-10 metal; alternatively, a Group 6-9 metal; alternatively, a Group 7-8 metal; alternatively, a Group 4 metal; alternatively, a Group 5 metal alternatively, a Group 6 metal; alternatively, a Group 7 metal; alternatively, a Group 8 metal; alternatively, a Group 9 metal; or alternatively, a Group 10 metal. In some embodiments, the metal salt can comprise titanium, zirconium, hafnium, vanadium, niobium, tantalum, chromium, molybdenum, tungsten, manganese, iron, cobalt, nickel, palladium, platinum, copper, or zinc; alternatively, titanium, zirconium, hafnium, vanadium, niobium, tantalum, chromium, molybdenum, tungsten, manganese, iron, or cobalt. In other embodiments, the metal salt can comprise titanium, zirconium, vanadium, chromium, molybdenum, tungsten, iron, cobalt, nickel, palladium, or platinum; alternatively, titanium, zirconium, vanadium, chromium, molybdenum, tungsten, iron, or cobalt; alternatively, chromium, iron, cobalt, or nickel; alternatively, chromium, iron, or cobalt; alternatively, titanium, zirconium or hafnium; alternatively, vanadium or niobium; alternatively, chromium, molybdenum or tungsten; alternatively, iron or cobalt; or alternatively, nickel, palladium, platinum, copper, or zinc; alternatively, palladium or platinum; or alternatively, copper or zinc. In other embodiments, the metal salt can comprise titanium; alternatively, zirconium; alternatively, hafnium; alternatively, vanadium; alternatively, niobium; alternatively, tantalum; alternatively, molybdenum; alternatively, tungsten; alternatively, manganese; alternatively, iron; alternatively, cobalt; alternatively, nickel; alternatively, palladium; alternatively, platinum; alternatively, copper; or alternatively, zinc. In an embodiment, the metal salt can comprise chromium.

Generally, the metal atom of the transition metal salt, $MX_p$ or $MX_pQ_q$, can have any positive oxidation state available to the metal atom. In an embodiment, the transition metal (general or specific) can have an oxidation state of from +2 to +6; alternatively, from +2 to +4; or alternatively, from +2 to +3. In some embodiments, the metal atom of the transition metal salt, $MX_p$ or $MX_pQ_q$, can have an oxidation state or +1; alternatively, +2; alternatively, +3; or alternatively, +4.

The anion X, of the transition metal salt can be any monoanion. In an embodiment, the monoanion, X, can be a halide, a carboxylate, a β-diketonate, a hydrocarboxide, a nitrate, or a chlorate. In some embodiments, the monoanion, X, can be a halide, a carboxylate, a β-diketonate, or a hydrocarboxide. In any aspect or embodiment, the hydrocarboxide can be an alkoxide, an aryloxide, or an aralkoxide. Generally, hydrocarboxide (and subdivisions of hydrocarboxide) are the anion analogues of the hydrocarboxy group. In other embodiments, the monoanion, X, can be a halide, a carboxylate, a β-diketonate, or an alkoxide; or alternatively, a halide or a β-diketonate. In other embodiments, the monoanion X can be a halide; alternatively, a carboxylate; alternatively, a β-diketonate; alternatively, a hydrocarboxide; alternatively, an alkoxide; or alternatively, an aryloxide. Generally, the number, p, of monoanions, X, can equal the oxidation state of the metal atom. In an embodiment, the number, p, of monoanions, X, can be from 2 to 6; alternatively, from 2 to 4; alternatively, from 2 to 3; alternatively, 1; alternatively, 2; alternatively, 3; or alternatively, 4.

Generally, each halide monoanion independently can be fluorine, chlorine, bromine, or iodine; or alternatively, chlorine, bromine, or iodine. In an embodiment, each halide monoanion can be chlorine; alternatively, bromine; or alternatively, iodine.

Generally, the carboxylate, β-diketonate, or hydrocarboxide (inclusive of alkoxide, aryloxide, or aralkoxide) can be any $C_1$ to $C_{20}$ carboxylate, β-diketonate, or hydrocarboxide (inclusive of alkoxide, aryloxide or aralkoxide); or alternatively, any $C_1$ to $C_{10}$ carboxylate, β-diketonate, or hydrocarboxide (inclusive of alkoxide, aryloxide, or aralkoxide). In some embodiments, the anion, X, can be a $C_1$ to $C_{20}$ carboxylate; alternatively, a $C_1$ to $C_{10}$ carboxylate; alternatively, a $C_1$ to $C_{20}$ β-diketonate; alternatively, a $C_1$ to $C_{10}$ β-diketonate; alternatively, a $C_1$ to $C_{20}$ hydrocarboxide; alternatively, a $C_1$ to $C_{10}$ hydrocarboxide; alternatively, a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide.

In an aspect, each carboxylate monoanion independently can be acetate, a propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, or an octadecanoate; or alternatively, a pentanoate, a hexanoate, a heptanoate, a octanoate, a nonanoate, a decanoate, a undecanoate, or a dodecanoate. In an embodiment, each carboxylate monoanion independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, laurate (n-dodecanoate), or stearate (n-octadecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate); or alternatively, 2-ethylhexanoate. In some embodiments, the carboxylate anion can be triflate (trifluoroacetate).

In an aspect, each β-diketonate independently can be acetylacetonate (alternatively 2,4-pentanedionate), hexafluoroacetylacetone (alternatively, 1,1,1,5,5,5-hexafluoro-2,4-pentanediuonate, or benzoylacetonate); alternatively, acetylacetonate; alternatively, hexafluoroacetylacetone; or alternatively, benzoylacetonate. In an aspect, each alkoxide monoanion independently can be methoxide, ethoxide, a propoxide, or a butoxide. In an embodiment, each alkoxide monoanion independently can be methoxide, ethoxide, iso-propoxide, or tert-butoxide; alternatively, methoxide; alternatively, an ethoxide; alternatively, an iso-propoxide; or alternatively, a tert-butoxide. In an aspect, the aryloxide can be phenoxide.

Neutral Ligand

Generally, the neutral ligand, Q, of the transition metal salt or the $N^2$-phosphinyl guanidine metal salt complex comprising a transition metal salt complexed to an $N^2$-phosphinyl guanidine compound, if present, independently can be any neutral ligand that forms an isolatable compound with the metal salt or $N^2$-phosphinyl guanidine metal salt complex comprising a transition metal salt complexed to an $N^2$-phosphinyl guanidine compound. In an aspect, each neutral ligand independently can be a nitrile or an ether. In an embodiment, the neutral ligand can be a nitrile; or alternatively, an ether. The number of neutral ligands, q, of the metal salt or $N^2$-phosphinyl guanidine metal salt complex comprising a transition metal salt complexed to an $N^2$-phosphinyl guanidine compound can be any number that forms an isolatable compound with the metal salt or $N^2$-phosphinyl guanidine metal salt complex comprising a transition metal salt complexed to an $N^2$-phosphinyl guanidine compound. In an aspect, the number of neutral ligands can be from 0 to 6; alternatively, 0 to 3; alternatively, 0; alternatively, 1; alternatively, 2; alternatively, 3; or alternatively, 4. It should be noted that the neutral ligand of the $N^2$-phosphinyl guanidine metal salt complex comprising a transition metal salt complexed to an $N^2$-phosphinyl guanidine compound does not have to be the same, if present, as the neutral ligand of the transition metal salt used to form the $N^2$-phosphinyl guanidine metal salt complex. Additionally, a metal salt not having a neutral ligand can be utilized to prepare an $N^2$-phosphinyl guanidine metal salt complex comprising a transition metal salt complexed to an $N^2$-phosphinyl guanidine compound having a neutral ligand.

Generally, each neutral nitrile ligand independently can be a $C_2$ to $C_{20}$ nitrile; or alternatively, a $C_2$ to $C_{10}$ nitrile. In an embodiment, each neutral nitrile ligand independently can be a $C_2$-$C_{20}$ aliphatic nitrile, a $C_7$-$C_{20}$ aromatic nitrile, a $C_8$-$C_{20}$ aralkane nitrile, or any combination thereof; alternatively, a $C_2$-$C_{20}$ aliphatic nitrile; alternatively, a $C_7$-$C_{20}$ aromatic nitrile; or alternatively, a $C_8$-$C_{20}$ aralkane nitrile. In some embodiments, each neutral nitrile ligand independently can be a $C_2$-$C_{10}$ aliphatic nitrile, a $C_7$-$C_{10}$ aromatic nitrile, a $C_8$-$C_{10}$ aralkane nitrile, or any combination thereof; alternatively, a $C_1$-$C_{10}$ aliphatic nitrile; alternatively, a $C_7$-$C_{10}$ aromatic nitrile; or alternatively, a $C_8$-$C_{10}$ aralkane nitrile.

In an embodiment, each aliphatic nitrile independently can be acetonitrile, propionitrile, a butyronitrile, or any combination thereof; alternatively, acetonitrile; alternatively, propionitrile; alternatively, or a butyronitrile. In an embodiment, each aromatic nitrile independently can be benzonitrile, 2-methylbenzonitrile, 3-methylbenzonitrile, 4-methylbenzonitrile, 2-ethylbenzonitrile, 3-ethylbenzonitrile, 4-ethylbenzonitrile, or any combination thereof; alternatively, benzonitrile; alternatively, 2-methylbenzonitrile; alternatively, 3-methylbenzonitrile; alternatively, 4-methylbenzonitrile;

alternatively, 2-ethylbenzonitrile; alternatively, 3-ethylbenzonitrile; or alternatively, 4-ethylbenzonitrile.

Generally, each neutral ether ligand independently can be a $C_2$ to $C_{40}$ ether; alternatively, a $C_2$ to $C_{30}$ ether; or alternatively, a $C_2$ to $C_{20}$ ether. In an embodiment, neutral ligand independently can be a $C_2$ to $C_{40}$ aliphatic acyclic ether, a $C_3$ to $C_{40}$ aliphatic cyclic ether, a $C_4$ to $C_{40}$ aromatic cyclic ether, or a $C_{12}$ to $C_{40}$ diaryl ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; alternatively, a $C_4$ to $C_{40}$ aromatic cyclic ether; or alternatively, a $C_{12}$ to $C_{40}$ diaryl ether. In some embodiments, each neutral ether ligand independently can be a $C_2$ to $C_{30}$ aliphatic acyclic ether, a $C_3$ to $C_{30}$ aliphatic cyclic ether, a $C_4$ to $C_{30}$ aromatic cyclic ether, or a $C_{12}$ to $C_{30}$ diaryl ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; alternatively, a $C_4$ to $C_{30}$ aromatic cyclic ether; or alternatively, a $C_{12}$ to $C_{30}$ diaryl ether. In other embodiments, each neutral ether ligand independently can be a $C_2$ to $C_{20}$ aliphatic acyclic ether, a $C_3$ to $C_{20}$ aliphatic cyclic ether, a $C_4$ to $C_{20}$ aromatic cyclic ether, or a $C_{12}$ to $C_{20}$ diaryl ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; alternatively, a $C_4$ to $C_{20}$ aromatic cyclic ether; or alternatively, a $C_{12}$ to $C_{20}$ diaryl ether.

In an embodiment, the aliphatic acyclic ether can be dimethyl ether, diethyl ether, a dipropyl ether, a dibutyl ether, methyl ethyl ether, a methyl propyl ether, a methyl butyl ether, or any combination thereof. In some embodiments, the aliphatic acyclic ether can be dimethyl ether; alternatively, diethyl ether; alternatively, a dipropyl ether; alternatively, a dibutyl ether; alternatively, methyl ethyl ether; alternatively, a methyl propyl ether; or alternatively, a methyl butyl ether.

In an embodiment, the aliphatic cyclic ether can be tetrahydrofuran, a substituted tetrahydrofuran, a dihydrofuran, a substituted dihydrofuran, 1,3-dioxolane, a substituted 1,3-dioxolane, tetrahydropyran, a substituted tetrahydropyran, a dihydropyran, a substituted dihydropyran, pyran, a substituted pyran, a dioxane, or a substituted dioxane; alternatively, tetrahydrofuran or a substituted tetrahydrofuran; alternatively, a dihydrofuran or a substituted dihydrofuran; alternatively, 1,3-dioxolane or a substituted 1,3-dioxolane; alternatively, tetrahydropyran or a substituted tetrahydropyran; alternatively, a dihydropyran or a substituted dihydropyran; alternatively, pyran or a substituted pyran; or alternatively, a dioxane or a substituted dioxane. In some embodiments, the aliphatic cyclic ether can be tetrahydrofuran, tetrahydropyran, or dioxane, or any combination thereof; alternatively, tetrahydrofuran; alternatively tetrahydropyran; or alternatively, dioxane. Substituents (general and specific) are independently disclosed herein and can be utilized without limitation to further describe a substituted tetrahydrofuran, a substituted dihydrofuran, a substituted 1,3-dioxolane, a substituted tetrahydropyran, a substituted dihydropyran, a substituted pyran, or a substituted dioxane which can be utilized as the neutral ligand.

In an embodiment, the aromatic cyclic ether can be furan, a substituted furan, benzofuran, a substituted benzofuran, isobenzofuran, a substituted isobenzofuran, dibenzofuran, a substituted dibenzofuran, or any combination thereof; alternatively, furan or a substituted furan; alternatively, benzofuran or a substituted benzofuran; alternatively, isobenzofuran or a substituted isobenzofuran; or alternatively, a dibenzofuran or a substituted dibenzofuran. In some embodiments, the aromatic cyclic ether can be furan, benzofuran, isobenzofuran, dibenzofuran, or any combination thereof; alternatively, furan; alternatively, benzofuran; alternatively, isobenzofuran; or alternatively, dibenzofuran. Substituents (general and specific) are independently disclosed herein and can be utilized without limitation to further describe a substituted furan, a substituted benzofuran, a substituted isobenzofuran, or a substituted dibenzofuran which can be utilized as the neutral ligand.

In an embodiment, the diaryl ether can be diphenyl ether, a substituted diphenyl ether, ditolyl ether, a substituted ditolyl ether, or any combination thereof; alternatively, diphenyl ether or a substituted diphenyl ether; or alternatively, ditolyl ether or a substituted ditolyl ether. In some embodiments, the diaryl ether can be diphenyl ether or ditolyl ether; alternatively, diphenyl ether; or ditolyl ether. Substituents (general and specific) are independently disclosed herein and can be utilized without limitation to further describe a substituted diphenyl ether or a substituted ditolyl ether which can be utilized as the neutral ligand.

The features of the transition metal salts have been independently described herein and can be utilized in any combination to describe the transition metal salt of the $N^2$-phosphinyl guanidine metal salt complex comprising a transition metal salt complexed to an $N^2$-phosphinyl guanidine compound.

In a non-limiting embodiment, the transition metal salts can be, comprise, or consist essentially of, a chromium(II) halide, a chromium(III) halide, a chromium(II) carboxylate, a chromium(III) carboxylate, a chromium(II) β-diketonate, a chromium(III) β-diketonate, a chromium(II) halide (THF) complex, a chromium(III) halide (THF) complex, an iron(II) halide, an iron(III) halide, an iron(II) carboxylate, an iron(III) carboxylate, an iron(II) β-diketonate, an iron(III) β-diketonate, a cobalt(II) halide, a cobalt(III) halide, a cobalt(II) carboxylate, a cobalt(III) carboxylate, a cobalt(II) β-diketonate, a cobalt(III) β-diketonate, a nickel(II) halide, a nickel(II) carboxylate, a nickel(II) β-diketonate, a palladium(II) halide, a palladium(II) carboxylate, a palladium(II) β-diketonate, a platinum(II) halide, a platinum(IV) halide, a platinum(II) carboxylate, or a platinum(IV) carboxylate. In some non-limiting embodiments, the transition metal salt can be, comprise, or consist essentially of, a chromium(II) halide, a chromium(III) halide, a chromium (II) carboxylate, a chromium (III) carboxylate, a chromium(II) β-diketonate, a chromium (III) β-diketonate, a chromium(II) halide (THF) complex, or a chromium(III) halide (THF) complex; alternatively, an iron (II) halide, an iron(III) halide, an iron(II) carboxylate, an iron(III) carboxylate, an iron(II) β-diketonate, or an iron(III) β-diketonate; alternatively, a cobalt(II) halide, a cobalt(III) halide, a cobalt(II) carboxylate, a cobalt(III) carboxylate, a cobalt(II) β-diketonate, or a cobalt(III) β-diketonate; alternatively, a nickel(II) halide, a nickel(II) carboxylate, or a nickel (II) β-diketonate; alternatively, a palladium(II) halide, a palladium(II) carboxylate, or a palladium(II) β-diketonate; or alternatively, a platinum(II) halide, a platinum(IV) halide, a platinum(II) carboxylate, or a platinum(IV) carboxylate. In some embodiments, the transition metal salt can be, comprise, or consist essentially of, a chromium(III) halide, a chromium(III) carboxylate, a chromium(III) β-diketonate, a chromium(III) halide (THF) complex; alternatively, an iron (III) halide, an iron(III) carboxylate, or an iron(III) β-diketonate; or alternatively, a cobalt(III) halide, a cobalt(III) carboxylate, or a cobalt(III) β-diketonate. In other embodiments, the transition metal salt can be, comprise, or consist essentially of, a chromium(II) halide; alternatively, a chromium (III) halide; alternatively, a chromium (II) carboxylate; alternatively, a chromium(III) carboxylate; alternatively, a chromium(II) β-diketonate; alternatively, a chromium(III) β-diketonate; alternatively, a chromium(II) halide (THF) complex; alternatively, a chromium(III) halide (THF) complex; alternatively, an iron(II) halide; alternatively, an iron (III) halide; alternatively, an iron(II) carboxylate; alternatively, an iron(III) carboxylate; alternatively, an iron(II) β-diketonate; alternatively, an iron(III) β-diketonate; alternatively, a cobalt(II) halide; alternatively, a cobalt(III) halide; alternatively, a cobalt(II) carboxylate; alternatively, a cobalt (III) carboxylate; alternatively, a cobalt(II) β-diketonate; alternatively, a cobalt(III) β-diketonate; alternatively, a nickel (II) halide; alternatively, a nickel(II) carboxylate; alternatively, a nickel(II) β-diketonate; alternatively, a palladium(II) halide; alternatively, a palladium(II) carboxylate; alternatively, a palladium(II) β-diketonate; alternatively, a platinum (II) halide; alternatively, a platinum(IV) halide; alternatively, a platinum(II) carboxylate; or alternatively, a platinum(IV) carboxylate.

In some non-limiting embodiments, the transition metal salt can be, comprise, or consist essentially of, chromium(II) chloride, chromium(III) chloride, chromium(II) fluoride, chromium(III) fluoride, chromium(II) bromide, chromium (III) bromide, chromium(II) iodide, chromium(III) iodide, chromium(III) chloride (THF) complex, chromium(II) acetate, chromium(III) acetate, chromium(II) 2-ethylhexanoate, chromium(III) 2-ethylhexanoate, chromium(II) triflate, chromium(III) triflate, chromium(III) nitrate, chromium(III) acetylacetonate, chromium(III) hexafluoracetylacetonate, chromium(III) benzoylacetonate, iron(II) chloride, iron(III) chloride, iron(II) fluoride, iron(III) fluoride, iron(II) bromide, iron(III) bromide, iron(II) iodide, iron(III) iodide, iron(II) acetate, iron(III) acetate, iron(II) acetylacetonate, iron(III) acetylacetonate, iron(II) 2-ethylhexanoate, iron(III) 2-ethylhexanoate, iron(II) triflate, iron (III) triflate, iron(III) nitrate, cobalt(II) chloride, cobalt(III) chloride, cobalt(II) fluoride, cobalt(III) fluoride, cobalt(II) bromide, cobalt(III) bromide, cobalt(II) iodide, cobalt(III) iodide, cobalt(II) acetate, cobalt(III) acetate, cobalt(II) acetylacetonate, cobalt(III) acetylacetonate, cobalt(II) 2-ethylhexanoate, cobalt(III) 2-ethylhexanoate, cobalt(II) triflate, cobalt (III) triflate, cobalt(III) nitrate, nickel(II) chloride, nickel(II) fluoride, nickel(II) bromide, nickel(II) iodide, nickel(II) acetate, nickel(II) 2-ethylhexanoate, nickel(II) triflate, nickel (II) nitrate, nickel(II) acetylacetonate, nickel(II) benzoylacetonate, nickel(II) hexafluoracetylacetonate, palladium(II) chloride, palladium(II) fluoride, palladium(II) bromide, palladium(II) iodide, palladium(II) acetate, palladium(II) acetylacetonate, palladium(II) nitrate, platinum(II) chloride, platinum(II) bromide, platinum(II) iodide, or platinum(IV) chloride. In other embodiments, the transition metal salt can be, comprise, or consist essentially of, chromium(II) chloride, chromium(III) chloride, chromium(II) fluoride, chromium(III) fluoride, chromium(II) bromide, chromium(III) bromide, chromium(II) iodide, chromium(III) iodide, chromium(III) chloride (THF) complex, chromium(II) acetate, chromium(III) acetate, chromium(II) 2-ethylhexanoate, chromium(III) 2-ethylhexanoate chromium(II) triflate, chromium(III) triflate, chromium(III) nitrate, chromium(III) acetylacetonate, chromium(III) hexafluoracetylacetonate, or chromium(III) benzoylacetonate; alternatively, iron(II) chloride, iron(III) chloride, iron(II) fluoride, iron(III) fluoride, iron(II) bromide, iron(III) bromide, iron(II) iodide, iron(III) iodide, iron(II) acetate, iron(III) acetate, iron(II) acetylacetonate, iron(III) acetylacetonate, iron(II) 2-ethylhexanoate, iron(III) 2-ethylhexanoate, iron(II) triflate, iron(III) triflate, or iron(III) nitrate; alternatively, cobalt(II) chloride, cobalt(III) chloride, cobalt(II) fluoride, cobalt(III) fluoride, cobalt(II) bromide, cobalt(III) bromide, cobalt(II) iodide, cobalt(III) iodide, cobalt(II) acetate, cobalt(III) acetate, cobalt(II) acetylacetonate, cobalt(III) acetylacetonate, cobalt(II) 2-ethylhexanoate, cobalt(III) 2-ethylhexanoate, cobalt(II) triflate, cobalt (III) triflate, or cobalt(III) nitrate; alternatively, nickel(II) chloride, nickel(II) fluoride, nickel(II) bromide, nickel(II) iodide, nickel(II) acetate, nickel(II) 2-ethylhexanoate, nickel (II) triflate, nickel(II) nitrate, nickel(II) acetylacetonate, nickel(II) benzoylacetonate, or nickel(II) hexafluoracetylacetonate; alternatively, palladium(II) chloride, palladium(II) fluoride, palladium(II) bromide, palladium(II) iodide, palladium(II) acetate, palladium(II) acetylacetonate, or palladium (II) nitrate; or alternatively, platinum(II) chloride, platinum (II) bromide, platinum(II) iodide, or platinum(IV) chloride. In yet other embodiments, the transition metal salt can be, comprise, or consist essentially of, chromium(III) chloride, chromium(III) fluoride, chromium(III) bromide, chromium (III) iodide, chromium(III) chloride (THF) complex, chromium(III) acetate, chromium(III) 2-ethylhexanoate, chromium(III) triflate, chromium(III) nitrate, chromium(III) acetylacetonate, chromium(III) hexafluoracetylacetonate, or chromium(III) benzoylacetonate; or alternatively, iron(III) chloride, iron(III) fluoride, iron(III) bromide, iron(III) iodide, iron(III) acetate, iron(III) acetylacetonate, iron(III) 2-ethylhexanoate, iron(III) triflate, or iron(III) nitrate. In further embodiments, the transition metal salt can be chromium(III) chloride, chromium(III) chloride (THF) complex, or chromium(III) acetylacetonate; or alternatively, iron(III) chloride, or iron(III) acetylacetonate.

In some non-limiting embodiments, the transition metal salts can be, comprise, or consist essentially of, chromium(II) chloride; alternatively, chromium(III) chloride; alternatively, chromium(II) fluoride; alternatively, chromium(III) fluoride; alternatively, chromium(II) bromide; alternatively, chromium(III) bromide; alternatively, chromium(II) iodide; alternatively, chromium(III) iodide; alternatively, chromium(III) chloride (THF) complex; alternatively, chromium(II) acetate; alternatively, chromium(III) acetate; alternatively, chromium (II) 2-ethylhexanoate; alternatively, chromium(III) 2-ethylhexanoate; alternatively, chromium(II) triflate; alternatively, chromium(III) triflate; alternatively, chromium(III) nitrate; alternatively, chromium(III) acetylacetonate; alternatively, chromium(III) hexafluoracetylacetonate; alternatively, chromium(III) benzoylacetonate; alternatively, iron(II) chloride; alternatively, iron(III) chloride; alternatively, iron(II) fluoride; alternatively, iron(III) fluoride; alternatively, iron(II) bromide; alternatively, iron(III) bromide; alternatively, iron (II) iodide; alternatively, iron(III) iodide; alternatively, iron (II) acetate; alternatively, iron(III) acetate; alternatively, iron (II) acetylacetonate; alternatively, iron(III) acetylacetonate; alternatively, iron(II) 2-ethylhexanoate; alternatively, iron (III) 2-ethylhexanoate; alternatively, iron(II) triflate; alternatively, iron(III) triflate; alternatively, iron(III) nitrate; alternatively, cobalt(II) chloride; alternatively, cobalt(III) chloride; alternatively, cobalt(II) fluoride; alternatively, cobalt(III) fluoride; alternatively, cobalt(II) bromide; alternatively, cobalt(III) bromide; alternatively, cobalt(II) iodide; alternatively, cobalt(III) iodide; alternatively, cobalt(II) acetate; alternatively, cobalt(III) acetate; alternatively, cobalt(II) acetylacetonate; alternatively, cobalt(III) acetylacetonate; alternatively, cobalt(II) 2-ethylhexanoate; alternatively, cobalt(III) 2-ethylhexanoate; alternatively, cobalt(II) triflate; alternatively, cobalt(III) triflate; alternatively, cobalt(III) nitrate; alternatively, nickel(II) chloride; alternatively, nickel (II) fluoride; alternatively, nickel(II) bromide; alternatively, nickel(II) iodide; alternatively, nickel(II) acetate; alternatively, nickel(II) 2-ethylhexanoate; alternatively, nickel(II) triflate; alternatively, nickel(II) nitrate; alternatively, nickel (II) acetylacetonate; alternatively, nickel(II) benzoylacetonate; alternatively, nickel(II) hexafluoracetylacetonate; alternatively, palladium(II) chloride; alternatively, palladium(II) fluoride; alternatively, palladium(II) bromide; alternatively, palladium(II) iodide; alternatively, palladium(II) acetate; alternatively, palladium(II) acetylacetonate; alternatively, palladium(II) nitrate; alternatively, platinum(II) chloride; alternatively, platinum(II) bromide; alternatively, platinum (II) iodide; or alternatively, platinum(IV) chloride.

It should be appreciated, that a given $N^2$-phosphinyl guanidine metal salt complex can have one or more neutral ligands even when the metal salt utilized to produce the $N^2$-phosphinyl guanidine metal salt complex did not have any neutral ligands. Additionally, a given $N^2$-phosphinyl guanidine metal salt complex can have more neutral ligands than present in the metal salt utilized to produce the $N^2$-phosphinyl guanidine metal salt complex.

Preparation of $N^2$-Phosphinyl Guanidine Metal Salt Complexes

In an aspect, this disclosure relates to a process of preparing an $N^2$-phosphinyl guanidine metal salt complex. Generally, the process of preparing the $N^2$-phosphinyl guanidine metal salt complex can comprise: a) contacting a metal salt with an $N^2$-phosphinyl guanidine compound; and b) forming the $N^2$-phosphinyl guanidine metal salt complex. Generally, the $N^2$-phosphinyl guanidine metal salt complex can be formed under conditions capable of forming an $N^2$-phosphinyl guanidine metal salt complex. In some embodiments, the $N^2$-phosphinyl guanidine metal salt complex can be isolated; alternatively purified; or alternatively, isolated and purified.

$N^2$-phosphinyl guanidine compounds are disclosed herein and can be utilized without limitation to further describe the process of preparing an $N^2$-phosphinyl guanidine metal salt complex. Metal salts are disclosed herein and can be utilized without limitation to further describe the process of preparing an $N^2$-phosphinyl guanidine metal salt complex.

Generally, the metal salt and the $N^2$-phosphinyl guanidine compound can be contacted at a metal salt to $N^2$-phosphinyl guanidine compound equivalent ratio of at least 0.9:1. In some embodiments, the metal salt and the $N^2$-phosphinyl guanidine compound can be contacted at a metal salt to $N^2$-phosphinyl guanidine compound equivalent ratio of at least 0.95:1; alternatively, of at least 0.975:1; or alternatively, of at least 0.99:1. In some embodiments, the metal salt and the $N^2$-phosphinyl guanidine compound can be contacted at a metal salt to $N^2$-phosphinyl guanidine compound equivalent ratio ranging from 0.9:1 to 1.25:1; alternatively, ranging from 0.95:1 to 1.20:1; alternatively, ranging from 0.975:1 to 1.15: 1; or alternatively, ranging from 0.99:1 to 1.10:1. In other embodiments, the metal salt and the $N^2$-phosphinyl guanidine compound can be contacted at a metal salt to $N^2$-phosphinyl guanidine compound equivalent ratio of about 1:1.

Conditions capable of forming an $N^2$-phosphinyl guanidine metal salt complex can comprise a contact temperature; alternatively, a contact time; or alternatively, a contact temperature and a contact time. In an embodiment, the contact temperature for forming an $N^2$-phosphinyl guanidine metal salt complex can include a contact temperature of at least 0° C.; alternatively, of at least 5° C.; alternatively, of at least 10° C.; or alternatively, of at least 15° C. In some embodiments, the contact temperature for forming the $N^2$-phosphinyl guanidine metal salt complex can include a contact temperature ranging from 0° C. to 60° C.; alternatively, ranging from 5° C. to 50° C.; alternatively, ranging from 10° C. to 45° C.; or alternatively, ranging from 15° C. to 40° C. In an embodiment, the contact time for forming the $N^2$-phosphinyl guanidine metal salt complex can include a contact time of at least 15 minutes; alternatively, of at least 30 minutes; alternatively, of at least 45 minutes; or alternatively, of at least 1 hour. In some embodiments, the contact time for forming the $N^2$-phosphinyl guanidine metal salt complex can include a contact time ranging from 15 minutes to 36 hours; alternatively, ranging from 30 minutes to 30 hours; alternatively, ranging from 45 minutes to 24 hours; or alternatively, ranging from 1 hour to 18 hours.

In an embodiment, the metal salt and the $N^2$-phosphinyl guanidine compound can be contacted in a solvent. In some embodiments, the metal salt and the $N^2$-phosphinyl guanidine compound can be contacted in a polar solvent. In some embodiments, the solvent is the same as the neutral ligand, Q, of the $N^2$-phosphinyl guanidine metal salt complex. Solvents (general and specific) and neutral ligands (general and specific) are generally disclosed herein and can be utilized, without limitation, to further describe the process of preparing the $N^2$-phosphinyl guanidine metal salt complex.

In an embodiment, the $N^2$-phosphinyl guanidine metal salt complex can be utilized without further isolation or purification. In some embodiments, the $N^2$-phosphinyl guanidine metal salt complex can be isolated; alternatively, purified; or alternatively, isolated and purified. In an embodiment, wherein the $N^2$-phosphinyl guanidine metal salt complex is prepared in a solvent, the process to prepare the $N^2$-phosphinyl guanidine metal salt complex can include a step of isolating the $N^2$-phosphinyl guanidine metal salt complex by evaporating the solvent. In an embodiment wherein the $N^2$-phosphinyl guanidine metal salt complex is prepared in a solvent, the process to prepare the $N^2$-phosphinyl guanidine metal salt complex can include the step of isolating the $N^2$-phosphinyl guanidine metal salt complex by filtering the solution to remove particulate materials and/or byproducts of the reaction and evaporating the solvent. In embodiments, the process to prepare the $N^2$-phosphinyl guanidine metal salt complex can include a purification step wherein the $N^2$-phosphinyl guanidine compound is purified by dissolving the $N^2$-phosphinyl guanidine metal salt complex in a solvent and filtering the solution to remove particulate materials and/or byproducts of the reaction. The solvent utilized to purify the $N^2$-phosphinyl guanidine metal salt complex can be the same solvent utilized to form the $N^2$-phosphinyl guanidine metal salt complex or it can be different than the solvent utilized to form the $N^2$-phosphinyl guanidine metal salt complex. In some embodiments, the process of preparing the $N^2$-phosphinyl guanidine metal salt complex can include a purification step of isolating the $N^2$-phosphinyl guanidine metal salt complex by washing the $N^2$-phosphinyl guanidine metal salt complex with a solvent. In other embodiments, the process of preparing the $N^2$-phosphinyl guanidine metal salt complex can include a purification step of recrystallizing the $N^2$-phosphinyl guanidine metal salt complex.

Generally, the evaporation of the solvent can be performed using any suitable method. In some embodiments, the solvent can be evaporated at ambient temperature (15° C. to 35° C.—no applied external heat source). In other embodiments, the solvent can be evaporated with gentle heating (e.g., at a temperature ranging from 25° C. to 50° C.). In further embodiments, the solvent can be evaporated at ambient temperature under reduced pressure. In yet other embodiments, the solvent can be evaporated with gentle heating under reduced pressure.

Catalyst Systems

In an aspect, the present disclosure relates to catalyst systems (or catalyst system compositions) comprising an $N^2$-phosphinyl guanidine compound and a metal salt; alternatively, an $N^2$-phosphinyl guanidine metal salt complex. In an embodiment, the catalyst system (or catalyst system composition) can comprise, or consist essentially of, an $N^2$-phosphinyl guanidine metal salt complex and a metal alkyl compound; or alternatively, an $N^2$-phosphinyl guanidine metal salt complex and an aluminoxane. In another aspect, the catalyst system (or catalyst system composition) can comprise, or consist essentially of, an $N^2$-phosphinyl guanidine compound, a metal salt, and a metal alkyl compound; or alternatively, an $N^2$-phosphinyl guanidine compound, a metal salt, and an aluminoxane. $N^2$-phosphinyl guanidine metal salt complexes, metal salts, $N^2$-phosphinyl guanidine compounds, metal alkyl compounds, and aluminoxanes which can be utilized in various aspects and/or embodiments of the catalyst systems (or catalyst system compositions) are independently described herein and can be utilized in any combination and without limitation to describe various catalyst systems of this disclosure.

Metal Alkyl

Generally, the metal alkyl compound which can be utilized in the catalyst system of this disclosure can be any heteroleptic or homoleptic metal alkyl compound. In an embodiment, the metal alkyl compound can comprise, consist essentially of, or consist of, a non-halide metal alkyl compound, a metal alkyl halide compound, or any combination thereof; alternatively a non-halide metal alkyl compound; or alternatively, a metal alkyl halide compound.

In an embodiment, the metal of the metal alkyl compound can comprise, consist essentially of, or consist of, a group 1, 2, 11, 12, 13, or 14 metal; or alternatively a group 13 or 14 metal; or alternatively, a group 13 metal. In some embodiments, the metal of the metal alkyl compound (non-halide metal alkyl compound or metal alkyl halide compound) can be lithium, sodium, potassium, rubidium, cesium, beryllium, magnesium, calcium, strontium, barium, zinc, cadmium, boron, aluminum, or tin; alternatively, lithium, sodium, potassium, magnesium, calcium, zinc, boron, aluminum, or tin; alternatively, lithium, sodium, or potassium; alternatively magnesium, calcium; alternatively, lithium; alternatively, sodium; alternatively, potassium; alternatively, magnesium; alternatively, calcium; alternatively, zinc; alternatively, boron; alternatively, aluminum; or alternatively, tin. In some embodiments, the metal alkyl compound (non-halide metal alkyl compound or metal alkyl halide compound) can comprise, consist essentially of, or consist of, a lithium alkyl compound, a sodium alkyl compound, a magnesium alkyl compound, a boron alkyl compound, a zinc alkyl compound, or an aluminum alkyl compound. In some embodiments, the metal alkyl compound (non-halide metal alkyl compound or metal alkyl halide compound) can comprise, consist essentially of, or consist of, an aluminum alkyl compound.

In an embodiment, the aluminum alkyl compound can be a trialkylaluminum compound, an alkylaluminum halide compound, an alkylaluminum alkoxide compound, an aluminoxane, or any combination thereof. In some embodiments, the aluminum alkyl compound can be a trialkylaluminum compound, an alkylaluminum halide compound, an aluminoxane, or any combination thereof; or alternatively, a trialkylaluminum compound, an aluminoxane, or any combination thereof. In other embodiments, the aluminum alkyl compound can be a trialkylaluminum compound; alternatively, an alkylaluminum halide compound; alternatively, an alkylaluminum alkoxide compound; or alternatively, an aluminoxane.

In a non-limiting embodiment, the aluminoxane can have a repeating unit depicted as Formula I:

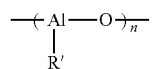

Formula I wherein R' is a linear or branched alkyl group. It should be noted that alkyl group, R', of the aluminoxane repeating unit having Formula I can be a mixture of different alkyl groups. Alkyl groups for metal alkyl compounds are independently described herein and can be utilized without limitation to further describe the aluminoxanes repeating unit having Formula I. Generally, n of Formula I is greater than 1; or alternatively greater than 2. In an embodiment, n can range from 2 to 15; or alternatively, range from 3 to 10.

In an aspect, each halide of any metal alkyl halide compound disclosed herein can independently be fluoride, chloride, bromide, or iodide; alternatively, chloride, bromide, or iodide. In an embodiment, each halide of any metal alkyl halide compound disclosed herein can be fluoride; alternatively, chloride; alternatively, bromide; or alternatively, iodide.

In an aspect, each alkyl group of any metal alkyl compound disclosed herein (non-halide metal alkyl compound, metal alkyl halide compound, and/or aluminoxane, among other described herein) independently can be a $C_1$ to $C_{20}$ alkyl group; alternatively, a $C_1$ to $C_{10}$ alkyl group; or alternatively, a $C_1$ to $C_6$ alkyl group. In an embodiment, each alkyl group independently can be a methyl group, an ethyl group, a propyl group, a butyl group, a pentyl group, a hexyl group, a heptyl group, or an octyl group; alternatively, a methyl group, a ethyl group, a butyl group, a hexyl group, or an octyl group. In some embodiments, each alkyl group independently can be a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, each alkoxide group of any metal alkyl alkoxide compound disclosed herein independently can be a $C_1$ to $C_{20}$ alkoxy group; alternatively, a $C_1$ to $C_{10}$ alkoxy group; or alternatively, a $C_1$ to $C_6$ alkoxy group. In an embodiment, each alkoxide group of any metal alkyl alkoxide compound disclosed herein independently can be a methoxy group, an ethoxy group, a propoxy group, a butoxy group, a pentoxy group, a hexoxy group, a heptoxy group, or an octoxy group; alternatively, a methoxy group, a ethoxy group, a butoxy group, a hexoxy group, or an octoxy group. In some embodiments, each alkoxide group of any metal alkyl alkoxide compound disclosed herein independently can be a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting embodiment, the metal alkyl compound can be, comprise, or consist essentially of, methyl lithium, n-butyl lithium, sec-butyl lithium, tert-butyl lithium, diethyl magnesium, di-n-butylmagnesium, ethylmagnesium chloride, n-butylmagnesium chloride, and diethyl zinc.

In a non-limiting embodiment, the trialkylaluminum compound can be, comprise, or consist essentially of, trimethylaluminum, triethylaluminum, tripropylaluminum, tributylaluminum, trihexylaluminum, trioctylaluminum, or mixtures thereof. In some non-limiting embodiments, the trialkylaluminum compound can be, comprise, or consist essentially of, trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting embodiments, the trialkylaluminum compound can be, comprise, or consist essentially of, trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting embodiment, the alkylaluminum halide compound can be, comprise, or consist essentially of, diethylaluminum chloride, diethylaluminum bromide, ethylaluminum dichloride, ethylaluminum sesquichloride, and mixtures thereof. In some non-limiting embodiments, the alkylaluminum halide can be, comprise, or consist essentially of, diethylaluminum chloride, ethylaluminum dichloride, ethylaluminum sesquichloride, and mixtures thereof. In other non-limiting embodiments, the alkylaluminum halides can be, comprise, or consist essentially of, diethylaluminum chloride; alternatively, diethylaluminum bromide; alternatively, ethylaluminum dichloride; or alternatively, ethylaluminum sesquichloride.

In a non-limiting embodiment, the aluminoxane can be, comprise, or consist essentially of, methylaluminoxane (MAO), ethylaluminoxane, modified methylaluminoxane (MMAO), n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, or mixtures thereof; In some non-limiting embodiments, the aluminoxane can be, comprise, or consist essentially of, methylaluminoxane (MAO), modified methylaluminoxane (MMAO), isobutyl aluminoxane, t-butyl aluminoxane, or mixtures thereof. In other non-limiting embodiments, useful aluminoxanes can include methylaluminoxane (MAO); alternatively, ethylaluminoxane; alternatively, modified methylaluminoxane (MMAO); alternatively, n-propylaluminoxane; alternatively, iso-propylaluminoxane; alternatively, n-butylaluminoxane; alternatively, sec-butylaluminoxane; alternatively, iso-butylaluminoxane; alternatively, t-butyl aluminoxane; alternatively, 1-pentylaluminoxane; alternatively, 2-pentylaluminoxane; alternatively, 3-pentylaluminoxane; alternatively, iso-pentylaluminoxane; or alternatively, neopentylaluminoxane.

Catalyst System Component Ratios

In an aspect, the metal alkyl and $N^2$-phosphinyl guanidine metal salt complex can be combined in any ratio that can form an active catalyst system (or catalyst system composition). In an embodiment, the metal of the metal alkyl compound to the metal of the $N^2$-phosphinyl guanidine metal salt complex molar ratio can be greater than or equal to 5:1; alternatively, greater than or equal to 10:1; alternatively, greater than or equal to 25:1; alternatively, greater than or equal to 50:1; or alternatively, greater than or equal to 100:1. In some embodiments, the metal of the metal alkyl compound to the metal of the $N^2$-phosphinyl guanidine metal salt complex molar ratio can range from 5:1 to 100,000:1; alternatively, range from 10:1 to 50,000:1; alternatively, range from 25:1 to 10,000:1; alternatively, range from 50:1 to 5,000:1; or alternatively, range from 100:1 to 2,500:1. When a metal alkyl compound having a specific metal and an $N^2$-phosphinyl guanidine metal salt complex having a specific metal is utilized the metal of the metal alkyl compound to the metal of the $N^2$-phosphinyl guanidine metal salt complex molar ratio can be stated as a specific metal of the metal alkyl to specific metal of the $N^2$-phosphinyl guanidine metal salt complex molar ratio. For example, when the metal alkyl compound is an alkylaluminum compound (e.g., trialkylaluminum compound, alkylaluminum halide compound, alkylaluminum alkoxide compound, and/or aluminoxane) and the $N^2$-phosphinyl guanidine metal salt complex is an $N^2$-phosphinyl guanidine chromium salt complex, the metal of the metal alkyl compound to metal of the metal salt can be an aluminum to chromium molar ratio. In some non-limiting embodiments, the aluminum to chromium molar ratio can be greater than or equal to 5:1; alternatively, greater than or equal to 10:1; alternatively, greater than or equal to 25:1; alternatively, greater than or equal to 50:1; alternatively, greater than or equal to 100:1; alternatively, range from 5:1 to 100,000:1; alternatively, range from 10:1 to 50,000:1; alternatively, range from 25:1 to 10,000:1; alternatively, range from 50:1 to 5,000:1; or alternatively, range from 100:1 to 2,500:1.

In another aspect, the metal alkyl, metal salt, and $N^2$-phosphinyl guanidine compound can be combined in any ratio that forms an active catalyst system (or catalyst system composition). Generally the ratio of the components of the catalyst system (or catalyst system composition) comprising, consisting essentially of, or consisting of a metal alkyl, metal salt, and $N^2$-phosphinyl guanidine compound can be provided as i) a molar ratio of the metal of the metal alkyl compound to metal of the metal salt, ii) an equivalent ratio of the $N^2$-phosphinyl guanidine compound to metal salt, or iii) a combination of a molar ratio of the metal of the metal alkyl compound to metal of the metal salt and an equivalent ratio of the $N^2$-phosphinyl guanidine compound to metal salt.

In an embodiment, the metal of the metal alkyl compound to the metal of the metal salt molar ratio can be greater than or equal to 5:1; alternatively, greater than or equal to 10:1; alternatively, greater than or equal to 25:1; alternatively, greater than or equal to 50:1; or alternatively, greater than or equal to 100:1. In some embodiments, the metal of the metal alkyl compound to the metal of the metal salt molar ratio can range from 5:1 to 100,000:1; alternatively, ranges from 10:1 to 50,000:1; alternatively, ranges from 25:1 to 10,000:1; alternatively, ranges from 50:1 to 5,000:1; or alternatively, ranges from 100:1 to 2,500:1. When a metal alkyl compound having a specific metal and a metal salt having a specific metal is utilized the metal of the metal alkyl compound to the metal of the metal salt molar ratio can be stated as a specific metal of the metal alkyl compound to specific metal of the metal salt molar ratio. For example, when the metal alkyl compound is an alkylaluminum compound (e.g., trialkylaluminum compound, alkylaluminum halide compound, alkylaluminum alkoxide compound, and/or aluminoxane) and the metal salt is a chromium salt, the metal of the metal alkyl compound to metal of the metal salt can be an aluminum to chromium molar ratio. In some non-limiting embodiments, the aluminum to chromium molar ratio can be greater than or equal to 5:1; alternatively, greater than or equal to 10:1; alternatively, greater than or equal to 25:1; alternatively, greater than or equal to 50:1; alternatively, greater than or equal to 100:1; alternatively, range from 5:1 to 100,000:1; alternatively, range from 10:1 to 50,000:1; alternatively, range from 25:1 to 10,000:1; alternatively, range from 50:1 to 5,000:1; or alternatively, range from 100:1 to 2,500:1

In an embodiment, the $N^2$-phosphinyl guanidine compound to metal salt equivalent ratio can be greater than or equal to 0.8:1; alternatively, greater than or equal to 0.9:1; or alternatively, greater than or equal to 0.95:1; or alternatively, greater than or equal to 0.98:1. In some embodiments, the $N^2$-phosphinyl guanidine compound to metal salt equivalent ratio can be range from 0.8:1 to 5:1; alternatively, range from 0.9:1 to 4:1; or alternatively, range from 0.95:1 to 3:1; or alternatively, range from 0.98:1 to 2.5:1. In other embodiments, the $N^2$-phosphinyl guanidine compound to metal salt equivalent ratio can range from 0.9:1 to 1.25:1; alternatively, ranging from 0.95:1 to 1.20:1; alternatively, ranging from 0.975:1 to 1.15:1; or alternatively, ranging from 0.99:1 to 1.10:1. In yet other embodiments, the $N^2$-phosphinyl guanidine compound to metal salt equivalent ratio can be about 1:1.

In an embodiment, the time between the isolation and/or purification of the $N^2$-phosphinyl guanidine metal salt complex and the formation of the catalyst system may impact aspects of the oligomerization. In an embodiment, increasing the time between the isolation and/or purification of the $N^2$-phosphinyl guanidine metal salt complex and the formation of the catalyst system can increase the catalytic activity and/or productivity of the catalyst system. In an embodiment increasing the time between the isolation and/or purification of the $N^2$-phosphinyl guanidine metal salt complex and the formation of the catalyst system can increase the percentage of polymer produced by the catalyst system. Without being limited by theory, it is believed that these effects can result from the disassociation of (or alternatively, evaporation of) neutral ligand, Q, from the $N^2$-phosphinyl guanidine metal salt complex and/or from the crystal lattice of the $N^2$-phosphinyl guanidine metal salt complex.

Controlling the time between the isolation and/or purification of the $N^2$-phosphinyl guanidine metal salt complex and the formation of the catalyst system can improve the oligomerization process or polymerization process. For instance, one can increase the activity and/or productivity of the catalyst system by increasing the time between the isolation and/or purification of the $N^2$-phosphinyl guanidine metal salt complex and formation of the catalyst system. Increasing the activity and/or the productivity of the catalyst system can provide increased oligomer (or polymer) product per unit of catalyst system.

However, it may not be possible to increase the time between the isolation and/or purification of the $N^2$-phosphinyl guanidine metal salt complex and formation of the catalyst system indiscriminately. As noted herein, increasing the time between the isolation and/or purification of the $N^2$-phosphinyl guanidine metal salt complex and the formation of the catalyst system can increase the percentage of polymer produced by the catalyst system. If the polymer production of the catalyst system utilizing the $N^2$-phosphinyl guanidine metal salt complex increases too much, polymer production can adversely impact the oligomerization process. For example, polymer could adhere to the oligomerization reactor walls or cooling apparatus and cause fouling which can necessitate a reactor shut down to remove polymer. Consequently, there can be a need to balance increases in catalyst system activity and/or productivity against increased polymer production.

In an embodiment, some of the effects of increasing the time between the isolation and/or purification of the $N^2$-phosphinyl guanidine metal salt complex and the formation of the catalyst system can be reversed by adding neutral ligand to the $N^2$-phosphinyl guanidine metal salt complex. The ability to reverse some of the effects of increasing the time between the isolation and/or purification of the $N^2$-phosphinyl guanidine metal salt complex and the formation of the catalyst system can negate potentially negative effects. Non-limiting examples of negative effects of increasing the time between the isolation and/or purification of the $N^2$-phosphinyl guanidine metal salt complex and the formation of the catalyst system can include 1) prohibiting the ability to use an $N^2$-phosphinyl guanidine metal salt complex by increasing the time between the isolation and/or purification of the $N^2$-phosphinyl guanidine metal salt complex and the formation of the catalyst system to a point wherein the formed catalyst system produces an undesirable quantity of polymer and 2) reducing the need to minimize the time between preparing the $N^2$-phosphinyl guanidine metal salt complex and the preparation of the catalyst system utilizing the $N^2$-phosphinyl guanidine metal salt complex. It should also be noted that the incremental loss of the neutral ligand can impact the catalyst system and its subsequent use in an oligomerization. Consequently, while adding neutral ligand can reverse the effect of neutral ligand loss from the $N^2$-phosphinyl guanidine metal salt complex, process and/or steps can be implemented that can limit the loss of neutral ligand loss from the $N^2$-phosphinyl guanidine metal salt complex as a method to control the effects associated with the neutral ligand loss from the $N^2$-phosphinyl guanidine metal salt complex. For example, the $N^2$-phosphinyl guanidine metal salt complex can be stored in a sealed container (among other methods know to those having ordinary skill in the art) to limit loss of neutral ligand from the $N^2$-phosphinyl guanidine metal salt complex.

However, without being limited by theory, it is believed that too much neutral ligand associated with the $N^2$-phosphinyl guanidine metal salt complex can significantly reduce or eliminate the catalyst system productivity. Consequently, in some embodiments, precautions can be taken to control the amount of neutral ligand provided to the $N^2$-phosphinyl guanidine metal salt complex. Generally, addition of the neutral ligand to the $N^2$-phosphinyl guanidine metal salt complex can be accomplished by any suitable method. For example, the $N^2$-phosphinyl guanidine metal salt complex can be recrystallized from a solution containing a neutral ligand or the $N^2$-phosphinyl guanidine metal salt complex can be placed in a solvent containing a neutral ligand. Excess neutral ligand can be removed from the $N^2$-phosphinyl guanidine metal salt complex by allowing the solvent to evaporate or by increasing the time between the treatment of the $N^2$-phosphinyl guanidine metal salt complex with the neutral ligand and the formation of the catalyst system.

In an aspect, the isolated and/or purified $N^2$-phosphinyl guanidine metal salt complex can be utilized in catalyst system for an oligomerization (or polymerization) process. Consequently, in an aspect, any process of producing a catalyst system disclosed herein or any oligomerization (or polymerization) process can further comprise a step of aging the $N^2$-phosphinyl guanidine metal salt complex. In another aspect, any process of producing a catalyst system disclosed herein or any oligomerization (or polymerization) process can further comprise a step of treating the $N^2$-phosphinyl guanidine metal salt complex with a neutral ligand; or alternatively, 1) treating the $N^2$-phosphinyl guanidine metal salt complex with a neutral ligand and 2) allowing the treated $N^2$-phosphinyl guanidine metal salt complex to age. In another aspect, any process of producing a catalyst system disclosed herein or any oligomerization (or polymerization) process can further comprise a step of treating an aged $N^2$-phosphinyl guanidine metal salt complex with a neutral ligand; or alternatively, 1) treating the $N^2$-phosphinyl guanidine metal salt complex with a neutral ligand and 2) allowing the treated $N^2$-phosphinyl guanidine metal salt complex to age.

In an aspect, the activity of any oligomerization (or polymerization) process described herein (using any catalyst system described herein comprising any $N^2$-phosphinyl guanidine metal salt complex described herein) can be controlled by aging the $N^2$-phosphinyl guanidine metal salt complex. In an aspect, the activity of any oligomerization (or polymerization) process described herein (using any catalyst system as described herein comprising any $N^2$-phosphinyl guanidine metal salt complex described herein) can be controlled by treating the $N^2$-phosphinyl guanidine metal salt complex with a neutral ligand; or alternatively, 1) treating the $N^2$-phosphinyl guanidine metal salt complex with a neutral ligand and 2) allowing the treated $N^2$-phosphinyl guanidine metal salt complex to age. In an aspect, the activity of any oligomerization (or polymerization) process described herein (using any catalyst system described herein comprising any $N^2$-phosphinyl guanidine metal salt complex described herein) can be controlled by treating an aged $N^2$-phosphinyl guanidine metal salt complex with a neutral ligand; or alternatively, 1) treating the $N^2$-phosphinyl guanidine metal salt complex with a neutral ligand and 2) allowing the treated $N^2$-phosphinyl guanidine metal salt complex to age.

The catalytic activity of any catalyst system described herein comprising any $N^2$-phosphinyl guanidine metal salt complex described herein in an oligomerization (or polymerization) process can be defined as the grams of olefin oligomer (or polymer) product (or liquid olefin oligomer/polymer product, or any other defined portion of the oligomerization/polymerization product) produced per gram of metal of the metal salt in the $N^2$-phosphinyl guanidine metal salt complex utilized. In an embodiment, the catalyst system activity of any catalyst system described herein comprising any $N^2$-phosphinyl guanidine metal salt complex described herein can be increased by utilizing an aged $N^2$-phosphinyl guanidine metal salt complex. This activity increase can be described as a percentage increase in the catalyst system activity and can be related to the activity of the catalyst system prepared using a fresh $N^2$-phosphinyl guanidine metal salt complex, $a_0$. Generally, a fresh $N^2$-phosphinyl guanidine metal salt complex is one which has been utilized to prepare a catalyst system within 7 days of its isolation and/or purification. It should be noted, a fresh $N^2$-phosphinyl guanidine metal salt complex does not contain excess neutral ligand which can give an inactive catalyst system (i.e. a catalyst system that produces less than 500 grams oligomer/polymer per gram metal of metal salt in the $N^2$-phosphinyl guanidine metal salt complex). The activity of the catalyst system based upon an aged $N^2$-phosphinyl guanidine metal salt complex can be denoted $a_x$.

In an embodiment, the $N^2$-phosphinyl guanidine metal salt complex can be aged for a maximum of 730 days; alternatively, 550 days; alternatively, 450 days; alternatively, 365 days; alternatively, 330 days; alternatively, 300 days; alternatively, 270 days; alternatively, 240 days; alternatively, 210 days; or alternatively, 180 days. In some embodiments, the $N^2$-phosphinyl guanidine metal salt complex can be aged for a minimum of 1 day; alternatively, 3 days; alternatively, 7 days; alternatively, 14 days; alternatively, 28 days. In other embodiments, the $N^2$-phosphinyl guanidine metal salt complex can be aged from any minimum aging time provided herein to any maximum aging time provided herein. In a non-limiting embodiment, the $N^2$-phosphinyl guanidine metal salt complex can be aged can be aged from 1 day to 730 days; alternatively, from 3 days to 550 days; alternatively, from 3 days to 330 days; or alternatively, from 7 days to 180 days. Other aging times are readily apparent from the present disclosure.

In an embodiment, aging the $N^2$-phosphinyl guanidine metal salt complex (for any time period described herein) can increase the activity of any catalyst system described herein utilizing any $N^2$-phosphinyl guanidine metal salt complex described herein by a minimum of 10%; alternatively, by at least 20%; alternatively, by at least 30%; alternatively, by at least 40%; or alternatively, by at least 50%. In other embodiments, aging the $N^2$-phosphinyl guanidine metal salt complex (for any time period described herein) can increase the activity of any catalyst system described herein utilizing any $N^2$-phosphinyl guanidine metal salt complex described herein by a maximum of 1500%; alternatively, 1000%; alternatively, 750%; alternatively, 600%; or alternatively, 500% In some embodiments, aging the $N^2$-phosphinyl guanidine metal salt complex (for any time period described herein) can increase the activity of any catalyst system described herein utilizing any $N^2$-phosphinyl guanidine metal salt complex described herein from any minimum value described herein to any maximum value described herein. In a non-limiting example, aging the $N^2$-phosphinyl guanidine metal salt complex (for any time period described herein) can increase the activity of any catalyst system described herein utilizing any $N^2$-phosphinyl guanidine metal salt complex described herein from 10% to 1500%; alternatively, from 20% to 1000%; alternatively, from 30% to 750%; alternatively, from 40% to 600%; or alternatively, from 50% to 500%. Other catalyst system activity ranges are readily apparent from the present disclosure.

In an embodiment, aging the $N^2$-phosphinyl guanidine metal salt complex (for any time period described herein) for any catalyst system described herein utilizing any $N^2$-phosphinyl guanidine metal salt complex described herein can provide an oligomerization catalyst system which can produce any defined percentage of polymer described herein. In an embodiment, aging the $N^2$-phosphinyl guanidine metal salt complex (for any time period described herein) for any catalyst system described herein utilizing any $N^2$-phosphinyl guanidine metal salt complex described herein can provide an oligomerization catalyst system which can produce less than 5 weight percent (wt. %) polymer; alternatively, equal to or less than 2 wt. % polymer; alternatively, equal to or less than 1.5 wt. % polymer, alternatively, equal to or less than 1 wt. % polymer r; alternatively, equal to or less than 0.75 wt. % polymer, alternatively, equal to or less than 2 wt. % polymer; alternatively, equal to or less than 0.5 wt. % polymer; alternatively, equal to or less than 0.4 wt. % polymer; alternatively, equal to or less than 0.3 wt. % polymer; alternatively, equal to or less than wt. % polymer; or alternatively, equal to or less than 0.1 wt. % polymer. Generally, the basis for weight percent polymer is based upon all oligomer products (alternatively, trimer product, tetramer product, or trimer and tetramer products) of the olefin oligomerization (olefin trimerization, olefin tetramerization, or olefin trimerization and tetramerization).

In some embodiments, any oligomerization catalyst system described herein utilizing an aged $N^2$-phosphinyl guanidine metal salt complex can have a combination of any increased activity described herein and any amount of polymer described herein. The oligomerization catalyst system described herein utilizing an aged $N^2$-phosphinyl guanidine metal salt complex can further be described utilizing, individually or in any combination, any other oligomerization catalyst system feature or oligomerization product feature described herein.

In an embodiment, a calibration curve can be produced depicting catalytic activity and or polymer product of any catalyst system described herein comprising any $N^2$-phosphinyl guanidine metal salt complex described herein in response to aging the phosphinyl guanidine metal salt complex. In some embodiments, a calibration curve (for catalyst activity and/or polymer production) can be depicted as a function of the period of $N^2$-phosphinyl guanidine metal salt complex age in order to derive a predictive equation. The calibration curve or predictive equation relating catalyst system activity and/or polymer production in response to $N^2$-phosphinyl guanidine metal salt complex age can be utilized to adjust one or more user and/or process parameters based upon the interpolation or extrapolation of the calibration curve and/or the predictive equation. It is contemplated that in some aspects, the extent to which $a_x$ increases with respect to $a_0$ can fall outside the instantly disclosed ranges and can be larger than would be expected based on the presently disclosed values depending on the conditions under which the $N^2$-phosphinyl guanidine metal salt complex is aged. For example, the $N^2$-phosphinyl guanidine metal salt complex can be subjected to aging for time periods that are 5 to 10 times longer than those presently recited or under conditions of elevated temperature and/or reduced pressure. The effects of aging the $N^2$-phosphinyl guanidine metal salt complex under such conditions can be subject to the herein mentioned analysis to provide predictive information that can lead one to conditions under which aging the $N^2$-phosphinyl guanidine metal salt complex can increase catalyst system activity using an aged $N^2$-phosphinyl guanidine metal salt complexes outside of the recited numerical ranges. It is contemplated that given the benefits of this disclosure and using routine experimentation one having ordinary skill in the art can modify the methodologies disclosed herein to alter the catalytic system activity using an aged $N^2$-phosphinyl guanidine metal salt complexes to a desired value or range. Such modifications fall within the scope of this disclosure.

In an embodiment, contacting of the $N^2$-phosphinyl guanidine metal salt complex (aged or otherwise) with a neutral ligand can be carried out using any suitable molar ratio of neutral ligand to $N^2$-phosphinyl guanidine metal salt. In an embodiment, the molar ratio of neutral ligand to $N^2$-phosphinyl guanidine metal salt complex can be at least 0.2:1; alternatively, at least 0.3:1; alternatively, at least 0.4:1; or alternatively, at least 0.5:1. In an embodiment, the molar ratio of neutral ligand to $N^2$-phosphinyl guanidine metal salt complex can be from 0.2:1 to 10,000:1; alternatively, 0.3:1 to 8,000:1; alternatively, from 0.4:1 to 6,000:1; or alternatively, from 0.5:1 to 5,000:1. In an embodiment, the contact of the $N^2$-phosphinyl guanidine metal salt complex can occur in a solvent consisting essentially of the neutral ligand; or alternatively, in a solvent comprising, or consisting essentially of, the neutral ligand and a non-complexing solvent.

When the $N^2$-phosphinyl guanidine metal salt complex is contacted with a solvent consisting essentially of the neutral ligand, the molar ratio of neutral ligand to $N^2$-phosphinyl guanidine metal salt can be any molar ratio of neutral ligand to $N^2$-phosphinyl guanidine metal salt disclosed herein. In other embodiments wherein the $N^2$-phosphinyl guanidine metal salt complex is contacted with a solvent consisting essentially of the neutral ligand, the molar ratio of neutral ligand to $N^2$-phosphinyl guanidine metal salt can be any molar ratio of neutral ligand to $N^2$-phosphinyl guanidine metal salt can be at least 5:1; alternatively, at least 7.5:1; alternatively, at least 10:1; alternatively, at least 10:1; alternatively, at least 15:1; alternatively, 5:1; alternatively, range from 7.5:1 to 10,000:1; alternatively, range from 10:1 to 8,000:1; alternatively, range from 10:1 to 6,000:1; or alternatively, range from 15:1 to 5,000:1.

When the $N^2$-phosphinyl guanidine metal salt complex is contacted with a solvent comprising, or consisting essentially of, the neutral ligand and a non-complexing solvent, the molar ratio of neutral ligand to $N^2$-phosphinyl guanidine metal salt can be any molar ratio of neutral ligand to $N^2$-phosphinyl guanidine metal salt disclosed herein. In other embodiments wherein the $N^2$-phosphinyl guanidine metal salt complex is contacted with a solvent comprising, or consisting essentially of, the neutral ligand and a non-complexing solvent, the molar ratio of neutral ligand to $N^2$-phosphinyl guanidine metal salt can be less than or equal to 500:1; less than or equal to 300:1; less than or equal to 200:1; alternatively, less than or equal to 100:1; alternatively range from 0.2:1 to 500:1; alternatively, range from 0.3:1 to 300:1; alternatively, range from 0.4:1 to 200:1; or alternatively, from 0.5:1 to 100:1. In some embodiments, wherein the $N^2$-phosphinyl guanidine metal salt complex is contacted with a solvent comprising, or consisting essentially of, the neutral ligand and a non-complexing solvent, the volumetric ratio of neutral ligand to non-complexing solvent can range from 1:1 to 10,000:1; alternatively, range from 5:1 to 8,000:1; alternatively, range from 7.5:1 to 6,000:1; or alternatively, range from 10:1 to 5,000:1.

In an embodiment, the neutral ligand can be any neutral ligand disclosed herein. In some embodiments, the neutral ligand utilized to treat the $N^2$-phosphinyl guanidine metal salt complex can be the same as the neutral ligand of the $N^2$-phosphinyl guanidine metal salt complex; or alternatively, the neutral ligand utilized to treat the $N^2$-phosphinyl guanidine metal salt complex can be different from the neutral ligand of the $N^2$-phosphinyl guanidine metal salt complex. In an embodiment, the non-complexing solvent utilized in an embodiment comprising, or consisting essentially of, a neutral ligand and a non-complexing solvent can be a hydrocarbon or a halogenated hydrocarbon; alternatively, a hydrocarbon or a halogenated hydrocarbon. Hydrocarbon and halogenated hydrocarbon solvents (general and specific) are disclosed herein and can be utilized, without limitation, to further describe any aspect and/or embodiment utilizing a solvent comprising, or consisting essentially of, a neutral ligand and a non-complexing solvent.

In an embodiment, the $N^2$-phosphinyl guanidine metal salt complex can be aged (whether or not it has been treated with a neutral ligand) utilizing any suitable methodology. In some embodiments, the $N^2$-phosphinyl guanidine metal salt complex can be aged (whether or not it has been treated with a neutral ligand) at ambient temperature (15-35° C.—no applied external heat source); or alternatively, at ambient temperature under an inert atmosphere. In other embodiments, the $N^2$-phosphinyl guanidine metal salt complex can be aged (whether or not it has been treated with a neutral ligand) with gentle heating (e.g., at a temperature ranging from 25° C. to 50° C.); alternatively, under reduced pressure; alternatively, at ambient temperature under reduced pressure; or alternatively, with gentle heating under reduced pressure.

In an embodiment, the aged $N^2$-phosphinyl guanidine metal salt complex, the neutral ligand treated $N^2$-phosphinyl guanidine metal salt complex, or the neutral ligand treated and aged $N^2$-phosphinyl guanidine metal salt complex can be utilized in a catalyst system, utilized in a process to prepare a catalyst system, and/or an oligomerization (or polymerization) process. Generally, the steps of aging the $N^2$-phosphinyl guanidine metal salt complex, the steps of treating the $N^2$-phosphinyl guanidine metal salt complex with a neutral ligand, and/or treating the $N^2$-phosphinyl guanidine metal salt complex with a neutral ligand and aging the neutral ligand treated the $N^2$-phosphinyl guanidine metal salt complex can be utilized, without limitation, to further describe the catalyst system, the process of preparing the catalyst system, and/or the oligomerization (or polymerization) process.

In an aspect, the step(s) for preparing the $N^2$-phosphinyl guanidine compound can be incorporated into the preparation of the $N^2$-phosphinyl guanidine metal salt complex, process of preparing the catalyst system, and/or an oligomerization (or polymerization) process. When the steps are combined, appropriate step identifiers (e.g., 1), 2), etc. . . . , a), b), etc. . . . , or i), ii), etc. . . . ) and compound/solvent identifiers (e.g., first, second, etc. . . . ) can be added to indicate individual and/or different steps/compounds/solvents utilized within the preparation of the guanidine compound, process of preparing the catalyst system, and/or an oligomerization (or polymerization) process without detracting from the general disclosure.

In an aspect, the present disclosure relates to an oligomerization process; or alternatively, a polymerization process. In an embodiment, the oligomerization process can comprise: a) contacting an olefin and a catalyst system (or catalyst system composition); and b) forming an oligomer product. In some embodiments, the oligomerization process can comprise, a) contacting an olefin, hydrogen, and a catalyst system (or catalyst system composition); and b) forming an oligomer product. In an embodiment, the polymerization process can comprise: a) contacting an olefin and a catalyst system (or catalyst system composition); and b) forming a polymer product. In some embodiments, the polymerization process can comprise a) contacting an olefin, hydrogen, and a catalyst system (or catalyst system composition) and b) forming a polymer product. The catalyst system (or catalyst system composition), olefin, and features of the oligomer product or polymer product are independently described herein and can be utilized, without limitation to further describe the oligomerization process or polymerization process. In an embodiment, the catalyst system can be prepared in a first solvent. In an embodiment, the olefin, catalyst system (or catalyst system composition), and optionally hydrogen, can be contacted in a second solvent. Generally, a solvent in which the catalyst system can be prepared and the solvent in which the olefin and catalyst system (or catalyst system compositions) can be contacted can be the same; or alternatively, can be different.

In an embodiment, the oligomerization process can comprise: a) forming a catalyst system mixture comprising an $N^2$-phosphinyl guanidine metal salt complex and a metal alkyl compound; b) contacting the catalyst system mixture with an olefin; and c) forming an oligomer product. In an embodiment, the polymerization process can comprise: a) forming a catalyst system mixture comprising an $N^2$-phosphinyl guanidine metal salt complex and a metal alkyl compound; b) contacting the catalyst system mixture with an olefin; and c) forming polymer product. In some embodiments, the step of contacting the catalyst system mixture with the olefin can be a step of contacting the catalyst system mixture with an olefin and hydrogen. In some embodiments, the catalyst system mixture can further comprise a solvent (e.g., a first solvent). In some embodiments, the catalyst system mixture and olefin can be contacted in a solvent (e.g., a second solvent when the catalyst system is prepared in a solvent). In an embodiment, the oligomerization process can comprise: a) forming a catalyst system mixture comprising, or consisting essentially of, an $N^2$-phosphinyl guanidine metal salt complex, a metal alkyl compound, and a first solvent; b) contacting the catalyst system mixture with an olefin and a second solvent; and c) forming an oligomer product. In an embodiment, the polymerization process can comprise: a) forming a catalyst system mixture comprising, or consisting essentially of, an $N^2$-phosphinyl guanidine metal salt complex, a metal alkyl compound, and a first solvent; b) contacting the catalyst system mixture with an olefin and a second solvent; and c) forming polymer product. In some embodiments, the step of contacting the catalyst system mixture with the olefin and the second solvent can be a step of contacting the catalyst system mixture with an olefin, a second solvent, and hydrogen. The $N^2$-phosphinyl guanidine metal salt complex, metal alkyl compound, olefin, solvents, and features of the oligomer product or polymer product are independently described herein (among other catalyst system and oligomerization or polymerization features) and can be utilized, without limitation to further describe the oligomerization process or polymerization process. In some embodiments, the first and second solvent can be the same; or alternatively, the first and second solvent can be different. In some embodiments, the metal alkyl compound can be, comprise, or consist essentially of, an aluminoxane. Ratios for the metal of the $N^2$-phosphinyl guanidine metal salt complex to the metal of the metal alkyl compound are independently provided herein (among other catalyst system and oligomerization or polymerization features) and can be utilized without limitation to further describe the oligomerization process or polymerization process.

In an embodiment, the oligomerization process can comprise: a) forming a composition comprising an $N^2$-phosphinyl guanidine metal salt complex; b) forming a mixture comprising an olefin and a metal alkyl compound; c) contacting the composition of step a) and the mixture of step b); and d) forming an oligomer product. In an embodiment, the polymerization process can comprise: a) forming a composition comprising a the $N^2$-phosphinyl guanidine metal salt complex; b) forming a mixture comprising an olefin and a metal alkyl compound; c) contacting the composition of step a) and the mixture of step b); and d) forming a polymer product. In some embodiments, the mixture comprising the olefin and the metal alkyl compound can further comprise hydrogen. In some embodiments the composition comprising the $N^2$-phosphinyl guanidine metal salt complex can further comprise a solvent (e.g., a first solvent). In some embodiments, the mixture comprising an olefin, a metal alkyl compound, and optionally hydrogen, can further comprise a solvent (e.g., a second solvent). In an embodiment, the oligomerization process can comprise: a) forming a composition comprising, or consisting essentially of, an $N^2$-phosphinyl guanidine metal salt complex and a first solvent; b) forming a mixture comprising an olefin, a metal alkyl compound, hydrogen, and a second solvent; c) contacting the composition of step a) and the mixture of step b); and d) forming an oligomer product. In an embodiment, the polymerization process can comprise: a) forming a composition comprising, or consisting essentially of, a the $N^2$-phosphinyl guanidine metal salt complex and a first solvent; b) forming a mixture comprising an olefin, a metal alkyl compound, hydrogen, and a second solvent; c) contacting the composition of step a) and the mixture of step b); and d) forming a polymer product. In an embodiment, the solvents used in the composition comprising the $N^2$-phosphinyl guanidine metal salt complex and the mixture comprising the olefin and the metal alkyl compound (and optionally hydrogen) can be the same; or alternatively, can be different. The $N^2$-phosphinyl guanidine metal salt complex, metal alkyl compound, olefin, solvents, and features of the oligomer product or polymer product (among other catalyst system and oligomerization or polymerization features) are independently described herein and can be utilized, without limitation to further describe the oligomerization process or polymerization process. In some embodiments, the metal alkyl compound can be, comprise, or consist essentially of an aluminoxane. Ratios for the metal of the $N^2$-phosphinyl guanidine metal salt complex to the metal of the metal alkyl compound are independently provided herein (among other catalyst system and oligomerization process or polymerization process features) and can be utilized without limitation to further describe the oligomerization process or polymerization process.

In an embodiment, the oligomerization process can comprise: a) forming a catalyst system mixture comprising an $N^2$-phosphinyl guanidine compound, a metal salt, and a metal alkyl compound; b) contacting the catalyst system mixture with an olefin; and c) forming an oligomer product. In an embodiment, the polymerization process can comprise: a) forming a catalyst system mixture comprising an $N^2$-phosphinyl guanidine compound, a metal salt, and a metal alkyl compound; b) contacting the catalyst system mixture with an olefin; and c) forming a polymer product. In some embodiments, the step of contacting the catalyst system mixture with the olefin can be a step of contacting the catalyst system mixture with an olefin and hydrogen. In some embodiments, the catalyst system mixture can further comprise a solvent (e.g., a first solvent). In some embodiments, the catalyst system mixture and olefin can be contacted in a solvent (e.g., a second solvent when the catalyst system is prepared in a solvent). In an embodiment, the oligomerization process can comprise: a) forming a catalyst system mixture comprising, or consisting essentially of, an $N^2$-phosphinyl guanidine compound, a metal salt, a metal alkyl compound, and a first solvent; b) contacting the catalyst system mixture with an olefin and a second solvent; and c) forming an oligomer product. In an embodiment, the polymerization process can comprise: a) forming a catalyst system mixture comprising, or consisting essentially of an $N^2$-phosphinyl guanidine compound, a metal salt, a metal alkyl compound, and a first solvent; b) contacting the catalyst system mixture with an olefin and a second solvent; and c) forming a polymer product. In some embodiments, the step of contacting the catalyst mixture with the olefin and the second solvent can be a step of contacting the catalyst system mixture with an olefin, a second solvent, and hydrogen. In some embodiments, the first and second solvent can be the same; or alternatively, the first and second can be different. The $N^2$-phosphinyl guanidine compound, metal salt, metal alkyl compound, olefin, solvents, and features of the oligomer product or polymer product are independently described herein (among other catalyst system and oligomerization or features) and can be utilized, without limitation to further describe the oligomerization process or polymerization process. In some embodiments, the first and second solvent can be the same; or alternatively, the first and second solvent can be different. In some embodiments, the metal alkyl compound can be, comprise, or consist essentially of, an aluminoxane. The $N^2$-phosphinyl guanidine compound, metal salt, metal alkyl compound, olefin, solvents, and features of the oligomer product or polymer product are independently described herein (among other catalyst system and oligomerization or polymerization features) and can be utilized, without limitation to further describe the oligomerization process or polymerization process. Ratios for the $N^2$-phosphinyl guanidine compound to metal salt and ratios for the metal of the metal alkyl compound to metal of the metal salt are independently provided herein (among other catalyst system and oligomerization process or polymerization process features) and can be utilized without limitation to further describe the oligomerization process or polymerization process.

In an embodiment, the oligomerization process can comprise: a) forming a composition comprising an $N^2$-phosphinyl guanidine compound and a metal salt; b) forming a mixture comprising an olefin and a metal alkyl compound; c) contacting the composition formed in step a) and the mixture formed in step b); and d) forming an oligomer product. In an embodiment, the polymerization process can comprise: a) forming a mixture comprising an $N^2$-phosphinyl guanidine compound and a metal salt; b) forming a mixture comprising an olefin and a metal alkyl compound; c) contacting the composition formed in step a) and the mixture formed in step b); and d) forming a polymer product. In some embodiments, the mixture comprising an olefin and a metal alkyl compound can further comprise hydrogen. In some embodiments, the composition of step a) can further comprise a solvent (e.g., a first solvent). In some embodiments, the mixture of step b) can further comprise a solvent (e.g., a second solvent when the catalyst system is prepared in a solvent). In an embodiment, the oligomerization process can comprise: a) forming a composition comprising, or consisting essentially of, an $N^2$-phosphinyl guanidine compound, a metal salt, and a first solvent; b) forming a mixture comprising an olefin, a metal alkyl compound, and a second solvent; c) contacting the composition formed in step a) and the mixture formed in step b); and d) forming an oligomer product. In an embodiment, the polymerization process can comprise: a) forming a composition comprising, or consisting essentially of, an $N^2$-phosphinyl guanidine compound, a metal salt, and a first solvent; b) forming a mixture comprising an olefin, a metal alkyl compound, and a second solvent; c) contacting the composition formed in step a) and the mixture formed in step b); and d) forming a polymer product. In some embodiments, the first and second solvent can be the same; or alternatively, the first and second solvent can be different. The $N^2$-phosphinyl guanidine compound, metal salt, metal alkyl compound, olefin, solvents, and features of the oligomer product or polymer product (among other catalyst system and oligomerization or polymerization features) are independently described herein and can be utilized, without limitation to further describe the oligomerization process or polymerization process. In some embodiments, the metal alkyl compound can be, comprise, or consist essentially of, an aluminoxane. Ratios for the $N^2$-phosphinyl guanidine compound to metal salt and ratios for the metal of the metal alkyl compound to metal of the metal salt are independently provided herein (among other catalyst system and oligomerization process or polymerization process features) and can be utilized without limitation to further describe the oligomerization process or polymerization process.

In an embodiment, a solvent utilized with the catalyst system, a mixture comprising an $N^2$-phosphinyl guanidine metal salt complex, a mixture comprising an $N^2$-phosphinyl guanidine metal salt complex and a metal alkyl compound, a composition comprising an $N^2$-phosphinyl guanidine compound and a metal salt, or a composition comprising an $N^2$-phosphinyl guanidine compound, a metal salt, and a metal alkyl compound can be a hydrocarbon solvent, a halogenated hydrocarbon solvent, or any combination thereof; alternatively, a hydrocarbon solvent; or alternatively, a halogenated hydrocarbon solvent. In some embodiments, a solvent utilized with a mixture comprising an $N^2$-phosphinyl guanidine metal salt complex, a mixture comprising an $N^2$-phosphinyl guanidine metal salt complex and a metal alkyl compound, a composition comprising an $N^2$-phosphinyl guanidine compound and a metal salt, or a composition comprising an $N^2$-phosphinyl guanidine compound, a metal salt, and a metal alkyl compound can be an aliphatic hydrocarbon solvent, a halogenated aliphatic hydrocarbon solvent, an aromatic hydrocarbon solvent, a halogenated aromatic solvent, or any combination thereof; alternatively, an aliphatic hydrocarbon solvent, a halogenated aliphatic hydrocarbon solvent, or any combination thereof; alternatively, an aromatic hydrocarbon solvent, a halogenated aromatic solvent, or any combination thereof; alternatively, an aliphatic hydrocarbon solvent; alternatively, a halogenated aliphatic hydrocarbon solvent; alternatively, an aromatic hydrocarbon solvent; or alternatively, a halogenated aromatic solvent. General and specific hydrocarbon solvents, halogenated hydrocarbon solvents, aliphatic hydrocarbon solvents, halogenated aliphatic hydrocarbon solvents, aromatic hydrocarbon solvents, and halogenated aromatic solvents are described herein and can be utilized without limitation to further describe the oligomerization process(es) or polymerization process(es) described herein.

In an embodiment, a solvent utilized in any mixture including the olefin or utilized to form the oligomer product or polymer product can be hydrocarbon solvent, a halogenated hydrocarbon solvent, or any combination thereof; alternatively, a hydrocarbon solvent; or alternatively, a halogenated hydrocarbon solvent. In some embodiments, a solvent utilized in any mixture including the olefin or utilized to form the oligomer product or polymer product can be an aliphatic hydrocarbon solvent, a halogenated aliphatic hydrocarbon solvent, an aromatic hydrocarbon solvent, a halogenated aromatic solvent, or any combination thereof; alternatively, an aliphatic hydrocarbon solvent, a halogenated aliphatic hydrocarbon solvent, or any combination thereof; alternatively, an aromatic hydrocarbon solvent, a halogenated aromatic solvent, or any combination thereof; alternatively, an aliphatic hydrocarbon solvent; alternatively, a halogenated aliphatic hydrocarbon solvent; alternatively, an aromatic hydrocarbon solvent; or alternatively, a halogenated aromatic solvent. General and specific hydrocarbon solvents, halogenated hydrocarbon solvents, aliphatic hydrocarbon solvents, halogenated aliphatic hydrocarbon solvents, aromatic hydrocarbon solvents, and halogenated aromatic solvents are described herein and can be utilized without limitation to further describe the oligomerization process or polymerization process described herein.

In some embodiments, the solvent utilized with the catalyst system, a mixture comprising an $N^2$-phosphinyl guanidine metal salt complex, a mixture comprising an $N^2$-phosphinyl guanidine metal salt complex and a metal alkyl, a composition comprising an $N^2$-phosphinyl guanidine compound and a metal salt, or a composition comprising an $N^2$-phosphinyl guanidine compound, a metal salt, and a metal alkyl and the solvent utilized in any mixture including the olefin or utilized to form the oligomer product or polymer product can be the same; or alternatively can be different. In an embodiment, the solvent utilized with the catalyst system, a mixture comprising an $N^2$-phosphinyl guanidine metal salt complex, a mixture comprising an $N^2$-phosphinyl guanidine metal salt complex and a metal alkyl, a composition comprising an $N^2$-phosphinyl guanidine compound and a metal salt, or a composition comprising an $N^2$-phosphinyl guanidine compound, a metal salt, and a metal alkyl and the solvent utilized in any mixture including the olefin or utilized to form the oligomer product or polymer product has a boiling point which allows for its easy separation (e.g., by distillation) from the oligomer product or polymer product.

Generally, the olefin which can be oligomerized or polymerized can comprise, or consist essentially of, a $C_2$ to $C_{30}$ olefin; alternatively, a $C_2$ to $C_{16}$ olefin; or alternatively, a $C_2$ to $C_{10}$ olefin. In an embodiment, the olefin can be an alpha olefin; alternatively, a linear alpha olefin; or alternatively a normal alpha olefin. In an embodiment, the olefin can comprise, or consist essentially of, ethylene, propylene, or a combination thereof; alternatively ethylene; or alternatively, propylene. When the olefin consists essentially of ethylene, the oligomerization process can be an ethylene oligomerization process or an ethylene polymerization process.

In an aspect, the oligomerization process can be a trimerization process; alternatively, a tetramerization process; or alternatively, a trimerization and tetramerization process. When the olefin is ethylene, the oligomerization process can be an ethylene trimerization process; alternatively, an ethylene tetramerization process; or alternatively, an ethylene trimerization and tetramerization process. When the process is an ethylene trimerization process, the oligomer product can comprise hexene; or alternatively, can comprise 1-hexene. When the process is an ethylene tetramerization process, the oligomer product can comprise octene; or alternatively, can comprise 1-octene. When the process is an ethylene trimerization and tetramerization process, the oligomer product can comprise hexene and octene; or can comprise 1-hexene and 1-octene.

Unless otherwise specified, the terms contacted, combined, and "in the presence of" refer to any addition sequence, order, or concentration for contacting or combining two or more components of the oligomerization process. Combining or contacting of oligomerization components, according to the various methods described herein can occur in one or more contact zones under suitable contact conditions such as temperature, pressure, contact time, flow rates, etc. . . . The contact zone can be disposed in a vessel (e.g., a storage tank, tote, container, mixing vessel, reactor, etc.), a length of pipe (e.g., a tee, inlet, injection port, or header for combining component feed lines into a common line), or any other suitable apparatus for bringing the components into contact. The processes can be carried out in a batch or continuous process as is suitable for a given embodiment.

In an embodiment, the oligomerization process or polymerization process can be a continuous process carried out in one or more reactors. In some embodiments, the continuous oligomerization reactor or polymerization reactor can comprise a loop reactor, a tubular reactor, a continuous stirred tank reactor (CSTR), or combinations thereof. In other embodiments, the continuous oligomerization reactor or polymerization reactor can be a loop reactor; alternatively, a tubular reactor; or alternatively, a continuous stirred tank reactor (CSTR). In other embodiments, the continuous oligomerization reactor or polymerization reactor can be employed in the form of different types of continuous reactors in combination, and in various arrangements.

In an embodiment, the oligomer product or polymer product can be formed under suitable oligomerization reaction conditions or polymerization reaction conditions such as temperature, pressure, and/or time. Temperatures, reaction pressures, and/or reaction times for forming the oligomer product or polymer product can be impacted by a number of factors such as the metal salt complex stability, metal salt complex activity, cocatalyst identity, cocatalyst activity, desired product distribution, and/or desired product purity, among other factors.

Generally, the oligomer product or polymer product can be formed using any $N^2$-phosphinyl guanidine compound, metal salt, or $N^2$-phosphinyl guanidine metal salt complex concentration that can form the desired oligomer product or polymer product (alternatively, oligomer or polymer). In an embodiment, the concentration of the $N^2$-phosphinyl guanidine compound, metal salt, or $N^2$-phosphinyl guanidine metal salt complex can be at least $1\times10^{-6}$ equivalents/liter; alternatively, at least $1\times10^{-5}$ equivalents/liter; or alternatively, at least $5\times10^{-4}$ equivalents/liter. In other embodiments, the concentration of the $N^2$-phosphinyl guanidine metal salt complex can range from $1\times10^{-6}$ equivalents/liter to 1 equivalents/liter; alternatively, range from $1\times10^{-5}$ equivalents/liter to $5\times10^{-1}$ equivalents/liter; or alternatively, range from $5\times10^{-4}$ equivalents/liter to $1\times10^{-1}$ equivalents/liter.

Generally, the oligomer product or polymer product can be formed at any pressure that can facilitate the oligomerization or polymerization of the olefin. In an embodiment, the pressure at which the oligomer product or polymer product is formed can be any pressure that produces the desired oligomer product or polymer product (alternatively, oligomer or polymer). In some embodiments, the oligomer product or polymer product can be formed at pressure can be greater than or equal to 0 psig (0 KPa); alternatively, greater than or equal to 50 psig (344 KPa); alternatively, greater than or equal to 100 psig (689 KPa); or alternatively, greater than or equal to 150 psig (1.0 MPa). In other embodiments, the oligomer product or polymer product can be formed at a pressure ranging from 0 psig (0 KPa) to 5,000 psig (34.5 MPa); alternatively, 50 psig (344 KPa) to 4,000 psig (27.6 MPa); alternatively, 100 psig (689 KPa) to 3,000 psig (20.9 MPa); or alternatively, 150 psig (1.0 MPa) to 2,000 psig (13.8 MPa). In embodiments wherein the monomer is a gas (e.g., ethylene), the oligomer product or polymer product can be formed under a monomer gas pressure. When the oligomerization or polymerization produces an ethylene oligomer product or polyethylene, the pressure can be the ethylene pressure. In some embodiments, the ethylene pressure can be greater than or equal to 0 psig (0 KPa); alternatively, greater than or equal to 50 psig (344 KPa); alternatively, greater than or equal to 100 psig (689 KPa); or alternatively, greater than or equal to 150 psig (1.0 MPa). In other embodiments, the ethylene pressure can range from 0 psig (0 KPa) to 5,000 psig (34.5 MPa); alternatively, 50 psig (344 KPa) to 4,000 psig (27.6 MPa); alternatively, 100 psig (689 KPa) to 3,000 psig (20.9 MPa); or alternatively, 150 psig (1.0 MPa) to 2,000 psig (13.8 MPa). In some cases when ethylene is the monomer, inert gases (and/or other gases; e.g., hydrogen) can form a portion of the total pressure. In the cases where inert gases (and/or other gases; e.g., hydrogen) form a portion of the pressure, the previously stated ethylene pressures can be the applicable ethylene partial pressures at which the oligomer product or the polymer product can be formed. In the situation where the monomer provides all or a portion of the oligomerization pressure or polymerization pressure, the reaction system pressure can decrease as the gaseous monomer is consumed. In this situation, additional gaseous monomer and/or inert gas can be added to maintain a desired pressure. In some embodiments, additional gaseous monomer can be added at a set rate (e.g., for a continuous flow reactor), or at different rates (e.g., to maintain a pressure in a batch reactor). In other embodiments, the oligomerization pressure or polymerization pressure can be allowed to decrease without adding any additional gaseous monomer and/or inert gas.

In embodiments wherein hydrogen is utilized, hydrogen can be added in any amount that can produce a desired effect. In some embodiments, the hydrogen partial pressure can be greater than or equal to 1 psig (kPa); alternatively, greater than or equal to 5 psig (34 kPa); alternatively, greater than or equal to 10 psig (69 kPa); or alternatively, greater than or equal to 15 psig (100 kPa). In other embodiments, the hydrogen partial pressure can range from 1 psig (6.9 kPa) to 500 psig (3.5 MPa); alternatively, 5 psig (34 kPa) to 400 psig (2.8 MPa); alternatively, 10 psig (69 kPa) to 300 psig (2.1 MPa); or alternatively, 15 psig (100 kPa) to 200 psig (1.4 MPa).

In an embodiment, a condition to form an oligomer product or polymer product can include a temperature at which the oligomer product or polymer product can be formed. Generally, oligomer product or polymer product can be formed at any temperature which can form the desired oligomer product or polymer product. In an embodiment, the temperature at which the oligomer product or polymer product is formed can be at least 0° C.; alternatively, at least 10° C.; alternatively, at least 20° C.; alternatively, at least 30° C.; alternatively, at least 40° C.; alternatively, at least 50° C.; alternatively, at least 50° C.; alternatively, at least 70° C.; alternatively, at least 80° C.; or alternatively, at least 90° C. In some embodiments, the maximum oligomerization temperature or polymerization temperature at which the oligomer product or polymer product is formed can be 200° C.; alternatively, 180° C.; alternatively, 160° C.; alternatively, 140° C.; alternatively, 120° C.; alternatively, 100° C.; alternatively, 90° C.; or alternatively, 80° C. In some embodiments, the oligomerization temperature (or polymerization temperature) at which the oligomer product or polymer product is formed can range from any minimum temperature described herein to any maximum temperature described herein. In a non-limiting example, the oligomerization temperature (or polymerization temperature) at which the oligomer product or polymer product is formed can range from 0° C. to 200° C.; alternatively, range from 10° C. to 160° C.; alternatively, range from 20° C. to 140° C.; alternatively, range from 30° C. to 120° C.; alternatively, range from 40° C. to 100° C.; alternatively, range from 50° C. to 100° C.; or alternatively, ranges from 60° C. to 140° C. Other temperature ranges at which the oligomer product or polymer product can be formed are readily apparent from the present disclosure.

In an embodiment, a condition to form an oligomer product or polymer product can include a time at which the oligomer product or polymer product can be formed. Generally, the time at which the oligomer product or polymer product is formed can be any time that can produce the desired quantity of oligomer product or polymer product; or alternatively, provide a desired catalyst system productivity; or alternatively, provide a desired conversion of monomer. In some embodiments, the time at which the oligomer product or polymer product is formed can range from 1 minute to 5 hours; alternatively, ranges from 5 minutes to 2.5 hours; alternatively, ranges from 10 minutes to 2 hours; or alternatively, ranges from 15 minutes to 1.5 hours. In an embodiment, the oligomer product or polymer product can be formed having a single pass olefin conversion of ethylene of at least 30 wt. % percent; alternatively, at least 35 wt. % percent; alternatively, at least 40 wt. % percent; or alternatively, at least 45 wt. % percent. When the olefin is ethylene, the olefin conversion can be the ethylene conversion.

In an embodiment, the oligomerization process can produce an oligomer product comprising an olefin trimer, an olefin tetramer, or mixtures thereof. In some embodiments, the oligomer product can comprise a liquid (under standard atmospheric conditions) product. In some embodiments, when the olefin is ethylene the oligomerization is an ethylene oligomerization process. In some embodiments, the oligomerization can produce an alpha olefin product having at least four carbon atoms. In an embodiment, the ethylene oligomerization process can produce an olefin product comprising an ethylene trimer (e.g., hexene; or alternatively, 1-hexene), an ethylene tetramer (e.g., octene; or alternatively, 1-octene), or a combination thereof; alternatively, hexene; alternatively, octene; alternatively, hexene and octene. In other embodiments, the ethylene oligomerization can produce an olefin product comprising 1-hexene, 1-octene, or a combination thereof; alternatively, 1-hexene; alternatively, 1-octene; alternatively 1-hexene and 1-octene. In an embodiment, when the olefin is ethylene and the oligomerization process produces an alpha olefin (e.g., 1-hexene, 1-octene, or a combination thereof) the olefin oligomerization process can be an alpha olefin production process.

In an embodiment, the ethylene oligomerization process can produce an oligomer product comprising a liquid oligomer product comprising at least 60 wt. % $C_6$ and $C_8$ olefins. In some embodiments, the olefin product comprises a liquid oligomer product comprising at least 70 wt. % $C_6$ and $C_8$ olefins; alternatively, at least 75 wt. % $C_6$ and $C_8$ olefins; alternatively, at least 80 wt. % $C_6$ and $C_8$ olefins; alternatively, at least 85 wt. % $C_6$ and $C_8$ olefins; or alternatively, at least 90 wt. % $C_6$ and $C_8$ olefins. In other embodiments, the ethylene oligomerization process can produce an liquid oligomer product comprising a liquid product having from 60 to 99.9 wt. % of $C_6$ and $C_8$ olefins; alternatively, from 70 to 99.8 wt. % $C_6$ and $C_8$ olefins; alternatively, from 75 to 99.7 wt. % $C_6$ and $C_8$ olefins; or alternatively, from 80 to 99.6 wt. % $C_6$ and $C_8$ olefins. Throughout this application, a liquid oligomer product refers to the oligomer product having from 4 to 18 carbon atoms.

In an embodiment, the $C_6$ oligomer product produced by the ethylene oligomerization process can comprise at least 85 wt. % 1-hexene. In some embodiments, the $C_6$ oligomer product produced by the ethylene oligomerization process can comprise at least 87.5 wt. % 1-hexene; alternatively, at least 90 wt % 1-hexene; alternatively, at least 92.5 wt. % 1-hexene; alternatively, at least 95 wt. percent 1-hexene; alternatively, at least 97 weight percent 1-hexene; or alternatively at least 98 weight percent 1-hexene. In other embodiments, the $C_6$ oligomer product produced by the ethylene oligomerization process can comprise from 85 to 99.9 wt % 1-hexene; alternatively, from 87.5 to 99.9 wt % 1-hexene; alternatively, from 90 to 99.9 wt % 1-hexene; alternatively, from 92.5 to 99.9 wt % 1-hexene; alternatively, from 95 to 99.9 wt. % 1-hexene; alternatively, from 97 to 99.9 wt. % 1-hexene; or alternatively, from 98 to 99.9 wt. % 1-hexene.

In an embodiment, the $C_8$ oligomer product produced by the ethylene oligomerization process can comprise at least 85 wt. % 1-octene. In some embodiments, the $C_8$ oligomer product produced by the ethylene oligomerization process can comprise at least 87.5 wt. % 1-octene; alternatively, at least 90 wt % 1-octene; alternatively, at least 92.5 wt. % 1-octene; alternatively, at least 95 wt. percent 1-octene; alternatively, at least 97 weight percent 1-octene; or alternatively at least 98 weight percent 1-octene. In other embodiments, the $C_8$ oligomer product produced by the ethylene oligomerization process can comprise from 85 to 99.9 wt % 1-octene; alternatively, from 87.5 to 99.9 wt % 1-octene; alternatively, from 90 to 99.9 wt % 1-octene; alternatively, from 92.5 to 99.9 wt % 1-octene; alternatively, from 95 to 99.9 wt. % 1-octene; alternatively, from 97 to 99.9 wt. % 1-octene; or alternatively, from 98 to 99.9 wt. % 1-octene.

In some aspects and/or embodiments, aging the catalyst system (or catalyst system composition) before contacting the catalyst system (or catalyst system composition) with the olefin to be oligomerized and/or polymerized can improve aspects of the oligomerization process and/or polymerization process; or alternatively, aging the catalyst system (or a catalyst system composition) in the substantial absence of an olefin can improve aspects of the oligomerization process and/or polymerization process. In some embodiments, aging the catalyst system can increase the productivity of the catalyst system. In other embodiments, aging the catalyst system can decrease the amount of polymer produced in an oligomerization process. In some oligomerization process aspects and/or embodiments, aging the catalyst system can increase the productivity of the catalyst system; alternatively, can decrease the amount of polymer produced in an oligomerization process; or alternatively, can increase the productivity of the catalyst system and decrease the amount of polymer produced in the oligomerization. In regards to aging the catalyst system (or catalyst system composition) in the substantial absence of an olefin, this can be taken to mean that the catalyst system (or catalyst system composition) can contain less than 1,000 ppm olefin, by weight. In some embodiments, the catalyst system (or catalyst system composition) can contain less than 500 ppm, by weight, olefin; alternatively, 250 ppm, by weight, olefin; alternatively, 100 ppm, by weight, olefin; alternatively, 75 ppm, by weight, olefin; alternatively, 50 ppm, by weight, olefin; alternatively, 25 ppm, by weight, olefin; alternatively, 15 ppm, by weight, olefin; alternatively, 10 ppm, by weight, olefin; alternatively, 5 ppm, by weight, olefin; alternatively, 2.5 ppm, by weight, olefin; or alternatively, 1 ppm, by weight, olefin.

The catalyst system aging impacts can be utilized to provide positive benefits to an oligomerization process and/or polymerization process. For example, increasing the activity and/or the productivity of the catalyst system can provide increased oligomer product (or polymer product) per unit of catalyst system. Additionally, in oligomerization processes, the decrease in polymer produced in an oligomerization upon aging the catalyst system can reduce polymer which could adhere to the oligomerization reactor walls or cooling apparatus. The reduction in polymer produced in the oligomerization process can reduce the need to shut down a reactor to remove the polymer which can cause fouling.

In any aspect or embodiment wherein an $N^2$-phosphinyl guanidine compound, a metal salt, and a metal alkyl are contacted prior to contacting the olefin, the mixture comprising the $N^2$-phosphinyl guanidine compound, the metal salt, and the metal alkyl can be allowed to age for a period of time prior to contacting the mixture comprising the $N^2$-phosphinyl guanidine compound, a metal salt, and a metal alkyl with an olefin (or a mixture comprising the olefin); or alternatively, catalyst system comprising the $N^2$-phosphinyl guanidine compound, the metal salt, and the metal alkyl can be allowed to age for a period of time in the substantial absence of (or in the absence of) an olefin (or a mixture comprising the olefin). In some embodiments, a mixture comprising an $N^2$-phosphinyl guanidine compound, a metal salt, and a metal alkyl can further comprise a solvent.

In any aspect or embodiment wherein an $N^2$-phosphinyl guanidine metal salt complex and a metal alkyl are contacted prior to contacting the olefin, the mixture comprising the $N^2$-phosphinyl guanidine metal salt complex and the metal alkyl can be allowed to age for a period of time prior to contacting the mixture comprising the $N^2$-phosphinyl guanidine metal salt complex and the metal alkyl with an olefin (or a mixture comprising the olefin) or alternatively, catalyst system comprising the $N^2$-phosphinyl guanidine metal salt complex and the metal alkyl can be allowed to age for a period of time in the substantial absence of (or in the absence of) an olefin (or a mixture comprising the olefin). In some embodiments, a mixture comprising an $N^2$-phosphinyl guanidine metal salt complex and a metal alkyl can further comprise a solvent.

In a non-limiting embodiment, the oligomerization process can comprise: a) preparing a catalyst system; b) allowing the catalyst system to age for a period of time; c) contacting the aged catalyst system with an olefin; and d) forming an oligomer product. In some non-limiting embodiments, the oligomerization process can comprise, a) preparing a catalyst system; b) allowing the catalyst system to age for a period of time; c) contacting the aged catalyst system with an olefin and hydrogen; and d) forming an oligomer product. The catalyst system, olefin, and other features of the oligomer product are independently described herein and can be utilized, without limitation, to further describe the olefin oligomerization process. In some embodiments, the catalyst system can be prepared in a first solvent. In an embodiment, the olefin, aged catalyst system, and optionally hydrogen, can be contacted in a second solvent. Generally, a solvent in which the catalyst system can be prepared and the solvent in which the olefin and aged catalyst system can be contacted can be the same; or alternatively, can be different. The catalyst system, features of aging the catalyst system, features of the oligomer product, and features of the impacts of aging the catalysts system, among other features, are independently described herein and can be utilized, without limitation, to further describe the oligomerization process. In some embodiments, the first and second solvent can be the same; or alternatively, the first and second solvent can be different.

In a non-limiting embodiment, the oligomerization process can comprise: a) forming a catalyst system mixture comprising an $N^2$-phosphinyl guanidine metal salt complex and metal alkyl compound; b) aging the catalyst system mixture; c) contacting the aged catalyst system mixture with an olefin; and c) forming an oligomer product. In another non-limiting embodiment, the oligomerization process can comprise: a) forming a catalyst system mixture comprising an $N^2$-phosphinyl guanidine compound, a metal salt, and a metal alkyl compound; b) aging the catalyst system mixture; c) contacting the aged catalyst system mixture with an olefin; and c) forming an oligomer product. In some embodiments, the catalyst system mixture can further comprise a solvent (e.g., a first solvent). In some embodiments, the catalyst system mixture and the olefin can be contacted in a solvent (e.g., a second solvent). In yet another non-limiting embodiment, the oligomerization process can comprise: a) forming a catalyst system mixture comprising (or consisting essentially of) an $N^2$-phosphinyl guanidine metal salt complex, a metal alkyl compound, and a first solvent; b) aging the catalyst system mixture; c) contacting the aged catalyst system mixture with an olefin and a second solvent; and c) forming an oligomer product. In a further non-limiting embodiment, the oligomerization process can comprise: a) forming a catalyst system mixture comprising (or consisting essentially of) an $N^2$-phosphinyl guanidine compound, a metal salt, a metal alkyl, and a first solvent; b) aging the catalyst system mixture; c) contacting the aged catalyst system mixture with an olefin and a second solvent; and d) forming an oligomer product.

In some embodiments, the step of contacting the aged catalyst system mixture with the olefin (and optionally a solvent—e.g., second solvent) can be a step of contacting the aged catalyst system mixture with an olefin and hydrogen. The $N^2$-phosphinyl guanidine compound, metal salt, the metal salt $N^2$-phosphinyl guanidine metal salt complex, the metal alkyl compound, the olefin, solvents, features of aging the catalyst system, features of the oligomer product, and features of the impacts of aging the catalysts system, among other features, are independently described herein and can be utilized, without limitation to further describe the oligomerization process. In some embodiments, the first and second solvent can be the same; or alternatively, the first and second solvent can be different. In some embodiments, the metal alkyl compound can be, comprise, or consist essentially of, an aluminoxane. Ratios for the $N^2$-phosphinyl guanidine compound to metal salt and ratios for the metal of the metal salt to metal of the metal salt or the metal of the $N^2$-phosphinyl guanidine metal salt complex, among other features, are independently described herein and can be utilized without limitation to further describe the oligomerization process.

In an embodiment, the catalyst system can be aged for up 14 days; alternatively, up to 10 days; alternatively, up to 8 days; alternatively, up to 6 days; alternatively, up to 4 days; alternatively, up to 3 days; alternatively, up to 48 hours; alternatively, up to 36 hours; alternatively, up to 24 hours; alternatively, up to 18 hours; alternatively, up to 10 hours; alternatively, up to 8 hours; alternatively, up to 6 hours; alternatively, up to 4 hours; or alternatively, up to 3 hours. In an embodiment, the catalyst system can be aged for at least 15 minutes; alternatively, at least 20 minutes; or alternatively, at least 30 minutes. In an embodiment, the catalyst system can be aged for a time ranging from any catalyst system aging minimum time disclosed herein to any catalyst system aging maximum time disclosed herein. In some non-limiting embodiments, the catalyst system can be aged for from 15 minutes to 14 days; alternatively, from 15 minutes to 10 days; alternatively, from 15 minutes to 8 days; alternatively, from 15 minutes to 6 days; alternatively, from 20 minutes to 4 days; alternatively, from 20 minutes to 3 days; alternatively, from 30 minutes to 48 hours; alternatively, from 30 minutes to 36 hours; alternatively, from 30 minutes to 24 hours; alternatively, from 30 minutes to 18 hours; alternatively, from 30 minutes to 10 hours; alternatively, from 30 minutes to 8 hours; alternatively, from 30 minutes to 6 hours; alternatively, from 30 minutes to 4 hours; or alternatively, from 30 minutes to 3 hours. Other catalyst system aging time ranges are readily apparent for the present disclosure.

In an embodiment, any catalyst system described herein can be aged at ambient temperature (15° C.-35° C.—no external heat source). In other embodiments, any catalyst system described herein can be aged at a temperature from 25° C. to 100° C.; alternatively, from 30° C. to 80° C.; or alternatively, from 35° C. to 60° C. In some embodiments, any catalyst system described herein can be aged under an inert atmosphere. Generally, one will recognize that the temperature at which the catalyst system is aged can have an impact upon the time necessary to achieve an increase in catalyst system activity and/or reduction in catalyst system polymer production. In any aspect or embodiment, the catalyst system can be aged at a combination of any catalyst system aging time described herein and any catalyst system aging temperature described herein.

The catalytic activity (oligomerization or polymerization) of any catalyst system described herein comprising i) any $N^2$-phosphinyl guanidine metal salt complex or ii) any $N^2$-phosphinyl guanidine compound described herein and any metal salt described herein can be defined as the grams of product (oligomer product or polymer product) produced per gram of metal of the metal salt in the $N^2$-phosphinyl guanidine metal salt complex (or metal of the metal salt) utilized and is measured over 30 minutes beginning from when complete catalyst system is contacted with the olefin. In an embodiment, any aged catalyst system described herein (using any aging time period described herein and/or any aging temperature described herein) can increase the oligomerization activity or polymerization activity of the catalyst system by at least 10%; alternatively, at least 20%; alternatively, at least 30%; alternatively, at least 40%; or alternatively, at least 50%. In some embodiments, any aged catalyst system described herein (using any aging time period described herein and/or any aging temperature described herein) can increase the oligomerization activity or polymerization activity of the catalyst system from 10% to 1000%; alternatively, from 20% to 800%; alternatively, from 30% to 600%; alternatively, from 40% to 500%; or alternatively, from 50% to 400%. Generally, the increase in the catalyst system activity (oligomerization or polymerization) as a result of aging the catalyst system is determined by comparing the activity of the aged catalyst system to the activity of a catalyst system that has been aged for less than 12 minutes.

In an embodiment, any aged catalyst system described herein (using any aging time period described herein and/or any aging temperature described herein) can provide a catalyst system which can produce a reduction in the percentage of polymer produced described herein. In some embodiments, aging of any catalyst system described herein can reduce (using any aging time period described herein and/or any aging temperature described herein) the amount of polymer produced in an oligomerization process by at least 5%; alternatively, 7.5%; alternatively, 10%; alternatively, 12.5%; or alternatively, at least 15%. In some embodiments, aging of any catalyst system described herein (for any time period described herein) can reduce the amount of polymer produced in an oligomerization by at least 20%; alternatively at least 25%; alternatively, at least 30%; or alternatively, at least 35%. Generally, the decrease in the catalyst system polymer production as a result of aging can be determined by comparing the polymer production of the aged catalyst system to the polymer production of a catalyst system that has been aged for less than 12 minutes.

In an embodiment, aging any oligomerization catalyst system described herein can have a combination of any increase in activity described herein and any reduction in the amount of polymer produced described herein.

In an embodiment, a calibration curve can be produced depicting the catalyst system activity and/or polymer production of any aged catalyst system described herein in response to one or more catalyst system aging variables (e.g., time, temperature, or time and temperature). In some embodiments the calibration curve can be depicted graphically as a function of a catalyst system aging variable(s) (e.g., time, temperature, or time and temperature); or alternatively, the calibration curve can be depicted as a predictive equation of a catalyst system aging variable(s) (e.g., time, temperature, or time and temperature). The graphical representation and/or predictive equation relating catalyst system activity and/or polymer production in response catalyst aging can be utilized to adjust one or more user and/or process parameters based upon the interpolation or extrapolation of the graphical representation or predictive equation. It is contemplated that in some aspects, the extent to which the catalyst system activity increases and/or the extent to which there is a decrease in polymer production with respect to catalyst system aging can fall outside the instantly disclosed ranges and can be larger than would be expected based on the presently disclosed values depending on conditions under which the catalyst system is aged. For example, the catalyst system can be subjected to aging for time periods that are longer than those presently recited and/or at temperatures greater than those presently recited. The effects of aging the catalyst system under such conditions can be subject to the herein mentioned analysis to provide predictive information that can lead one to conditions under which catalyst system aging increases the catalyst system activity and/or reduces the polymer production in the oligomerization to within some user and/or process desired range of values. It is contemplated that given the benefits of this disclosure and using routine experimentation one having ordinary skill in the art can modify the methodologies disclosed herein to alter the catalytic system activity of a disclosed catalyst system and/or reduce the amount of polymer produced in an oligomerization process to a desired value or range. Such modifications fall within the scope of this disclosure.

It has also been discovered that when the metal alkyl is an alumoxane, aging the alumoxane can improve aspects of the oligomerization. For example, it has been observed that aging the alumoxane prior to its contact with the other components of the catalyst system can decrease the amount of polymer produced in the oligomerization process. In some embodiments, any process for preparing the catalyst system described herein and/or any oligomerization process described herein can include a step (or steps) for aging an alumoxane.

In an embodiment, the alumoxane can be aged at ambient temperature (15° C.-35° C.—no external heat source) for at least 60 days; at least 120 days; at least 180 days; or at least 240 days. In some embodiments, the alumoxane can be aged for up to 1,440 days; up to 1080 days; up to 900 days; or up to 720 days. In some embodiments, the alumoxane can be aged at ambient temperature (15° C.-35° C.—no external heat source) from 60 days to 1,440 days; from 120 days to 1080 days; from 180 to 900 days; or from 240 days to 720 days. Other, alumoxane aging times at ambient temperature are readily apparent form the present disclosure. In some embodiments, the alumoxane can be aged under an inert atmosphere.

The aging of the alumoxane can be performed at elevated temperature. It has been discovered that the aging of the alumoxane at elevated temperature can reduce the time need to achieve the benefits observed when the aged alumoxane is utilized in a catalyst system. In an embodiment, the alumoxane can be aged at a temperature from 30° C. to 100° C.; from 35° C. to 90° C.; from 40° C. to 80° C.; or 45° C. to 70° C. In an embodiment, the alumoxane can be aged at any elevated temperature disclosed herein for at least 12 hours; at least 18 hours; at least 24 hours; or at least 36 hours. In an embodiment, the alumoxane can be aged at any elevated temperature disclosed herein for up to 360 days; up to 270 days; up to 180 days; or up to 90 days. In some embodiments, the alumoxane can be aged at any elevated temperature disclosed herein for a time ranging from any minimum alumoxane aging time disclosed herein to any maximum alumoxane aging time disclosed herein. In a non-limiting example the alumoxane can be aged at any elevated temperature disclosed herein for a time ranging from 12 hours to 360 days; alternatively, from 12 hours to 270 days; alternatively, from 18 hours to 270 days; or alternatively, from 18 hours to 180 days. Other alumoxane aging times at elevated temperatures are readily apparent from the present disclosure. In some embodiments, the alumoxane can be aged under an inert atmosphere.

In an embodiment, any aging of the alumoxane described herein can provide any reduction in the percentage of polymer produced by the oligomerization process described herein. In some embodiments, any aging of the alumoxane described herein can reduce the amount of polymer produced in an oligomerization process by at least 20%; at least 40%; at least 60%; at least 70%; at least 75%; at least 80%; or at least 85%.

In an embodiment, a calibration curve can be produced depicting the catalyst system polymer production of any catalyst system described herein utilizing an aged alumoxane in response to one or more alumoxane aging variables (e.g., time, temperature, or time and temperature). In some embodiments the alumoxane aging calibration curve can be depicted graphically as a function of an alumoxane aging variable(s) (e.g., time, temperature, or time and temperature); alternatively, the calibration curve can be depicted as a predictive equation of an alumoxane aging variable(s) (e.g., time, temperature, or time and temperature). The graphical representation and/or predictive equation relating catalyst system polymer production in response to alumoxane aging can be utilized to adjust one or more user and/or process parameters based upon the interpolation or extrapolation of the graphical representation or predictive equation. It is contemplated that in some aspects, the extent to which the polymer production of the catalyst system decreases with respect to alumoxane aging can fall outside the instantly disclosed ranges and can be larger than would be expected based on the presently disclosed values depending on the conditions under which alumoxane is aged. For example, the catalyst system can be subjected to aging for time periods that are longer than those presently recited and/or at temperatures greater than those presently recited. The effects of alumoxane aging under such conditions can be subject to the herein mentioned analysis to provide predictive information that can lead to conditions under which alumoxane aging can reduce the polymer production of the catalyst system in the oligomerization. It is contemplated that given the benefits of this disclosure and using routine experimentation one having ordinary skill in the art can modify the methodologies disclosed herein to alter a reduction in the amount of polymer produced in an oligomerization process. Such modifications fall within the scope of this disclosure.

Various aspects and embodiments described herein refer to non-hydrogen substituents (or alternatively, substituent or substituent group). Each non-hydrogen substituent can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group. Each non-hydrogen substituent of any aspect or embodiment calling for a substituent independently can be a halide, a $C_1$ to $C_{10}$ hydrocarbyl group, or a $C_1$ to $C_{10}$ hydrocarboxy group; alternatively, a halide or a $C_1$ to $C_{10}$ hydrocarbyl group; alternatively, a halide or a $C_1$ to $C_{10}$ hydrocarboxy group; alternatively, a $C_1$ to $C_{10}$ hydrocarbyl group or a $C_1$ to $C_{10}$ hydrocarboxy group; alternatively, a halide; alternatively, a $C_1$ to $C_{10}$ hydrocarbyl group; or alternatively, a $C_1$ to $C_{10}$ hydrocarboxy group. In other embodiments, each non-hydrogen substituent of any aspect or embodiment calling for a substituent independently can be a halide, a $C_1$ to $C_5$ hydrocarbyl group, or a $C_1$ to $C_5$ hydrocarboxy group; alternatively, a halide or a $C_1$ to $C_5$ hydrocarbyl group; alternatively, a halide or a $C_1$ to $C_5$ hydrocarboxy group; alternatively, a $C_1$ to $C_5$ hydrocarbyl group or a $C_1$ to $C_5$ hydrocarboxy group; alternatively, a halide; alternatively, a $C_1$ to $C_5$ hydrocarbyl group; or alternatively, a $C_1$ to $C_5$ hydrocarboxy group.

In an embodiment, each halide substituent of any aspect or embodiment calling for a substituent independently can be a fluoride, chloride, bromide, or iodide; alternatively, a fluoride or chloride. In some embodiments, each halide substituent of any aspect or embodiment calling for a substituent independently can be a fluoride; alternatively, a chloride; alternatively, a bromide; or alternatively, an iodide.

In an embodiment, each hydrocarbyl substituent of any aspect or embodiment calling for a substituent independently can be an alkyl group, an aryl group, or an aralkyl group; alternatively, an alkyl group; alternatively, an aryl group; or alternatively, an aralkyl group. In an embodiment, each alkyl substituent of any aspect or embodiment calling for a substituent independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, each aryl substituent of any aspect or embodiment calling for a substituent independently can be phenyl group, a tolyl group, a xylyl group, or a 2,4,6-trimethylphenyl group; alternatively, a phenyl group; alternatively, a tolyl group; alternatively, a xylyl group; or alternatively, a 2,4,6-trimethylphenyl group. In an embodiment, each aralkyl substituent of any aspect or embodiment calling for a substituent independently can be benzyl group or an ethylphenyl group (2-phenyleth-1-yl or 1-phenyleth-1-yl); alternatively, a benzyl group; alternatively, an ethylphenyl group; alternatively a 2-phenyleth-1-yl group; or alternatively, a 1-phenyleth-1-yl group.

In an embodiment, each hydrocarboxy substituent of any aspect or embodiment calling for a substituent independently can be an alkoxy group, an aryloxy group, or an aralkoxy group; alternatively, an alkoxy group; alternatively, an aryloxy group, or an aralkoxy group. In an embodiment, each alkoxy substituent of any aspect or embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, each aryloxy substituent of any aspect or embodiment calling for a substituent independently can be phenoxy group, a toloxy group, a xyloxy group, or a 2,4,6-trimethylphenoxy group; alternatively, a phenoxy group; alternatively, a toloxy group; alternatively, a xyloxy group; or alternatively, a 2,4,6-trimethylphenoxy group. In an embodiment, each aralkoxy substituent of any aspect or embodiment calling for a substituent independently can be benzoxy group.

In an embodiment, non-hydrogen substituents (or alternatively, substituent or substituent group) which can be utilized in various aspects or embodiments can be a trihydrocarbylsilyl group. Generally, each hydrocarbyl group of the trihydrocarbylsilyl group independently can be any hydrocarbyl group (general or specific) which has be disclosed herein as a non-hydrogen substituent. In some embodiments, the trihydrocarbylsilyl group which can be utilized as a substituent can be a trimethylsilyl group, a triethylsilyl group, a tripropylsilyl group, a triphenylsilyl group, or a tribenzylsilyl group; alternatively, a trimethylsilyl group, a triethylsilyl group, or a tripropylsilyl group; alternatively, a trimethylsilyl group; alternatively, a triethylsilyl group; alternatively, a tripropylsilyl group; alternatively, a triphenylsilyl group; or alternatively, a tribenzylsilyl group.

In an embodiment, non-hydrogen substituents (or alternatively, substituent or substituent group) which can be utilized in various aspects or embodiments can be a trihydrocarbylsiloxy group. Generally, each hydrocarbyl group of the trihydrocarbylsiloxy group independently can be any hydrocarbyl group (general or specific) which has be disclosed herein as a non-hydrogen substituent. In some embodiments, the trihydrocarbylsiloxy group which can be utilized as a substituent can be a trimethylsiloxy group, a triethylsiloxy group, a tripropylsiloxy group, a triphenylsiloxy group, or a tribenzylsiloxy group; alternatively, a trimethylsiloxy group, a triethylsiloxy group, or a tripropylsiloxy group; alternatively, a trimethylsiloxy group; alternatively, a triethylsiloxy group; alternatively, a tripropylsiloxy group; alternatively, a triphenylsiloxy group; or alternatively, a tribenzylsiloxy group.

Solvents

The processes and methods described herein can utilize one or more solvents. Solvents which can be utilized in aspects and/or embodiments of the present disclosure include without limitation hydrocarbons, halogenated hydrocarbons, ethers, carbonates, esters, ketones, aldehydes, alcohols, nitriles, and combinations thereof. Some aspects and/or embodiments and aspects of this disclosure can call for a polar solvent. Polar solvents which can be utilized include without limitation ethers, carbonates, esters, ketones, aldehydes, alcohols, nitriles, and mixtures thereof; alternatively, ethers, carbonates, esters, ketones, aldehydes, alcohols, nitriles, and mixtures thereof; alternatively, ethers, esters, ketones, alcohols, nitriles, and mixtures thereof; alternatively, ethers; alternatively, carbonates; alternatively, esters; alternatively, ketones; alternatively, aldehydes; alternatively, alcohols; or alternatively, nitriles. Some aspects and/or embodiments of this disclosure can call for an aprotic polar solvent. Aprotic polar solvents which can be utilized include without limitation ethers, esters, ketones, aldehydes, nitriles, and mixtures thereof; alternatively, ethers, nitriles and mixtures thereof; alternatively, esters, ketones, aldehydes and mixtures thereof; alternatively, ethers; alternatively, esters; alternatively, ketones; alternatively, aldehydes; or alternatively, nitriles. Other aspects and/or embodiments of the disclosure can call for a non-polar solvent. Non-polar solvents include without limitation hydrocarbons, halogenated hydrocarbons, or mixtures thereof; alternatively, a hydrocarbon; or alternatively, a halogenated hydrocarbon. Yet other aspects and/or embodiments of the present disclosure can call for a solvent that is substantially unreactive with a metal alkyl. Solvents which are unreactive with a metal alkyl include without limitation ethers, hydrocarbons, and mixtures thereof; alternatively, ethers; or alternatively, hydrocarbons.

Hydrocarbons and halogenated hydrocarbon can include, for example, aliphatic hydrocarbons, aromatic hydrocarbons, petroleum distillates, halogenated aliphatic hydrocarbons, halogenated aromatic hydrocarbons, or combinations thereof; alternatively aliphatic hydrocarbons, aromatic hydrocarbons, halogenated aliphatic hydrocarbons, halogenated aromatic hydrocarbons, and combinations thereof; alternatively, aliphatic hydrocarbons; alternatively, aromatic hydrocarbons; alternatively, halogenated aliphatic hydrocarbons; or alternatively, halogenated aromatic hydrocarbons. Aliphatic hydrocarbons which can be useful as a solvent include $C_3$ to $C_{20}$ aliphatic hydrocarbons; alternatively $C_4$ to $C_{15}$ aliphatic hydrocarbons; or alternatively, $C_5$ to $C_{10}$ aliphatic hydrocarbons. The aliphatic hydrocarbons can be cyclic or acyclic and/or can be linear or branched, unless otherwise specified. Non-limiting examples of suitable acyclic aliphatic hydrocarbon solvents that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, propane; alternatively, iso-butane; alternatively, n-butane; alternatively, butane (n-butane or a mixture of linear and branched $C_4$ acyclic aliphatic hydrocarbons); alternatively, pentane (n-pentane or a mixture of linear and branched $C_5$ acyclic aliphatic hydrocarbons); alternatively, hexane (n-hexane or mixture of linear and branched $C_6$ acyclic aliphatic hydrocarbons); alternatively, heptane (n-heptane or mixture of linear and branched $C_7$ acyclic aliphatic hydrocarbons); or alternatively, octane (n-octane or a mixture of linear and branched $C_8$ acyclic aliphatic hydrocarbons). Non-limiting examples of suitable cyclic aliphatic hydrocarbon solvents include cyclohexane, methyl cyclohexane; alternatively cyclohexane; or alternatively, methylcyclohexane. Aromatic hydrocarbons which can be useful as a solvent include $C_6$ to $C_{20}$ aromatic hydrocarbons; or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene.

Halogenated aliphatic hydrocarbons which can be useful as a solvent include $C_1$ to $C_{15}$ halogenated aliphatic hydrocarbons; alternatively, $C_1$ to $C_{10}$ halogenated aliphatic hydrocarbons; or alternatively, $C_1$ to $C_5$ halogenated aliphatic hydrocarbons. The halogenated aliphatic hydrocarbons can be cyclic or acyclic and/or can be linear or branched, unless otherwise specified. Non-limiting examples of suitable halogenated aliphatic hydrocarbons which can be utilized include methylene chloride, chloroform, carbon tetrachloride, dichloroethane, trichloroethane, and combinations thereof; alternatively, methylene chloride, chloroform, dichloroethane, trichloroethane, and combinations thereof; alternatively, methylene chloride; alternatively, chloroform; alternatively, carbon tetrachloride; alternatively, dichloroethane; or alternatively, trichloroethane. Halogenated aromatic hydrocarbons which can be useful as a solvent include $C_6$ to $C_{20}$ halogenated aromatic hydrocarbons; or alternatively, $C_6$ to $C_{10}$ halogenated aromatic hydrocarbons. Non-limiting examples of suitable halogenated aromatic hydrocarbons include chlorobenzene, dichlorobenzene, and combinations thereof; alternatively chlorobenzene and dichlorobenzene.

Ethers, carbonates, esters, ketones, aldehydes, or alcohols which can be useful as a solvent include $C_2$ to $C_{20}$ ethers, carbonates, esters, ketones, aldehydes, or alcohols; alternatively, $C_2$ to $C_{10}$ ethers, carbonates, esters, ketones, aldehydes, or alcohols; or alternatively, $C_2$ to $C_5$ ethers, carbonates, esters, ketones, aldehydes, or alcohols. Suitable ether solvents can be cyclic or acyclic. Non-limiting examples of suitable ethers which can be useful as a solvent include dimethyl ether, diethyl ether, methyl ethyl ether, monoethers or diethers of glycols (e.g., dimethyl glycol ether), furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group. $C_1$ to $C_5$ alkyl substituent groups are disclosed herein and can be utilized without limitation of further describe the substituted tetrahydrofuran, dihydrofuran, furan, 1,3-dioxane, or 1,4 dioxane solvents. Non-limiting examples of suitable carbonates which can be utilized as a solvent include ethylene carbonate, propylene carbonate, diethyl carbonate, diethyl carbonate, glycerol carbonate, and combinations thereof. Non-limiting examples of suitable esters which can be utilized as a solvent include ethyl acetate, propyl acetate, butyl acetate, isobutyl isobutyrate, methyl lactate, ethyl lactate, and combinations thereof. Non-limiting examples of suitable ketones which can be utilized as a solvent include acetone, ethyl methyl ketone, methyl isobutyl ketone, and combinations thereof. Non-limiting examples of suitable alcohols which can be utilized as a solvent include methanol, ethanol, propanol, isopropanol, n-butanol, isobutanol, pentanol, hexanol, heptanol, octanol, benzyl alcohol, phenol, cyclohexanol, and the like, or combinations thereof.

While the present disclosure presents various aspects and embodiments as independent elements, one can readily recognize that these aspects and embodiments can be combined to form additional aspects and embodiments. Some non-limiting combinations of aspects and embodiments are herein presented as exemplary combinations. These exemplary combinations are not to be construed as the only combinations of aspects and embodiments of the concepts present herein which can be envisioned and/or supported by the present disclosure. All combinations of the various aspects and embodiments disclosed herein are fully contemplated by the present disclosure.

In a first embodiment, the present disclosure includes a composition comprising an $N^2$-phosphinyl guanidine metal salt complex comprising a chromium salt complexed to an $N^2$-phosphinyl guanidine compound. In a second embodiment, the present disclosure includes the composition of the first embodiment wherein the $N^2$-phosphinyl guanidine metal salt complex has a Structure CrGu1 wherein $R^1$ is a $C_1$ to $C_{30}$ organyl group, $R^{2a}$ and $R^{2b}$ independently are $C_1$ to $C_{30}$ organyl groups consisting essentially of inert functional groups, $R^3$ is hydrogen or a $C_1$ to $C_{30}$ organyl group consisting essentially of inert functional groups, $R^4$ and $R^5$ each independently are $C_1$ to $C_{30}$ organyl groups consisting essentially of inert functional groups, $CrX_p$ represents a chromium salt where X is a monoanion, and p ranges from 2 to 6, and Q is a neutral ligand, and q ranges from 0 to 6. In a third embodiment, the present disclosure includes the composition of the second embodiment wherein a) $R^1$ and $R^{2a}$ can be joined to form a ring or a ring system, b) $R^{2a}$ and $R^{2b}$ can be joined to form a ring or a ring system, c) $R^{2b}$ and $R^3$ can be joined to form a ring or a ring system, or d) $R^1$ and $R^{2a}$ can be joined to form a ring or a ring system and $R^{2b}$ and $R^3$ can be joined to form a ring or a ring system. In a fourth embodiment, the present disclosure includes the composition of the first or the second embodiments, wherein the $N^2$-phosphinyl guanidine metal salt complex has Structure CrGu2 wherein $L^{12}$ is a $C_2$ to $C_{15}$ organylene group consisting of inert functional groups (or alternatively, a $C_2$ to $C_{15}$ hydrocarbylene groups), $R^3$ is hydrogen or a $C_1$ to $C_{30}$ organyl group consisting essentially of inert functional groups (or a $C_1$ to $C_{30}$ hydrocarbyl group), $R^4$ and $R^5$ independently are $C_1$ to $C_{30}$ organyl groups consisting essentially of inert functional groups (or $C_1$ to $C_{30}$ hydrocarbyl groups). $CrX_p$ represents a chromium salt where X is a monoanion and p ranges from 2 to 6, Q is a neutral ligand, and q ranges from 0 to 6; alternatively, wherein the $N^2$-phosphinyl guanidine metal salt complex has Structure CrGu3 wherein $R^1$ is a $C_1$ to $C_{30}$ organyl group consisting essentially of inert functional groups (or a $C_1$ to $C_{30}$ hydrocarbyl group), $L^{23}$ is a $C_2$ to $C_{15}$ organylene group consisting of inert functional groups (or alternatively, a $C_2$ to $C_{15}$ hydrocarbylene groups), $R^4$ and $R^5$ independently are $C_1$ to $C_{30}$ organyl groups consisting essentially of inert functional groups (or $C_1$ to $C_{30}$ hydrocarbyl groups). $CrX_p$ represents a chromium salt where X is a monoanion and p ranges from 2 to 6, Q is a neutral ligand, and q ranges from 0 to 6; alternatively, wherein the $N^2$-phosphinyl guanidine metal salt complex has Structure CrGu4 wherein $L^{12}$ and $L^{23}$ independently are $C_2$ to $C_{15}$ organylene group consisting of inert functional groups (or alternatively, hydrocarbylene groups), $R^4$ and $R^5$ independently are $C_1$ to $C_{30}$ organyl groups consisting essentially of inert functional groups (or $C_1$ to $C_{30}$ hydrocarbyl groups). $CrX_p$ represents a chromium salt where X is a monoanion and p ranges from 2 to 6, Q is a neutral ligand, and q ranges from 0 to 6; alternatively, wherein the $N^2$-phosphinyl guanidine metal salt complex has Structure CrGu5 wherein $R^1$ is a $C_1$ to $C_{30}$ organyl group consisting essentially of inert functional groups (or a $C_3$ to $C_{20}$ hydrocarbyl group), $L^{22}$ is a $C_3$ to $C_{20}$ organylene group consisting of inert functional groups (or alternatively, a $C_2$ to $C_{15}$ hydrocarbylene groups), $R^3$ is hydrogen or a $C_1$ to $C_{30}$ organyl group consisting essentially of inert functional groups (or a $C_1$ to $C_{30}$ hydrocarbyl group), $R^4$ and $R^5$ independently are $C_1$ to $C_{30}$ organyl groups consisting essentially of inert functional groups (or $C_1$ to $C_{30}$ hydrocarbyl groups), $CrX_p$ represents a chromium salt where X is a monoanion and p ranges from 2 to 6, Q is a neutral ligand, and q ranges from 0 to 6. In a fifth embodiment, the present disclosure includes the composition of the first embodiment wherein the chromium salt comprises a chromium(III) carboxylate, a chromium(III) β-diketonate, or a chromium(III) halide; or alternatively, the composition of the second through the fourth embodiments wherein X is a carboxylate, a β-diketonate, or a halide, and p is 3. In a sixth embodiment, the present disclosure includes the composition of the first embodiment wherein the chromium salt comprises a chromium(III) halide; or alternatively, the composition of the second through the fourth embodiments wherein X is a halide, and p is 3. In a seventh embodiment, the present disclosure includes the composition of the second through the sixth embodiments wherein Q comprises a $C_1$ to $C_{20}$ nitrile or a $C_1$ to $C_{40}$ ether. In a eighth embodiment, the present disclosure includes the composition of the second through the fourth embodiments wherein $CrX_p$ comprises a chromium (III) halide and each Q independently is a $C_2$ to $C_{30}$ aliphatic acyclic ether or a $C_3$ to $C_{30}$ aliphatic cyclic ether. In a ninth embodiment, the present disclosure includes the composition of the first embodiment wherein the $N^2$-phosphinyl guanidine metal salt complex has Structure $CrCl_3 \cdot THF$ Gu I, Structure $CrCl_3 \cdot THF$ Gu VII, or Structure $CrCl_3 \cdot THF$ Gu XI: alternatively, Structure CrCl$_3$·THF Gu I; alternatively, Structure CrCl$_3$·THF Gu VII; or alternatively, Structure CrCl$_3$·THF Gu XI.

In a tenth embodiment, the present disclosure includes a catalyst system composition comprising a) an N$^2$-phosphinyl guanidine metal salt complex described in any of first through the ninth embodiments, and b) a metal alkyl compound. In an eleventh embodiment, the present disclosure includes the catalyst system composition of the tenth embodiment wherein the metal alkyl compound comprises an aluminoxane. In a twelfth embodiment, the present disclosure includes the catalyst system composition of the eleventh embodiment wherein the aluminoxane comprises methylaluminoxane (MAO), modified methylaluminoxane (MMAO), ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, and mixtures thereof. In a thirteenth embodiment, the present disclosure includes the catalyst system composition of the tenth embodiment wherein the aluminoxane comprises modified methylaluminoxane (MMAO); or alternatively, the catalyst system composition of the eleventh embodiment wherein the aluminoxane comprises modified methylaluminoxane (MMAO). In a fourteenth embodiment, the present disclosure includes the catalyst system composition of the eleventh through thirteenth embodiments wherein a metal of the metal alkyl compound to chromium of the N$^2$-phosphinyl guanidine metal salt complex molar ratio is at least 5:1; or alternatively, wherein an aluminum of the aluminoxane to chromium of the N$^2$-phosphinyl guanidine metal salt complex molar ratio is at least 5:1.

In a fifteenth embodiment, the present disclosure includes a process of preparing a catalyst system composition comprising contacting an N$^2$-phosphinyl guanidine metal salt complex described in any of first through the ninth embodiments and a metal alkyl compound (or alternatively, an aluminoxane). In a sixteenth embodiment, the present disclosure includes the method of the fifteenth embodiment, wherein the catalyst system composition is aged in the substantial absence of an olefin for at least 15 minutes. In a seventeenth embodiment, the present disclosure includes the process of the sixteenth embodiment, wherein the aged catalyst system composition displays a) increased oligomerization catalytic activity when compared to an otherwise similar catalyst system that has not been aged, b) reduced percentage of produced polymer when compared to an otherwise similar catalyst system that has not been aged, or c) increased oligomerization catalytic activity and a reduced percentage of produced polymer when compared to an otherwise similar catalyst system that has not been aged.

In an eighteenth embodiment, the present disclosure includes an oligomerization process comprising a) contacting i) an olefin, and ii) a catalyst system comprising (a) an N$^2$-phosphinyl guanidine metal salt complex described in any of first through the ninth embodiments, and (b) a metal alkyl compound (or alternatively, an aluminoxane), to form an oligomer product and b) recovering an oligomer; or alternatively, a) contacting i) an olefin, and ii) a catalyst system described in any of tenth through the fourteenth embodiments, and b) recovering an oligomer. In a nineteenth embodiment, the present disclosure includes the process of the eighteenth embodiment, wherein the catalyst system, the olefin, and hydrogen are contacted to form an oligomer product. In a twentieth embodiment, the present disclosure includes the process of the eighteenth through the nineteenth embodiments, wherein the oligomer product is formed at a temperature ranging from 20° C. to 150° C. In a twenty-first embodiment, the present disclosure includes the process of the eighteenth through the twentieth embodiments, wherein the olefin comprises ethylene, and wherein the oligomer product comprises a liquid oligomer product comprising from 60 to 99.9 wt. % C$_6$ and C$_8$ olefins. In a twenty-second embodiment, the present disclosure includes the process of the eighteenth through the twenty-first embodiments, wherein the olefin comprises ethylene and wherein a C$_6$ oligomer product comprises at least 90 wt. % 1-hexene. In a twenty-third embodiment, the present disclosure includes the process of the eighteenth through the twenty-second embodiments, wherein the olefin comprises ethylene and wherein a C$_8$ oligomer product comprises at least 90 wt. % 1-octene. In a twenty-fourth embodiment, the present disclosure includes the process of the nineteenth through the twenty-third embodiments, wherein the catalyst system, the olefin, and hydrogen are contacted to form an oligomer product, wherein the olefin comprises ethylene, wherein the oligomer product is formed at an ethylene partial pressure ranging from 150 psig to 2,000 psig and a hydrogen partial pressure ranging from 5 psig to 400 psig.

General Disclosure Information

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

Unless indicated otherwise, when a range of any type is disclosed or claimed, for example a range of the number of carbon atoms, molar ratios, temperatures, and the like, it is intended to disclose or claim individually each possible number that such a range could reasonably encompass, including any sub-ranges encompassed therein. For example, when describing a range of the number of carbon atoms, each possible individual integral number and ranges between integral numbers of atoms that the range includes are encompassed therein. Thus, by disclosing a C$_1$ to C$_{10}$ alkyl group or an alkyl group having from 1 to 10 carbon atoms or "up to" 10 carbon atoms, Applicants' intent is to recite that the alkyl group can have 1, 2, 3, 4, 5, 6, 7, 8, 9, or 10 carbon atoms, and these methods of describing such a group are interchangeable. When describing a range of measurements such as molar ratios, every possible number that such a range could reasonably encompass can, for example, refer to values within the range with one significant digit more than is present in the end points of a range. In this example, a molar ratio between 1.03:1 and 1.12:1 includes individually molar ratios of 1.03:1, 1.04:1, 1.05:1, 1.06:1, 1.07:1, 1.08:1, 1.09:1, 1.10:1, 1.11:1, and 1.12:1. Applicants' intent is that these two methods of describing the range are interchangeable. Moreover, when a range of values is disclosed or claimed, which Applicants intent to reflect individually each possible number that such a range could reasonably encompass, Applicants also intend for the disclosure of a range to reflect, and be interchangeable with, disclosing any and all sub-ranges and combinations of sub-ranges encompassed therein. In this aspect, Applicants' disclosure of a C$_1$ to C$_{10}$ alkyl group is intended to literally encompass a C$_1$ to C$_6$ alkyl, a C$_4$ to C$_8$ alkyl, a $C_2$ to $C_7$ alkyl, a combination of a $C_1$ to $C_3$ and a $C_5$ to $C_7$ alkyl, and so forth. When describing a range in which the end points of the range have different numbers of significant digits, for example, a molar ratio from 1:1 to 1.2:1, every possible number that such a range could reasonably encompass can, for example, refer to values within the range with one significant digit more than is present in the end point of a range having the greatest number of significant digits, in this case 1.2:1. In this example, a molar ratio from 1:1 to 1.2:1 includes individually molar ratios of 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, and 1.20, all relative to 1, and any and all sub-ranges and combinations of sub-ranges encompassed therein. Accordingly, Applicants reserve the right to proviso out or exclude any individual members of any such group, including any sub-ranges or combinations of sub-ranges within the group, if for any reason Applicants choose to claim less than the full measure of the disclosure, for example, to account for a reference that Applicants are unaware of at the time of the filing of the application.

In any application before the United States Patent and Trademark Office, the Abstract of this application is provided for the purpose of satisfying the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can suggest themselves to one of ordinary skill in the art without departing from the spirit of the present invention or the scope of the appended claims.

The data and descriptions provided in the following examples are given to show particular aspects and embodiments of the compounds, catalyst systems, and oligomerization and/or polymerization methods disclosed, and to demonstrate a number of the practices and advantages thereof. The examples are given as a more detailed demonstration of some of the aspects and embodiments described herein and are not intended to limit the disclosure or claims in any manner.

EXAMPLES $N^2$-phosphinyl guanidine metal salt complexes were prepared and their utility as oligomerization catalysts evaluated.

Guanidine Compound Syntheses

All chemicals and compounds used were purchased from commercial sources. Diethyl ether was distilled from sodium-benzophenone to eliminate water and oxygen. Anhydrous benzene (dry benzene) was degassed and stored over molecular sieves. The synthesis of the guanidine compounds were performed using the general procedure in Li, D.; Guang, J.; Zhang, W.-X.; Wang, Y.; Xi, Z. *Org. Biomol. Chem.* 2010, 8, 1816-1820 which is incorporated herein by reference in its entirety. Table 3 summarizes the amines and carbodiimides utilized in guanidine syntheses 1-5 along with the produced guanidine compounds.

Guanidine Synthesis 1—Guanidine A 2,6 dimethylaniline (20 mmol, 2.608 ml) was dissolved in 50 ml of benzene in a 100 ml Schlenk flask. To this solution, N,N'-diisopropylcarbodiimide (20 mmol, 3.09 ml) and zinc trifluoromethanesulfonate (0.6 mmol, 0.2200 g) were also added to give a clear and colorless solution. This solution was refluxed for 12 hours. After refluxing the reaction mixture was cloudy but still colorless. The benzene solvent was removed and the white solid that remained was dissolved in diethyl ether, filtered, and taken to dryness to give a white powder (4.3951 g, 88.1% yield). NMR ($C_6D_6$) δ: 7.16 (doublet, 2H), 6.95 (triplet, 1H), 3.17 (broad doublet, 2H), 2.33 (singlet, 6H), 0.87 (broad doublet, 12H) ppm.

Guanidine Synthesis 2—Guanidine B

Aniline (10 mmol, 0.9137 ml), Zn(OTF)$_2$ (0.3 mmol, 0.1100 g), and N,N'-diisopropylcarbodiimide (10 mmol, 1.546 ml) were transferred to a 50 ml Schlenk flask and dissolved in 25 ml of benzene. The reaction mixture was refluxed for 72 hours. The solution changed color from dark brown to translucent dark green that began to solidify as the flask was allowed to cool to room temperature. The flask was heated to redissolve the mixture and the benzene solvent was removed by vacuum. The product was isolated by dissolving in warm diethyl ether followed by filtration. The green solution was reduced in volume until solid began to form. The solution was placed in a freezer for 1 hour before filtering (1.3320 g, 60.7% yield). NMR ($C_6D_6$) δ: 7.26 (triplet, 2H), 7.14 (singlet, 2H), 6.92 (triplet, 1H), 3.64 (broad singlet, 2H), 3.42 (broad multiplet, 2H), 0.88 (doublet, 13H) ppm.

Guanidine Synthesis 3—Guanidine C 2-5-di-tert-butylaniline (10 mmol, 2.0535 g), a white, powdery solid, Zn(OTF)$_2$ (0.3 mmol, 0.1100 g), and N,N'-diisopropylcarbodiimide (10 mmol, 1.546 ml) were transferred to a 50 ml Schlenk flask and dissolved in 25 ml of benzene to give a clear and colorless solution. This solution was refluxed for 12 hours. After reflux the solution remained colorless but became more translucent. The flask was allowed to cool to room temperature and solvent was removed under vacuum to give a white solid. This solid was dissolved in diethyl ether to give a colorless solution with a fine white precipitate and was allowed to stir for 30 minutes before filtering to give a clear and colorless filtrate. The solvent was removed by vacuum to give a white powder (3.0554, 92.2% yield). NMR ($C_6D_6$) δ: 7.46 (doublet, 2H), 7.01 (doublet, 1H), 6.97 (singlet, 1H), 3.68 (broad, 2H), 3.43 (broad doublet, 2H), 1.66 (singlet, 9H), 1.30 (singlet, 9H), 0.94 (doublet, 12H) ppm.

Guanidine Synthesis 4—Guanidine D

Guanidine D was prepared in the same manner and same millimolar proportions as described for the synthesis for Guanidine C. The synthesis provided 4.68 g, 94.5% yield, of Guanidine D. NMR ($C_6D_6$) δ: 7.25 (doublet, 1H), 7.19 (doublet, 1H), 6.98 (multiplet, 2H), 3.63 (broad, 2H), 3.39 (broad, 2H), 2.80 (quartet, 2H), 1.31 (triplet, 3H), 0.90 (doublet, 12H) ppm.

Guanidine Synthesis 5—Guanidine E

Guanidine E was prepared in the same manner and same millimolar proportions as described for the synthesis for Guanidine C. The synthesis provided 5.3461, 97.0% yield, of Guanidine E. NMR ($C_6D_6$) δ: 7.33 (doublet, 2H), 7.12 (doublet, 2H), 3.68 (broad peak, 4H), 1.26 (singlet, 9H), 0.92 (doublet, 12H) ppm.

Synthesis of $N^2$-Phosphinyl Guanidine Compounds

All chemicals and compounds not prepared as disclosed in the herein Examples were purchased from commercial sources. The $N^2$-phosphinyl guanidine compounds were performed under an argon atmosphere. Diethyl ether was distilled from sodium-benzophenone to eliminate water and

TABLE 3

Amines, Carbodiimides, and Product Guanidine Compounds of Guanidine Syntheses 1-5

| Synthesis Designation | Amine | Carbodiimide | Guanidine |
|---|---|---|---|
| Guanidine Synthesis 1 | 2,6-dimethylaniline | diisopropylcarbodiimide | Guanidine A |
| Guanidine Synthesis 2 | aniline | diisopropylcarbodiimide | Guanidine B |
| Guanidine Synthesis 3 | 2,5-di-tert-butylaniline | diisopropylcarbodiimide | Guanidine C |
| Guanidine Synthesis 4 | 2-ethylaniline | diisopropylcarbodiimide | Guanidine D |
| Guanidine Synthesis 5 | 4-tert-butylaniline | diisopropylcarbodiimide | Guanidine E | oxygen. Anhydrous benzene (dry benzene) were degassed and stored over molecular sieves.

N²-Phosphinyl Guanidine Synthesis 1—N²-Phosphinyl Guanidine Structure XIX

Guanidine A (3 mmol, 0.7415 g) dissolved in 50 ml of diethyl ether in a 100 ml Schlenk flask to give a clear and colorless solution. The reaction mixture was placed in an ice bath under argon purge. A 10% molar excess of butyl lithium (2M, 1.65 ml) was added drop-wise and the solution was allowed to stir for 2 hours at room temperature. A 10% molar excess of p-chlorodiphenylphosphine (3.3 mmol, 0.592 ml) was added in one part. After a few minutes the solution changed from clear and colorless to orange-yellow with a fine white precipitate suspended in solution. The mixture was filtered to give a clear solution. Solvent was removed from the filtrate under vacuum to give viscous yellow oil (1.3359 g, quantitative yield). NMR ($C_6D_6$): δ 7.67 (triplet, 4H), 7.13 (multiplet, 8H), 6.90 (triplet, 1H), 4.51 (multiplet, 1H), 4.32 (doublet, 1H), 3.18 (multiplet, 1H), 2.38 (singlet, 6H), 1.46 (doublet, 6H), 0.46 (doublet, 6H) ppm.

N²-Phosphinyl Guanidine Synthesis 2—N²-Phosphinyl Guanidine Structure XVIII

The N²-phosphinyl guanidine compound having Structure XVIII was prepared using the same procedure and millimolar quantities as utilized in N²-phosphinyl guanidine synthesis 1 using chloro-diisopropylphosphine and Guanidine A as reagents. When p-chlorodiisopropylphosphine was added the solution remained clear and colorless with fine white precipitate suspended in solution. Two filtrations were necessary to remove the solid from the filtrate to give a clear and colorless solution. The ether was removed and a clear and colorless oil remained (1.1082, quantitative yield). NMR ($C_6D_6$): δ 6.94 (singlet, 3H), 3.34 (multiplet, 1H), 3.23 (multiplet, 2H), 3.04 (multiplet, 1H), 2.97 (doublet, 1H), 2.51 (singlet, 6H), 1.22 (multiplet, 19H), 0.53 (doublet, 6H) ppm.

N²-Phosphinyl Guanidine Synthesis 3—N²-Phosphinyl Guanidine Structure XVII

The N²-phosphinyl guanidine compound having Structure XVII was prepared using the same procedure millimolar quantities as utilized in N²-Phosphinyl Guanidine Synthesis 1 using chlorodiphenyl-phosphine and Guanidine B as reagents. One molar equivalent each of butyl lithium and chlorodiphenyl-phosphine were used as reagents. Filtering the reaction mixture removed the lithium chloride salt and gave a clear, slightly yellow solution. The solvent was removed to give a yellow oil (0.9885 g, 48.9% Yield). NMR indicated that the product probably consisted of a mixture of isomers.

N²-Phosphinyl Guanidine Synthesis 4—N²-Phosphinyl Guanidine Structure XXII

The N²-phosphinyl guanidine compound having Structure XVII was prepared using the same procedure as utilized in N²-Phosphinyl Guanidine Synthesis 1 using chlorodiphenylphosphine and Guanidine C as reagents. Guanidine C (5 mmol, 1.6578 g) was dissolved in 50 ml of dry diethyl ether in a 100 ml Schlenk flask and cooled in an ice bath. Butyllithium (5 mmol, 2M, 2.5 ml) was added drop-wise. After the addition, the mixture was allowed to stir for two hours at room temperature. Chlorodiphenyl-phosphine (5 mmol, 0.898 ml) was added in one addition. The mixture became slightly yellow and in a few minutes a fine white precipitate began to form. The mixture was passed through a fine filtered frit funnel to remove the lithium chloride salt and give a clear, light yellow solution. The solvent was removed to give a light yellow powder (2.3109 g, 89.6% Yield). NMR ($C_6D_6$): δ 7.67 (multiplet, 4H), 7.41 (2 singlets, 1H), 7.15 (multiplet, 6H), 7.20 (triplet, 2H), 7.02 (doublet, 1H), 6.89 (singlet, 1H), 4.00 (multiplet, 1H), 3.79 (singlet, 2H), 1.65 (singlet, 9H), 1.35 (doublet, 6H), 1.29 (singlet, 9H), 0.79 (doublet, 6H) ppm.

N²-Phosphinyl Guanidine Synthesis 5—N²-Phosphinyl Guanidine Structure XX

The N²-phosphinyl guanidine compound having Structure XX was prepared using the same procedure as utilized in N²-Phosphinyl Guanidine Synthesis 1 using chlorodiphenylphosphine and Guanidine D as reagents. Guanidine D (5 mmol, 1.2373 g) was dissolved in dry diethyl ether, cooled in an ice bath, and treated with butyl lithium (2M, 2.5 ml). After complete addition, the mixture was allowed to stir for 2 hours at room temperature. Chlorodiphenylphosphine was added, the solution changed from green to light yellow with a fine white precipitate, and was allowed to stir over night. The white lithium chloride salt was removed by vacuum filtration through a fine fritted filter funnel to give a green-yellow solution. The solvent was removed and the compound that remained began to solidify. The solid was dissolved in pentane, filtered, and taken to dryness, yielding a greenish-beige solid (1.9474 g, 90.0% Yield). NMR ($C_6D_6$): δ 7.65 (triplet, 4H), 7.07 (multiplet, 7H), 6.94 (triplet, 2H), 6.81 (doublet, 1H), 4.10 (multiplet, 2H), 3.52 (multiplet, 1H), 2.85 (quartet, 2H), 1.36 (singlet, 2H), 1.33 (singlet, 3H), 1.32 (doublet, 1H), 0.91 (doublet, 2H), 0.67 (doublet, 4H) ppm.

N²-Phosphinyl Guanidine Synthesis 6—N²-Phosphinyl Guanidine Structure XXI

The N²-phosphinyl guanidine compound having Structure XXI was prepared using the same procedure and millimolar quantities as utilized N²-Phosphinyl Guanidine Synthesis 1 using chloro-diphenylphosphine and Guanidine E as reagents. The product was a very viscous yellow oil (1.9047 g, 81.1% Yield). NMR indicated that the product probably consisted of a mixture of isomers.

N²-Phosphinyl Guanidine Synthesis 7—N²-Phosphinyl Guanidine Structure VII

Triazabicyclo[4.4.0]dec-5-ene (5 mmol, 0.696 g) was suspended in 50 ml of dry diethyl either under an argon atmosphere and cooled in an ice bath. One molar equivalent of butyllithium (2 M, 2.5 ml) was added drop-wise and the solution was allowed to stir for 2 hours at room temperature. The reaction mixture became milky white with a fine white precipitate suspended in solution. After 2 hours, one molar equivalent of p-chlorodiisopropylphosphine (5 mmol, 0.797 ml) was added in one portion and a fine white precipitate began to form. This mixture was allowed to stir for one hour at room temperature. Lithium chloride was removed by filtration to give a clear and colorless filtrate. Solvent was removed leaving a clear and colorless liquid (1.1851 g, 92.8% Yield). NMR ($C_6D_6$): δ 3.40 (triplet, 2H), 3.31 (multiplet, 2H), 3.08 (multiplet, 2H), 2.66 (triplet, 2H), 2.52 (triplet, 2H), 1.53 (multiplet, 2H), 1.47 (multiplet, 2H), 1.25-1.14 (multiplet, 12H) ppm.

$N^2$-Phosphinyl Guanidine Synthesis 8—$N^2$-Phosphinyl Guanidine Structure XI The $N^2$-phosphinyl guanidine compound having Structure XI was prepared using the same procedure and millimolar quantities as utilized in $N^2$-Phosphinyl Guanidine Synthesis 7 using chloro-diphenylphosphine and triazabicyclo[4.4.0]dec-5-ene as reagents. After the addition of chlorodiphenylphosphine the reaction mixture became significantly thicker with more precipitate. The ether was removed and the white solid was dissolved in dry benzene and filtered. The benzene was removed under vacuum to give a white solid that partially melts under warm conditions (1.2646 g, 81.2% Yield). NMR ($C_6D_6$): δ 7.54 (multiplet, 4H), 7.12 (multiplet, 5H), 3.49 (triplet, 2H), 2.88 (triplet, 2H), 2.66 (triplet, 2H), 2.52 (triplet, 2H), 1.56 (multiplet, 2H), 1.29 (multiplet, 2H) ppm

$N^2$-Phosphinyl Guanidine Synthesis 9—$N^2$-Phosphinyl Guanidine Structure X The $N^2$-phosphinyl guanidine compound having Structure X was prepared using the same procedure and millimolar quantities as utilized in $N^2$-Phosphinyl Guanidine Synthesis 7 using chloro-dicyclohexylphosphine and triazabicyclo[4.4.0]dec-5-ene as reagents. The product was a liquid at room temperature (1.1409 g, 71.0% Yield). NMR ($C_6D_6$): δ 3.46 (broad triplet, 2H), 3.27 (triplet, 2H), 2.94 (broad singlet, 2H), 2.63 (triplet, 2H), 2.52 (triplet, 2H), 2.02 (broad, 2H), 1.89 (broad multiplet, 4H), 1.77 (broad doublet, 2H), 1.68 (broad doublet, 2H), 1.52-1.33 (broad multiplet, 14H) ppm.

$N^2$-Phosphinyl Guanidine Synthesis 10—$N^2$-Phosphinyl Guanidine Structure XXIII The $N^2$-phosphinyl guanidine compound having Structure XXIII was prepared using the same procedure and millimolar quantities as utilized in $N^2$-Phosphinyl Guanidine Synthesis 7 using chloro-diethylphosphine and triazabicyclo[4.4.0]dec-5-ene as reagents. The product was a white powder (0.8302 g, 83.0% Yield). NMR ($C_6D_6$): δ 3.64 (broad singlet, 2H), 2.73 (broad singlet, 2H), 2.56 (triplet, 2H), 2.47 (triplet, 2H), 1.71 (broad multiplet, 2H), 1.49, (multiplet, 2H), 1.31-1.10 (multiplet, 10H) ppm.

$N^2$-Phosphinyl Guanidine Synthesis 11—$N^2$-Phosphinyl Guanidine Structure I The $N^2$-phosphinyl guanidine compound having Structure I was prepared using the same procedure and millimolar quantities as utilized in $N^2$-Phosphinyl Guanidine Synthesis 7 using chloro-diisopropylphosphine and 1,3-di-o-tolylguanidine as reagents. The product was a viscous oil (1.320 g, 74.3% Yield). NMR ($C_6D_6$): δ 9.05 (broad singlet, 1H), 7.20 (multiplet, 6H), 6.90 (multiplet, 2H), 4.20 (broad singlet, 1H), 2.28 (singlet, 6H), 0.81-0.69 (multiplet, 12H) ppm.

Synthesis of Chromium Trichloride $N^2$-Phosphinyl Guanidine Complexes

All chemicals and compounds not prepared as disclosed in the herein Examples were purchased from commercial sources. The $N^2$-phosphinyl guanidine compounds were performed under an argon atmosphere. Tetrahydrofuran were distilled from sodium-benzophenone to eliminate water and oxygen. Anhydrous pentane, benzene, and toluene were degassed and stored over molecular sieves.

$N^2$-Phosphinyl Guanidine Chromium Trichloride Complex Synthesis 1—$N^2$-Phosphinyl Guanidine Chromium Trichloride Complex Structure $CrCl_3Gu$ XIX $CrCl_3(THF)_3$ (0.5 mmol, 0.1873 g) was suspended in 25 ml of toluene in a 50 ml Schlenk flask to give a dark purple solution with suspended solids. One molar equivalent of the $N^2$-phosphinyl guanidine compound having Structure XIX was transferred to the flask. The mixture was stirred for three days and was then filtered through a fritted funnel and washed with pentane to give a dark green solid (0.1470 g, 49.5% Yield).

$N^2$-Phosphinyl Guanidine Chromium Trichloride Complex Synthesis 2—$N^2$-Phosphinyl Guanidine Chromium Trichloride Complex Structure $CrCl_3Gu$ XVIII $CrCl_3(THF)_3$ (0.5 mmol, 0.1873 g) was dissolved in 25 ml of tetrahydrofuran in a 50 ml Schlenk flask to give a clear, purple solution. One molar equivalent of the $N^2$-phosphinyl guanidine compound having Structure XVIII was transferred to the flask. The mixture immediately changed color from clear and purple to very dark green. The reaction was allowed to stir for one hour to ensure the reaction continued to completion. The resulting solution was filtered to give a clear solution. The solvent was removed slowly under vacuum to give a dark green solid (0.5868 g, 98.4% Yield).

$N^2$-Phosphinyl Guanidine Chromium Trichloride Complex Synthesis 3—$N^2$-Phosphinyl Guanidine Chromium Trichloride Complex Structure $CrCl_3Gu$ XVII The $N^2$-phosphinyl guanidine chromium trichloride complex having Structure XVII was prepared using the same procedure and millimolar quantities as utilized in $N^2$-Phosphinyl Guanidine Chromium Trichloride Complex Synthesis 2 using the $N^2$-phosphinyl guanidine compound having Structure XVII. The procedure provided a dark blue solid (0.2699 g, 85.1% Yield).

$N^2$-Phosphinyl Guanidine Chromium Trichloride Complex Synthesis 4—$N^2$-Phosphinyl Guanidine Chromium Trichloride Complex Structure $CrCl_3Gu$ XXII The $N^2$-phosphinyl guanidine chromium trichloride complex having Structure XXII was prepared using the same procedure and millimolar quantities as utilized in $N^2$-Phosphinyl Guanidine Chromium Trichloride Complex Synthesis 1 using the $N^2$-phosphinyl guanidine compound having Structure XXII. The procedure provided a blue solid (0.1007 g, 27.0% Yield).

$N^2$-Phosphinyl Guanidine Chromium Trichloride Complex Synthesis 5—$N^2$-Phosphinyl Guanidine Chromium Trichloride Complex Structure CrCl$_3$Gu XX The $N^2$-phosphinyl guanidine chromium trichloride complex having Structure XX was prepared using the same procedure and millimolar quantities as utilized in $N^2$-Phosphinyl Guanidine Chromium Trichloride Complex Synthesis 2 using the $N^2$-phosphinyl guanidine compound having Structure XX. The procedure provided a dark green solid (0.3066 g, 92.6% Yield).

$N^2$-Phosphinyl Guanidine Chromium Trichloride Complex Synthesis 6—$N^2$-Phosphinyl Guanidine Chromium Trichloride Complex Structure CrCl$_3$Gu XXI The $N^2$-phosphinyl guanidine chromium trichloride complex having Structure XXI was prepared using the same procedure and millimolar quantities as utilized in $N^2$-Phosphinyl Guanidine Chromium Trichloride Complex Synthesis 2 using the $N^2$-phosphinyl guanidine compound having Structure XXI. The procedure provided a green solid (0.2885 g, 82.5% Yield).

$N^2$-Phosphinyl Guanidine Chromium Trichloride Complex Synthesis 7—$N^2$-Phosphinyl Guanidine Chromium Trichloride Complex Structure CrCl$_3$Gu VII The $N^2$-phosphinyl guanidine chromium trichloride complex having Structure VII was prepared using the same procedure as utilized in $N^2$-Phosphinyl Guanidine Chromium Trichloride Complex Synthesis 2 except the procedure utilized 2.0 mmoles of the $N^2$-phosphinyl guanidine compound having Structure VII and 2.0 mmoles of CrCl$_3$(THF)$_3$. The procedure provided a greenish-blue solid (0.8721 g, 89.9% Yield).

$N^2$-Phosphinyl Guanidine Chromium Trichloride Complex Synthesis 8—$N^2$-Phosphinyl Guanidine Chromium Trichloride Complex Structure CrCl$_3$Gu XI The $N^2$-phosphinyl guanidine chromium trichloride complex having Structure XI was prepared using the same procedure as utilized in $N^2$-Phosphinyl Guanidine Chromium Trichloride Complex Synthesis 2 except the procedure utilized 2.0 mmoles of the $N^2$-phosphinyl guanidine compound having Structure XI and 2.0 mmoles of CrCl$_3$(THF)$_3$. The procedure provided a dark blue solid (1.081, 86.0% Yield).

$N^2$-Phosphinyl Guanidine Chromium Trichloride Complex Synthesis 9—$N^2$-Phosphinyl Guanidine Chromium Trichloride Complex Structure CrCl$_3$Gu X The $N^2$-phosphinyl guanidine chromium trichloride complex having Structure X was prepared using the same procedure and millimolar quantities as utilized in $N^2$-Phosphinyl Guanidine Chromium Trichloride Complex Synthesis 2 using the $N^2$-phosphinyl guanidine compound having Structure X. The procedure provided a dark blue solid (0.2000 g, 72.6% Yield).

$N^2$-Phosphinyl Guanidine Chromium Trichloride Complex Synthesis 10—$N^2$-Phosphinyl Guanidine Chromium Trichloride Complex Structure CrCl$_3$Gu XXIII The $N^2$-phosphinyl guanidine chromium trichloride complex having Structure XXIII was prepared using the same procedure and millimolar quantities as utilized in $N^2$-Phosphinyl Guanidine Chromium Trichloride Complex Synthesis 2 using the $N^2$-phosphinyl guanidine compound having Structure XXIII. The procedure provided a dark blue solid (0.1590 g, 71.3% Yield).

$N^2$-Phosphinyl Guanidine Chromium Trichloride Complex Synthesis 11—$N^2$-Phosphinyl Guanidine Chromium Trichloride Complex Structure CrCl$_3$Gu I The $N^2$-phosphinyl guanidine chromium trichloride complex having Structure I was prepared using the same procedure and millimolar quantities as utilized in $N^2$-Phosphinyl Guanidine Chromium Trichloride Complex Synthesis 2 using the $N^2$-phosphinyl guanidine compound having Structure I. The procedure provided a dark blue solid (0.2467 g, 84.4% Yield).

Olefin Oligomerization

The $N^2$-phosphinyl guanidine compounds and $N^2$-phosphinyl guanidine metal salt complexes were utilized as prepared using the methods described herein. The MMAO-3A (7 wt % aluminum in heptanes) was utilized as obtained from the chemical supplier Akzo-Nobel. The solvents were dried and/or purified using conventional methods and stored under conditions to limit their ability to pick-up water. In the product analyses, reference to an amount of $C_6$ or $C_8$ products refer to all oligomer products having 6 or 8 carbon atoms, respectively, within the oligomer product. References to weight percent of 1-hexene or 1-octene refer to the weight percent of 1-hexene or 1-octene in the $C_6$ or $C_8$ product portion of the oligomer product, respectively (e.g., product purities).

Ethylene Oligomerization Run-Standard Method

A 1 L stainless steel reactor was dried under vacuum at 110° C. for at least 8 hours prior to use. The reactor was then cooled to 50° C. In the drybox, a 20 mL glass vial was charged with an $N^2$-phosphinyl guanidine metal salt complex and ethylbenzene (1.0 g). MMAO-3A (3.3 g, 7.6 wt % Al solution in heptanes) was added to the blue heterogeneous solution of the $N^2$-phosphinyl metal salt complex resulting in formation of a yellow solution. The catalyst system was then allowed to set overnight (approximately 18 hours). The yellow solution was then added to 0.5 L glass charger containing 400 ml cyclohexane. This solution was removed from the drybox and charged into the reactor. Hydrogen (50 psig) was added followed by ethylene (850 psig, fed on-demand). The reaction was allowed to proceed for 30 minutes (starting from the introduction of ethylene) at 50° C. After 30 minutes, water cooling was applied to the reactor system. Once the temperature reached 35° C., the unreacted ethylene and hydrogen gas was vented to the atmosphere. A liquid sample was collected and analyzed by GC-FID; for this run ethylbenzene was used as the internal standard. Solids were collected by filtering the solution and cleaning the reactor walls and cooling coil. The $N^2$-phosphinyl guanidine metal salt complexes and amount of materials utilized for each ethylene oligomerization are provided are summarized in Table 4 along with the results of each oligomerization run.

TABLE 4

Ethylene Oligomerization Runs

| Complex Structure Designation | CrCl₃•THF Gu VII | CrCl₃•THF Gu XI | CrCl₃•THF Gu XI | CrCl₃•THF Gu I |
|---|---|---|---|---|
| Catalyst System and Oligomerization Parameters | | | | |
| MW complex (g/mole) | 484.79 | 623.92 | 623.92 | 656.01 |
| mg complex | 5 | 6 | 6 | 6 |
| mmol complex | 0.0103 | 0.0096 | 0.0096 | 0.0091 |
| mg Cr | 0.54 | 0.50 | 0.50 | 0.48 |
| MMAO (g 7.6 wt. % Al solution in heptanes) | 3.3 | 3.3 | 3.3 | 3.3 |
| Al:Cr molar ratio | 600 | 600 | 600 | 600 |
| Bulk solvent | 0.4 L, cyH | 0.4 L, cyH | 0.4 L, cyH | 0.4 L, cyH |
| rxn time (min) | 20 | 20 | 20 | 30 |
| $C_2H_4$ (psig) | 875 | 875 | 875 | 875 |
| $H_2$ (psig) | 25 | 25 | 25 | 25 |
| rxn temp (° C.) | 70 | 70 | 70 | 70 |
| Product Analysis | | | | |
| g polymer | 0.6 | 0.4 | 0.6 | 2.4 |
| g liquid product | 101.7 | 5 | 6.4 | 15.1 |
| Polymer | 0.6 | 7.4 | 8.6 | 13.7 |
| Carbon Number Distribution | | | | |
| $C_6$, (wt. %) | 67.4 | 33.6 | 37.0 | 60.7 |
| $C_8$, (wt. %) | 30.3 | 36.8 | 41.7 | 26.9 |
| $C_{10}$, (wt. %) | 1.3 | 7.3 | 7.2 | 2.2 |
| $C_{12}$, (wt. %) | 0.7 | 5.9 | 9.0 | 1.6 |
| $C_{14+}$, (wt. %) | 0.3 | 16.4 | 5.1 | 8.6 |
| ($C_6 + C_8$) (wt. %) | 97.7 | 70.4 | 78.7 | 87.6 |
| Productivity ($C_6 + C_8$) | 185,300 | 7,000 | 10,100 | 27,800 |
| purity $C_6$ (wt. %) | 91.51 | 46.01 | 44.74 | 94.13 |
| purity $C_8$ (wt. %) | 97.66 | 84.59 | 84.96 | 96.71 |

What is claimed:

1. A composition comprising an $N^2$-phosphinyl guanidine metal salt complex comprising a chromium salt complexed to an $N^2$-phosphinyl guanidine compound.

2. The composition of claim 1, wherein the $N^2$-phosphinyl guanidine metal salt complex has a general structure:

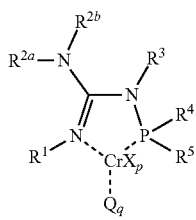

wherein:

$R^1$ is a $C_1$ to $C_{30}$ organyl group, $R^2$ and $R^{2b}$ independently are $C_1$ to $C_{30}$ organyl groups consisting essentially of inert functional groups, $R^3$ is hydrogen or a $C_1$ to $C_{30}$ organyl group consisting essentially of inert functional groups, $R^4$ and $R^5$ each independently are $C_1$ to $C_{30}$ organyl groups consisting essentially of inert functional groups, $CrX_p$ represents a chromium salt where X is a monoanion, and p ranges from 2 to 6, and Q is a neutral ligand, and q ranges from 0 to 6, wherein the inert functional groups are selected from the group consisting of halo groups, nitro groups, hydrocarboxy groups, hydrocarbosulfidyl groups, or combinations thereof.

3. The composition of claim 2, wherein
a) $R^1$ and $R^{2a}$ can be joined to form a ring or a ring system,
b) $R^{2a}$ and $R^{2b}$ can be joined to form a ring or a ring system,
c) $R^{2b}$ and $R^3$ can be joined to form a ring or a ring system, or
d) $R^1$ and $R^{2a}$ can be joined to form a ring or a ring system, and $R^{2b}$ and $R^3$ can be joined to form a ring or a ring system.

4. The composition of claim 2, wherein the $N^2$-phosphinyl guanidine metal salt complex has the general structure:

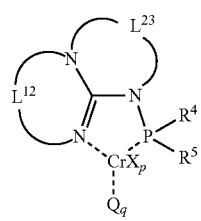

wherein $L^{12}$ and $L^{23}$ independently are $C_2$ to $C_{15}$ organylene group consisting of inert functional groups, wherein the inert functional groups are selected from the group consisting of halo groups, nitro groups, hydrocarboxy groups, hydrocarbosulfidyl groups, or combinations thereof.

5. The composition of claim 1, wherein the chromium salt comprises a chromium(III) carboxylate, a chromium(III) β-diketonate, or a chromium(III) halide.

6. The composition of claim 1, wherein the chromium salt comprises a chromium(III) halide.

7. The composition of claim 2, wherein Q comprises a $C_1$ to $C_{20}$ nitrile or a $C_1$ to $C_{40}$ ether.

8. The conposition of claim 2, wherein $CrX_p$ comprises a chromium(III) halide and each Q independently is a $C_2$ to $C_{30}$ aliphatic acyclic ether or a $C_3$ to $C_{30}$ aliphatic cyclic ether.

9. The composition of claim 1 wherein the $N^2$-phosphinyl guanidine metal salt complex has the structure:

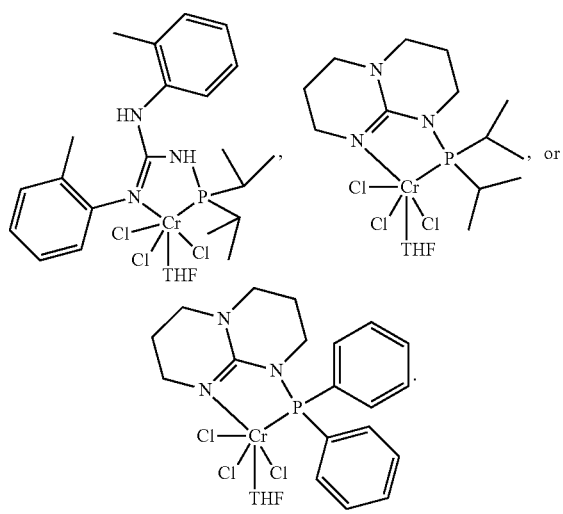

10. A catalyst system composition comprising:
a) an $N^2$-phosphinyl guanidine metal salt complex comprising a chromium salt complexed to an $N^2$-phosphinyl guanidine compound; and
b) a metal alkyl compound.

11. The catalyst system composition of claim 10, wherein the metal alkyl compound comprises an aluminoxane.

12. The catalyst system composition of claim 11, the aluminoxane comprises methyauminoxane, modified methylalumninoxane, ethylaluminoxane, n-propylaluminoxane, isopropylaluminoxane, n-butylaluminoxane, sec-butylaluminoxane, iso-butylaluminoxane, t-butyl aluminoxane, 1pentylaluminoxane, 2pentylaluminoxane, 3pentylaluminoxane, iso-pentylaluminoxane, neopentylaluminoxane, and mixtures thereof.

13. The catalyst system composition of claim 11, wherein the metal alkyl comprises modified methylaluminoxane.

14. The catalyst system composition of claim 12, wherein an aluminum of the aluminoxane to chromium of the $N^2$-phosohinyl guanidine metal salt complex molar ratio is at least 5:1.

15. A process of preparing a catalyst system composition comprising contacting an $N^2$-phosphinyl guanidine metal salt complex comprising a chromium salt complexed to an $N^2$-phosphinyl guanidine compound and a metal alkyl compound.

16. The process of claim 15, wherein the catalyst system composition is aged in the substantial absence of an olefin for at least 15 minutes.

17. The process of claim 16, wherein the aged catalyst system composition displays a) increased oligomerization catalytic activity when compared to an otherwise similar catalyst system that has not been aged, b) reduced percentage of produced polymer when compared to an otherwise similar catalyst system that has not been aged, or c) increased oligomerization catalytic activity and a reduced percentage of produced polymer when compared to an otherwise similar catalyst system that has not been aged.

18. An oligomerization process comprising:
a) contacting
i) an olefin, and
ii) a catalyst system comprising
(a) $N^2$-phosphinyl guanidine metal salt complex comprising a chromium salt complexed to an $N^2$-phosphinyl guanidine compound, and
(b) a metal alkyl compound,
to form an oligomer product; and
b) recovering an oligomer.

19. The process of claim 18, wherein the catalyst system, olefin, and hydrogen are contacted to form an oligomer product.

20. The process of claim 18, wherein the oligomer product is formed at a temperature ranging from 20 °C to 150 °C.

21. The process of claim 18, wherein the olefin comprises ethylene and wherein the oligomer product comprises a liquid oligomer product comprising from 60 to 99.9 wt. % $C_6$ and $C_8$ olefins.

22. The process of claim 18, wherein the olefin comprises ethylene and wherein a $C_6$ oligomer product comprises at least 90 wt. % 1-hexene.

23. The process of claim 18, wherein the olefin comprises ethylene and wherein a $C_8$ oligomer product comprises at least 90 wt. % 1-octene.

24. The process of claim 18, wherein the catalyst system, the olefin, and hydrogen are contacted to form an oligomer product,
wherein the olefin comprises ethylene,
wherein the oligomer product is formed at;
(a) an ethylene partial pressure ranging from 150 psig to 2000 psig.
(b) a hydrogen partial pressure; ranging from 5 psig to 400 psig, and
(c) a temperature ranging from 20 °C to 150 °C, and
wherein the oligomer prpduct comprises a liquid oligomer product comprising from 60 to 99.9 wt. % wt. % $C_6$ and $C_8$ olefins, a $C_6$ oligomer product comprises at least 90 wt. % 1-hexene and a $C_8$ oligomer product comprises at least 90 wt. % 1-octene.

* * * * *